(12) United States Patent
Dorsch et al.

(10) Patent No.: US 11,174,241 B2
(45) Date of Patent: Nov. 16, 2021

(54) QUINOLIN-2-ONE DERIVATIVES

(71) Applicant: MERCK PATENT GMBH, Darmstadt (DE)

(72) Inventors: Dieter Dorsch, Ober-Ramstadt (DE); Mathilde Muzerelle, Martigny (CH); Lars Burgdorf, Frankfurt am Main (DE); Margarita Wucherer-Plietker, Messel (DE); Paul Czodrowski, Mainz (DE); Christina Esdar, Darmstadt (DE); Christos Tsaklakidis, Weinheim (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 16/796,046

(22) Filed: Feb. 20, 2020

(65) Prior Publication Data

US 2020/0190055 A1 Jun. 18, 2020

Related U.S. Application Data

(62) Division of application No. 16/069,326, filed as application No. PCT/EP2016/002118 on Dec. 16, 2016, now Pat. No. 10,669,251.

(30) Foreign Application Priority Data

Jan. 11, 2016 (EP) .................................. 16150717

(51) Int. Cl.
| | | |
|---|---|---|
| C07D 401/04 | (2006.01) | |
| C07D 413/14 | (2006.01) | |
| C07D 417/14 | (2006.01) | |
| C07D 487/04 | (2006.01) | |
| C07D 487/10 | (2006.01) | |
| C07D 403/04 | (2006.01) | |
| C07D 497/10 | (2006.01) | |
| C07D 407/14 | (2006.01) | |
| C07D 403/14 | (2006.01) | |
| A61K 31/4375 | (2006.01) | |
| A61K 31/4709 | (2006.01) | |
| A61K 31/496 | (2006.01) | |
| A61K 31/5377 | (2006.01) | |
| A61K 31/551 | (2006.01) | |
| A61K 45/06 | (2006.01) | |
| C07D 401/14 | (2006.01) | |
| C07D 471/04 | (2006.01) | |
| C07D 491/107 | (2006.01) | |
| C07D 498/10 | (2006.01) | |

(52) U.S. Cl.
CPC ........ *C07D 401/04* (2013.01); *A61K 31/4375* (2013.01); *A61K 31/4709* (2013.01); *A61K 31/496* (2013.01); *A61K 31/5377* (2013.01); *A61K 31/551* (2013.01); *A61K 45/06* (2013.01); *C07D 401/14* (2013.01); *C07D 403/04* (2013.01); *C07D 403/14* (2013.01); *C07D 407/14* (2013.01); *C07D 413/14* (2013.01); *C07D 417/14* (2013.01); *C07D 471/04* (2013.01); *C07D 487/04* (2013.01); *C07D 487/10* (2013.01); *C07D 491/107* (2013.01); *C07D 497/10* (2013.01); *C07D 498/10* (2013.01)

(58) Field of Classification Search
CPC .. C07D 401/04; C07D 401/14; C07D 471/04; C07D 491/107; C07D 498/10; C07D 413/14; C07D 497/10; C07D 407/14; C07D 403/04; C07D 403/14; A61K 31/4375; A61K 31/4709; A61K 31/496; A61K 31/5377; A61K 31/551; A61K 45/06
USPC ........................................................ 546/156
See application file for complete search history.

(56) References Cited

U.S. PATENT DOCUMENTS

| | | | |
|---|---|---|---|
| 10,669,251 B2* | 6/2020 | Dorsch | ................... A61P 35/00 |
| 2005/0049274 A1 | 3/2005 | Wall | |
| 2015/0238480 A1 | 8/2015 | Daugan | |

FOREIGN PATENT DOCUMENTS

| | | |
|---|---|---|
| WO | 2005009967 A2 | 2/2005 |
| WO | 2012119978 A1 | 9/2012 |
| WO | 2013184119 A1 | 12/2013 |

OTHER PUBLICATIONS

Search Report in corresponding Russian Patent Application No. 2018 128 642 dated Apr. 15, 2020 (pp. 1-8).
Belikov V. G. Pharmacevtičeskaâ himiâ [Pharmaceutical Chemistry]. Moscow: MEDpressinform, 2007, pp. 27-29 . See also English translation.

(Continued)

*Primary Examiner* — Taylor V Oh
(74) *Attorney, Agent, or Firm* — Millen, White, Zelano & Branigan, PC; Ryan Pool

(57) ABSTRACT

Compounds of the formula I

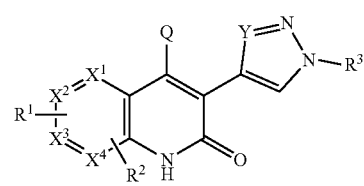

in which $X^1$, $X^2$, $X^3$, $X^4$, $R^1$, $R^2$, $R^3$, Q and Y have the meanings indicated in Claim 1,
are inhibitors of c-Kit kinase, and can be employed for the treatment of cancer.

8 Claims, No Drawings

(56) References Cited

OTHER PUBLICATIONS

Dyson G., May P. Himiâ sintetičeskih lekarstvennyh sredstv [Chemistry of Synthetic Drugs]. (Transl.) Moscow: Mir, 1964, pp. 12-19. See also English translation.

Sof'ina Z. P. et al. Ocenka informativnosti eksperimental'nyh testov, ispol'zuemyh diâ prognoza kliničeskoj aktivnosti protivoopuholevyh preparatov [Evaluation of the informational value of experimental tests used for the prognosis of the clinical activity of antitumour medicaments]. Vestnik onkologičeskogo naučnogo centra RAMN, 1993 4(S), pp. 4-8, table 1). See also English translation.

International Search Report PCT/EP2016/002118 dated Mar. 9, 2017.

\* cited by examiner

QUINOLIN-2-ONE DERIVATIVES

BACKGROUND OF THE INVENTION

The invention had the object of finding novel compounds having valuable properties, in particular those which can be used for the preparation of medicaments.

The present invention relates to quinolin-2-one derivatives which inhibit c-KIT kinase across a wide range of c-KIT mutations and secondary mutations (V654A secondary resistance mutation in Exon 13) that may arise in GIST (gastrointestinal stromal tumor) patients.

The compounds of this invention are therefore useful in treating diseases such as cancer.

The present invention also provides methods for preparing these compounds, pharmaceutical compositions comprising these compounds, the compounds for use for the treatment of diseases and methods of treating diseases utilizing pharmaceutical compositions comprising these compounds.

Mutated forms of the receptor tyrosine kinase c-KIT are "drivers" in several cancers and are attractive targets for therapy. While benefits have been obtained from use of inhibitors of KIT kinase activity such as imatinib, especially in GIST, primary resistance occurs with certain oncogenic mutations.

Furthermore, resistance frequently develops due to secondary mutations (L. K. Ashman & R. Griffith (2013) Expert Opinion on Investigational Drugs, 22:1, 103-115).

L. L. Chen et al. describe "A Missense Mutation in KIT kinase domain 1 correlates with imatinib resistance in gastrointestinal stromal tumors" in Cancer res. 2004; 64:5913-5919.

K. G. Roberts et al. describe "Resistance to c-KIT kinase inhibitors conferred by V654A mutation" in Mol. Cancer Ther. 2007; 6:1159-1166.

Gastrointestinal stromal tumors (GISTs) are the most common mesenchymal tumors of the gastrointestinal (GI) tract.

GISTs are defined as c-KIT (CD117, stem cell factor receptor)-positive mesenchymal spindle cell or epitheloid neoplasms.

GISTs have commonly primary activating mutations of the KIT gene (90%) leading to ligand-independent activation of the receptor tyrosine kinase c-KIT rendering the tumor dependent on oncogenic KIT activity.

Imatinib treatment of GISTs with primary mutation has an initial response rate of ~70% but secondary resistance emerges in almost all tumors.

Approximately 60-70% of patients failing on Imatinib harbor the secondary V654A resistance mutation in c-KIT.

There is a high unmet medical need for development of a safe and specific inhibitor against KIT V654A resistance mutation.

It has been found that the compounds according to the invention and salts thereof have very valuable pharmacological properties while being well tol-erated.

The present invention specifically relates to compounds of the formula I which inhibit c-KIT kinase, preferably the mutant V654A of c-KIT kinase.

Moreover, compounds of the formula I inhibit PDGFRα (V651D). The gain-of-function mutations of PDGFRα appear to play an important role in development of GISTs without KIT mutations (S. Hirota et al., Gastroenterology 2003; 125:660-667).

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

T. N. Glasnov and C. O. Kappe describe in *QSAR Comb. Sci* 2007, 26, 1261 the compound
6,7-dimethoxy-3-(1-phenyl-1H-1,2,3-triazol-4-yl)quinolin-2(1H)-one

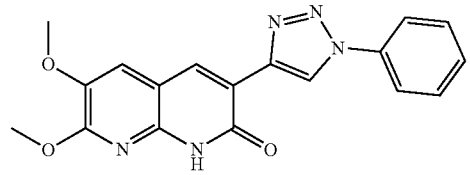 [SMILES: COc1cc2cc(-c3cn(-c4ccccc4)nn3)c(=O)[nH]c2nc1OC]

having fluorescent characteristics.

Dihydronaphthyridines and related compounds are described in WO 2013/184119 A1 as inhibitors of c-Kit mutants including the V654A mutant.

SUMMARY OF THE INVENTION

The invention relates to compounds of the formula I

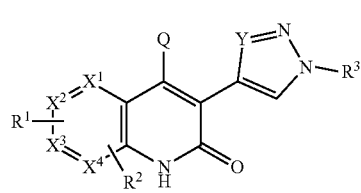

in which
$X^1$, $X^2$, $X^3$, $X^4$ each, independently of one another, denote CH or N,
Y denotes N or CH,
Q denotes H or $CH_3$,
$R^1$ denotes H, F, Cl, Br, CN, $CH_3$, $CF_3$ or $OCH_3$, $R^2$ denotes H, F or Cl, $R^3$ denotes phenyl, naphthyl, pyridyl, pyrimidinyl, quinolinyl, isoquinolinyl, indolyl, indazolyl, thiophenyl, dihydroisoindolyl or benzimidazolyl, each of which is unsubstituted or mono-, di- or trisubstituted by Hal, CN, $NO_2$, A, $(CR^4)_nOR^4$, $(CR^4)_nN(R^4)_2$, $(CR^4)_nS(O)_mR^4$, $(CR^4)_nCON(R^4)_2$, $(CR^4)_nCOHet$, $(CR^4)_nSO_2N(R^4)_2$, $(CR^4)_nSO_2Het$, $(CR^4)_nN(R^4)_2$, $(CR^4)_nHet$, $O(CR^4)_nCO\text{-}Het$, $(CR^4)_nO(CR^4)_nHet$, $(CR^4)_nN(R^4)(CR^4)_nHet$, $(CR^4)_nCON(R^4)(CR^4)_nHet$, $(CR^4)_nCON(R^4)(CR^4)_nN(R^4)_2$, $(CR^4)_nN(R^4)COA$, $(CR^4)_nN(R^4)COHet'$, $(CR^4)_nOCyc$ and/or $(CR^4)_nCOOR^4$, $R^4$ denotes H or A', A denotes unbranched or branched alkyl with 1-10 C-atoms, wherein two adjacent carbon atoms may form a double bond and/or one or two non-adjacent CH- and/or $CH_2$- groups may be replaced by N-, O- and/or S-atoms and wherein 1-7H-atoms may be replaced by $R^5$, or cyclic alkyl having 3-7 C atoms, A' denotes unbranched or branched alkyl with 1-6 C-atoms, wherein one or two non-adjacent CH- and/or $CH_2$-groups may be replaced by O-atoms, Cyc denotes cyclobutyl, cyclopentyl or cyclohexyl, each of which is unsubstituted or mono- or disubstituted by A, Hal, $OR^4$, $N(R^4)_2$, Het', $(CR^4)_nO(CR^4)_nHet'$, $CON(R^4)_2$ and/or =O, $R^5$ denotes F, Cl or OH, Het denotes pyrrolidinyl, morpholinyl, piperidinyl, piperazinyl, [1,4]-diazepanyl, oxazolidinyl, hexahydro-pyrrolo[3,4-c]pyrrolyl, 2-oxa-6-aza-spiro[3.4]octanyl, 2-oxa-6-aza-spiro[3.5]nonanyl, 2-oxa-7-aza-spiro[3.5]nonanyl, 2,5-dioxa-8-aza-spiro[3.5]nonanyl, oxetanyl, 2-oxa-5-aza-spiro[3.4]octanyl, 2-oxa-6-aza-spiro[3.3]heptanyl, 3-aza-bicyclo[3.1.0]hexanyl, 2-oxa-7-aza-spiro[3.5]nonanyl, isoxazolidinyl, azetidinyl, 2,6-diaza-spiro[3.4]octanyl, hexahydro-pyrrolo[3,4-b]pyrrolyl, tetrahydrofuranyl or isothiazolidinyl, each of which is unsubstituted or mono-, di- or trisubstituted by A, Hal, $OR^4$, OCOA, COA, $(CR^4)_nN(R^4)_2$, $(CR^4)_nHet'$, $(CR^4)_nO(CR^4)_nHet'$, $CON(R^4)_2$, $COHet'$, $(CR^4)_nS(O)_mR^4$, and/or =O, Het' denotes pyrrolidinyl, morpholinyl, piperidinyl, oxetanyl, tetrahydrofuranyl, tetrahydropyranyl, pyridyl, pyrazolyl or piperazinyl, each of which is unsubstituted or mono- or disubstituted by A, Hal, $OR^4$, $N(R^4)_2$ and/or =O, Hal denotes F, Cl, Br or I, n denotes 0, 1, 2 or 3, m denotes 0, 1 or 2, with the proviso that only one or two of $X^1$, $X^2$, $X^3$, $X^4$ denote N, and pharmaceutically acceptable salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides. It is understood, that the invention also relates to the solvates of the salts. The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues.

In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syn-drome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically acceptable salts, solvates, tautomers and stereoisomers thereof, characterised in that a) for the preparation of compounds of the formula I, wherein $X^1$, $X^2$, $X^3$, $X^4$ denote CH and Y denotes N, a compound of the formula II

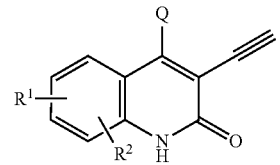

II in which $R^1$, $R^2$ and Q have the meanings indicated in Claim 1,
is reacted with a compound of formula III

 III in which $R^3$ has the meanings indicated in Claim 1,
or b) for the preparation of compounds of the formula I, wherein
Y denotes N,
a compound of the formula IV

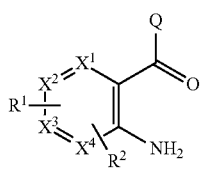 IV in which
and $X^1$, $X^2$, $X^3$, $X^4$, $R^1$, $R^2$ and Q have the meanings indicated in Claim 1,
is reacted with a compound of formula V

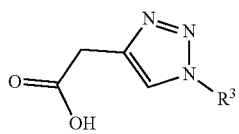 V in which $R^3$ has the meanings indicated in Claim 1,
or c) a radical $R^3$ is converted into another radical $R^3$ by
i) converting a carboxylic group into an amide,
ii) acylating or alkylating an amino group,
or d) that a compound of formula I is liberated from one of its functional derivatives by treatment with a solvolysing or hydrogenolysing agent,
and/or
a base or acid of the formula I is converted into one of its salts.

Above and below, the radicals $X^1$, $X^2$, $X^3$, $X^4$, $R^1$, $R^2$, $R^3$, Q and Y have the meanings indicated for the formula I, unless explicitely stated otherwise.

A denotes alkyl, this is unbranched (linear) or branched, and has 1, 2, 3, 4, 5, 6, 7, 8, 9 or 10 C atoms. A preferably denotes methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Cyclic alkyl preferably denotes cyclopropyl, cyclobutyl, cyclopentyl or cyclohexyl.
Moreover, A denotes preferably $CH_2OCH_3$, $CH_2CH_2OH$ or $CH_2CH_2OCH_3$.

A' denotes alkyl, this is unbranched (linear) or branched, and has 1, 2, 3, 4, 5 or 4 6 atoms. A' preferably denotes methyl, ethyl, propyl, isopropyl, butyl, isobutyl, sec-butyl or tert-butyl. Moreover, A' denotes preferably $CH_2OCH_3$, $CH_2CH_2OH$ or $CH_2CH_2OCH_3$.

$R^1$ preferably denotes H, F, Cl, Br, CN, $CH_3$, $CF_3$ or $OCH_3$; particularly preferably F or Cl.

$R^2$ preferably denotes H or F; particularly preferably F.

$R^3$ preferably denotes phenyl, pyridyl, pyrimidinyl, indolyl, indazolyl, thiophenyl, dihydroisoindolyl or benzimidazolyl, each of which is unsubstituted or mono-, di- or trisubstituted by Hal, A, $(CR^4)_nOR^4$, $(CR^4)_nN(R^4)_2$, $(CR^4)_nS(O)_mR^4$, $(CR^4)_nCON(R^4)_2$, $(CR^4)_nCOHet$, $(CR^4)_nSO_2Het$, $(CR^4)_nHet$, $O(CR^4)_nCOHet$, $(CR^4)_nO(CR^4)_nHet$, $(CR^4)_nN(R^4)(CR^4)_nHet$, $(CR^4)_nCON(R^4)(CR^4)_nHet$, $(CR^4)_nCON(R^4)(CR^4)_nN(R^4)_2$, $(CR^4)_nN(R^4)COA$, $(CR^4)_nN(R^4)COHet'$, $(CR^4)_nOCyc$ and/or $(CR^4)_nCOOR^4$.

$R^3$ more preferably denotes phenyl, which is unsubstituted or mono-, di- or trisubstituted by Hal, A, $(CR^4)_nOR^4$, $(CR^4)_nN(R^4)_2$, $(CR^4)_nS(O)_mR^4$, $(CR^4)_nCON(R^4)_2$, $(CR^4)_nCOHet$, $(CR^4)_nSO_2Het$, $(CR^4)_nHet$, $O(CR^4)_nCOHet$, $(CR^4)_nO(CR^4)_nHet$, $(CR^4)_nN(R^4)(CR^4)_nHet$, $(CR^4)_nCON(R^4)(CR^4)_nHet$, $(CR^4)_nCON(R^4)(CR^4)_nN(R^4)_2$, $(CR^4)_nN(R^4)COA$, $(CR^4)_nN(R^4)COHet'$, $(CR^4)_nOCyc$ and/or $(CR^4)_nCOOR^4$;

A preferably denotes unbranched or branched alkyl with 1-10 C-atoms, wherein two adjacent carbon atoms may form a double bond and/or one or two non-adjacent CH- and/or $CH_2$-groups may be replaced by N- and/or O-atoms and wherein 1-7H-atoms may be replaced by $R^5$.

Het' preferably denotes pyrrolidinyl.

$X^1$, $X^2$, $X^3$, $X^4$ preferably denote CH.

Y preferably denotes N.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to If, which conform to the formula I and in which the radicals not designated in greater detail have the meaning indicated for the formula I, but in which in Ia $R^1$ denotes H, F, Cl, Br, CN, $CH_3$, $CF_3$ or $OCH_3$,
$R^2$ denotes H or F;

in Ib $R^3$ denotes phenyl, pyridyl, pyrimidinyl, indolyl, indazolyl, thiophenyl, dihydroisoindolyl or benzimidazolyl, each of which is unsubstituted or mono-, di- or trisubstituted by Hal, A, $(CR^4)_nOR^4$, $(CR^4)_nN(R^4)_2$, $(CR^4)_nS(O)_mR^4$, $(CR^4)_nCON(R^4)_2$, $(CR^4)_nCOHet$, $(CR^4)_nSO_2Het$, $(CR^4)_nHet$, $O(CR^4)_nCOHet$, $(CR^4)_nO(CR^4)_nHet$, $(CR^4)_nN(R^4)(CR^4)_nHet$, $(CR^4)_nCON(R^4)(CR^4)_nHet$, $(CR^4)_nCON(R^4)(CR^4)_nN(R^4)_2$, $(CR^4)_nN(R^4)COA$, $(CR^4)_nN(R^4)COHet'$, $(CR^4)_nOCyc$ and/or $(CR^4)_nCOOR^4$;

in Ic A denotes unbranched or branched alkyl with 1-10 C-atoms, wherein two adjacent carbon atoms may form a double bond and/or one or two non-adjacent CH- and/or $CH_2$-groups may be replaced by N- and/or O-atoms and wherein 1-7H-atoms may be replaced by $R^5$;

in Id Het' denotes pyrrolidinyl;

in Ie $X^1$, $X^2$, $X^3$, $X^4$ each, independently of one another, denote CH or N, Y denotes N or CH,
Q denotes H or CH$_3$,
R$^1$ denotes H, F, Cl, Br, CN, CH$_3$, CF$_3$ or OCH$_3$,
R$^2$ denotes H or F,
R$^3$ denotes phenyl, pyridyl, pyrimidinyl, indolyl, indazolyl, thiophenyl, dihydroisoindolyl or benzimidazolyl, each of which is unsubstituted or mono-, di- or trisubstituted by Hal, A, (CR$^4$)$_n$OR$^4$, (CR$^4$)$_n$N(R$^4$)$_2$, (CR$^4$)$_n$S(O)$_m$R$^4$, (CR$^4$)$_n$CON(R$^4$)$_2$, (CR$^4$)$_n$COHet, (CR$^4$)$_n$SO$_2$Het, (CR$^4$)$_n$Het, O(CR$^4$)$_n$COHet, (CR$^4$)$_n$O(CR$^4$)$_n$Het, (CR$^4$)$_n$N(R$^4$)(CR$^4$)$_n$Het, (CR$^4$)$_n$CON(R$^4$)(CR$^4$)$_n$Het, (CR$^4$)$_n$CON(R$^4$)(CR$^4$)$_n$N(R$^4$)$_2$, (CR$^4$)$_n$N(R$^4$)COA, (CR$^4$)$_n$N(R$^4$)COHet', (CR$^4$)$_n$OCyc and/or (CR$^4$)$_n$COOR$^4$,
R$^4$ denotes H or A',
A denotes unbranched or branched alkyl with 1-10 C-atoms, wherein two adjacent carbon atoms may form a double bond and/or one or two non-adjacent CH- and/or CH$_2$-groups may be replaced by N- and/or O-atoms and wherein 1-7H-atoms may be replaced by R$^5$,
Cyc denotes cyclobutyl, cyclopentyl or cyclohexyl, each of which is unsubstituted or mono- or disubstituted by A, Hal, OR$^4$, N(R$^4$)$_2$, Het', (CR$^4$)$_n$O(CR$^4$)$_n$Het', CON(R$^4$)$_2$ and/or =O,
A' denotes unbranched or branched alkyl with 1-6 C-atoms, wherein one or two non-adjacent CH- and/or CH$_2$-groups may be replaced by O-atoms,
R$^5$ denotes F, Cl or OH,
Het denotes pyrrolidinyl, morpholinyl, piperidinyl, piperazinyl, [1,4]-diazepanyl, oxazolidinyl, hexahydro-pyrrolo[3,4-c]pyrrolyl, 2-oxa-6-aza-spiro[3.4]octanyl, 2-oxa-6-aza-spiro[3.5]nonanyl, 2-oxa-7-aza-spiro[3.5]nonanyl, 2,5-dioxa-8-aza-spiro[3.5]nonanyl, oxetanyl, 2-oxa-5-aza-spiro[3.4]octanyl, 2-oxa-6-aza-spiro[3.3]heptanyl, 3-aza-bicyclo[3.1.0]hexanyl, 2-oxa-7-aza-spiro[3.5]nonanyl, isoxazolidinyl, azetidinyl, 2,6-di-aza-spiro[3.4]octanyl, hexahydro-pyrrolo[3,4-b]pyrrolyl, tetrahydrofuranyl or isothiazolidinyl, each of which is unsubstituted or mono-, di- or trisubstituted by A, Hal, OR$^4$, OCOA, COA, (CR$^4$)$_n$N(R$^4$)$_2$, (CR$^4$)$_n$Het', (CR$^4$)$_n$O(CR$^4$)$_n$Het', CON(R$^4$)$_2$, COHet', (CR$^4$)$_n$S(O)$_m$R$^4$, and/or =O,
Het' denotes pyrrolidinyl, oxetanyl, tetrahydrofuranyl, tetrahydropyranyl, pyridyl or pyrazolyl,
Hal denotes F, Cl, Br or I,
n denotes 0, 1, 2 or 3,
m denotes 0, 1 or 2,
in If X$^1$, X$^2$, X$^3$, X$^4$ denote CH,
Y denotes N,
Q denotes H or CH$_3$,
R$^1$ denotes H, F, Cl, Br, CN, CH$_3$, CF$_3$ or OCH$_3$,
R$^2$ denotes H or F,
R$^3$ denotes phenyl, which is unsubstituted or mono-, di- or trisubstituted by Hal, A, (CR$^4$)$_n$OR$^4$, (CR$^4$)$_n$N(R$^4$)$_2$, (CR$^4$)$_n$S(O)$_m$R$^4$, (CR$^4$)$_n$CON(R$^4$)$_2$, (CR$^4$)$_n$OCOHet, (CR$^4$)$_n$SO$_2$Het, (CR$^4$)$_n$Het, O(CR$^4$)$_n$COHet, (CR$^4$)$_n$O(CR$^4$)$_n$Het, (CR$^4$)$_n$N(R$^4$)(CR$^4$)$_n$Het, (CR$^4$)$_n$CON(R$^4$)(CR$^4$)$_n$Het, (CR$^4$)$_n$CON(R$^4$)(CR$^4$)$_n$N(R$^4$)$_2$, (CR$^4$)$_n$N(R$^4$)COA, (CR$^4$)$_n$N(R$^4$)COHet', (CR$^4$)$_n$OCyc and/or (CR$^4$)$_n$COOR$^4$,
R$^4$ denotes H or A',
A denotes unbranched or branched alkyl with 1-10 C-atoms, wherein two adjacent carbon atoms may form a double bond and/or one or two non-adjacent CH- and/or CH$_2$-groups may be replaced by N- and/or O-atoms and wherein 1-7H-atoms may be replaced by R$^5$,
Cyc denotes cyclobutyl, cyclopentyl or cyclohexyl, each of which is unsubstituted or mono- or disubstituted by A, Hal, OR$^4$, N(R$^4$)$_2$, Het', (CR$^4$)$_n$O(CR$^4$)$_n$Het', CON(R$^4$)$_2$ and/or =O,
A' denotes unbranched or branched alkyl with 1-6 C-atoms, wherein one or two non-adjacent CH- and/or CH$_2$-groups may be replaced by O-atoms,
R$^5$ denotes F, Cl or OH,
Het denotes pyrrolidinyl, morpholinyl, piperidinyl, piperazinyl, [1,4]-diazepanyl, oxazolidinyl, hexahydro-pyrrolo[3,4-c]pyrrolyl, 2-oxa-6-aza-spiro[3.4]octanyl, 2-oxa-6-aza-spiro[3.5]nonanyl, 2-oxa-7-aza-spiro[3.5]nonanyl, 2,5-dioxa-8-aza-spiro[3.5]nonanyl, oxetanyl, 2-oxa-5-aza-spiro[3.4]octanyl, 2-oxa-6-aza-spiro[3.3]heptanyl, 3-aza-bicyclo[3.1.0]hexanyl, 2-oxa-7-aza-spiro[3.5]nonanyl, isoxazolidinyl, azetidinyl, 2,6-di-aza-spiro[3.4]octanyl, hexahydro-pyrrolo[3,4-b]pyrrolyl, tetrahydrofuranyl or isothiazolidinyl, each of which is unsubstituted or mono-, di- or trisubstituted by A, Hal, OR$^4$, OCOA, COA, (CR$^4$)$_n$N(R$^4$)$_2$, (CR$^4$)$_n$Het', (CR$^4$)$_n$O(CR$^4$)$_n$Het', CON(R$^4$)$_2$, COHet', (CR$^4$)$_n$S(O)$_m$R$^4$, and/or =O,
Het' denotes pyrrolidinyl, oxetanyl, tetrahydrofuranyl, tetrahydropyranyl, pyridyl or pyrazolyl,
Hal denotes F, Cl, Br or I,
n denotes 0, 1, 2 or 3,
m denotes 0, 1 or 2,
and pharmaceutically acceptable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formula II and III are generally known. If they are novel, however, they can be prepared by methods known per se. Compounds of the formula I can preferably be obtained by reacting a compound of the formula II with a compound of the formula III. The reactions is known as "Click-reaction" and is generally carried out in an inert solvent, preferably in the presence of CuSO$_4$ and sodium ascorbate or isoascorbate.

Depending on the conditions used, the reaction time is between a few minutes and 14 days, the reaction temperature is between about 0° and 140°, normally between 20° and 130°, in particular between about 80° and about 120°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to DMF.

The starting compounds of the formula IV and V are generally known. If they are novel, however, they can be prepared by methods known per se.

Compounds of the formula I can preferably be obtained by reacting a compound of the formula IV with a compound of the formula V.

The reaction is generally carried out in the presence of an acid-binding agent, preferably an organic base, such as DIPEA, triethylamine, dimethylaniline, pyridine or quinoline.

Moreover, the reaction is generally carried out in the presence of [dimethylamino-([1,2,3]triazolo[4,5-b]pyridin-3-yloxy)-methylene]-dimethyl-ammonium hexafluorophosphate (HATU).

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF. Alternatively, the reaction is carried out under modified Frielaender quinolone synthesis conditions, with a carboxylic acid anhydride, such as acetic acid anhydride, as solvent and condensing agent and with an acid binding agent, such as trimethylamine or DIPEA.

It is furthermore possible to convert a compound of the formula I into another compound of the formula I, for example by reducing nitro groups to amino groups (for example by hydrogenation on Raney nickel or Pd/carbon in an inert solvent, such as methanol or ethanol).

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The alkylation also can be performed under reducing alkylating conditions, such as the use of HCHO and NaBH$_3$CN.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an aminoprotecting group instead of an H atom bonded to an N atom, for example those which conform to the formula I, but contain an NHR' group (in which R' is an aminoprotecting group, for example BOC or CBZ) instead of an NH$_2$ group.

Preference is furthermore given to starting materials which carry a hydroxylprotecting group instead of the H atom of a hydroxyl group, for example those which conform to the formula I, but contain an R"O-phenyl group (in which R" is a hydroxylprotecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "aminoprotecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxy-methyl or aralkyl groups. Since the aminoprotecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred aminoprotecting groups are BOC and Mtr, furthermore CBZ, Fmoc, benzyl and acetyl.

The term "hydroxylprotecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxylprotecting groups are not crucial since they are removed again after the desired chemical reaction or reaction sequence; preference is given to groups having 1-20, in particular 1-10, carbon atoms. Examples of hydroxylprotecting groups are, inter alia, tert-butoxycarbonyl, benzyl, p-nitrobenzoyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-300.

Moreover, compounds of the formula I can preferably be obtained by converting a radical $R^3$ into another radical $R^3$ by converting a carboxylic group into an amide.

The reaction is generally carried out in the presence of a coupling agent such as HATU and an acid binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −100 and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, formate, galacterate (from mucic acid), galacturonate, gluco-heptanoate, gluconate, glutamate, glycerophosphate, hemisuccinate, hemi-sulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphos-phate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di($C_1$-$C_4$)alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl($C_1-C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other iso-topes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t½), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable salts, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an ab-sorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be en-capsulated in microcapsules. The formulation can also be prepared in such a way that the release is extended or retarded, such as, for example, by coating or embedding of particulate material in polymers, wax and the like.

The compounds of the formula I and pharmaceutically salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxy-ethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal pas-sages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, tautomers and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically acceptable salts, tautomers and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, tautomers and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula I can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula I is an amount that inhibits c-KIT kinase in a cell, such as, for example, in vitro or in vivo. In some embodiments, the effective amount of the compound of formula I inhibits tankyrase in a cell by 10%, 20%, 30%, 40%, 50%, 60%, 70%, 80%, 90% or 99%, compared to the activity of c-KIT kinase in an untreated cell. The effective amount of the compound of formula I, for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans, in the treatment of cancer, such as gastrointestinal stromal tumor.

The present invention encompasses the use of the compounds of the formula I and/or pharmaceutically acceptable salts, tautomers and stereoisomers thereof for the preparation of a medicament for the treatment or prevention of cancer, preferably for the treatment of gastrointestinal stromal tumor.

Preferably, the present invention relates to a method for treating a disease, wherein the disease is a cancer, preferably a gastrointestinal stromal tumor.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating Agents such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA Altering Agents such as amrubicin, bisantrene, decitabine, mitoxantrone, procarbazine, trabectedin, clofarabine;
amsacrine, brostallicin, pixantrone, laromustine[1,3];

Topoisomerase Inhibitors such as etoposide, irinotecan, razoxane, sobuzoxane, teniposide, topotecan; amonafide, belotecan, elliptinium acetate, voreloxin;

Microtubule Modifiers such as cabazitaxel, docetaxel, eribulin, ixabepilone, paclitaxel, vinblastine, vincristine, vinorelbine, vindesine, vinflunine;
fosbretabulin, tesetaxel;

Antimetabolites such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;
doxifluridine, elacytarabine, raltitrexed, sapacitabine, tegafur[2,3], trimetrexate;

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin;
aclarubicin, peplomycin, pirarubicin;

Hormones/Antagonists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol;

acolbifene, danazol, deslorelin, epitiostanol, orteronel, enzalutamide[1,3];

Aromatase Inhibitors such as aminoglutethimide, anastrozole, exemestane, fadrozole, letrozole, testolactone;

formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers such as methoxsalen[3];

porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];

catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates such as denileukin diftitox, ibritumomab tiuxetan, iobenguane 1123, prednimustine, trastuzumab emtansine, estramustine, gemtuzumab, ozogamicin, aflibercept;

cintredekin besudotox, edotreotide, inotuzumab ozogamicin, naptumomab estafenatox, oportuzumab monatox, technetium (99mTc) arcitumomab[1,3], vintafolid[1,3];

Vaccines such as sipuleucel[3], vitespen[3], emepepimut-S[3], oncoVAX[4], rindopepimut[3], troVax[4], MGN-1601[4], MGN-1703[4];

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat;

celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

[1] Prop. INN (Proposed International Nonproprietary Name)
[2] Rec. INN (Recommended International Nonproprietary Names)
[3] USAN (United States Adopted Name)
[4] no INN.

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), CDCl$_3$ (deuterated chloroform), CD$_3$OD (deuterated methanol), CH$_3$CN (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-d$_6$ (deuterated dimethylsulfoxide), EDC (1-(3-dimethyl-amino-propyl)-3-ethylcarbodiimide), ESI (Electro-spray ionization), EtOAc (ethyl acetate), Et$_2$O (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), MeOH (methanol), MgSO$_4$ (magnesium sulfate), MS (mass spectrometry), MTBE (Methyl tert-butyl ether), NaHCO$_3$ (sodium bicarbonate), NaBH$_4$ (sodium borohydride), NMM (N-methyl morpholine), NMR (Nuclear Magnetic Resonance), PyBOP (benzotriazole-1-yloxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

$^1$H NMR was recorded on Bruker DPX-300, DRX-400, AVII-400 or on a 500 MHz spectrometer, using residual signal of deuterated solvent as internal reference. Chemical shifts ($\delta$) are reported in ppm relative to the residual solvent signal ($\delta$=2.49 ppm for $^1$H NMR in DMSO-d$_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

HPLC/MS conditions A:
HPLC/MS: Agilent 1200/6100
eluent A: water+0.05% formic acid
eluent B: acetonitrile+0.04% formic acid
column: Chromolith HR RP-18e; 50-4.6 mm
flow rate: 3.3 ml/min
gradient: 0%→100% B: 0.0→2.0 min|100% B: 2.0→2.5 min
UV detection: 220 nm
MS detection: 65-800 amu positive HPLC/MS conditions B:
HPLC/MS: Agilent 1200/6100
eluent A: water+0.05% formic acid
eluent B: acetonitrile+0.04% formic acid
column: Kinetex XB-C18; 2.6 μm; 50-4.6 mm
flow rate: 2.5 ml/min
gradient: 0%→100% B: 0.0→1.4 min|100% B: 1.4→2.0 min
UV detection: 220 nm
MS detection: 65-800 amu positive
UPLC/MS conditions:
UPLC/MS: Waters Acquity/SQD
eluent A: water+0.05% formic acid
eluent B: acetonitrile+0.04% formic acid
column: Kinetex XB-C18; 1.7 μm; 50-2.1 mm
flow rate: 0.9 ml/min
gradient: 2%→100% B: 0.0→1.0 min|100% B: 1.0→1.3 min
UV detection: 220 nm/254 nm/MaxPlot/TotalPlot
MS detection: 61-800 amu positive
Assays
c-Kit(V654A) assay:
c-Kit(V654A) (N-terminal GST-tagged, recombinant human c-Kit, amino acids 544-end containing the V654A mutation) is incubated with 8 mM MOPS pH 7.0, 0.2 mM EDTA, 250 μM GGMEDIYEFMGGKKK, 10 mM MgAcetate and [gamma-33P-ATP] (specific activity approx. 500 cpm/pmol, concentration 200 μM). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

PDGFRalpha(V561 D) assay:
PDGFRalpha(V561 D) (N-terminal 6His-tagged, recombinant human PDGFRalpha, amino acids 550-end containing the V561 D mutation) is incubated with 8 mM MOPS pH 7.0, 0.2 mM EDTA, 250 μM GGMEDIYEFMGGKKK, 10 mM MgAcetate and [gamma-33P-ATP] (specific activity approx. 500 cpm/pmol, concentration 200 μM). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

Pharmacological Data

TABLE 1

Inhibition ($IC_{50}$) of c-KIT (V654A) and PDGFRα (V561D) of compounds of the formula I

| Compound No. | c-KIT (V654A) [M] | PDGFRα (V561D) [M] | Compound No. | c-KIT (V654A) [M] | PDGFRα (V561D) [M] |
|---|---|---|---|---|---|
| "A1"  | 6E−09  | 2E−09  | "A81"  | 1.7E−08 | 6E−09  |
| "A2"  | 5.1E−08 | 1.2E−08 | "A82"  | 1.4E−08 | 3E−09  |
| "A3"  | 5.3E−08 | 1.6E−08 | "A83"  | 1E−08  | 3E−09  |
| "A4"  | 3.4E−08 | 1.9E−08 | "A84"  | 4.8E−08 | 5E−09  |
| "A5"  |        |        | "A85"  | 1.3E−06 | 1.7E−06 |
| "A6"  | 4.3E−07 |        | "A86"  | 1.1E−08 | 2E−09  |
| "A7"  | 4.9E−07 |        | "A87"  | 2.5E−08 | 1.2E−08 |
| "A8"  | 1.7E−07 | 1.4E−08 | "A88"  | 9E−08  | 6E−09  |
| "A9"  | 7.6E−07 | 2.3E−07 | "A89"  | 3.6E−08 | 8E−09  |
| "A10" | 8.2E−08 | 3.2E−08 | "A90"  | 2E−08  | 2.9E−08 |
| "A11" | 2.2E−07 | 2.6E−08 | "A91"  | 1.9E−08 | 8.2E−08 |
| "A12" | 6.9E−08 | 6.3E−08 | "A92"  | 2.1E−08 | 5.9E−09 |
| "A13" |        | 5E−07  | "A93"  | 3.2E−07 | 3.1E−07 |
| "A14" | 2.3E−08 | 2E−08  | "A94"  | 3.6E−06 | 2.3E−06 |
|       |        |        | "A94a" | 6.0E−08 | 5.4E−08 |
| "A15" | 4.9E−08 | 4.7E−08 | "A95"  | 9.0E−09 | 3.7E−07 |
| "A16" |        | 3.3E−08 | "A96"  | 5.2E−09 | 3.3E−10 |
| "A17" | 2.9E−07 | 6.7E−08 | "A97"  | 1.7E−08 | 1.0E−08 |
| "A18" | 1.5E−08 | 5E−09  | "A98"  | 1.8E−07 | 7.5E−08 |
| "A19" | 3.8E−08 | 1.4E−08 | "A99"  | 3.3E−08 | 7.6E−08 |
| "A20" | 2E−07  | 5.2E−08 | "A100" | 2E−08  | 6.3E−08 |
|       |        |        | "A100a"| 1.8E−08 | 5.4E−08 |
| "A21" | 7.9E−08 | 3.2E−08 | "A101" | 3.3E−08 | 2.9E−07 |
| "A22" | 2.7E−08 | 6E−09  | "A102" | 1.1E−08 | 4.8E−08 |
| "A23" |        | 2.5E−07 | "A103" | 8.6E−09 | 3.5E−08 |
| "A24" | 1.1E−07 | 2.6E−08 | "A104" | 2.4E−08 | 1.5E−07 |
| "A25" | 1.5E−08 | 3E−09  | "A105" | 9.7E−09 | 3.4E−07 |
| "A26" | 1.5E−08 | 1E−08  | "A106" | 9.1E−09 | 9E−10  |
| "A27" | 5E−08  | 3.2E−08 | "A107" | 4.4E−08 | 2.3E−08 |
| "A28" | 3.6E−08 | 2.9E−08 | "A108" | 8.3E−08 | 8.1E−08 |
| "A29" | 1.5E−07 | 2.3E−08 | "A109" | 1.2E−08 | 3.4E−09 |
| "A30" | 2.2E−06 | 1.5E−07 | "A110" | 3.9E−08 | 2.8E−08 |
| "A31" | 9.9E−08 | 1.3E−08 | "A111" | 7.7E−09 | 1.8E−08 |
| "A32" | 6.4E−08 | 1.1E−08 | "A112" | 1.6E−08 | 6.4E−08 |
| "A33" | 2E−08  | 3E−09  | "A113" | 8.6E−09 | 3.6E−08 |
| "A34" | 5.8E−06 | 1.1E−07 | "A114" | 2.0E−08 | 1.4E−07 |
| "A35" | 6.5E−07 | 4.9E−08 | "A115" | 1.8E−07 | 1.4E−06 |
|       |        |        | "A115a"| 1.6E−07 | 1.5E−06 |
| "A36" | 2.9E−08 | 1.7E−08 | "A116" |        |        |
| "A37" | 3.8E−08 | 9E−09  | "A117" | 2.8E−08 | 1.1E−08 |
| "A38" | 3.2E−06 | 5.8E−7 | "A118" | 1.6E−08 | 5E−09  |
| "A39" | 7.4E−08 | 2.3E−08 | "A119" | 9E−09  | 4.6E−08 |

TABLE 1-continued

Inhibition (IC$_{50}$) of c-KIT (V654A) and PDGFRα (V561D) of compounds of the formula I

| Compound No. | c-KIT (V654A) [M] | PDGFRα (V561D) [M] | Compound No. | c-KIT (V654A) [M] | PDGFRα (V561D) [M] |
|---|---|---|---|---|---|
| "A40" | 2.6E−08 | 7E−09 | "A120" | 2.8E−07 | 2.3E−07 |
| "A41" | 2.4E−07 | 4.4E−08 | "A121" | 4E−08 | 1.6E−08 |
| "A42" | 8.4E−08 | 3.8E−08 | "A122" | 7.3E−08 | 5E−08 |
| "A43" | 1.4E−07 | 1.7E−07 | "A123" | 5E−09 | 1E−09 |
| "A44" | | | "A124" | 6.6E−08 | 9E−09 |
| "A45" | 1.1E−06 | 3.3E−07 | "A125" | 3.4E−08 | 6E−09 |
| "A46" | 3.7E−07 | 1.5E−07 | "A126" | 1.9E−08 | 4.2E−08 |
| "A47" | 2.4E−08 | 7E−09 | "A127" | 3.8E−08 | 7.9E−08 |
| "A48" | 1.7E−08 | 1.9E−08 | "A128" | 4.1E−08 | 9.7E−09 |
| "A49" | 1.5E−07 | 4.2E−08 | "A129" | 1.3E−08 | 4.8E−08 |
| "A50" | 2.4E−08 | 1.4E−08 | "A130" | 3.5E−08 | 1.7E−07 |
| "A51" | 9.1E−08 | 2.2E−08 | "A131" | 9.7E−09 | 3.8E−08 |
| "A52" | 2.2E−08 | 2.7E−08 | "A132" | 7.5E−09 | 8E−10 |
| "A53" | 1.1E−08 | 9E−09 | "A133" | 1.1E−08 | 6.4E−09 |
| "A54" | 4.9E−07 | 1.6E−07 | "A134" | 1.7E−08 | 1.6E−08 |
| "A55" | 1.4E−08 | 1.4E−08 | "A135" | 1.8E−07 | 3.1E−07 |
| "A56" | 7E−09 | 5E−09 | "A136" | 1.5E−08 | 1.8E−08 |
| "A57" | 1.5E−08 | 6E−09 | "A137" | 4.0E−08 | 4.2E−08 |
| "A58" | 4.4E−08 | 2.1E−08 | "A138" | 1.1E−08 | 8.6E−08 |
| "A59" | 7.6E−08 | 4.6E−08 | "A139" | 1.2E−08 | 3.8E−06 |
| "A60" | 3.8E−08 | 3.3E−08 | "A140" | 1.4E−08 | 2.8E−08 |
| "A61" | 2.9E−08 | 1.1E−08 | "A141" | 3.8E−09 | 2.8E−09 |
| "A62" | 2E−07 | 4.6E−08 | "A142" | 2.8E−07 | 2.8E−06 |
| "A63" | 1.3E−07 | 4E−08 | "A143" | 1.9E−08 | 3.1E−07 |
| "A64" | 4.4E−08 | 1.6E−08 | "A144" | 1.2E−08 | 1.7E−07 |
| "A65" | 1.2E−06 | 1.5E−07 | "A145" | 2.2E−08 | 1.8E−07 |
| "A66" | 6.4E−07 | 1.9E−07 | "A146" | | |
| "A67" | 2.4E−08 | 4E−09 | "A147" | | |
| "A68" | 2.8E−08 | 7E−09 | "A148" | | |
| "A69" | 1.4E−08 | 1E−08 | "A149" | 6E−09 | 1.2E−08 |
| "A70" | 1.4E−08 | 5E−09 | "A150" | 4.9E−08 | 3.7E−08 |
| "A71" | 8E−09 | 4E−09 | "A151" | 3E−09 | 1E−09 |
| "A72" | 1.1E−08 | 4E−09 | "A152" | 1.1E−08 | 2.3E−08 |
| "A73" | | 4.4E−07 | "A153" | 2.4E−08 | 4E−09 |
| "A74" | 8E−09 | 6E−09 | "A154" | 1.1E−08 | 3E−09 |
| "A75" | 4.8E−08 | 1.8E−08 | "A155" | 8.1E−08 | 6.1E−08 |
| "A76" | 4.9E−08 | 3E−08 | "A156" | 2.6E−08 | 4.0E−08 |
| "A77" | 4.7E−07 | 1.1E−07 | "A157" | 5.9E−09 | 3.2E−10 |
| "A78" | 1.7E−08 | 3.1E−08 | "A158" | 1.3E−08 | 4.6E−08 |
| "A79" | 3.3E−08 | 3.1E−08 | "A159" | 2E−08 | 9.1E−08 |
| "A80" | 1.2E−07 | 4.4E−08 | "A160" | 1.6E−08 | 7.5E−08 |
| "A161" | 3.5E−08 | 1.5E−08 | "A171" | 1.7E−08 | 1.9E−07 |
| "A162" | 8.2E−08 | 9.7E−08 | "A172" | 6.3E−09 | 2.5E−08 |
| "A163" | 9.9E−09 | 4.5E−08 | "A173" | | |
| "A164" | 8.4E−09 | 1.1E−08 | "A174" | | |
| "A165" | 3.0E−08 | 3.3E−08 | "A175" | 9.2E−08 | 6E−09 |
| "A166" | 8.0E−09 | 4.3E−08 | "A176" | 6.7E−09 | 1.6E−09 |
| "A167" | 1.8E−08 | 2.1E−08 | "A177" | 1.7E−08 | 5.7E−08 |
| "A168" | 3.7E−08 | 1.0E−07 | "A178" | 3.9E−09 | 1.3E−09 |
| "A169" | 1.4E−08 | 4.3E−07 | "A179" | 1.4E−08 | 1.6E−09 |
| "A170" | 1.8E−06 | 1.2E−05 | "A180" | 9.5E−09 | 5.0E−10 |
| "A181" | 8.5E−09 | 7.1E−10 | "A191" | 1.5E−08 | 2.4E−07 |
| "A182" | 1.3E−08 | 1.2E−09 | "A192" | 2.3E−07 | 2.0E−07 |
| "A183" | 7.5E−09 | 2.6E−08 | "A193" | 2.3E−07 | 2.0E−07 |
| "A184" | 1.8E−08 | 1.1E−08 | "A194" | 4.9E−08 | 9.1E−08 |
| "A185" | 5.1E−07 | | "A195" | 6.8E−08 | 9.3E−08 |
| "A186" | | | "A196" | 4.4E−08 | 1.1E−07 |
| "A187" | 3.6E−08 | 7.6E−08 | "A197" | 2.8E−08 | 3.2E−08 |
| "A188" | 2.6E−08 | 1.6E−06 | "A198" | 3.0E−08 | 2.0E−07 |
| "A189" | 1.1E−07 | 4.3E−07 | "A199" | 1.6E−08 | 2.2E−08 |
| "A190" | 9.7E−09 | 6.4E−08 | "A200" | 1.8E−08 | 1.4E−07 |
| "A201" | 9.7E−08 | 9.2E−08 | "A211" | 1.9E−07 | 8.5E−08 |
| "A202" | 5.7E−08 | 1.6E−08 | "A212" | 1.3E−06 | 1.6E−07 |
| "A203" | 3.6E−08 | 4.9E−07 | "A213" | 6.5E−08 | 3.7E−08 |
| "A204" | 5.5E−08 | 1.1E−07 | "A214" | 7.2E−08 | 7.9E−08 |
| "A205" | 3.6E−08 | 9.4E−08 | "A215" | 6.4E−08 | 2.2E−07 |
| "A206" | 2.4E−08 | 4.8E−08 | "A216" | 5.2E−08 | 2.9E−08 |
| "A207" | 5.2E−08 | 3.1E−07 | "A217" | 3.5E−07 | 4.6E−08 |
| "A208" | 1.8E−08 | 1.8E−07 | "A218" | 6.4E−08 | 5.9E−08 |
| "A209" | 5.3E−08 | 5.8E−07 | "A219" | 1.6E−06 | 3.2E−07 |
| "A210" | 4.6E−08 | 3.0E−07 | "A220" | 9.8E−07 | 5.0E−07 |
| "A221" | 2.0E−07 | 3.8E−07 | "A231" | 9.0E−08 | 3.4E−07 |
| "A222" | 7.2E−08 | 2.1E−07 | "A232" | 1.6E−07 | 9.8E−07 |
| "A223" | 3.5E−07 | 4.1E−07 | "A233" | 9.6E−08 | 6.0E−07 |

TABLE 1-continued

Inhibition (IC$_{50}$) of c-KIT (V654A) and PDGFRα
(V561D) of compounds of the formula I

| Compound No. | c-KIT (V654A) [M] | PDGFRα (V561D) [M] | Compound No. | c-KIT (V654A) [M] | PDGFRα (V561D) [M] |
|---|---|---|---|---|---|
| "A224" | 7.0E−08 | 2.8E−07 | "A234" | 5.0E−08 | 7.4E−07 |
| "A225" | 1.9E−07 | 5.8E−07 | "A235" | 4.2E−08 | 1.4E−07 |
| "A226" | 5.5E−08 | 8.9E−08 | "A236" | 5.3E−08 | 5.6E−07 |
| "A227" | 9.2E−08 | 1.4E−07 | "A237" | 8.1E−08 | 4.9E−07 |
| "A228" | 7.4E−08 | 3.0E−07 | "A238" | 7.9E−08 | 6.2E−07 |
| "A229" | 4.1E−08 | 1.5E−07 | "A239" | 3.3E−07 | 1.2E−06 |
| "A230" | 4.9E−08 | 9.5E−08 | "A240" | 1.3E−07 | 2.5E−07 |
| "A241" | 1.0E−07 | 2.9E−07 | "A251" | 1.6E−07 | 4.0E−07 |
| "A242" | 1.1E−08 | 1.7E−08 | "A252" | 9.8E−08 | 9.3E−08 |
| "A243" | 3.0E−08 | 1.4E−08 | "A253" | 4.4E−08 | 2.1E−08 |
| "A244" | 3.6E−08 | 1.3E−08 | "A254" | 5.7E−08 | 2.4E−08 |
| "A245" | 6.5E−08 | 4.7E−07 | "A255" | 2.2E−08 | 2.6E−09 |
| "A246" | 2.3E−08 | 7.4E−09 | "A256" | 2.7E−08 | 4.3E−09 |
| "A247" | 2.3E−08 | 4.5E−08 | "A257" | 2.7E−08 | 3.7E−09 |
| "A248" | 3.5E−08 | 4.5E−08 | "A258" | 4.7E−08 | 8.6E−08 |
| "A249" | 3.5E−08 | 2.6E−07 | "A259" | 5.7E−08 | 8.4E−09 |
| "A250" | 4E−08 | 7.6E−08 | "A260" | 5.1E−08 | 1.0E−07 |
| "A261" | 4.4E−08 | 3.7E−08 | "A271" | 5E−08 | 5.1E−10 |
| "A262" | 9.4E−08 | 1.1E−07 | "A272" | 4.8E−08 | 8.9E−10 |
| "A263" | 9.4E−08 | 9.1E−10 | "A273" | 4E−08 | 4.1E−09 |
| "A264" | 7.5E−08 | 1.2E−09 | "A274" | 6.1E−08 | 3.3E−09 |
| "A265" | 4.9E−08 | 1.6E−09 | "A275" | 4.5E−08 | 2.1E−10 |
| "A266" | 4.0E−08 | 1.1E−09 | "A276" | 5.4E−08 | 1.4E−09 |
| "A267" | 1.7E−08 | 1.4E−09 | "A277" | 3E−08 | 2.6E−09 |
| "A268" | 1.6E−08 | 6.7E−10 | "A278" | 1.7E−08 | 1.5E−09 |
| "A269" | 3.1E−08 | 1.5E−09 | "A279" | 1.4E−08 | 7.2E−10 |
| "A270" | 2.6E−08 | 2E−10 | "A280" | 7.7E−08 | 5.3E−08 |
| "A281" | 5.7E−08 | 1.0E−08 | "A291" | 7.5E−09 | |
| "A282" | 1.6E−08 | | "A292" | | |
| "A283" | 1.9E−08 | | "A293" | | |
| "A284" | 1.7E−08 | | "A294" | | |
| "A285" | 5.6E−09 | | "A295" | | |
| "A286" | 5.1E−09 | | "A296" | 3.8E−08 | 1.4E−08 |
| "A287" | 2.5E−08 | | "A297" | 6.6E−08 | 2.4E−07 |
| "A288" | 6.5E−09 | | "A298" | 4.1E−08 | 2.1E−08 |
| "A289" | 2.5E−08 | | "A299" | 5.8E−08 | 2.3E−08 |
| "A290" | 1.4E−08 | | "A300" | 6.8E−08 | 7.6E−10 |
| "A301" | 4.3E−08 | 1.0E−09 | "A311" | 2.1E−08 | 3.1E−07 |
| "A302" | 3.1E−08 | 1.2E−09 | "A312" | 6.1E−08 | 2.9E−07 |
| "A303" | 3.7E−08 | 6E−09 | "A313" | 2.6E−08 | 3.3E−07 |
| "A304" | 1.6E−08 | | "A314" | 7.2E−08 | 1.8E−07 |
| "A305" | 7.7E−09 | | "A315" | 2.0E−07 | 1.4E−06 |
| "A306" | 4.5E−08 | 2.4E−07 | "A316" | 1.2E−07 | 5.2E−07 |
| "A307" | 1.7E−08 | 2.4E−07 | "A317" | 1.2E−07 | 1.4E−06 |
| "A308" | 1.0E−08 | 9.74E−08 | "A318" | 2E−08 | 1.7E−07 |
| "A309" | 6.3E−08 | 1.3E−07 | "A319" | 2.7E−08 | 3.6E−08 |
| "A310" | 4.4E−08 | 8.5E−08 | "A320" | 4.8E−08 | 9.9E−08 |
| "A321" | 4.4E−08 | 3.7E−07 | "A331" | 6.3E−08 | 5.7E−07 |
| "A322" | 2.5E−08 | 6.5E−08 | "A332" | 7.1E−08 | 1.0E−07 |
| "A323" | 2.2E−07 | 2.2E−07 | "A333" | 6.3E−08 | 1.2E−07 |
| "A324" | 2.7E−07 | 7.2E−09 | "A334" | 1.5E−08 | 4.1E−08 |
| "A325" | 1.7E−08 | 3.8E−09 | "A335" | 1.7E−07 | 6.8E−07 |
| "A326" | 1.8E−07 | 9.4E−07 | "A336" | 1.8E−07 | 2.4E−07 |
| "A327" | 1.4E−08 | 2.2E−07 | "A337" | 7.5E−08 | 2.3E−07 |
| "A328" | 4.0E−08 | 9.7E−08 | "A338" | 3.9E−08 | 1.6E−07 |
| "A329" | 7.3E−08 | 9.2E−08 | "A339" | 9.2E−09 | |
| "A330" | 4.8E−08 | 2.1E−08 | "A340" | | |
| "A341" | | | "A351" | 1.4E−08 | |
| "A342" | 2.5E−08 | 3.6E−08 | "A352" | 2.6E−07 | 4.4E−07 |
| "A343" | 9E−09 | 8.5E−08 | "A353" | 9.4E−08 | 1.9E−07 |
| "A344" | 9.7E−09 | 1.6E−08 | "A354" | 3.1E−06 | 4.2E−07 |
| "A345" | 1.2E−08 | 1.5E−06 | "A355" | 8.9E−08 | 1.6E−06 |
| "A346" | 1.6E−08 | | "A356" | 9.6E−08 | 1.5E−07 |
| "A347" | 2.6E−08 | | "A357" | | |
| "A348" | 1.6E−08 | | "A358" | 1.9E−08 | |
| "A349" | 5.1E−08 | | "A359" | 1.3E−08 | |
| "A350" | 1.6E−08 | | "A360" | 2.2E−08 | |
| "A361" | 1.1E−08 | | "A371" | 3.4E−08 | 1.1E−08 |
| "A362" | 1.6E−08 | | "A372" | 2.1E−08 | |
| "A363" | | | "A373" | 1.5E−08 | |
| "A364" | 2.1E−08 | | "A374" | 1.7E−08 | |
| "A365" | | | "A375" | 9.5E−09 | |
| "A366" | | | "A376" | 4.9E−09 | |
| "A367" | 1.9E−08 | 7.0E−08 | | | |

TABLE 1-continued

Inhibition ($IC_{50}$) of c-KIT (V654A) and PDGFRα
(V561D) of compounds of the formula I

| Compound No. | c-KIT (V654A) [M] | PDGFRα (V561D) [M] | Compound No. | c-KIT (V654A) [M] | PDGFRα (V561D) [M] |
|---|---|---|---|---|---|
| "A368" | 2.3E−08 | 3.4E−08 | | | |
| "A369" | 1.3E−08 | 3.4E−08 | | | |
| "A370" | 3.1E−08 | 5.8E−08 | | | |

Explanation: 1.4E-06 means $1.4 \times 10^{-6}$

The compounds shown in Table 1 are particularly preferred compounds according to the invention.

Synthesis of Intermediates

Bromoquinolones and Bromonaphthyridones

Synthesis of 3-bromo-6-fluoro-1H-quinolin-2-one

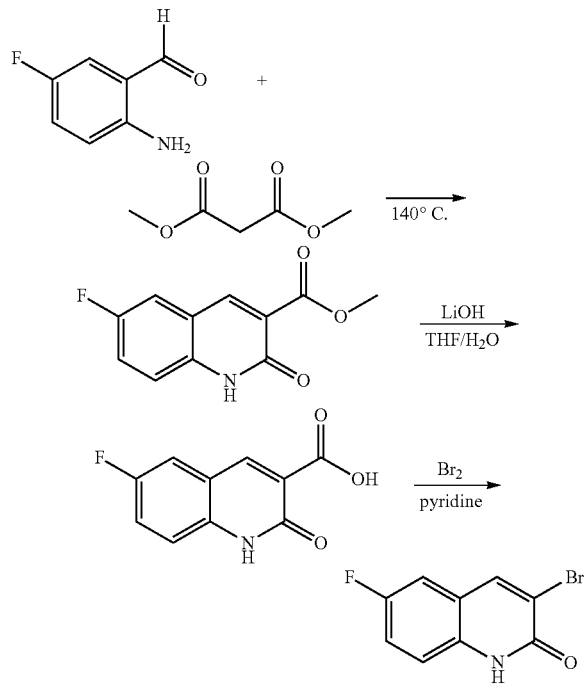

A solution of 2-amino-5-fluoro-benzaldehyde (7.42 g, 53.3 mmol) in dimethyl malonate (45 ml) is heated to 140° C. and stirred at this temperature for 16 hours. The reaction mixture is allowed to reach room temperature. The resultant precipitate is filtered off, washed with tert-butyl methyl ether and dried under vacuum to afford 6-fluoro-2-oxo-1,2-dihydro-quinoline-3-carboxylic acid methyl ester as light ochre solid; HPLC/MS 1.17 min (B), $[M+H]^+$ 222.

$^1$H NMR (400 MHz, DMSO-$d_6$) δ 12.11 (s, 1H), 8.49 (s, 1H), 7.70 (dd, J=9.0, 2.9 Hz, 1H), 7.52 (td, J=8.9, 2.9 Hz, 1H), 7.35 (dd, J=9.1, 4.7 Hz, 1H), 3.81 (s, 3H).

To a slurry of 6-fluoro-2-oxo-1,2-dihydro-quinoline-3-carboxylic acid methyl ester (6.92 g, 31.3 mmol) in a mixture of THF (30 ml) and water (38 ml) is added lithium hydroxide (6.59 g, 275 mmol) and the mixture is stirred for 2 hours at 65° C. After cooling to room temperature, 1 N aqueous hydrochloric acid is added until a pH value of 1 is reached. The resultant precipitate is filtered off, washed with water and dried under vacuum to afford 6-fluoro-2-oxo-1,2-dihydro-quinoline-3-carboxylic acid as light yellow solid; HPLC/MS 1.18 min (B), $[M+H]^+$ 208.

A suspension of 6-fluoro-2-oxo-1,2-dihydro-quinoline-3-carboxylic acid (6.70 g, 32.3 mmol) in pyridine (108 ml) is cooled to 0° C. Under stirring and continuous external cooling, bromine (6.63 ml, 129 mmol) is added dropwise. The reaction mixture is heated to 65° C. and stirred at this temperature for 1 hour. After cooling to room temperature, the reaction mixture is poured into water (160 ml). 37% aqueous hydrochloric acid is added until a pH value of 4 is reached. The resultant precipitate is filtered off and washed with water. The filtrate is extracted three times with dichloromethane; the organic phases are combined, dried over sodium sulfate and evaporated. The residue is combined with the precipitate and chromatographed on a silica gel column with dichloromethane/methanol as eluent to afford 3-bromo-6-fluoro-1H-quinolin-2-one as light yellow solid; HPLC/MS 1.26 min (B), $[M+H]^+$ 242,244.

$^1$H NMR (400 MHz, DMSO-$d_6$) δ 12.31 (s, 1H), 8.49 (s, 1H), 7.54 (dd, J=9.1, 2.8 Hz, 1H), 7.46 (td, J=8.8, 2.8 Hz, 1H), 7.36 (dd, J=9.0, 4.8 Hz, 1H).

The following compounds are prepared similarly

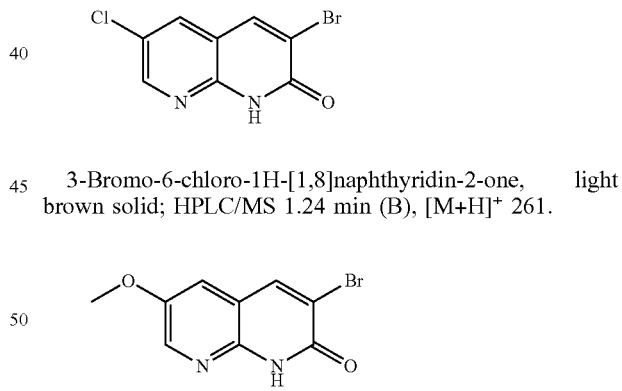

3-Bromo-6-chloro-1H-[1,8]naphthyridin-2-one, light brown solid; HPLC/MS 1.24 min (B), $[M+H]^+$ 261.

3-Bromo-6-methoxy-1H-[1,8]naphthyridin-2-one, brown solid; HPLC/MS 1.12 min (B), $[M+H]^+$ 255,257.

$^1$H NMR (400 MHz, DMSO-d6) δ 12.59 (s, 1H), 8.49 (s, 1H), 8.36 (d, J=3.0 Hz, 1H), 7.75 (d, J=3.0 Hz, 1H), 3.86 (s, 3H).

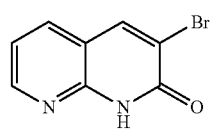 [SMILES: O=c1[nH]c2ncccc2cc1Br]

3-Bromo-1H-[1,8]naphthyridin-2-one, brown solid; HPLC/MS 1.09 min (B), [M+H]+ 225,227.

¹H NMR (400 MHz, DMSO-d6) δ 12.74 (s, 1H), 8.56 (m, 2H), 8.13 (d, 1H), 7.30 (dd, 1H).

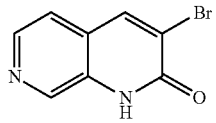 [SMILES: O=c1[nH]c2cnccc2cc1Br]

3-Bromo-1H-[1,7]naphthyridin-2-one, orange-brown solid; HPLC/MS 1.00 min (B), [M+H]+ 225,227.

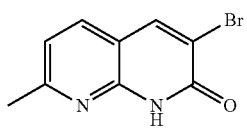

3-Bromo-7-methyl-1H-[1,8]naphthyridin-2-one, light yellow solid; HPLC/MS 1.16 min (B), [M+H]+ 239,241.

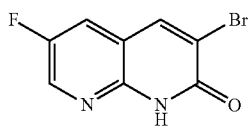

3-Bromo-6-fluoro-1H-[1,8]naphthyridin-2-one, beige solid; HPLC/MS 1.15 min (B), [M+H]+ 243,245.

¹H NMR (500 MHz, DMSO-d6) δ 12.80 (s, 1H), 8.62 (d, J=2.8 Hz, 1H), 8.52 (s, 1H), 8.08 (dd, J=8.5, 2.9 Hz, 1H).

Ethynyl-Quinolones and Ethynyl-Naphthyridones

Synthesis of 3-ethynyl-1H-quinolin-2-one

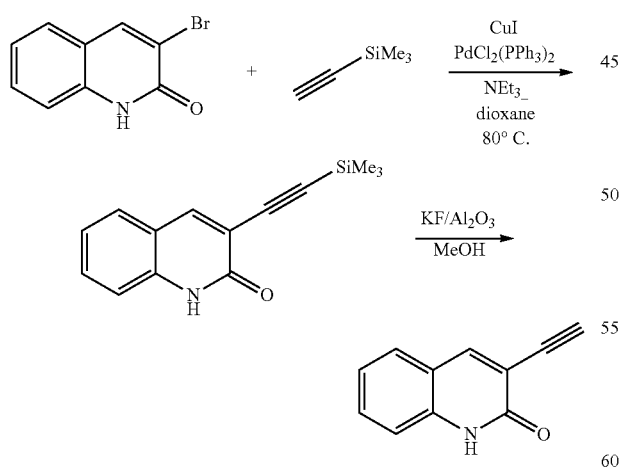

To a suspension of 3-bromo-1H-quinolin-2-one (2.24 g, 10.0 mmol) in dioxane (40 ml) are added triethylamine (3.67 ml, 26.5 mmol) and copper(I) iodide (1.90 g, 10.0 mmol). The reaction mixture is purged with nitrogen and bis(triphenylphosphine)palladium(II) chloride (286 mg, 0.40 mmol) and trimethylsilyl-acetylene (2.37 ml, 17.1 mmol) are added. The reaction mixture is flushed with nitrogen and stirred in a closed reaction vial for 16 hours at 80° C. The reaction mixture is allowed to reach room temperature and filtered through a plug of kieselguhr. The residue is washed with dichloromethane and the filtrate is evaporated. The residue is chromatographed on a silica gel column with cyclohexane/ethyl acetate as eluent to afford 3-trimethylsilanylethynyl-1H-quinolin-2-one as light brown solid; HPLC/MS 1.52 min (B), [M+H]+ 242.

To a solution of 3-trimethylsilanylethynyl-1H-quinolin-2-one (2.16 g, 8.95 mmol) in methanol (18 ml) is added potassium fluoride on aluminium oxide (1.04 g, 5.7 mmol fluoride) and the reaction mixture is stirred at room temperature for 30 minutes. The reaction mixture is poured into ice water. The solids are filtered off, washed with water and dried under vacuum. The residue is chromatographed on a silica gel column with dichloromethane/methanol as eluent to afford 3-ethynyl-1H-quinolin-2-one as light brown solid; HPLC/MS 1.18 min (B), [M+H]+ 170.

1H NMR (400 MHz, DMSO-d₆) δ 12.02 (s, 1H), 8.23 (s, 1H), 7.67 (dd, J=7.9, 1.4 Hz, 1H), 7.53 (ddd, J=8.5, 7.2, 1.5 Hz, 1H), 7.34-7.27 (m, 1H), 7.20 (ddd, J=8.1, 7.2, 1.1 Hz, 1H), 4.34 (s, 1H).

The following compounds are prepared similarly:

6-Chloro-3-ethynyl-1H-[1,8]naphthyridin-2-one, light beige solid; HPLC/MS 1.20 min (B), [M+H]+ 205.

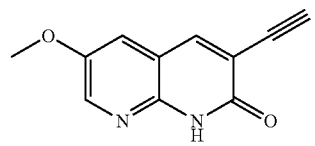

3-Ethynyl-6-methoxy-1H-[1,8]naphthyridin-2-one, beige solid; HPLC/MS 1.11 min (B), [M+H]+ 201.

¹H NMR (400 MHz, DMSO-d₆) δ 12.34 (s, 1H), 8.30 (d, J=3.0 Hz, 1H), 8.18 (s, 1H), 7.72 (d, J=3.0 Hz, 1H), 4.41 (s, 1H), 3.84 (s, 3H).

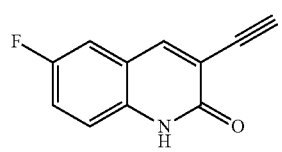

3-Ethynyl-6-fluoro-1H-quinolin-2-one, beige solid; HPLC/MS 1.27 min (A), [M+H]+ 188.

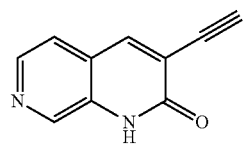

3-Ethynyl-1H-[1,7]naphthyridin-2-one, beige powder; HPLC/MS 0.97 min (B), [M+H]+ 171;

$^1$H NMR (400 MHz, DMSO-d$_6$) δ 12.28 (bs, 1H) 8.60 (s, 1H), 8.22 (d, J=5.2 Hz, 1H), 8.14 (s, 1H), 7.51 (d, J=5.2 Hz, 1H), 4.41 (s, 1H).

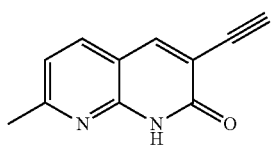

3-Ethynyl-7-methyl-1H-[1,8]naphthyridin-2-one, beige solid; HPLC/MS 1.13 min (B), [M+H]+ 185;

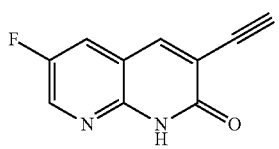

3-Ethynyl-6-fluoro-1H-[1,8]naphthyridin-2-one, orange-beige solid; HPLC/MS 1.11 min (B), [M+H]+ 189;

$^1$H NMR (500 MHz, DMSO-d$_6$) δ 12.45 (s, 1H), 8.47 (d, J=2.8 Hz, 1H), 8.10 (s, 1H), 7.96 (dd, J=8.5, 3.0 Hz, 1H), 4.38 (s, 1H).

Aromatic Azides

Synthesis of 4-(4-azido-phenyl)-3-oxo-piperazine-1-carboxylic Acid Tert-Butyl Ester

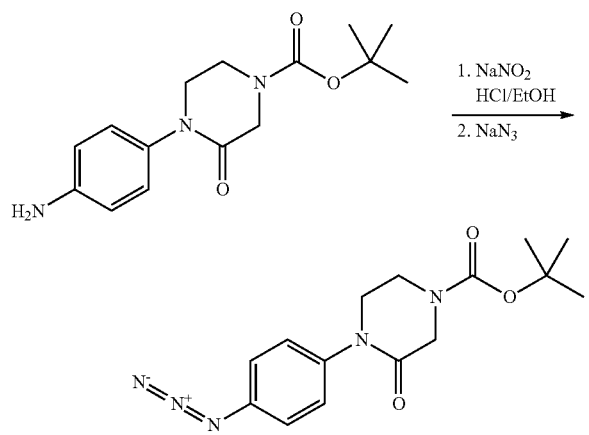

To a stirred solution of 4-(4-amino-phenyl)-3-oxo-piperazine-1-carboxylic acid tert-butyl ester (4.37 g, 15.0 mmol) in a mixture of ethanol (47 ml) and water (47 ml) is added aqueous hydrochloric acid (37%, 9.15 ml). The solution is cooled to 0° C. and a solution sodium nitrite (1.24 g, 18.0 mmol) in water (10 ml) is added slowly. The reaction mixture is stirred for 10 minutes at room temperature. Then sodium azide (1.46 g, 22.5 mmol) is added in portions and the reaction mixture is stirred for 2 hours at room temperature. The reaction mixture is poured into water, the solids are filtered off, washed with water and dried under vacuum to afford 4-(4-azido-phenyl)-3-oxo-piperazine-1-carboxylic acid tert-butyl ester as beige solid; HPLC/MS 1.60 min (A), [M+H]+ 318.

$^1$H NMR (400 MHz, DMSO-d$_6$) δ 7.39 (d, J=8.8 Hz, 2H), 7.14 (d, J=8.8 Hz, 2H), 4.06 (s, 2H), 3.76-3.62 (m, 4H), 1.44 (s, 9H).

The following compounds are prepared similarly

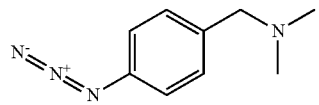

(4-Azido-benzyl)-dimethyl-amine; $^1$H NMR (400 MHz, CDCl$_3$) δ 7.46 (d, 2H), 6.99 (d, 2H), 3.38 (s, 2H), 2.25 (s, 6H).

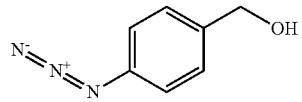 [SMILES: [N-]=[N+]=Nc1ccc(CO)cc1]

(4-Azido-phenyl)-methanol; $^1$H NMR (400 MHz, DMSO-d$_6$) δ 7.36 (d, 2H), 7.07 (d, 2H), 5.25 t, 1H), 4.49 (d, 2H).

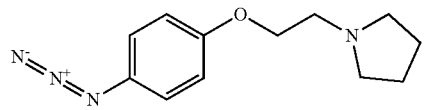 [SMILES: [N-]=[N+]=Nc1ccc(OCCN2CCCC2)cc1]

1-[2-(4-Azido-phenoxy)-ethyl]-pyrrolidine, brown oil; HPLC/MS 1.07 min (B), [M+H]+ 233.

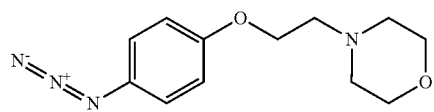 [SMILES: [N-]=[N+]=Nc1ccc(OCCN2CCOCC2)cc1]

4-[2-(4-Azido-phenoxy)-ethyl]-morpholine, brown oil; HPLC/MS 1.05 min (B), [M+H]+ 249.

$^1$H NMR (400 MHz, DMSO-d$_6$) δ 7.08-6.96 (m, 4H), 4.08 (t, J=5.8 Hz, 2H), 3.56-3.60 (m, 4H), 2.68 (t, J=5.8 Hz, 2H), 2.44-2.49 (m, 2H).

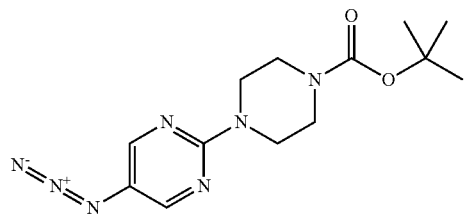 [SMILES: CC(C)(C)OC(=O)N1CCN(c2ncc(N=[N+]=[N-])cn2)CC1]

4-(5-Azido-pyrimidin-2-yl)-piperazine-1-carboxylic acid tert-butyl ester, brown solid; HPLC/MS 1.83 min (A), [M-$^t$bu]+ 250.

$^1$H NMR (300 MHz, DMSO-d$_6$) δ 8.29 (s, 2H), 3.72-3.65 (m, 4H), 3.46-3.36 (m, 4H), 1.42 (s, 9H).

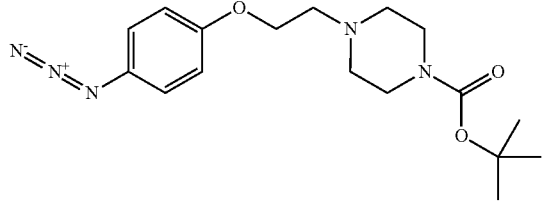 [SMILES: CC(C)(C)OC(=O)N1CCN(CCOc2ccc(N=[N+]=[N-])cc2)CC1]

4-[2-(4-Azido-phenoxy)-ethyl]-piperazine-1-carboxylic acid tert-butyl ester, beige powder; HPLC/MS 1.30 min (A), [M+H]+ 348.

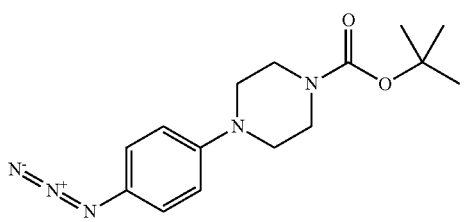 [SMILES: CC(C)(C)OC(=O)N1CCN(c2ccc(N=[N+]=[N-])cc2)CC1]

4-(4-Azido-phenyl)-piperazine-1-carboxylic acid tert-butyl ester, brown solid; HPLC/MS 1.94 min (A), [M+H]+ 304.

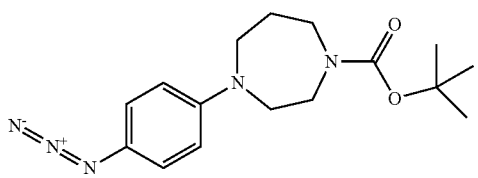 [SMILES: CC(C)(C)OC(=O)N1CCCN(c2ccc(N=[N+]=[N-])cc2)CC1]

4-(4-Azido-phenyl)-[1,4]diazepane-1-carboxylic acid tert-butyl ester, brown oil; HPLC/MS 1.97 min (A), [M+H]+ 318.

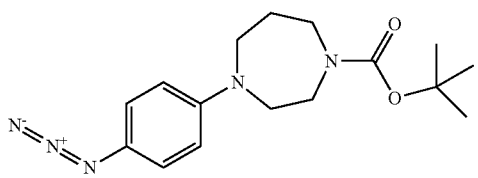 [SMILES: CC(C)(C)OC(=O)N1CCCN(c2ccc(N=[N+]=[N-])cc2)CC1]

4-(4-Azido-phenyl)-[1,4]diazepane-1-carboxylic acid tert-butyl ester, brown oil; HPLC/MS 1.97 min (A), [M+H]+ 318.

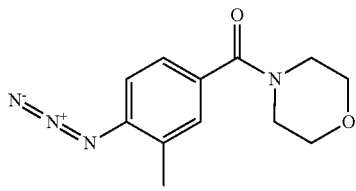 [SMILES: Cc1cc(C(=O)N2CCOCC2)ccc1N=[N+]=[N-]]

(4-Azido-3-methyl-phenyl)-morpholin-4-yl-methanone, yellow resin; HPLC/MS 1.42 min (A), [M+H]+ 247.

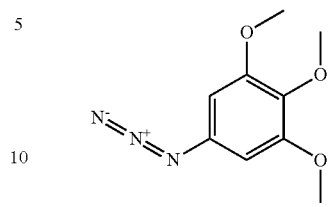

5-Azido-1,2,3-trimethoxy-benzene, beige solid; HPLC/MS 1.56 min (A), [M+H]+ 210.
$^1$H NMR (400 MHz, DMSO-$d_6$) δ 6.42 (s, 2H), 3.80 (s, 6H), 3.64 (s, 3H).

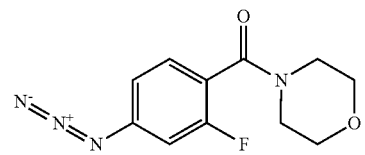 [SMILES: [N-]=[N+]=Nc1ccc(C(=O)N2CCOCC2)c(F)c1]

(4-Azido-2-fluoro-phenyl)-morpholin-4-yl-methanone, light brown oil; HPLC/MS 1.31 min (A), [M+H]+ 251.

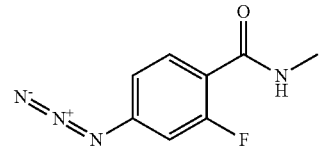

4-Azido-2-fluoro-N-methyl-benzamide, light brown oil; HPLC/MS 1.23 min (A), [M+H]+ 195.

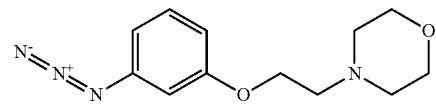 [SMILES: [N-]=[N+]=Nc1cccc(OCCN2CCOCC2)c1]

4-[2-(3-Azido-phenoxy)-ethyl]-morpholine, brown oil; HPLC/MS 1.03 min (A), [M+H]+ 249.

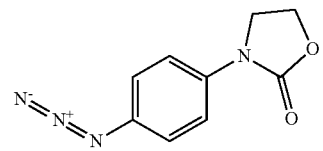 [SMILES: [N-]=[N+]=Nc1ccc(N2CCOC2=O)cc1]

3-(4-Azido-phenyl)-oxazolidin-2-one, pale brown powder; HPLC/MS 1.44 min (A), [M+H]+ 205. $^1$H NMR (400 MHz, DMSO-$d_6$) δ 7.60 (d, J=9.0 Hz, 2H), 7.15 (d, J=9.0 Hz, 2H), 4.59-4.33 (m, 2H), 4.10-4.00 (m, 2H).

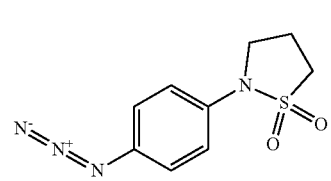 [SMILES: [N-]=[N+]=Nc1ccc(N2CCCS2(=O)=O)cc1]

2-(4-Azido-phenyl)-isothiazolidine 1,1-dioxide, beige powder; HPLC/MS 1.47 min (A), [M+H]⁺ 239.

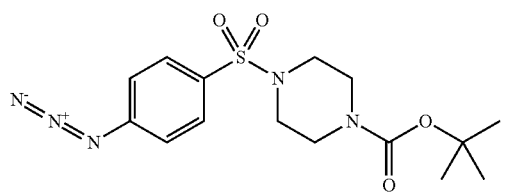 [SMILES: CC(C)(C)OC(=O)N1CCN(S(=O)(=O)c2ccc(N=[N+]=[N-])cc2)CC1]

4-(4-Azido-benzenesulfonyl)-piperazine-1-carboxylic acid tert-butyl ester, light yellow solid; UPLC/MS 0.90 min, [M+H]⁺ 268.

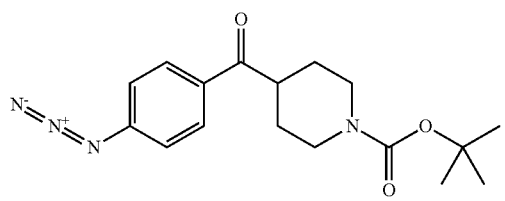 [SMILES: CC(C)(C)OC(=O)N1CCC(C(=O)c2ccc(N=[N+]=[N-])cc2)CC1]

4-(4-Azido-benzenesulfonyl)-piperazine-1-carboxylic acid tert-butyl ester, beige solid; HPLC/MS 1.93 min (A), [M+H]⁺ 275.

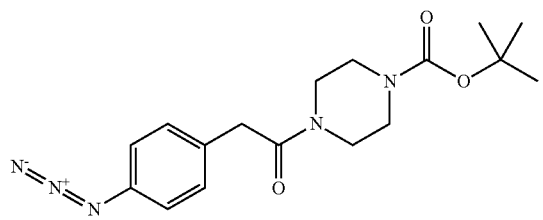 [SMILES: CC(C)(C)OC(=O)N1CCN(C(=O)Cc2ccc(N=[N+]=[N-])cc2)CC1]

4-[2-(4-Azido-phenyl)-acetyl]-piperazine-1-carboxylic acid tert-butyl ester, light yellow solid; UPLC/MS 1.13 min, [M-$^t$Bu]⁺ 290. $^1$H NMR (400 MHz, DMSO-$d_6$) δ 7.31-7.25 (m, 2H), 7.15-7.04 (m, 2H), 3.72 (s, 2H), 3.50-3.42 (m, 4H), 3.30-3.23 (m, 4H), 1.41 (s, 9H).

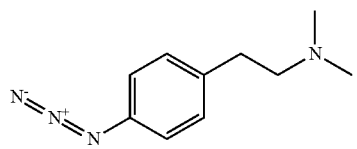

[2-(4-Azido-phenyl)-ethyl]-dimethyl-amine, red-brown oil; UPLC/MS 0.77 min, [M+H]⁺ 191. $^1$H NMR (500 MHz, DMSO-$d_6$) δ 7.27 (d, J=8.4 Hz, 2H), 7.07-6.99 (m, 2H), 2.75-2.66 (m, 2H), 2.47-2.38 (m, 2H), 2.17 (s, 6H).

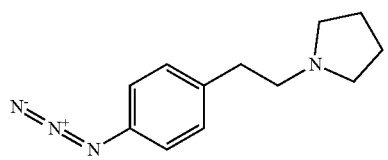 [SMILES: [N-]=[N+]=Nc1ccc(CCN2CCCC2)cc1]

1-[2-(4-Azido-phenyl)-ethyl]-pyrrolidine, red-brown oil; UPLC/MS 0.78 min, [M+H]⁺ 217. $^1$H NMR (500 MHz, DMSO-$d_6$) δ 7.30-7.26 (m, 1H), 7.06-7.01 (m, 1H), 2.73 (t, J=7.6 Hz, 1H), 2.60 (t, J=7.6 Hz, 1H), 2.49-2.43 (m, 3H), 1.71-1.63 (m, 4H).

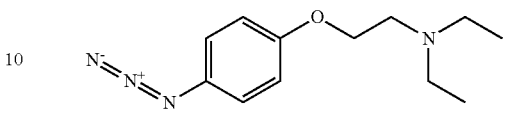

[2-(4-Azido-phenoxy)-ethyl]-diethyl-amine, brown liquid; HPLC/MS 1.08 min (A), [M+H]⁺ 235.

Synthesis of 4-(4-azido-phenyl)-morpholin-3-one

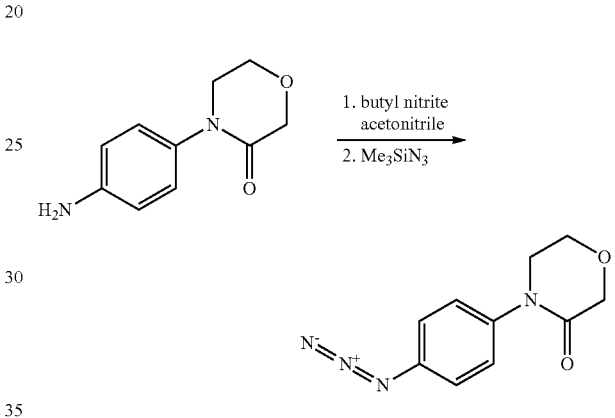

A suspension of 4-(4-amino-phenyl)-morpholin-3-one (3.00 g, 15.6 mmol) in acetonitrile (35 ml) is cooled to 0° C. Then butyl nitrite (2.43 g, 23.6 mmol) is added dropwise. The reaction mixture is stirred for 15 minutes at 0° C. Then trimethylsilyl azide is added dropwise. The reaction mixture is stirred for 20 hours at room temperature. The reaction mixture is concentrated under reduced pressure and the residue is chromatographed on a silica gel column with cyclohexane/ethyl acetate as eluent to afford 4-(4-azido-phenyl)-morpholin-3-one as beige solid; HPLC/MS 1.21 min (B), [M+H]⁺ 219.

$^1$H NMR (300 MHz, DMSO-$d_6$) δ 7.45 (d, J=8.8 Hz, 2H), 7.16 (d, J=8.8 Hz, 2H), 4.20 (s, 2H), 4.04-3.92 (m, 2H), 3.81-3.66 (m, 2H).

The following compounds are prepared similarly

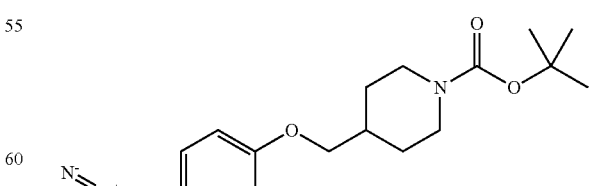

4-(4-Azido-phenoxymethyl)-piperidine-1-carboxylic acid tert-butyl ester, beige solid; HPLC/MS 1.85 min (B), [M-$^t$bu]⁺ 277.

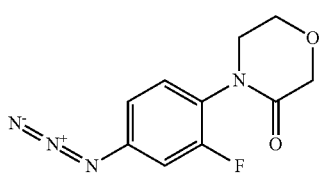 [SMILES: [N-]=[N+]=Nc1ccc(N2CCOCC2=O)c(F)c1]

4-(4-Azido-2-fluoro-phenyl)-morpholin-3-one, yellow powder; HPLC/MS 1.27 min (A), [M+H]+ 237.

$^1$H NMR (400 MHz, DMSO-d$_6$) δ 7.49 (t, J=8.4 Hz, 1H), 7.17 (dd, J=11.0, 2.5 Hz, 1H), 7.05 (ddd, J=8.6, 2.5, 1.0 Hz, 1H), 4.22 (s, 2H), 4.03-3.82 (m, 2H), 3.73-3.58 (m, 2H).

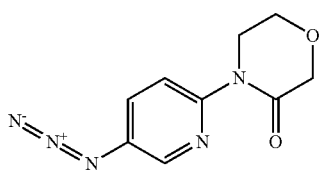 [SMILES: [N-]=[N+]=Nc1ccc(N2CCOCC2=O)nc1]

4-(5-Azido-pyridin-2-yl)-morpholin-3-one, yellow solid; HPLC/MS 1.15 min (A), [M+H]+ 220.

$^1$H NMR (400 MHz, DMSO-d$_6$) δ 8.27 (dd, J=2.9, 0.7 Hz, 1H), 8.05 (dd, J=8.9, 0.7 Hz, 1H), 7.69 (dd, J=8.9, 2.9 Hz, 1H), 4.27 (s, 2H), 4.05-3.90 (m, 4H).

Synthesis of 2-(4-azido-phenyl)-propan-2-ol

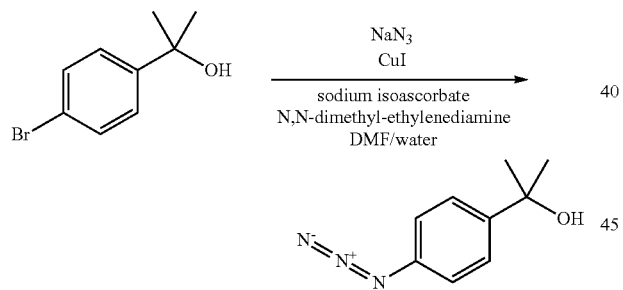

To a suspension of 2-(4-bromo-phenyl)-propan-2-ol (1.00 g, 4.65 mmol), copper(I) iodide (177 mg, 0.93 mmol) and sodium (2R)-2-[(2R)-3,4-dihydroxy-5-oxo-2H-furan-2-yl]-2-hydroxy-ethanolate hydrate (100 mg, 0.46 mmol in a mixture of DMF (4 ml) and water (5 ml) are added sodium azide (605 mg, 9.3 mmol) and N,N'-dimethyl-ethane-1,2-diamine (123 mg, 1.39 mmol). The reaction mixture is stirred at room temperature for 19 hours. The reaction mixture is poured into 40 ml saturated aqueous sodium chloride solution. The mixture is extracted with ethyl acetate. The organic phase is dried over sodium sulfate and evaporated. The residue is chromatographed on a silica gel column with cyclohexane/ethyl acetate as eluent to afford 2-(4-azido-phenyl)-propan-2-ol as light brown oil; HPLC/MS 1.47 min (B), [M-N$_2$—OH]+ 132.

$^1$H NMR (400 MHz, DMSO-d$_6$) δ 7.49 (d, J=8.4 Hz, 2H), 7.04 (d, J=8.4 Hz, 2H), 5.01 (s, 1H), 1.41 (s, 6H).

The following compounds are prepared similarly

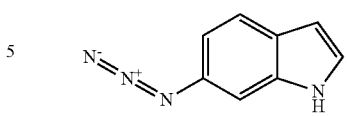

5-Azido-1H-indole, dark brown oil; HPLC/MS 1.46 min (B), [M+H]+ 159.

$^1$H NMR (300 MHz, DMSO-d$_6$) δ 11.19 (s, 1H), 7.43 (dt, J=8.6, 0.8 Hz, 1H), 7.40 (t, J=2.8 Hz, 1H), 7.29 (dt, J=2.2, 0.7 Hz, 1H), 6.84 (dd, J=8.6, 2.2 Hz, 1H), 6.42 (ddd, J=3.0, 2.0, 0.9 Hz, 1H).

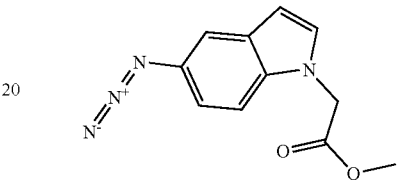

(5-Azido-indol-1-yl)-acetic acid methyl ester, black gum; HPLC/MS 1.72 min (A), [M+H]+ 231.

$^1$H NMR (400 MHz, DMSO-d$_6$) δ 7.47 (d, J=8.7 Hz, 1H), 7.41 (d, J=3.2 Hz, 1H), 7.32 (d, J=2.1 Hz, 1H), 6.91 (d, J=2.2 Hz, 1H), 6.89 (d, J=2.2 Hz, 1H), 6.47 (dd, J=3.2, 0.8 Hz, 2H), 5.16 (s, 1H), 3.69 (s, 3H).

Synthesis of (4-azido-phenyl)-morpholin-4-yl-methanone

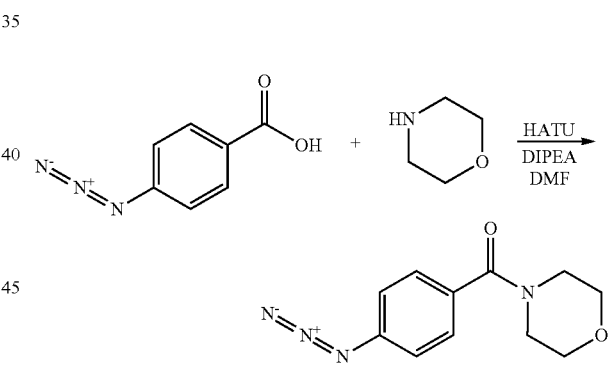

To a solution of 4-azidobenzoic acid (2.50 g, 15.3 mmol), morpholine (1.35 ml, 15.5 mmol) and [dimethylamino(triazolo[4,5-b]pyridin-3-yloxy)methylene]-dimethyl-ammonium hexafluorophosphate (HATU; 5.85 g, 15.4 mmol) in DMF (30 ml) is added ethyl-diisopropyl-amine (7.90 ml, 46.5 mmol) and the reaction mixture is stirred for 16 hours at room temperature. To the reaction mixture is added ethyl acetate, saturated aqueous Na$_2$CO$_3$ solution and water. The organic phase is separated, washed with water, with 2 N aqueous HCl solution and saturated sodium chloride solution. The organic phase is dried over sodium sulfate and evaporated. The residue is chromatographed on a silica gel column with cyclohexane/ethyl acetate as eluent to afford (4-azido-phenyl)-morpholin-4-yl-methanone as colourless oil, which crystallizes on standing; HPLC/MS 1.27 min (A), [M+H]+ 233.

$^1$H NMR (400 MHz, DMSO-d$_6$) δ 7.48 (d, J=8.5 Hz, 2H), 7.20 (d, J=8.5 Hz, 2H), 3.38-3-66 (m, 8H).

The following compounds are prepared similarly:

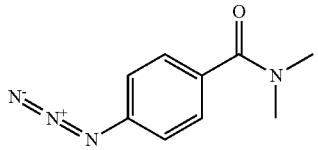

4-Azido-N,N-dimethylbenzamide, brown oil; HPLC/MS 2.24 min (A), [M+H]⁺ 191.

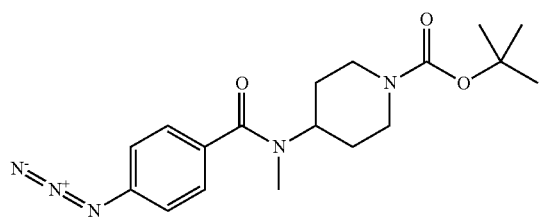

4-[(4-Azido-benzoyl)-methyl-amino]-piperidine-1-carboxylic acid tert-butyl ester, yellow oil; HPLC/MS 1.42 min (B), [M-$^t$bu]⁺304.
$^1$H NMR (400 MHz, DMSO-d$_6$) δ 7.44 (d, J=8.5 Hz, 2H), 7.24-7.08 (m, 1H), 4.41 (m, 1H), 4.02 (m, 4H), 2.79 (s, 3H), 1.73-1.51 (m, 4H), 1.41 (s, 9H).

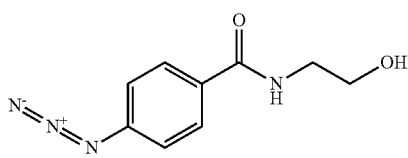 [SMILES: [N-]=[N+]=Nc1ccc(C(=O)NCCO)cc1]

4-Azido-N-(2-hydroxy-ethyl)-benzamide, white crystals; HPLC/MS 1.10 min (B), [M+H]⁺ 207.

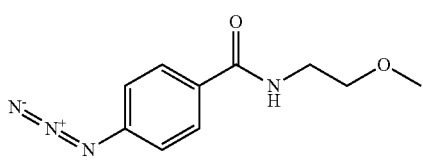 [SMILES: COCCNC(=O)c1ccc(N=[N+]=[N-])cc1]

4-Azido-N-(2-methoxy-ethyl)-benzamide.

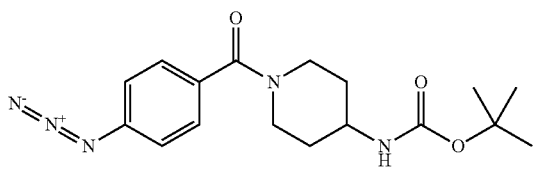 [SMILES: CC(C)(C)OC(=O)NC1CCN(C(=O)c2ccc(N=[N+]=[N-])cc2)CC1]

[1-(4-Azido-benzoyl)-piperidin-4-yl]-carbamic acid tert-butyl ester, light yellow glass; HPLC/MS 1.45 min (B), [M+H]⁺ 346.
$^1$H NMR (400 MHz, DMSO-d$_6$) δ 7.40 (d, J=8.5 Hz, 1H), 7.17 (d, J=8.5 Hz, 1H), 6.84 (d, J=7.8 Hz, 1H), 4.10-4.40 (m, 1H), 3.45-3.60 (m, 2H), 2.85-3.15 (m, 2H), 1.65-1.85 (m, 2H), 1.38 (s, 9H), 1.20-1.40 (m, 2H).

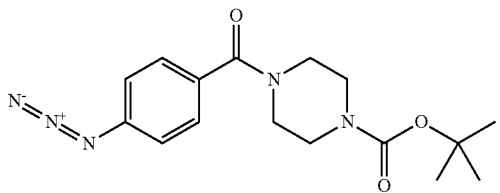 [SMILES: CC(C)(C)OC(=O)N1CCN(C(=O)c2ccc(N=[N+]=[N-])cc2)CC1]

4-(4-Azido-benzoyl)-piperazine-1-carboxylic acid tert-butyl ester, light yellow solid; HPLC/MS 1.49 min (B), [M-tbu]⁺276.
$^1$H NMR (300 MHz, DMSO-d$_6$) δ 7.47 (d, J=8.5 Hz, 2H), 7.19 (d, J=8.5 Hz, 2H), 3.30-3.62 (m, 8H), 1.42 (s, 9H).

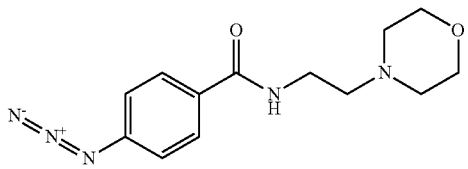 [SMILES: [N-]=[N+]=Nc1ccc(C(=O)NCCN2CCOCC2)cc1]

4-Azido-N-(2-morpholin-4-yl-ethyl)-benzamide, brown glass; HPLC/MS 0.98 min (B), [M+H]⁺ 276.

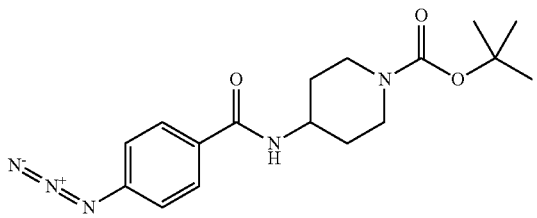 [SMILES: CC(C)(C)OC(=O)N1CCC(NC(=O)c2ccc(N=[N+]=[N-])cc2)CC1]

4-(4-Azido-benzoylamino)-piperidine-1-carboxylic acid tert-butyl ester, light yellow solid; HPLC/MS 1.49 min (B), [M-tbu]⁺290.
$^1$H NMR (400 MHz, DMSO-d$_6$) δ 8.26 (d, J=7.8 Hz, 1H), 7.90 (d, J=8.6 Hz, 2H), 7.20 (d, J=8.6 Hz, 2H), 3.90-4.03 (m, 3H), 2.77-2.94 (m, 2H), 1.75-1.82 (m, 2H), 1.42 (s, 9H), 1.36-1.48 (m, 2H).

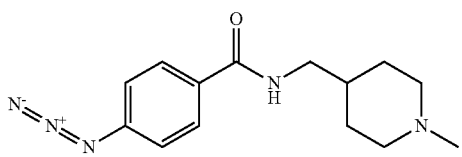 [SMILES: CN1CCC(CNC(=O)c2ccc(N=[N+]=[N-])cc2)CC1]

4-Azido-N-(1-methyl-piperidin-4-ylmethyl)-benzamide, light yellow oil; HPLC/MS 1.00 min (B), [M+H]⁺ 274.

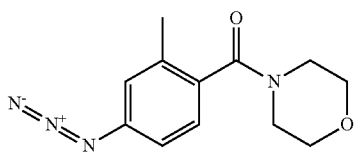 [SMILES: Cc1cc(N=[N+]=[N-])ccc1C(=O)N1CCOCC1]

(4-Azido-2-methyl-phenyl)-morpholin-4-yl-methanone, brown resin; HPLC/MS 1.35 min (A), [M+H]⁺ 247

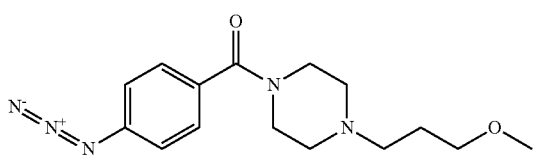 [SMILES: COCCCN1CCN(C(=O)c2ccc(N=[N+]=[N-])cc2)CC1]

(4-Azido-phenyl)-[4-(3-methoxy-propyl)-piperazin-1-yl]-methanone, brown oil; HPLC/MS 1.00 min (A), [M+H]+ 304.

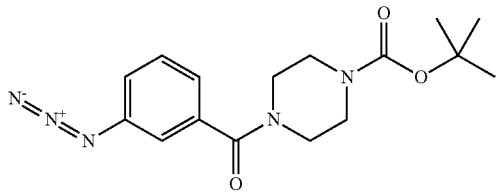 [SMILES: CC(C)(C)OC(=O)N1CCN(C(=O)c2cccc(N=[N+]=[N-])c2)CC1]

4-(3-Azido-benzoyl)-piperazine-1-carboxylic acid tert-butyl ester, beige solid; HPLC/MS 1.69 min (A), [M+H]+ 232.

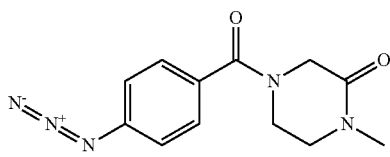 [SMILES: CN1CCN(C(=O)c2ccc(N=[N+]=[N-])cc2)CC1=O]

4-(4-Azido-benzoyl)-1-methyl-piperazin-2-one, light yellow gum; HPLC/MS 1.18 min (A), [M+H]+ 269.

$^1$H NMR (400 MHz, DMSO-$d_6$) δ 7.55-7.47 (m, 2H), 7.24-7.17 (m, 2H), 4.06 (s, 1H), 3.87-3.54 (m, 2H), 3.36 (t, J=5.5 Hz, 1H), 2.86 (s, 3H).

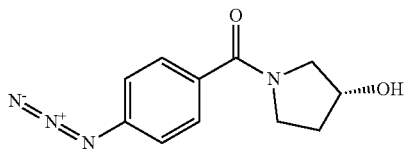 [SMILES: [N-]=[N+]=Nc1ccc(C(=O)N2CC[C@@H](O)C2)cc1]

(4-Azido-phenyl)-((R)-3-hydroxy-pyrrolidin-1-yl)-methanone, pale brown oil; HPLC/MS 1.16 min (A), [M+H]+ 233.

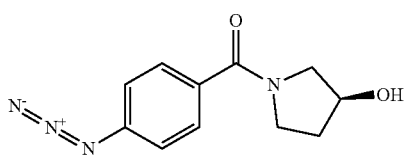 [SMILES: [N-]=[N+]=Nc1ccc(C(=O)N2CC[C@H](O)C2)cc1]

(4-Azido-phenyl)-((S)-3-hydroxy-pyrrolidin-1-yl)-methanone, pale brown oil; HPLC/MS 1.16 min (A), [M+H]+ 233.

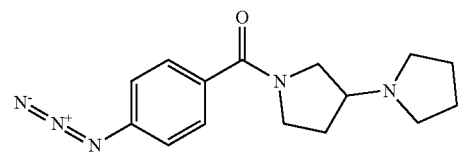 [SMILES: [N-]=[N+]=Nc1ccc(C(=O)N2CCC(N3CCCC3)C2)cc1]

(4-Azido-phenyl)-[1,3']bipyrrolidinyl-1'-methanone, brown gum; HPLC/MS 0.94 min (A), [M+H]+ 286.

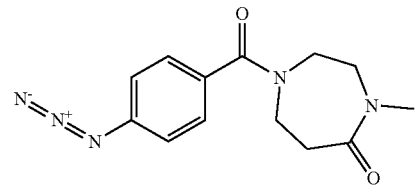 [SMILES: CN1CCN(C(=O)c2ccc(N=[N+]=[N-])cc2)CCC1=O]

1-(4-Azido-benzoyl)-4-methyl-[1,4]diazepan-5-one, yellow resin; UPLC/MS 0.51 min, [M+H]+ 274.

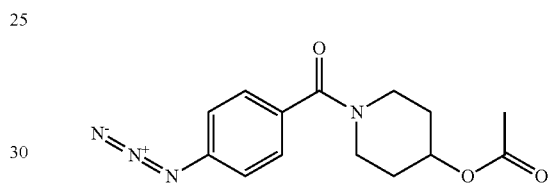

Acetic acid 1-(4-azido-benzoyl)-piperidin-4-yl ester, yellow resin; HPLC/MS 1.48 min (A), [M+H]+ 289.

$^1$H NMR (400 MHz, DMSO-$d_6$) δ 7.38 (d, J=8.5 Hz, 2H), 7.16-6.99 (m, 2H), 4.87 (tt, J=7.9, 3.8 Hz, 1H), 4.06-3.11 (m, 4H), 1.93 (s, 3H), 1.80 (bs, 2H), 1.53 (bs, 2H).

Synthesis of 4-[2-(5-azido-indol-1-yl)-acetyl]-piperazine-1-carboxylic Acid Tert-Butyl Ester

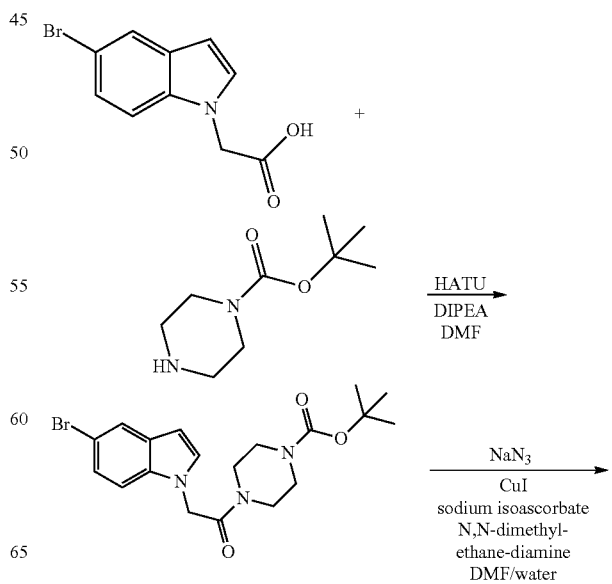

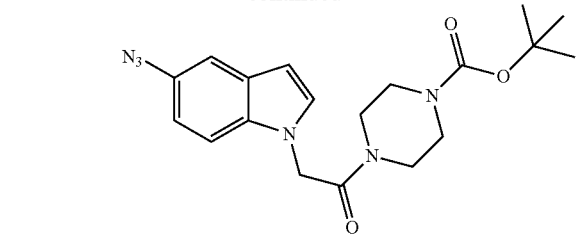

4-[2-(5-azido-indol-1-yl)-acetyl]-piperazine-1-carboxylic acid tert-butyl ester, light beige solid; UPLC/MS 0.84 min, [M+H]+ 329.

Synthesis of 4-[2-(4-azido-phenoxy)-acetyl]-piperazine-1-carboxylic Acid Tert-Butyl Ester

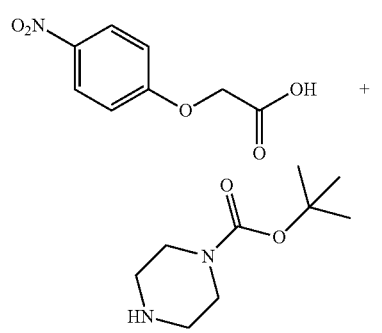

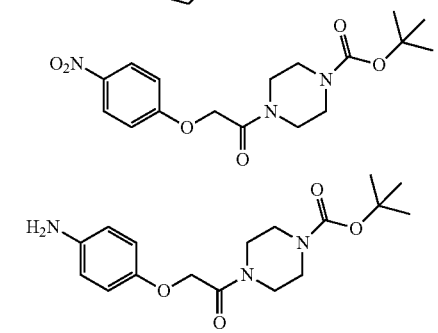

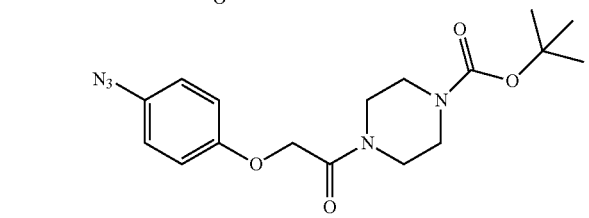

4-[2-(4-Azido-phenoxy)-acetyl]-piperazine-1-carboxylic acid tert-butyl ester, yellow solid; UPLC/MS 0.84 min, [M+H]+ 306.

Synthesis of 4-[2-(5-azido-indazol-1-yl)-acetyl]-piperazine-1-carboxylic Acid Tert-Butyl Ester

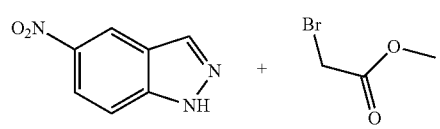

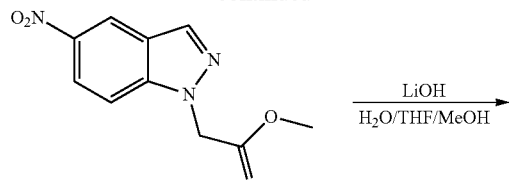

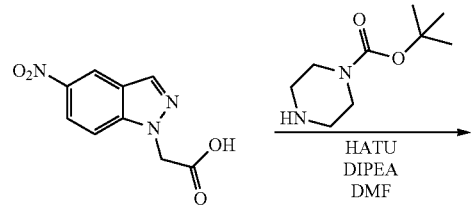

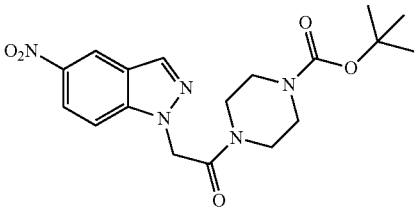

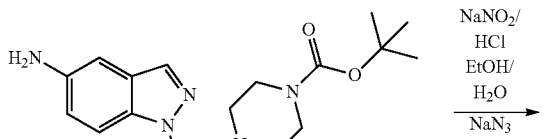

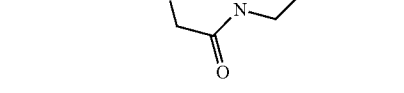

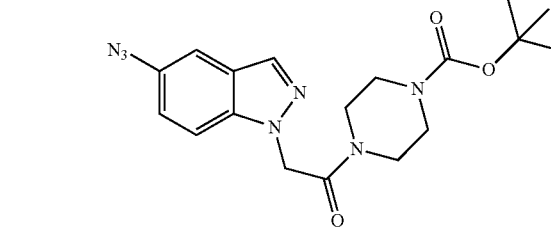

4-[2-(5-Azido-indazol-1-yl)-acetyl]-piperazine-1-carboxylic acid tert-butyl ester, purple solid, UPLC/MS 1.04 min, [M+H]+ 386.

Triazolyl-Acetic Acids

Synthesis of 4-[4-(4-carboxymethyl-[1,2,3]triazol-1-yl)-benzoyl]-piperazine-1-carboxylic Acid Tert-Butyl Ester

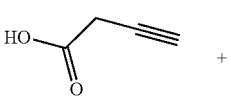

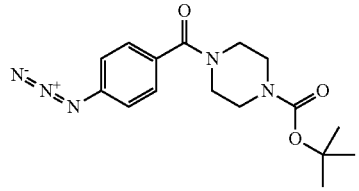

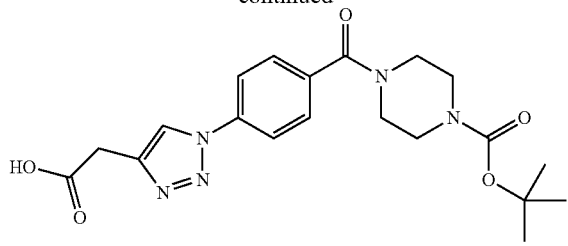

To a suspension of copper(II) sulfate pentahydrate (86 mg, 0.54 mmol) and sodium (2R)-2-[(2R)-3,4-dihydroxy-5-oxo-2H-furan-2-yl]-2-hydroxy-ethanolate hydrate (116 mg, 0.54 mmol in a mixture of tert-butanol (10 ml) and water (10 ml) are added 3-butynoic acid (451 mg, 5.37 mmol) and 4-(4-azido-benzoyl)-piperazine-1-carboxylic acid tert-butyl ester (1.78 g, 5.37 mmol). The reaction mixture is stirred at 80° C. for 19 hours. The reaction mixture is allowed to reach room temperature and poured into water. The resultant precipitate is filtered off, washed with water and dried. The residue is triturated with tert-butyl methyl ether to afford 4-[4-(4-carboxymethyl-[1,2,3]triazol-1-yl)-benzoyl]-piperazine-1-carboxylic acid tert-butyl ester as beige powder. A second crop can be obtained by extracting the filtrate with ethyl acetate. HPLC/MS 1.36 min (A), [M+H]+ 416. $^1$H NMR (400 MHz, DMSO-d$_6$, d-TFA) δ 8.59 (s, 1H), 7.99 (d, J=8.5 Hz, 2H), 7.64 (d, J=8.5 Hz, 2H), 3.84 (s, 2H), 3.35-3.75 (m, 8H), 1.45 (s, 9H).

The following compounds are prepared similarly:

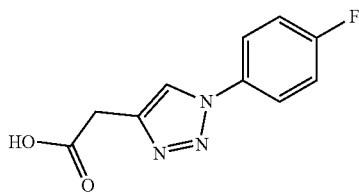 [SMILES: O=C(O)Cc1cn(-c2ccc(F)cc2)nn1]

[1-(4-Fluoro-phenyl)-1H-[1,2,3]triazol-4-yl]-acetic acid, light brown solid; HPLC/MS 1.18 min (B), [M+H]+ 222.

$^1$H NMR (400 MHz, DMSO-d$_6$, d-TFA) δ 8.48 (s, 1H), 7.86 (dd, J=9.0, 4.6 Hz, 2H), 7.27 (t, J=8.7 Hz, 2H), 3.73 (s, 2H).

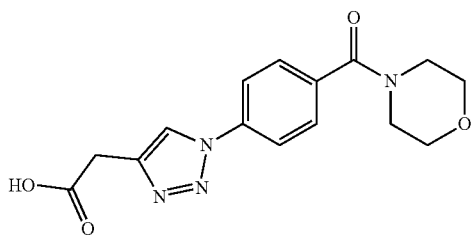 [SMILES: O=C(O)Cc1cn(-c2ccc(C(=O)N3CCOCC3)cc2)nn1]

{1-[4-(Morpholine-4-carbonyl)-phenyl]-1H-[1,2,3]triazol-4-yl}-acetic acid, beige solid; HPLC/MS 1.01 min (A), [M+H]+ 317.

$^1$H NMR (400 MHz, DMSO-d$_6$) δ 12.58 (s, 1H), 8.73 (s, 1H), 8.35-7.83 (m, 2H), 7.86-7.52 (m, 2H), 3.80 (s, 2H), 3.48 (d, J=124.8 Hz, 9H).

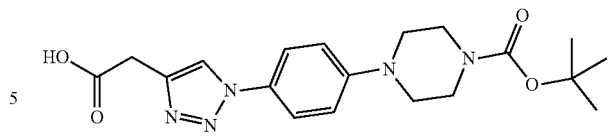

4-[4-(4-Carboxymethyl-[1,2,3]triazol-1-yl)-phenyl]-piperazine-1-carboxylic acid tert-butyl ester, grey solid; HPLC/MS 1.51 min (A), [M+H]+ 388.

$^1$H NMR (400 MHz, DMSO-d$_6$, d-TFA) δ 8.56 (s, 1H), 7.85 (d, J=8.7 Hz, 2H), 7.34 (d, J=8.8 Hz, 2H), 3.81 (s, 2H), 3.58-3.64 (m, 4H), 3.33-3.39 (m, 4H), 1.46 (s, 9H).

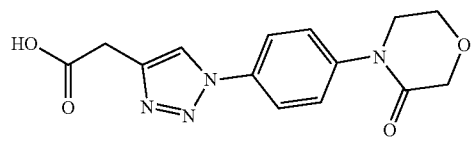 [SMILES: O=C(O)Cc1cn(-c2ccc(N3CCOCC3=O)cc2)nn1]

{1-[4-(3-Oxo-morpholin-4-yl)-phenyl]-1H-[1,2,3]triazol-4-yl}-acetic acid, beige solid; HPLC/MS 1.06 min (A), [M+H]+ 303.

$^1$H NMR (400 MHz, DMSO-d$_6$, TFA-d1) δ 8.58 (s, 1H), 7.90 (d, J=8.8 Hz, 2H), 7.60 (d, J=8.8 Hz, 2H), 4.21 (s, 2H), 3.99-3.95 (m, 2H), 3.82-3.71 (m, 4H).

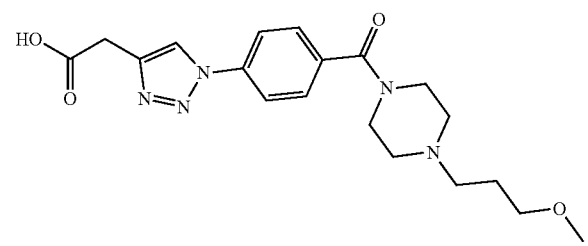 [SMILES: COCCCN1CCN(C(=O)c2ccc(-n3cc(CC(=O)O)nn3)cc2)CC1]

(1-{4-[4-(3-Methoxy-propyl)-piperazine-1-carbonyl]-phenyl}-1H-[1,2,3]triazol-4-yl)-acetic acid, beige solid; HPLC/MS 0.86 min (A), [M+H]+ 388.

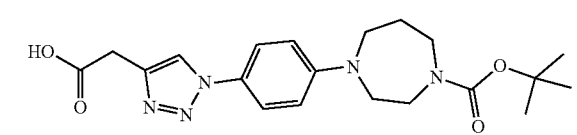 [SMILES: CC(C)(C)OC(=O)N1CCCN(c2ccc(-n3cc(CC(=O)O)nn3)cc2)CC1]

4-[4-(4-Carboxymethyl-[1,2,3]triazol-1-yl)-phenyl]-[1,4]diazepane-1-carboxylic acid tert-butyl ester, violet solid; HPLC/MS 1.52 min (A), [M+H]+ 402.

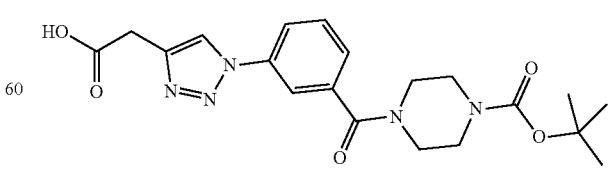

4-(3-Azido-benzoyl)-piperazine-1-carboxylic acid tert-butyl ester, beige solid; HPLC/MS 1.38 min (A), [M+H]+ 416.

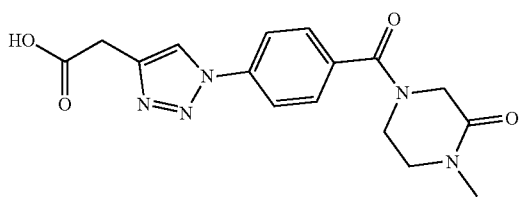 [SMILES: CN1CCN(C(=O)c2ccc(-n3cc(CC(=O)O)nn3)cc2)CC1=O]

{1-[4-(4-Methyl-3-oxo-piperazine-1-carbonyl)-phenyl]-1H-[1,2,3]triazol-4-yl}-acetic acid, light yellow powder; UPLC/MS 0.40 min, [M+H]$^+$ 344.

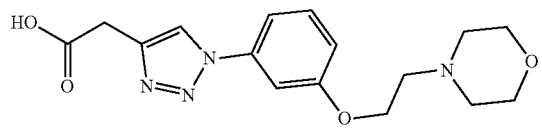 [SMILES: O=C(O)Cc1cn(-c2cccc(OCCN3CCOCC3)c2)nn1]

{1-[3-(2-Morpholin-4-yl-ethoxy)-phenyl]-1H-[1,2,3]triazol-4-yl}-acetic acid, beige solid; HPLC/MS 0.88 min (A), [M+H]$^+$ 333.

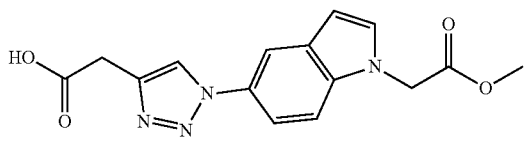 [SMILES: COC(=O)Cn1ccc2cc(-n3cc(CC(=O)O)nn3)ccc21]

[1-(1-Methoxycarbonylmethyl-1H-indol-6-yl)-1H-[1,2,3]triazol-4-yl]-acetic acid, light brown solid; HPLC/MS 1.25 min (A), [M+H]$^+$ 315. $^1$H NMR (400 MHz, DMSO-d$_6$) δ 12.61 (bs, 1H), 8.56 (s, 1H), 8.03 (t, J=1.3 Hz, 1H), 7.63-7.61 (m, 2H), 7.51 (d, J=3.2 Hz, 1H), 6.62 (d, J=3.2 Hz, 1H), 5.24 (s, 2H), 3.78 (s, 2H), 3.71 (s, 3H).

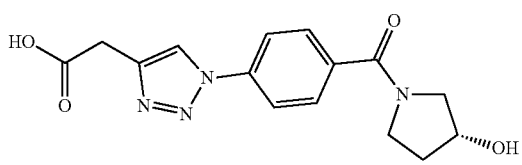 [SMILES: O=C(O)Cc1cn(-c2ccc(C(=O)N3CC[C@@H](O)C3)cc2)nn1]

{1-[4-((R)-3-Hydroxy-pyrrolidine-1-carbonyl)-phenyl]-1H-[1,2,3]triazol-4-yl}-acetic acid, dark brown oil; HPLC/MS 0.95 min (A), [M+H]$^+$ 317.

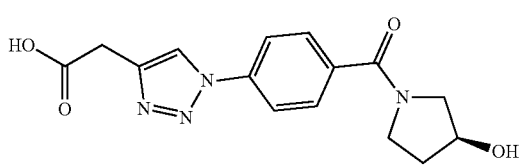 [SMILES: O=C(O)Cc1cn(-c2ccc(C(=O)N3CC[C@H](O)C3)cc2)nn1]

{1-[4-((S)-3-Hydroxy-pyrrolidine-1-carbonyl)-phenyl]-1H-[1,2,3]triazol-4-yl}-acetic acid, dark brown oil; HPLC/MS 0.95 min (A), [M+H]$^+$ 317.

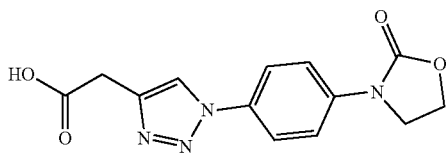 [SMILES: O=C(O)Cc1cn(-c2ccc(N3CCOC3=O)cc2)nn1]

{1-[4-(2-Oxo-oxazolidin-3-yl)-phenyl]-1H-[1,2,3]triazol-4-yl}-acetic acid, brown powder; HPLC/MS 1.08 min (A), [M+H]$^+$ 289. $^1$H NMR (400 MHz, DMSO-d$_6$, TFA-d$_1$) δ 8.63 (s, 1H), 8.19-7.87 (m, 2H), 7.87-7.70 (m, 2H), 4.50 (m, 2H), 4.16 (m, 2H), 3.80 (s, 2H).

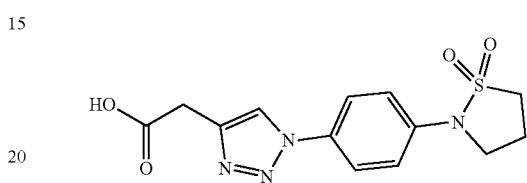

{1-[4-(1,1-Dioxo-isothiazolidin-2-yl)-phenyl]-1H-[1,2,3]triazol-4-yl}-acetic acid, brown powder; HPLC/MS 1.11 min (A), [M+H]$^+$ 323.

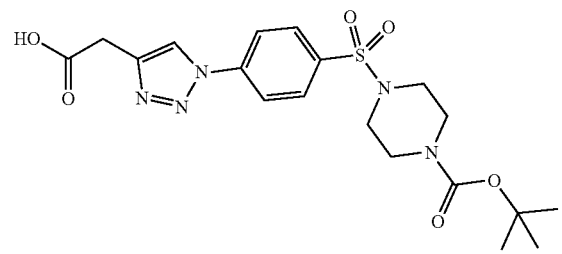 [SMILES: CC(C)(C)OC(=O)N1CCN(S(=O)(=O)c2ccc(-n3cc(CC(=O)O)nn3)cc2)CC1]

{1-[4-(1,1-Dioxo-isothiazolidin-2-yl)-phenyl]-1H-[1,2,3]triazol-4-yl}-acetic acid, brown powder; HPLC/MS 1.11 min (A), [M+H]$^+$ 323.

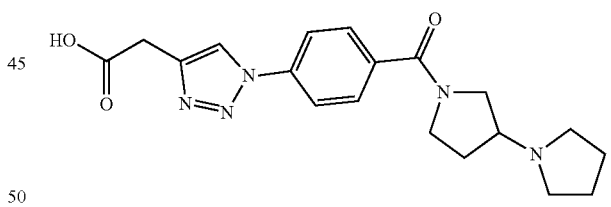

{1-[4-([1,3']Bipyrrolidinyl-1'-carbonyl)-phenyl]-1H-[1,2,3]triazol-4-yl}-acetic acid, brown solid; HPLC/MS 0.84 min (A), [M+H]$^+$ 370.

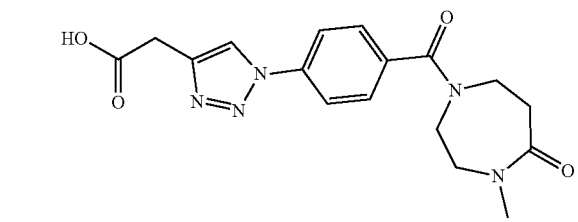 [SMILES: CN1CCN(C(=O)c2ccc(-n3cc(CC(=O)O)nn3)cc2)CCC1=O]

{1-[4-(4-Methyl-5-oxo-[1,4]diazepane-1-carbonyl)-phenyl]-1H-[1,2,3]triazol-4-yl}-acetic acid, brown solid; UPLC/MS 0.40 min, [M+H]$^+$ 358.

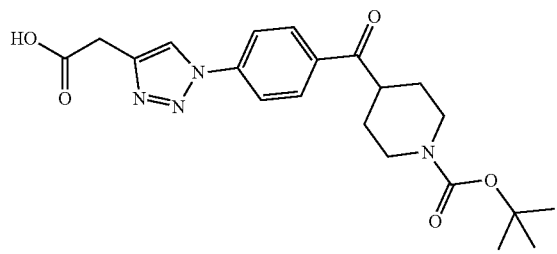 [SMILES: CC(C)(C)OC(=O)N1CCC(C(=O)c2ccc(-n3cc(CC(=O)O)nn3)cc2)CC1]

4-[4-(4-Carboxymethyl-[1,2,3]triazol-1-yl)-benzoyl]-piperidine-1-carboxylic acid tert-butyl ester, beige solid; HPLC/MS 1.57 min (A), [M+H]⁺ 415.

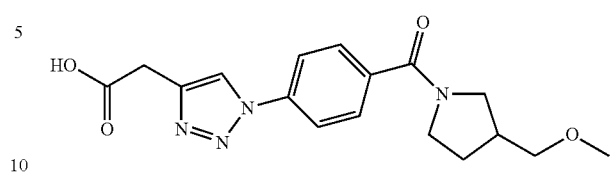

{1-[4-(3-Methoxymethyl-pyrrolidine-1-carbonyl)-phenyl]-1H-[1,2,3]triazol-4-yl}-acetic acid, brown foam; HPLC/MS 1.13 min (A), [M+H]⁺ 345.

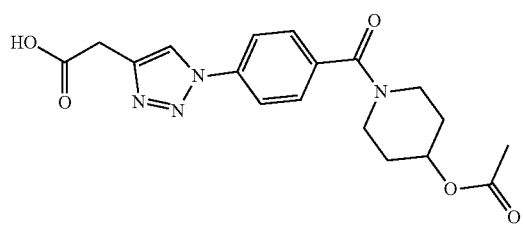 [SMILES: CC(=O)OC1CCN(C(=O)c2ccc(-n3cc(CC(=O)O)nn3)cc2)CC1]

{1-[4-(4-Acetoxy-piperidine-1-carbonyl)-phenyl]-1H-[1,2,3]triazol-4-yl}-acetic acid, beige solid; HPLC/MS 1.17 min (A), [M+H]⁺ 373.

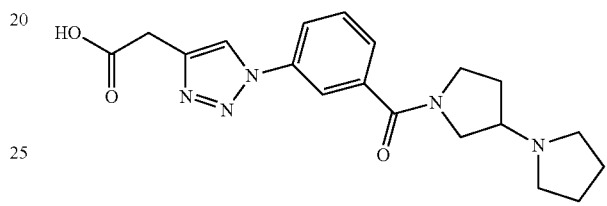

{1-[3-([1,3']Bipyrrolidinyl-1'-carbonyl)-phenyl]-1H-[1,2,3]triazol-4-yl}-acetic acid, light brown solid; HPLC/MS 0.84 min (A), [M+H]⁺ 370.

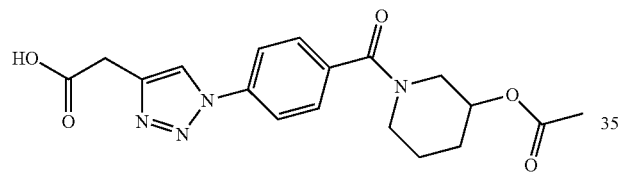

{1-[4-(3-Acetoxy-piperidine-1-carbonyl)-phenyl]-1H-[1,2,3]triazol-4-yl}-acetic acid, light brown foam; HPLC/MS 1.18 min (A), [M+H]⁺ 373.

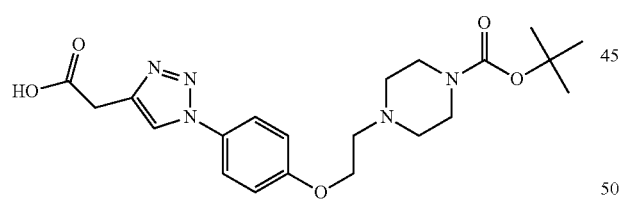

4-{2-[4-(4-Carboxymethyl-[1,2,3]triazol-1-yl)-phenoxy]-ethyl}-piperazine-1-carboxylic acid tert-butyl ester, brown solid; HPLC/MS 1.10 min (A), [M+H]⁺ 432.

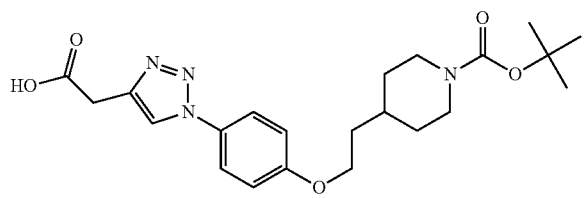

4-{2-[4-(4-Carboxymethyl-[1,2,3]triazol-1-yl)-phenoxy]-ethyl}-piperidine-1-carboxylic acid tert-butyl ester, brown oil, which crystallizes slowly; HPLC/MS 1.73 min (A), [M+H]⁺ 431.

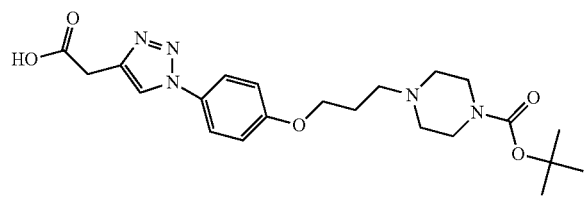 [SMILES: CC(C)(C)OC(=O)N1CCN(CCCOc2ccc(-n3cc(CC(=O)O)nn3)cc2)CC1]

4-{3-[4-(4-Carboxymethyl-[1,2,3]triazol-1-yl)-phenoxy]-propyl}-piperazine-1-carboxylic acid tert-butyl ester, brown powder; HPLC/MS 1.12 min (A), [M+H]⁺ 446.

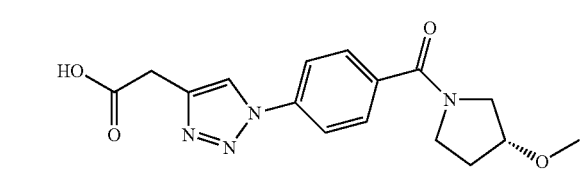 [SMILES: CO[C@@H]1CCN(C(=O)c2ccc(-n3cc(CC(=O)O)nn3)cc2)C1]

{1-[4-((R)-3-Methoxy-pyrrolidine-1-carbonyl)-phenyl]-1H-[1,2,3]triazol-4-yl}-acetic acid, green resin; UPLC/MS 0.73 min, [M+H]⁺ 331.

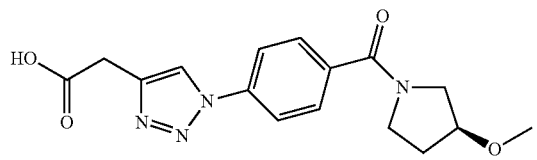 [SMILES: CO[C@H]1CCN(C(=O)c2ccc(-n3cc(CC(=O)O)nn3)cc2)C1]

{1-[4-((S)-3-Methoxy-pyrrolidine-1-carbonyl)-phenyl]-1H-[1,2,3]triazol-4-yl}-acetic acid, green resin; UPLC/MS 0.73 min, [M+H]$^+$ 331.

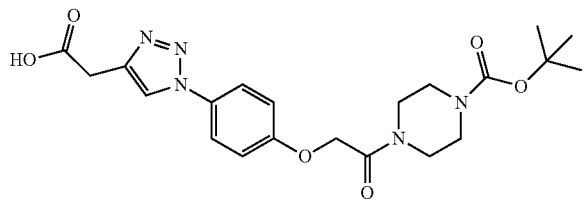

4-{2-[4-(4-Carboxymethyl-[1,2,3]triazol-1-yl)-phenoxy]-acetyl}-piperazine-1-carboxylic acid tert-butyl ester, off-white solid; UPLC/MS 0.92 min, [M+H]$^+$ 446.

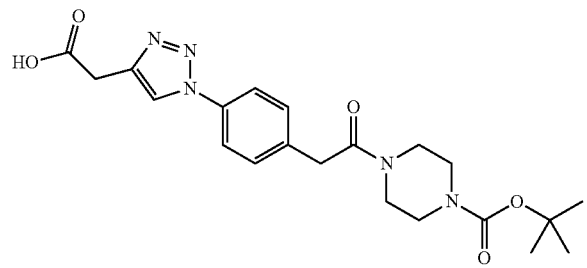 [SMILES: CC(C)(C)OC(=O)N1CCN(C(=O)Cc2ccc(-n3cc(CC(=O)O)nn3)cc2)CC1]

4-{2-[4-(4-Carboxymethyl-[1,2,3]triazol-1-yl)-phenyl]-acetyl}-piperazine-1-carboxylic acid tert-butyl ester, beige solid; UPLC/MS 0.92 min [M+H]$^+$ 430.

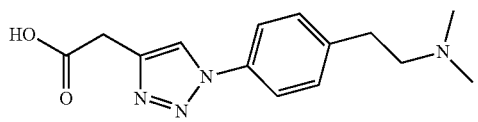 [SMILES: CN(C)CCc1ccc(-n2cc(CC(=O)O)nn2)cc1]

{1-[4-(2-Dimethylamino-ethyl)-phenyl]-1H-[1,2,3]triazol-4-yl}-acetic acid, dark brown residue; UPLC/MS 0.63 min, [M+H]$^+$ 275.

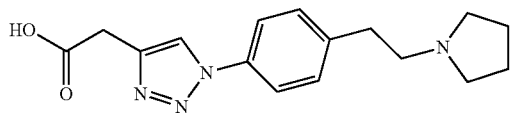 [SMILES: O=C(O)Cc1cn(-c2ccc(CCN3CCCC3)cc2)nn1]

{1-[4-(2-Pyrrolidin-1-yl-ethyl)-phenyl]-1H-[1,2,3]triazol-4-yl}-acetic acid, dark brown solid; UPLC/MS 0.65 min, [M+H]$^+$ 301.

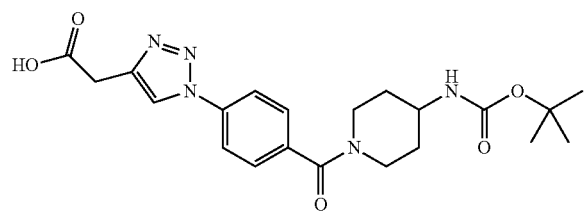

{1-[4-(4-tert-Butoxycarbonylamino-piperidine-1-carbonyl)-phenyl]-1H-[1,2,3]triazol-4-yl}-acetic acid, beige solid; UPLC/MS 0.90 min [M+H]$^+$ 430. $^1$H NMR (500 MHz, DMSO-d$_6$) δ 12.59 (s, 1H), 8.72 (s, 1H), 8.12-7.73 (m, 2H), 7.58 (d, J=8.5 Hz, 2H), 6.88 (d, J=7.7 Hz, 1H), 4.33 (bs, 1H), 3.80 (s, 2H), 3.55 (bs, 2H), 3.14 (bs, 1H), 2.99 (bs, 1H), 1.77 (m, 2H), 1.40 (m, 11H).

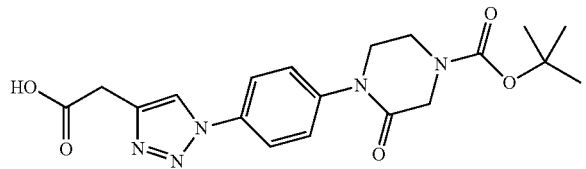 [SMILES: CC(C)(C)OC(=O)N1CCN(c2ccc(-n3cc(CC(=O)O)nn3)cc2)C(=O)C1]

4-[4-(4-Carboxymethyl-[1,2,3]triazol-1-yl)-phenyl]-3-oxo-piperazine-1-carboxylic acid tert-butyl ester, beige solid; HPLC/MS 1.34 min (A), [M+H]$^+$ 402.

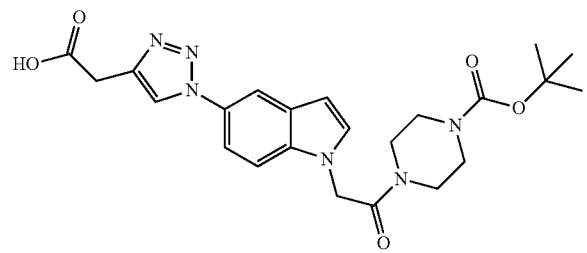

4-{2-[5-(4-Carboxymethyl-[1,2,3]triazol-1-yl)-indol-1-yl]-acetyl}-piperazine-1-carboxylic acid tert-butyl ester, beige solid; UPLC/MS 0.92 min, [M+H]$^+$ 469.

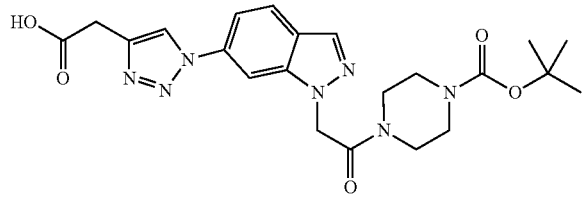 [SMILES: CC(C)(C)OC(=O)N1CCN(C(=O)Cn2ncc3ccc(-n4cc(CC(=O)O)nn4)cc32)CC1]

4-{2-[5-(4-Carboxymethyl-[1,2,3]triazol-1-yl)-indazol-1-yl]-acetyl}-piperazine-1-carboxylic acid tert-butyl ester, gray powder; UPLC/MS 0.88 min, [M+H]$^+$ 470.

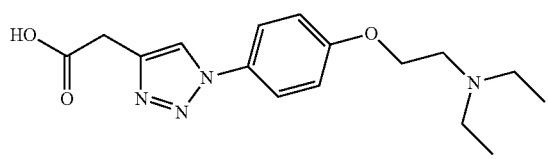 [SMILES: CCN(CC)CCOc1ccc(-n2cc(CC(=O)O)nn2)cc1]

{1-[4-(2-Diethylamino-ethoxy)-phenyl]-1H-[1,2,3]tri-azol-4-yl}-acetic acid, brown residue; HPLC/MS 0.91 min (A), [M+H]⁺ 391.

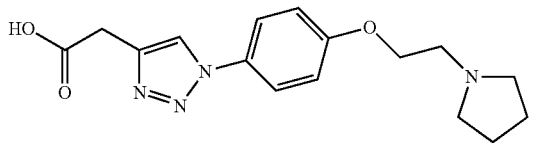 [SMILES: O=C(O)Cc1cn(-c2ccc(OCCN3CCCC3)cc2)nn1]

{1-[4-(2-Pyrrolidin-1-yl-ethoxy)-phenyl]-1H-[1,2,3]tri-azol-4-yl}-acetic acid, brown solid foam; HPLC/MS 0.89 min (A), [M+H]⁺ 317.

2-Aminobenzaldehydes

Synthesis of 6-amino-2,3-difluoro-benzaldehyde

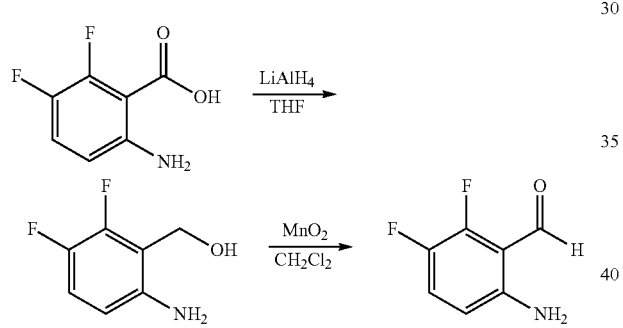

A suspension of 2,3-difluoro-6-aminobenzoic acid (1.00 g, 5.78 mmol) in THF (30 ml) is cooled to 0° C. under nitrogen. Lithium aluminium hydride (1.0 M solution in THF, 8.7 ml, 8.7 mmol) is added dropwise within 30 minutes. The reaction mixture is stirred for 1 hour at 0° C. and for 18 hours at room temperature. The reaction mixture is quenched with water and filtered over kieselguhr. The filtrate is concentrated in vacuo and the residue is partitioned between water and ethyl acetate. The organic phase is dried over sodium sulfate and evaporated. The residue is chromatographed on a silica gel column with dichloromethane/methanol as eluent to afford (6-amino-2,3-difluoro-phenyl)-methanol as brown solid; HPLC/MS 0.99 min (A), [M+H]⁺ 160. ¹H NMR (400 MHz, DMSO-d₆) δ 7.01 (dt, J=10.6, 9.0 Hz, 1H), 6.42 (ddd, J=8.9, 4.1, 1.9 Hz, 1H), 5.13 (s, 2H), 5.07 (t, J=5.5 Hz, 1H), 4.47 (dd, J=5.5, 2.3 Hz, 2H).

To a solution of (6-amino-2,3-difluoro-phenyl)-methanol (565 mg, 3.56 mmol) in dichloromethane (8 ml) is added manganese dioxide (620 mg, 7.13 mmol) and the reaction mixture is stirred at 80° C. for 3 hours. The reaction mixture is allowed to reach room temperature and filtered over kieselguhr. The filtrate is evaporated to afford 6-amino-2,3-difluoro-benzaldehyde as brown solid; HPLC/MS 1.44 min (A), [M+H]⁺ 158, ¹H NMR (400 MHz, DMSO-d₆) δ 10.16 (d, J=0.5 Hz, 1H), 7.44 (dt, J=10.5, 9.3 Hz, 1H), 7.34 (s, 2H), 6.57 (dddd, J=9.4, 3.8, 2.0, 0.7 Hz, 1H).

The following compounds are prepared similarly

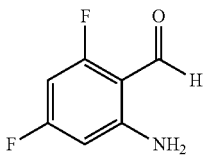

2-Amino-4,6-difluoro-benzaldehyde, dark red solid; HPLC/MS 1.47 min (A), [M+H]⁺ 158;
¹H NMR (400 MHz, DMSO-d₆) δ 10.08 (d, J=0.6 Hz, 1H), 7.73 (s, 2H), 6.42-6.34 (m, 2H).

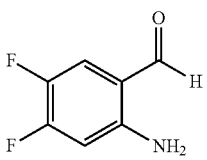

2-Amino-4,5-difluoro-benzaldehyde, dark brown residue; UPLC/MS 0.65 min, [M+H]⁺ 158.
¹H NMR (400 MHz, DMSO-d₆) δ 9.73 (s, 1H), 7.66 (dd, J=11.0, 9.1 Hz, 1H), 7.23 (s, 2H), 6.70 (dd, J=13.2, 6.7 Hz, 1H).

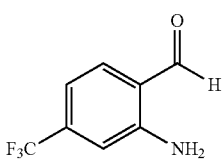

2-Amino-4-trifluoromethyl-benzaldehyde, light orange solid; UPLC/MS 1.05 min, [M+H]⁺ 190.
¹H NMR (500 MHz, DMSO-d₆) δ 9.95 (d, J=0.6 Hz, 1H), 7.79 (d, J=8.1 Hz, 1H), 7.40 (s, 2H), 7.13 (s, 1H), 6.90 (dd, J=8.1, 1.7 Hz, 1H).

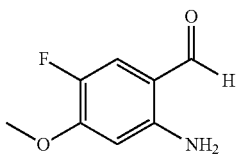

2-Amino-5-fluoro-4-methoxy-benzaldehyde, beige solid; HPLC/MS 1.31 min (A), [M+H]⁺ 170.

EXAMPLE 1

6-fluoro-3-{1-[4-(morpholine-4-carbonyl)-phenyl]-1H-[1,2,3]triazol-4-yl}-1H-quinolin-2-one ("A1")

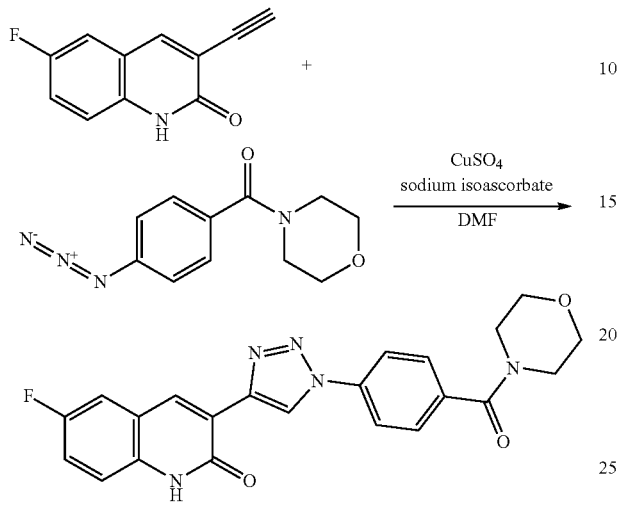

To a suspension of 3-ethynyl-6-fluoro-1H-quinolin-2-one (46.8 mg, 0.25 mmol), copper(II) sulfate pentahydrate (4.0 mg, 0.03 mmol) and sodium (2R)-2-[(2R)-3,4-dihydroxy-5-oxo-2H-furan-2-yl]-2-hydroxy-ethanolate hydrate (5.4 mg, 0.03 mmol) in DMF (0.5 ml) is added (4-azido-phenyl)-morpholin-4-yl-methanone (65.0 mg, 0.28 mmol). The reaction mixture is heated to 110° C. and stirred at this temperature for 22 hours. The reaction mixture is allowed to reach room temperature. Water is added and the resultant precipitate is filtered off, washed with water and dried. The residue is chromatographed on a silica gel column with dichloromethane/methanol as eluent to afford 6-fluoro-3-{1-[4-(morpholine-4-carbonyl)-phenyl]-1H-[1,2,3]triazol-4-yl}-1H-quinolin-2-one as off-white powder; HPLC/MS 1.44 min (A), [M+H]$^+$ 420.

$^1$H NMR (400 MHz, DMSO-d$_6$) δ 12.27 (s, 1H), 9.28 (s, 1H), 8.85 (s, 1H), 8.10 (d, J=8.5 Hz, 2H), 7.80 (dd, J=9.3, 2.7 Hz, 1H), 7.65 (d, J=8.5 Hz, 2H), 7.47 (dd, J=9.0, 2.7 Hz, 1H), 7.45-7.39 (m, 1H), 3.75-3.35 (m, 8H).

The following compounds are prepared similarly:

3-{1-[4-(morpholine-4-carbonyl)-phenyl]-1H-[1,2,3]triazol-4-yl}-1H-quinolin-2-one ("A2")

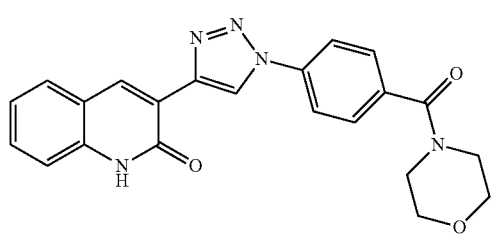 [SMILES: O=C(c1ccc(-n2cc(-c3cc4ccccc4[nH]c3=O)nn2)cc1)N1CCOCC1]

beige solid, HPLC/MS 1.27 min (B), [M+H]$^+$ 402; $^1$H NMR (400 MHz, DMSO-d$_6$) δ 12.21 (s, 1H), 9.28 (s, 1H), 8.85 (s, 1H), 8.11 (d, J=8.2 Hz, 2H), 7.92 (d, J=7.9 Hz, 1H), 7.67 (d, J=8.2 Hz, 2H), 7.57 (t, J=7.7 Hz, 1H), 7.42 (d, J=8.3 Hz, 1H), 7.27 (t, J=7.5 Hz, 1H), 3.75-3.35 (m, 8H).

N,N-dimethyl-4-[4-(2-oxo-1,2-dihydro-[1,8]naphthyridin-3-yl)-[1,2,3]triazol-1-yl]-benzamide ("A3")

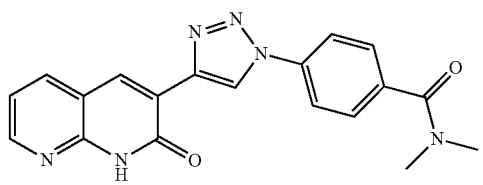 [SMILES: CN(C)C(=O)c1ccc(-n2cc(-c3cc4cccnc4[nH]c3=O)nn2)cc1]

beige powder; $^1$H NMR (400 MHz, DMSO-d$_6$) δ 12.58 (s, 1H), 9.28 (s, 1H), 8.87 (s, 1H), 8.59 (s, 1H), 8.38 (d, J=7.8 Hz, 1H), 8.09 (d, J=8.1 Hz, 2H), 7.66 (d, J=8.1 Hz, 2H), 7.34 (t, J=6.3 Hz, 1H), 3.02 (s, 3H), 3.00 (s, 3H).

N,N-dimethyl-4-[4-(2-oxo-1,2-dihydro-quinolin-3-yl)-[1,2,3]triazol-1-yl]-benzamide ("A4")

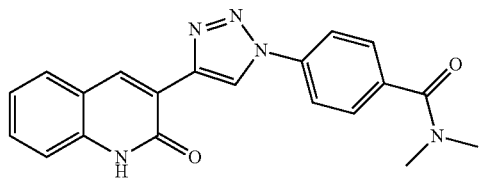 [SMILES: CN(C)C(=O)c1ccc(-n2cc(-c3cc4ccccc4[nH]c3=O)nn2)cc1]

light yellow solid, HPLC/MS 1.28 min (B), [M+H]$^+$ 360; $^1$H NMR (400 MHz, DMSO-d$_6$) δ 12.22 (s, 1H), 9.26 (s, 1H), 8.84 (s, 1H), 8.14-8.04 (m, 2H), 7.91 (dd, J=7.9, 1.4 Hz, 1H), 7.68-7.62 (m, 2H), 7.56 (ddd, J=8.5, 7.1, 1.4 Hz, 1H), 7.41 (d, J=8.1 Hz, 1H), 7.26 (ddd, J=8.1, 7.2, 1.1 Hz, 1H), 3.02 (s, 4H), 2.97 (s, 3H).

3-[1-(4-dimethylaminomethyl-phenyl)-1H-[1,2,3]triazol-4-yl]-1H-[1,8]naphthyridin-2-one ("A5")

$^1$H NMR (400 MHz, DMSO-d$_6$, TFA-d$_1$) δ 9.25 (br s, 1H), 8.83 (br s, 1H), 8.57 (br s, 1H), 8.31 (d, 1H), 8.08 (d, 2H), 7.70 (d, 2H), 7.27 (br s, 1H), 4.34 (s, 2H), 2.74 (s, 6H).

3-(1-phenyl-1H-[1,2,3]triazol-4-yl)-1H-[1,8]naph-thyridin-2-one ("A6")

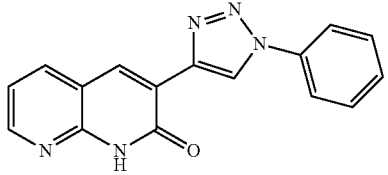 [SMILES: O=c1[nH]c2ncccc2cc1-c1cn(-c2ccccc2)nn1]

$^1$H NMR (400 MHz, DMSO-d$_6$, TFA-d$_1$) δ 9.22 (br s, 1H), 8.85 (br s, 1H), 8.57 (brs, 1H), 8.35 (d, 1H), 7.98 (d, 1H), 7.59 (m, 2H), 7.50 (m, 2H), 7.30 (br s, 1H).

3-[1-(4-hydroxymethyl-phenyl)-1H-[1,2,3]triazol-4-yl]-1H-[1,8]naphthyridin-2-one ("A7")

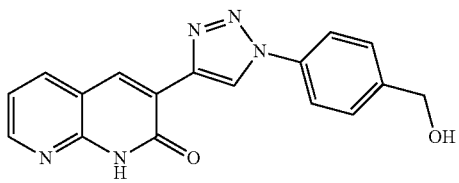 [SMILES: O=c1[nH]c2ncccc2cc1-c1cn(-c2ccc(CO)cc2)nn1]

$^1$H NMR (400 MHz, DMSO-d$_6$, TFA-d$_1$) δ 9.20 (br s, 1H), 8.81 (br s, 1H), 8.55 (br s, 1H), 8.30 (d, 1H), 7.80 (d, 1H), 5.70 (s, 2H), 7.47 (d, 2H), 7.27 (d, 1H), 4.53 (s, 2H).

N-(2-hydroxy-ethyl)-4-[4-(2-oxo-1,2-dihydro-[1,8]naphthyridin-3-yl)-[1,2,3]triazol-1-yl]-benzamide ("A8")

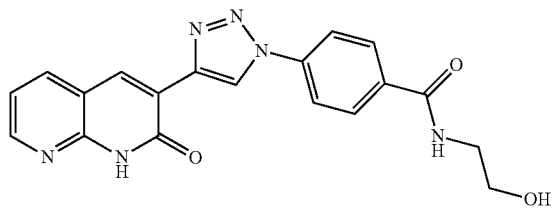 [SMILES: O=C(NCCO)c1ccc(-n2cc(-c3cc4cccnc4[nH]c3=O)nn2)cc1]

$^1$H NMR (400 MHz, DMSO-d$_6$, TFA-d$_1$) δ 9.31 (br s, 1H), 8.87 (br s, 1H), 8.57 (br s, 1H), 8.36 (d, 1H), 8.13 (dd, 4H), 7.31 (br s, 1H), 3.51 (m, 2H), 3.37 (m, 2H).

N-(2-methoxy-ethyl)-4-[4-(2-oxo-1,2-dihydro-[1,8]naphthyridin-3-yl)-[1,2,3]triazol-1-yl]-benzamide ("A9")

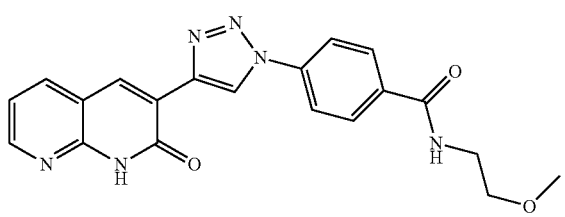 [SMILES: COCCNC(=O)c1ccc(-n2cc(-c3cc4cccnc4[nH]c3=O)nn2)cc1]

$^1$H NMR (400 MHz, DMSO-d$_6$, TFA-d$_1$) δ 9.29 (br s, 1H), 8.83 (br s, 1H), 8.55 (br s, 1H), 8.30 (br s, 1H), 8.05 (br s, 4H), 7.83 (br s, 0.5H), 7.54 (br s, 0.5H), 7.26 (br s, 1H), 3.44 (s, 4H), 3.23 (s, 3H).

3-[1-(4-methoxy-phenyl)-1H-[1,2,3]triazol-4-yl]-1H-quinolin-2-one ("A10")

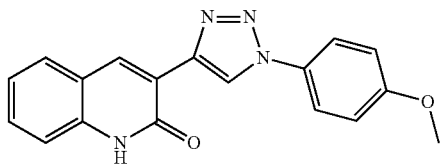 [SMILES: COc1ccc(-n2cc(-c3cc4ccccc4[nH]c3=O)nn2)cc1]

yellow-brown solid; HPLC/MS 1.43 min (B), [M+H]$^+$ 319; $^1$H NMR (400 MHz, DMSO-d$_6$) δ 12.19 (s, 1H), 9.09 (s, 1H), 8.82 (s, 1H), 7.95-7.86 (m, 3H), 7.55 (ddd, J=8.5, 7.1, 1.4 Hz, 1H), 7.40 (d, J=8.1 Hz, 1H), 7.25 (ddd, J=8.2, 7.2, 1.1 Hz, 1H), 7.19-7.11 (m, 2H), 3.85 (s, 3H).

4-[4-(6-chloro-2-oxo-1,2-dihydro-[1,8]naphthyridin-3-yl)-[1,2,3]triazol-1-yl]-N,N-dimethyl-benzamide ("A11")

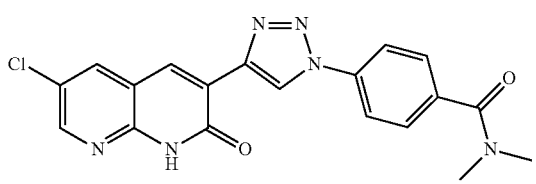 [SMILES: CN(C)C(=O)c1ccc(-n2cc(-c3cc4cc(Cl)cnc4[nH]c3=O)nn2)cc1]

light brown solid; HPLC/MS 1.31 min (B), [M+H]$^+$ 395; $^1$H NMR (500 MHz, DMSO-d$_6$) δ 12.78 (s, 1H), 9.29 (s, 1H), 8.85 (s, 1H), 8.60 (d, J=2.5 Hz, 1H), 8.55 (d, J=2.5 Hz, 1H), 8.08 (d, J=8.6 Hz, 2H), 7.65 (d, J=8.5 Hz, 2H), 3.02 (s, 3H), 2.97 (s, 3H).

3-[1-(4-fluoro-phenyl)-1H-[1,2,3]triazol-4-yl]-1H-quinolin-2-one ("A12")

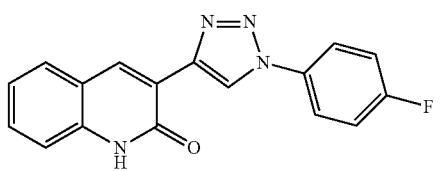 [SMILES: O=c1[nH]c2ccccc2cc1-c1cn(-c2ccc(F)cc2)nn1]

light yellow solid; HPLC/MS 1.44 min (B), [M+H]$^+$ 307; $^1$H NMR (400 MHz, DMSO-d$_6$) δ 12.20 (s, 1H), 9.19 (s, 1H), 8.83 (s, 1H), 8.12-8.02 (m, 2H), 7.90 (dd, J=7.9, 1.4 Hz, 1H), 7.56 (ddd, J=8.5, 7.2, 1.4 Hz, 1H), 7.51-7.43 (m, 2H), 7.40 (dd, J=8.2, 1.0 Hz, 1H), 7.25 (ddd, J=8.1, 7.2, 1.1 Hz, 1H).

3-[1-(2-fluoro-phenyl)-1H-[1,2,3]triazol-4-yl]-1H-quinolin-2-one ("A13")

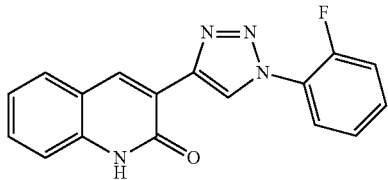 [SMILES: O=c1[nH]c2ccccc2cc1-c1cn(-c2ccccc2F)nn1]

light yellow solid; HPLC/MS 1.43 min (B), [M+H]⁺ 307; ¹H NMR (400 MHz, DMSO-d₆) δ 12.20 (s, 1H), 9.06 (d, J=2.4 Hz, 1H), 8.85 (s, 1H), 7.95 (td, J=7.9, 1.6 Hz, 1H), 7.91 (dd, J=8.0, 1.4 Hz, 1H), 7.68-7.52 (m, 3H), 7.51-7.44 (m, 1H), 7.41 (dd, J=8.2, 1.0 Hz, 1H), 7.26 (ddd, J=8.1, 7.2, 1.1 Hz, 1H).

3-{1-[4-(2-pyrrolidin-1-yl-ethoxy)-phenyl]-1H-[1,2,3]triazol-4-yl}-1H-quinolin-2-one ("A14")

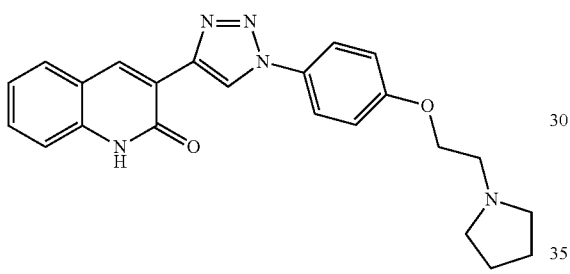

light brown crystals; HPLC/MS 1.13 min (B), [M+H]⁺ 402; ¹H NMR (500 MHz, DMSO-d₆) δ 12.17 (s, 1H), 9.08 (s, 1H), 8.81 (s, 1H), 7.91-7.86 (m, 3H), 7.55 (ddd, J=8.4, 7.1, 1.4 Hz, 1H), 7.40 (d, J=8.1 Hz, 1H), 7.28-7.22 (m, 1H), 7.19-7.11 (m, 2H), 4.16 (t, J=5.9 Hz, 2H), 2.82 (t, J=5.8 Hz, 2H), 2.56-2.52 (m, 3H), 1.72-1.68 (m, 4H).

N-(1-methyl-piperidin-4-ylmethyl)-4-[4-(2-oxo-1,2-dihydro-quinolin-3-yl)-[1,2,3]triazol-1-yl]-benzamide ("A15")

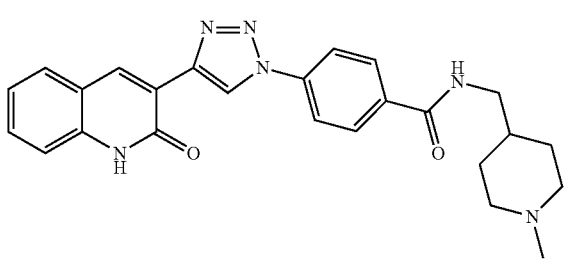 [SMILES: CN1CCC(CNC(=O)c2ccc(-n3cc(-c4cc5ccccc5[nH]c4=O)nn3)cc2)CC1]

brown solid; HPLC/MS 1.50 min (B), [M+H]⁺ 443; ¹H NMR (500 MHz, DMSO-d₆) δ 12.21 (s, 1H), 9.29 (s, 1H), 8.85 (s, 1H), 8.63 (t, J=5.8 Hz, 1H), 8.13 (d, J=8.7 Hz, 2H), 8.08 (d, J=8.8 Hz, 2H), 7.91 (dd, J=8.0, 1.3 Hz, 1H), 7.56 (ddd, J=8.4, 7.0, 1.4 Hz, 1H), 7.41 (d, J=8.2 Hz, 1H), 7.26 (t, J=7.7 Hz, 1H), 3.19 (t, J=6.3 Hz, 2H), 2.84-2.74 (m, 2H), 2.19 (s, 3H), 2.06-1.73 (m, 2H), 1.75-1.64 (m, 2H), 1.62-1.50 (m, 1H), 1.32-1.13 (m, 2H).

4-[4-(6-methoxy-2-oxo-1,2-dihydro-[1,8]naphthyridin-3-yl)-[1,2,3]triazol-1-yl]-N,N-dimethyl-benzamide ("A16")

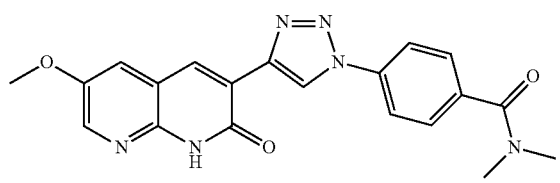

yellow solid; HPLC/MS 1.23 min (B), [M+H]⁺ 391; ¹H NMR (500 MHz, DMSO-d6) δ 12.51 (s, 1H), 9.29 (s, 1H), 8.85 (s, 1H), 8.36 (d, J=3.0 Hz, 1H), 8.13-8.06 (m, 2H), 8.03 (d, J=3.0 Hz, 1H), 7.71-7.62 (m, 2H), 3.91 (s, 3H), 3.03 (s, 3H), 2.98 (s, 3H).

4-[4-(2-oxo-1,2-dihydro-quinolin-3-yl)-[1,2,3]triazol-1-yl]-pyridine-2-carboxylic acid methyl ester ("A17")

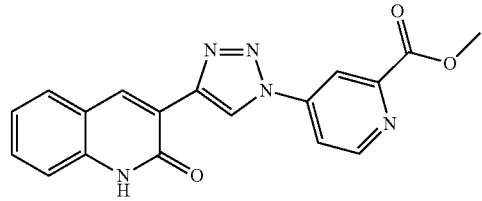 [SMILES: COC(=O)c1cc(-n2cc(-c3cc4ccccc4[nH]c3=O)nn2)ccn1]

brown solid; HPLC/MS 1.30 min (B), [M+H]⁺ 348; ¹H NMR (400 MHz, DMSO-d₆) δ 12.23 (s, 1H), 9.52 (s, 1H), 8.91 (d, J=5.3 Hz, 1H), 8.87 (s, 1H), 8.66 (d, J=2.1 Hz, 1H), 8.38 (dd, J=5.3, 2.2 Hz, 1H), 7.91 (d, J=7.6 Hz, 1H), 7.57 (ddd, J=8.4, 7.1, 1.4 Hz, 1H), 7.41 (d, J=8.2 Hz, 1H), 7.26 (t, J=7.4 Hz, 1H), 3.96 (s, 3H).

4-[4-(6-fluoro-2-oxo-1,2-dihydro-quinolin-3-yl)-[1,2,3]triazol-1-yl]-N, N-dimethyl-benzamide ("A18")

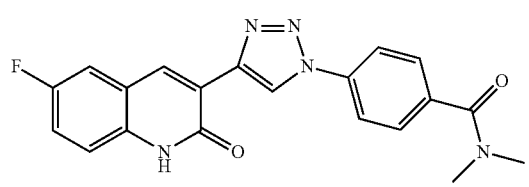 [SMILES: CN(C)C(=O)c1ccc(-n2cc(-c3cc4cc(F)ccc4[nH]c3=O)nn2)cc1]

light yellow solid; HPLC/MS 1.31 min (B), [M+H]⁺ 378; ¹H NMR (400 MHz, DMSO-d₆) δ 12.28 (s, 1H), 9.29 (s, 1H), 8.86 (s, 1H), 8.14-8.07 (m, 2H), 7.81 (dd, J=9.2, 2.6 Hz, 1H), 7.70-7.63 (m, 2H), 7.52-7.40 (m, 2H), 3.03 (s, 3H), 2.99 (s, 3H).

N-(2-hydroxy-ethyl)-4-[4-(2-oxo-1,2-dihydro-quinolin-3-yl)-[1,2,3]triazol-1-yl]-benzamide ("A19")

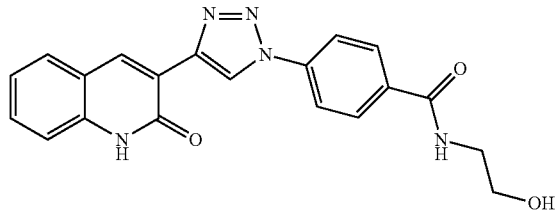 [SMILES: O=C(NCCO)c1ccc(-n2cc(-c3cc4ccccc4[nH]c3=O)nn2)cc1]

light brown crystals; HPLC/MS 1.20 min (B), [M+H]+ 376; H NMR (400 MHz, DMSO-d6) δ 12.20 (s, 1H), 9.29 (s, 1H), 8.85 (s, 1H), 8.60 (t, J=5.6 Hz, 1H), 8.14 (d, J=8.8 Hz, 2H), 8.09 (d, J=8.8 Hz, 2H), 7.91 (d, J=7.1 Hz, 0H), 7.56 (ddd, J=8.5, 7.2, 1.5 Hz, 1H), 7.41 (d, J=8.3 Hz, 1H), 7.30-7.21 (m, 1H), 4.73 (t, J=5.6 Hz, 1H), 3.55 (q, J=6.0 Hz, 2H), 3.37 (q, J=6.0 Hz, 2H).

3-[1-(1H-indol-5-yl)-1H-[1,2,3]triazol-4-yl]-1H-quinolin-2-one ("A20")

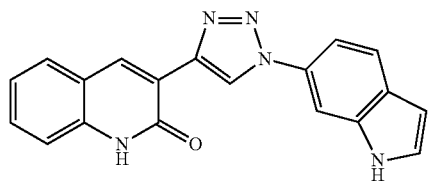 [SMILES: O=c1[nH]c2ccccc2cc1-c1cn(-c2ccc3cc[nH]c3c2)nn1]

brown solid; HPLC/MS 1.38 min (B), [M+H]+ 328; ¹H NMR (400 MHz, DMSO-d6) δ 12.19 (s, 1H), 11.43 (s, 1H), 9.09 (s, 1H), 8.83 (s, 1H), 8.11 (s, 1H), 7.91 (d, J=7.9 Hz, 1H), 7.70-7.50 (m, 4H), 7.41 (d, J=8.2 Hz, 1H), 7.26 (t, J=7.5 Hz, 1H), 6.60 (s, 1H).

N-(2-morpholin-4-yl-ethyl)-4-[4-(2-oxo-1,2-dihydro-quinolin-3-yl)-[1,2,3]triazol-1-yl]-benzamide ("A21")

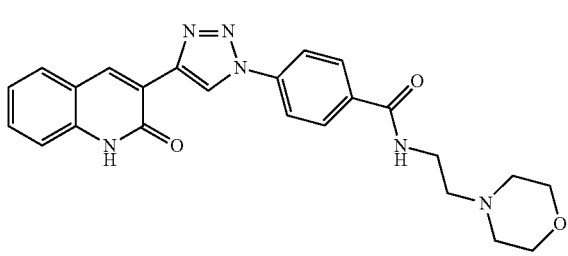 [SMILES: O=C(NCCN1CCOCC1)c1ccc(-n2cc(-c3cc4ccccc4[nH]c3=O)nn2)cc1]

light brown powder; HPLC/MS 1.10 min (B), [M+H]+ 445; ¹H NMR (500 MHz, DMSO-d6) δ 12.21 (s, 1H), 9.29 (s, 1H), 8.85 (s, 1H), 8.58 (t, J=5.7 Hz, 1H), 8.20-8.11 (m, 2H), 8.11-8.02 (m, 2H), 7.91 (d, J=8.0, 1.4 Hz, 1H), 7.56 (ddd, J=8.4, 7.1, 1.4 Hz, 1H), 7.41 (d, J=8.2 Hz, 0H), 7.26 (ddd, J=8.1, 7.2, 1.1 Hz, 1H), 3.60-3.56 (m, 4H), 3.43 (q, J=6.8 Hz, 2H), 2.52-2.48 (m, 2H), 2.47-2.39 (m, 4H).

4-[4-(6-fluoro-2-oxo-1,2-dihydro-quinolin-3-yl)-[1,2,3]triazol-1-yl]-N-(1-methyl-piperidin-4-ylmethyl)-benzamide ("A22")

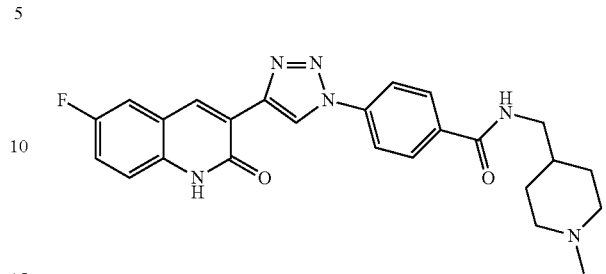

red-brown solid; HPLC/MS 1.12 min (B), [M+H]+ 461; ¹H NMR (400 MHz, DMSO-d6) δ 12.28 (s, 1H), 9.31 (s, 1H), 8.85 (s, 1H), 8.62 (t, J=5.8 Hz, 1H), 8.13 (d, J=8.8 Hz, 2H), 8.07 (d, J=8.8 Hz, 2H), 7.80 (dd, J=9.2, 2.6 Hz, 1H), 7.53-7.34 (m, 2H), 3.18 (t, J=6.3 Hz, 2H), 2.81-2.71 (m, 2H), 2.15 (s, 3H), 1.93-1.75 (m, 2H), 1.71-1.61 (m, 1H), 1.60-1.48 (m, 1H), 1.26-1.14 (m, 2H).

3-[4-(2-oxo-1,2-dihydro-quinolin-3-yl)-[1,2,3]triazol-1-yl]-benzoic Acid Methyl Ester ("A23")

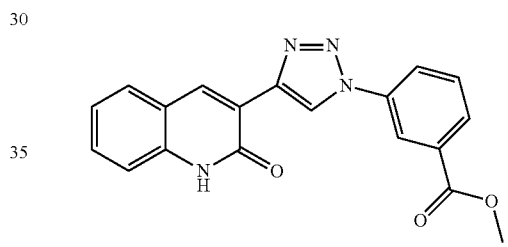

light brown solid; HPLC/MS 1.45 min (B), [M+H]+ 347; ¹H NMR (400 MHz, DMSO-d6) δ 12.21 (s, 1H), 9.31 (s, 1H), 8.85 (s, 1H), 8.50 (t, J=2.0 Hz, 1H), 8.32 (dd, J=8.1, 1.4 Hz, 1H), 8.08 (dt, J=7.8, 1.3 Hz, 1H), 7.91 (dd, J=8.0, 1.3 Hz, 1H), 7.78 (t, J=8.0 Hz, 1H), 7.56 (ddd, J=8.4, 7.2, 1.4 Hz, 1H), 7.41 (d, J=8.2 Hz, 1H), 7.26 (t, J=7.4 Hz, 1H), 3.94 (s, 3H).

3-[1-(3-methoxy-phenyl)-1H-[1,2,3]triazol-4-yl]-1H-quinolin-2-one ("A24")

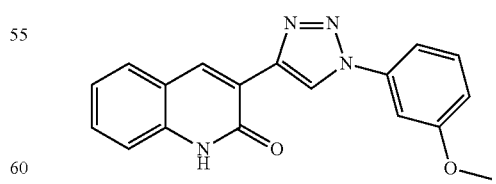

yellow solid; HPLC/MS 1.45 min (B), [M+H]+ 319; ¹H NMR (400 MHz, DMSO-d6) δ 12.17 (s, 1H), 9.22 (s, 1H), 8.82 (s, 1H), 7.90 (dd, J=8.1, 1.4 Hz, 1H), 7.60-7.48 (m, 4H), 7.43-7.38 (m, 1H), 7.25 (ddd, J=8.1, 7.2, 1.1 Hz, 1H), 7.08 (ddd, J=8.1, 2.4, 1.2 Hz, 1H), 3.89 (s, 3H).

3-{1-[4-(3-oxo-morpholin-4-yl)-phenyl]-1H-[1,2,3]triazol-4-yl}-1H-quinolin-2-one ("A25")

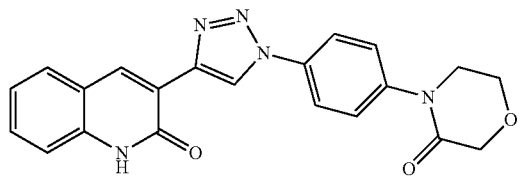 [SMILES: O=C1COCCN1c1ccc(-n2cc(-c3cc4ccccc4[nH]c3=O)nn2)cc1]

white solid; HPLC/MS 1.27 min (B), [M+H]+ 388; 1H NMR (400 MHz, DMSO-d6) δ 12.20 (s, 1H), 9.23 (s, 1H), 8.85 (s, 1H), 8.11-8.03 (m, 2H), 7.95-7.88 (m, 1H), 7.74-7.65 (m, 2H), 7.57 (ddd, J=8.4, 7.1, 1.4 Hz, 1H), 7.42 (d, J=8.2 Hz, 1H), 7.32-7.22 (m, 1H), 4.27 (s, 2H), 4.01-4.05 (m, 2H), 3.87-3.82 (m, 2H).

3-{1-[4-(2-morpholin-4-yl-ethoxy)-phenyl]-1H-[1,2,3]triazol-4-yl}-1H-quinolin-2-one ("A26")

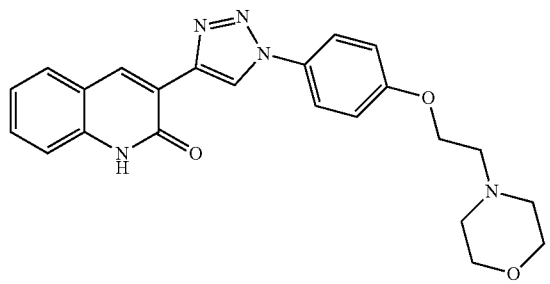 [SMILES: O=c1[nH]c2ccccc2cc1-c1cn(-c2ccc(OCCN3CCOCC3)cc2)nn1]

beige solid; HPLC/MS 1.08 min (B), [M+H]+ 418; 1H NMR (400 MHz, DMSO-d6) δ 12.17 (s, 1H), 9.09 (s, 1H), 8.82 (s, 1H), 7.92-7.87 (m, 3H), 7.56 (ddd, J=8.4, 7.2, 1.4 Hz, 1H), 7.45-7.38 (m, 1H), 7.32-7.24 (m, 1H), 7.22-7.13 (m, 2H), 4.20 (t, J=5.7 Hz, 2H), 3.65-3.57 (m, 4H), 2.75 (t, J=5.7 Hz, 2H), 2.52-2.49 (m, 4H).

3-(1-phenyl-1H-[1,2,3]triazol-4-yl)-1H-quinolin-2-one ("A27")

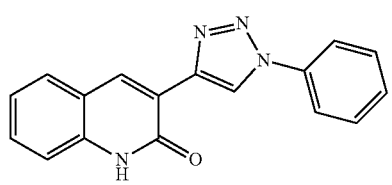 [SMILES: O=c1[nH]c2ccccc2cc1-c1cn(-c2ccccc2)nn1]

yellow crystals; HPLC/MS 1.43 min (B), [M+H]+ 289; 1H NMR (500 MHz, DMSO-d6) δ 12.19 (s, 1H), 9.19 (s, 1H), 8.83 (s, 1H), 8.03-7.97 (m, 2H), 7.90 (dd, J=7.9, 1.3 Hz, 1H), 7.67-7.59 (m, 2H), 7.59-7.49 (m, 1H), 7.43-7.39 (m, 1H), 7.26 (ddd, J=8.1, 7.2, 1.1 Hz, 1H).

3-[1-(3H-benzimidazol-5-yl)-1H-[1,2,3]triazol-4-yl]-1H-quinolin-2-one ("A28")

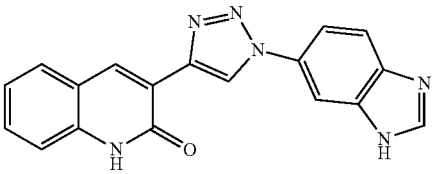 [SMILES: O=c1[nH]c2ccccc2cc1-c1cn(-c2ccc3nc[nH]c3c2)nn1]

beige solid; HPLC/MS 1.09 min (B), [M+H]+ 329; 1H NMR (400 MHz, DMSO-d6, TFA-d1) δ 9.67 (s, 1H), 9.32 (s, 1H), 8.82 (s, 1H), 8.47 (d, J=2.0 Hz, 1H), 8.21 (dd, J=8.9, 2.0 Hz, 1H), 8.03 (d, J=8.9 Hz, 1H), 7.82 (dd, J=8.0, 1.3 Hz, 1H), 7.49 (ddd, J=8.4, 7.0, 1.4 Hz, 1H), 7.41 (d, J=8.2 Hz, 1H), 7.27-7.12 (m, 1H).

3-{1-[4-(morpholine-4-carbonyl)-phenyl]-1H-[1,2,3]triazol-4-yl}-1H-[1,7]naphthyridin-2-one ("A29")

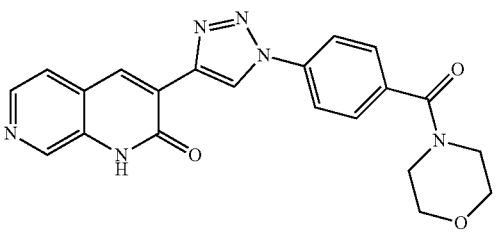 [SMILES: O=C(c1ccc(-n2cc(-c3cc4ccncc4[nH]c3=O)nn2)cc1)N1CCOCC1]

beige solid; HPLC/MS 1.11 min (B), [M+H]+ 403; 1H NMR (400 MHz, DMSO-d6) δ 12.47 (s, 1H), 9.37 (s, 1H), 8.88 (s, 1H), 8.85 (bs, 1H), 8.48 (bs, 1H), 8.17-8.06 (m, 2H), 7.91 (b, 1H), 7.75-7.60 (m, 2H), 3.80-3.35 (m, 8H).

7-methyl-3-{1-[4-(morpholine-4-carbonyl)-phenyl]-1H-[1,2,3]triazol-4-yl}-1H-[1,8]naphthyridin-2-one ("A30")

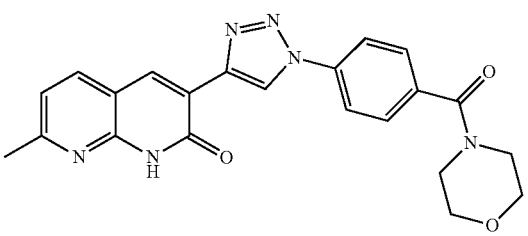 [SMILES: Cc1ccc2cc(-c3cn(-c4ccc(C(=O)N5CCOCC5)cc4)nn3)c(=O)[nH]c2n1]

brown solid; HPLC/MS 1.24 min (B), [M+H]+ 417; 1H NMR (500 MHz, DMSO-d6) δ 12.46 (s, 1H), 9.24 (s, 1H), 8.82 (s, 1H), 8.24 (d, J=7.9 Hz, 1H), 8.13-8.05 (m, 2H), 7.96 (s, 1H), 7.71-7.61 (m, 2H), 7.22 (d, J=7.9 Hz, 1H), 3.64 (bs, 4H), 2.51 (bs, 4H), 1.25 (s, 3H).

6-fluoro-3-{1-[4-(morpholine-4-carbonyl)-phenyl]-1H-[1,2,3]triazol-4-yl}-1H-[1,8]naphthyridin-2-one ("A31")

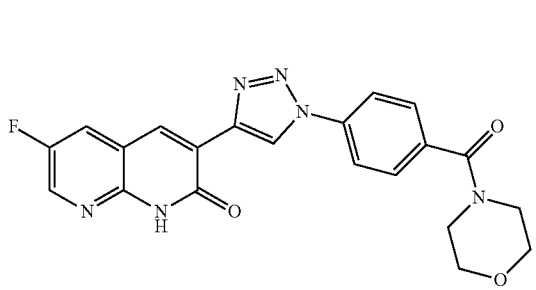 [SMILES: O=C(c1ccc(-n2cc(-c3cc4cc(F)cnc4[nH]c3=O)nn2)cc1)N1CCOCC1]

brown solid, HPLC/MS 1.24 min (B), [M+H]⁺ 421; ¹H NMR (400 MHz, DMSO-d₆) δ 12.73 (s, 1H), 9.31 (s, 1H), 8.88 (s, 1H), 8.63 (d, J=2.9 Hz, 1H), 8.36 (dd, J=8.7, 3.0 Hz, 1H), 8.17-8.04 (m, 2H), 7.77-7.55 (m, 2H), 3.75-3.40 (m, 8H).

3-{1-[3-fluoro-4-(3-oxo-morpholin-4-yl)-phenyl]-1H-[1,2,3]triazol-4-yl}-1H-quinolin-2-one ("A32")

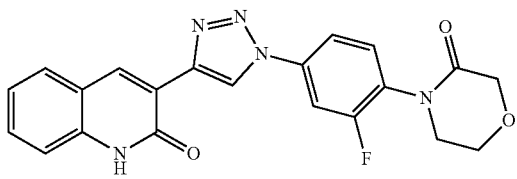 [SMILES: O=C1COCCN1c1ccc(-n2cc(-c3cc4ccccc4[nH]c3=O)nn2)cc1F]

beige powder, HPLC/MS 1.42 min (A), [M+H]⁺ 406; ¹H NMR (400 MHz, DMSO-d₆) δ 12.21 (s, 1H), 9.32 (s, 1H), 8.84 (s, 1H), 8.12 (dd, J=11.0, 2.4 Hz, 1H), 8.04-7.95 (m, 1H), 7.90 (dd, J=8.0, 1.4 Hz, 1H), 7.73 (t, J=8.4 Hz, 1H), 7.56 (ddd, J=8.4, 7.2, 1.4 Hz, 1H), 7.41 (d, J=8.2 Hz, 1H), 7.26 (td, J=7.6, 1.1 Hz, 1H), 4.28 (s, 2H), 4.05-4.00 (m, 2H), 3.81-3.65 (m, 2H).

6-fluoro-3-{1-[3-fluoro-4-(3-oxo-morpholin-4-yl)-phenyl]-1H-[1,2,3]triazol-4-yl}-1H-quinolin-2-one ("A33")

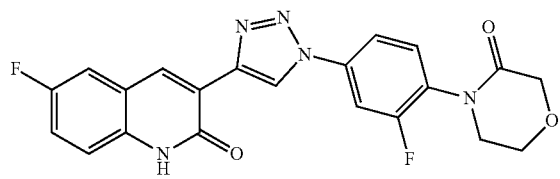 [SMILES: O=C1COCCN1c1ccc(-n2cc(-c3cc4cc(F)ccc4[nH]c3=O)nn2)cc1F]

beige powder, HPLC/MS 1.47 min (A), [M+H]⁺ 424; ¹H NMR (400 MHz, DMSO-d₆) δ 12.28 (s, 1H), 9.34 (s, 1H), 8.85 (s, 1H), 8.13 (dd, J=11.0, 2.4 Hz, 1H), 8.01-7.95 (m, 1H), 7.80 (dd, J=9.3, 2.7 Hz, 1H), 7.73 (t, J=8.4 Hz, 1H), 7.52-7.38 (m, 2H), 4.28 (s, 2H), 4.08-3.99 (m, 2H), 3.90-3.66 (m, 2H).

3-{1-[6-(3-oxo-morpholin-4-yl)-pyridin-3-yl]-1H-[1,2,3]triazol-4-yl}-1H-quinolin-2-one ("A34")

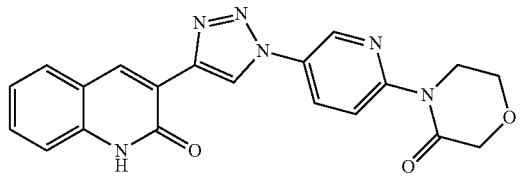 [SMILES: O=C1COCCN1c1ccc(-n2cc(-c3cc4ccccc4[nH]c3=O)nn2)cn1]

beige solid, HPLC/MS 1.41 min (A), [M+H]⁺ 389; ¹H NMR (400 MHz, DMSO-d₆) δ 12.21 (s, 1H), 9.32 (s, 1H), 9.11 (d, J=2.7 Hz, 1H), 8.86 (s, 1H), 8.50 (dd, J=9.1, 2.8 Hz, 1H), 8.31 (d, J=9.0 Hz, 1H), 7.95-7.90 (m, 1H), 7.57 (ddd, J=8.4, 7.1, 1.4 Hz, 1H), 7.42 (d, J=8.2 Hz, 1H), 7.31-7.24 (m, 1H), 4.33 (s, 2H), 4.05 (s, 4H).

3-{1-[2-methyl-4-(morpholine-4-carbonyl)-phenyl]-1H-[1,2,3]triazol-4-yl}-1H-quinolin-2-one ("A35")

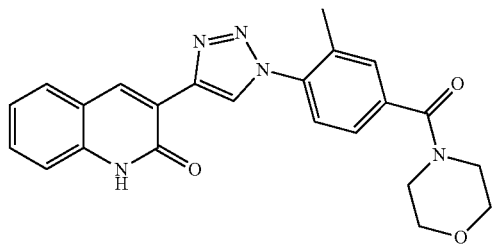 [SMILES: Cc1cc(C(=O)N2CCOCC2)ccc1-n1cc(-c2cc3ccccc3[nH]c2=O)nn1]

beige solid, HPLC/MS 1.40 min (A), [M+H]⁺ 416; ¹H NMR (300 MHz, DMSO-d₆) δ 12.16 (s, 1H), 8.92 (s, 1H), 8.84 (s, 1H), 7.89 (dd, J=8.0, 1.4 Hz, 1H), 7.61 (d, J=8.1 Hz, 1H), 7.59-7.52 (m, 2H), 7.46 (dd, J=8.1, 1.9 Hz, 1H), 7.40 (d, J=8.4 Hz, 1H), 7.26 (ddd, J=8.1, 7.2, 1.2 Hz, 1H), 3.75-3.35 (m, 8H), 2.26 (s, 3H).

3-{1-[4-(1-hydroxy-1-methyl-ethyl)-phenyl]-1H-[1,2,3]triazol-4-yl}-1H-quinolin-2-one ("A36")

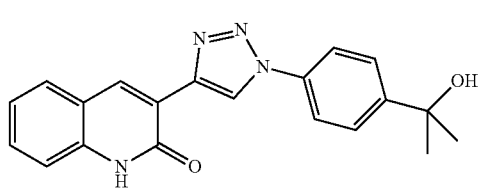 [SMILES: CC(C)(O)c1ccc(-n2cc(-c3cc4ccccc4[nH]c3=O)nn2)cc1]

light brown solid, HPLC/MS 1.47 min (A), [M+H]⁺ 347; ¹H NMR (400 MHz, DMSO-d₆) δ 12.18 (s, 1H), 9.15 (s, 1H), 8.82 (s, 1H), 7.93-7.88 (m, 3H), 7.73-7.66 (m, 2H), 7.55 (ddd, J=8.5, 7.1, 1.4 Hz, 1H), 7.41 (dd, J=8.2, 1.0 Hz, 1H), 7.25 (ddd, J=8.1, 7.2, 1.1 Hz, 1H), 5.17 (s, 1H), 1.49 (s, 6H).

3-{1-[3-fluoro-4-(morpholine-4-carbonyl)-phenyl]-1H-[1,2,3]triazol-4-yl}-1H-quinolin-2-one ("A37")

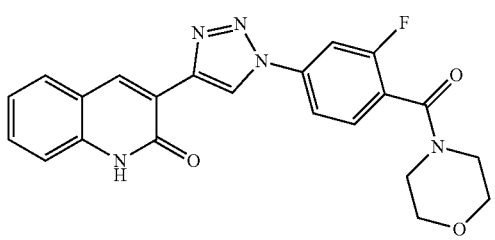 [SMILES: O=C(c1ccc(-n2cc(-c3cc4ccccc4[nH]c3=O)nn2)cc1F)N1CCOCC1]

yellow solid, HPLC/MS 1.45 min (A), [M+H]+ 420; 1H NMR (400 MHz, DMSO-d6) δ 12.22 (s, 1H), 9.35 (s, 1H), 8.86 (s, 1H), 8.12 (dd, J=10.4, 2.0 Hz, 1H), 8.02 (dd, J=8.3, 2.0 Hz, 1H), 7.92 (dd, J=8.1, 1.4 Hz, 1H), 7.68 (dd, J=8.3, 7.4 Hz, 1H), 7.58 (ddd, J=8.5, 7.1, 1.4 Hz, 1H), 7.42 (d, J=8.2 Hz, 1H), 7.27 (ddd, J=8.1, 7.1, 1.1 Hz, 1H), 3.69 (s, 4H), 3.61-3.56 (m, 2H), 3.35-3-30 (m, 2H).

3-[1-(3,4,5-trimethoxy-phenyl)-1H-[1,2,3]triazol-4-yl]-1H-quinolin-2-one ("A38")

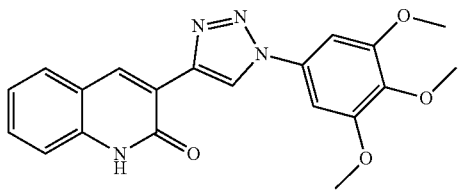 [SMILES: COc1cc(-n2cc(-c3cc4ccccc4[nH]c3=O)nn2)cc(OC)c1OC]

beige solid, HPLC/MS 1.57 min (A), [M+H]+ 379; 1H NMR (400 MHz, DMSO-d6) δ 12.18 (s, 1H), 9.27 (s, 1H), 8.83 (s, 1H), 7.91 (dd, J=8.0, 1.4 Hz, 1H), 7.56 (ddd, J=8.4, 7.1, 1.4 Hz, 1H), 7.42 (d, J=7.7 Hz, 1H), 7.31 (s, 2H), 7.26 (ddd, J=8.2, 7.2, 1.1 Hz, 1H), 3.93 (s, 6H), 3.75 (s, 3H).

2-fluoro-N-methyl-4-[4-(2-oxo-1,2-dihydro-quinolin-3-yl)-[1,2,3]triazol-1-yl]-benzamide ("A39")

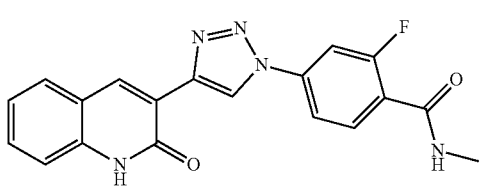 [SMILES: CNC(=O)c1ccc(-n2cc(-c3cc4ccccc4[nH]c3=O)nn2)cc1F]

beige solid, HPLC/MS 1.42 min (A), [M+H]+ 364; 1H NMR (500 MHz, DMSO-d6) δ 12.23 (s, 1H), 9.36 (s, 1H), 8.86 (s, 1H), 8.42-8.35 (m, 1H), 8.11 (dd, J=11.3, 2.1 Hz, 1H), 8.00 (dd, J=8.4, 2.1 Hz, 1H), 7.92 (dd, J=8.0, 1.3 Hz, 1H), 7.86 (t, J=8.1 Hz, 1H), 7.57 (ddd, J=8.4, 7.1, 1.4 Hz, 1H), 7.42 (d, J=8.2 Hz, 1H), 7.33-7.23 (m, 1H), 2.83 (d, J=4.6 Hz, 3H).

3-{1-[3-methyl-4-(morpholine-4-carbonyl)-phenyl]-1H-[1,2,3]triazol-4-yl}-1H-quinolin-2-one ("A40")

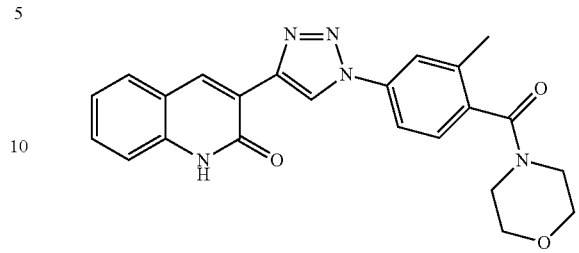

yellow powder, HPLC/MS 1.43 min (A), [M+H]+ 416; 1H NMR (400 MHz, DMSO-d6) δ 12.21 (s, 1H), 9.25 (s, 1H), 8.85 (s, 1H), 8.00 (d, J=2.5 Hz, 1H), 7.93-7.89 (m, 2H), 7.57 (ddd, J=8.5, 7.1, 1.4 Hz, 1H), 7.46-7.40 (m, 2H), 7.27 (ddd, J=8.1, 7.2, 1.1 Hz, 1H), 3.70 (s, 4H), 3.55 (s, 2H), 3.21 (s, 2H), 2.37 (s, 3H).

EXAMPLE 2

3-{1-[4-(morpholine-4-carbonyl)-phenyl]-1H-[1,2,3]triazol-4-yl}-1H-[1,6]naphthyridin-2-one ("A41")

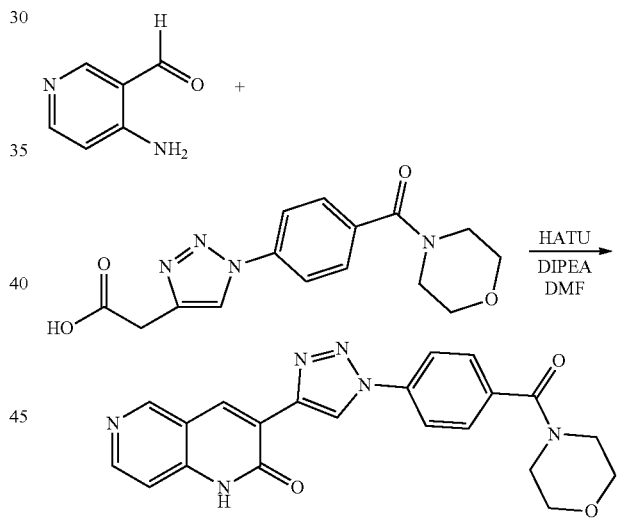

To a solution of 4-Amino-pyridine-3-carbaldehyde (61.1 mg, 0.50 mmol), {1-[4-(morpholine-4-carbonyl)-phenyl]-1H-[1,2,3]triazol-4-yl}-acetic acid (158 mg, 0.50 mmol) and [dimethylamino-([1,2,3]triazolo[4,5-b]pyridin-3-yloxy)-methylene]-dimethyl-ammonium hexafluorophosphate (HATU; 380 mg, 1.0 mmol) in DMF (1.3 ml) is added N-ethyldiisopropylamine (257 µl, 1.5 mmol) and the reaction mixture is stirred for 17 hours at room temperature. Water is added to the reaction mixture. The resultant precipitate is filtered off, dried and chromatographed on a silica gel column with dichloromethane/methanol as eluent to afford 3-{1-[4-(morpholine-4-carbonyl)-phenyl]-1H-[1,2,3]triazol-4-yl}-1H-[1,6]naphthyridin-2-one as beige solid; HPLC/MS 1.02 min (A), [M+H]+ 403. 1H NMR (400 MHz, DMSO-d6) δ 12.46 (s, 1H), 9.28 (s, 1H), 9.10 (s, 1H), 8.93 (s, 1H), 8.52 (d, J=5.7 Hz, 1H), 8.11 (d, J=8.6 Hz, 1H), 7.67 (d, J=8.6 Hz, 2H), 7.30 (d, J=5.7 Hz, 1H), 3.35-3.75 (m, 8H).

The following compounds are prepared similarly:

N,N-dimethyl-4-[4-(2-oxo-1,2-dihydro-[1,7]naphthyridin-3-yl)-[1,2,3]triazol-1-yl]-benzamide ("A42")

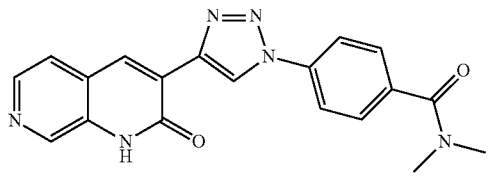 [SMILES: CN(C)C(=O)c1ccc(-n2cc(-c3cc4ccncc4[nH]c3=O)nn2)cc1]

brown powder, MS-ESI: [M+H]+ 361.

3-(1-phenyl-1H-pyrazol-4-yl)-1H-[1,8]naphthyridin-2-one ("A43")

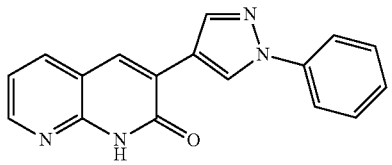 [SMILES: O=c1[nH]c2ncccc2cc1-c1cnn(-c2ccccc2)c1]

brown powder, HPLC/MS 1.34 min (B), [M+H]+ 289; H NMR (400 MHz, DMSO-$d_6$) δ 12.40 (s, 1H), 9.12 (s, 1H), 8.51 (dd, J=4.7, 1.7 Hz, 1H), 8.44 (s, 1H), 8.42 (s, 1H), 8.11 (dd, J=7.8, 1.8 Hz, 1H), 7.96-7.82 (m, 2H), 7.63-7.50 (m, 2H), 7.40-7.33 (m, 1H), 7.29 (dd, J=7.7, 4.7 Hz, 1H).

3-(1-phenyl-1H-pyrazol-4-yl)-1H-[1,7]naphthyridin-2-one ("A44")

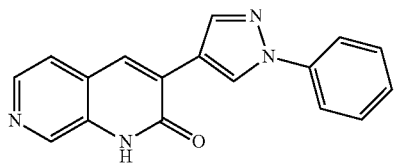 [SMILES: O=c1[nH]c2cnccc2cc1-c1cnn(-c2ccccc2)c1]

brown powder, HPLC/MS 1.21 min (B), [M+H]+ 289; $^1$H NMR (400 MHz, DMSO-$d_6$) δ 12.27 (s, 1H), 9.19 (s, 1H), 8.69 (s, 1H), 8.50 (s, 1H), 8.44 (s, 1H), 8.35 (d, J=5.2 Hz, 1H), 7.97-7.80 (m, 2H), 7.60 (d, J=5.0 Hz, 1H), 7.58-7.50 (m, 2H), 7.42-7.26 (m, 1H).

3-[1-(4-fluoro-phenyl)-1H-[1,2,3]triazol-4-yl]-1H-[1,6]naphthyridin-2-one ("A45")

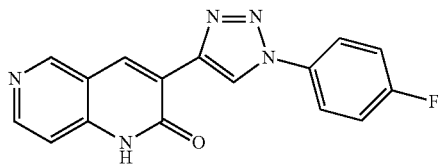 [SMILES: O=c1[nH]c2ccncc2cc1-c1cn(-c2ccc(F)cc2)nn1]

brown solid, HPLC/MS 1.09 min (B), [M+H]+ 308; $^1$H NMR (500 MHz, DMSO-$d_6$, TFA-$d_1$) δ 9.44 (s, 1H), 9.17 (s, 1H), 9.07 (s, 1H), 8.61 (d, J=6.7 Hz, 1H), 8.02-7.92 (m, 2H), 7.70 (d, J=6.7 Hz, 1H), 7.31 (t, J=8.7 Hz, 2H).

3-(1-phenyl-1H-pyrazol-4-yl)-1H-[1,6]naphthyridin-2-one ("A46")

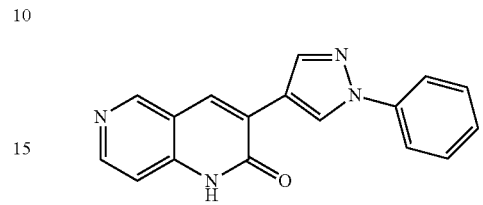

beige powder, HPLC/MS 1.06 min (B), [M+H]+ 289; $^1$H NMR (400 MHz, DMSO-$d_6$) δ 12.27 (s, 1H), 9.11 (s, 1H), 8.86 (d, J=0.7 Hz, 1H), 8.50 (s, 1H), 8.46 (d, J=5.5 Hz, 2H), 7.91-7.85 (m, 2H), 7.57-7.50 (m, 2H), 7.39-7.32 (m, 1H), 7.25 (d, J=5.7 Hz, 1H).

3-{1-[4-(morpholine-4-carbonyl)-phenyl]-1H-[1,2,3]triazol-4-yl}-1H-[1,8]naphthyridin-2-one "A47")

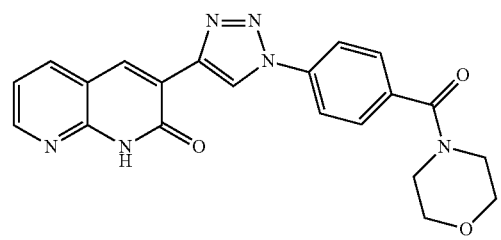 [SMILES: O=C(c1ccc(-n2cc(-c3cc4cccnc4[nH]c3=O)nn2)cc1)N1CCOCC1]

beige solid, HPLC/MS 1.27 min (A), [M+H]+ 403; $^1$H NMR (400 MHz, DMSO-$d_6$) δ 12.58 (s, 1H), 9.28 (s, 1H), 8.87 (s, 1H), 8.59 (dd, J=4.7, 1.8 Hz, 1H), 8.38 (dd, J=7.8, 1.8 Hz, 1H), 8.11 (d, J=8.6 Hz, 2H), 7.78-7.60 (m, 2H), 7.34 (dd, J=7.8, 4.7 Hz, 1H), 3.76-3.36 (m, 8H).

5-fluoro-3-{1-[4-(morpholine-4-carbonyl)-phenyl]-1H-[1,2,3]triazol-4-yl}-1H-quinolin-2-one ("A48")

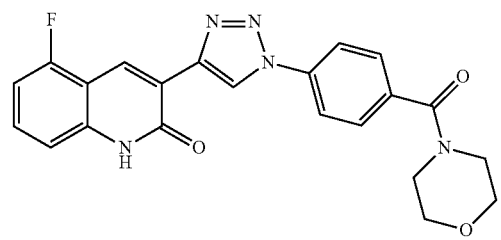 [SMILES: O=C(c1ccc(-n2cc(-c3cc4c(F)cccc4[nH]c3=O)nn2)cc1)N1CCOCC1]

beige solid, HPLC/MS 1.45 min (A), [M+H]+ 420; 1H NMR (400 MHz, DMSO-$d_6$) δ 12.44 (s, 1H), 9.28 (s, 1H), 8.82 (s, 1H), 8.10 (d, J=8.6 Hz, 2H), 7.66 (d, J=8.6 Hz, 2H), 7.57 (td, J=8.2, 6.0 Hz, 1H), 7.24 (d, J=8.4 Hz, 1H), 7.18-7.05 (m, 1H), 3.75-3.35 (m, 8H).

3-{1-[4-(3-oxo-morpholin-4-yl)-phenyl]-1H-[1,2,3]triazol-4-yl}-1H-[1,7]naphthyridin-2-one ("A49")

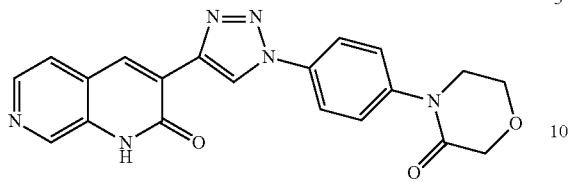

beige solid, HPLC/MS 1.45 min (A), [M+H]+ 420; 1H NMR (400 MHz, DMSO-d$_6$) δ 12.44 (s, 1H), 9.28 (s, 1H), 8.82 (s, 1H), 8.10 (d, J=8.6 Hz, 2H), 7.66 (d, J=8.6 Hz, 2H), 7.57 (td, J=8.2, 6.0 Hz, 1H), 7.24 (d, J=8.4 Hz, 1H), 7.18-7.05 (m, 1H), 3.75-3.35 (m, 8H).

EXAMPLE 3

3-{1-[4-(piperazine-1-carbonyl)-phenyl]-1H-[1,2,3]triazol-4-yl}-1H-quinolin-2-one ("A50")

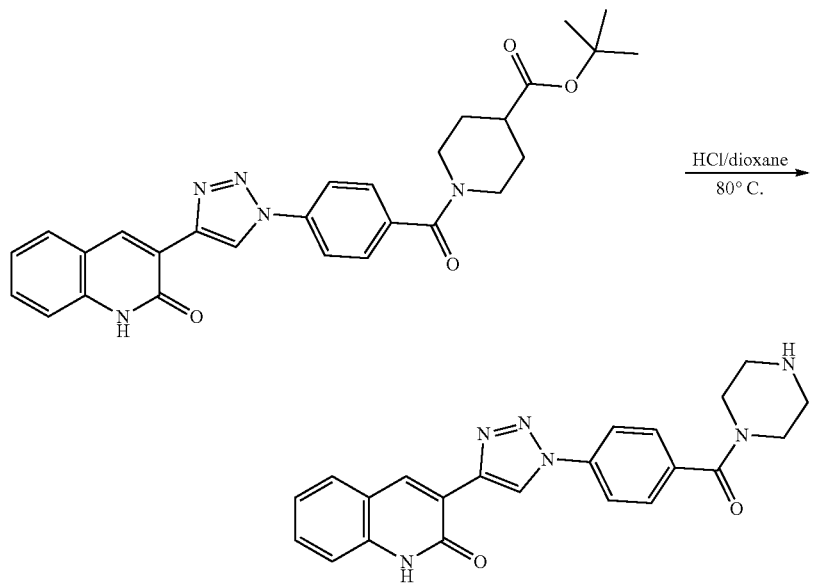

A suspension of 4-{4-[4-(2-oxo-1,2-dihydro-quinolin-3-yl)-[1,2,3]triazol-1-yl]-benzoyl}-piperazine-1-carboxylic acid tert-butyl ester (43 mg, 0.09 mmol; synthesized in analogy to example 1) in a 4 M solution of hydrochloric acid in dioxane (0.5 ml) is heated to 80° C. and stirred at this temperature in a closed reaction vial for 1 hour. The reaction mixture is allowed to reach room temperature. The solids are filtered off and washed with THF. The residue is treated with aqueous sodium carbonate solution. The solid is filtered off, washed with water and ethanol and dried under vacuum to afford 3-{1-[4-(piperazine-1-carbonyl)-phenyl]-1H-[1,2,3]triazol-4-yl}-1H-quinolin-2-one as light grey powder; HPLC/MS 1.07 min (B), [M+H]+ 401.

1H NMR (400 MHz, DMSO-d$_6$) δ 12.21 (s, 1H), 9.26 (s, 1H), 8.84 (s, 1H), 8.08 (d, J=8.0 Hz, 2H), 7.90 (d, J=7.9 Hz, 1H), 7.61 (d, J=8.0 Hz, 2H), 7.56 (t, J=7.6 Hz, 1H), 7.41 (d, J=8.3 Hz, 1H), 7.26 (t, J=7.5 Hz, 1H), 3.65-3.35 (m, 4H), 2.8-2.6 (m, 4H).

The following compounds are prepared similarly:

4-[4-(2-oxo-1,2-dihydro-[1,8]naphthyridin-3-yl)-[1,2,3]triazol-1-yl]-N-piperidin-4-yl-benzamide ("A51")

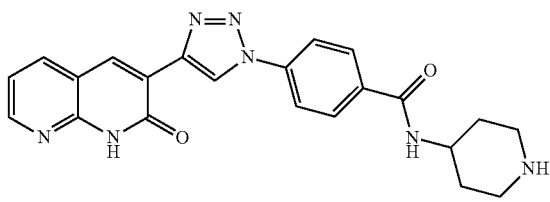 [SMILES: O=C(NC1CCNCC1)c1ccc(-n2cc(-c3cc4cccnc4[nH]c3=O)nn2)cc1]

trifluoroacetate: 1H NMR (400 MHz, DMSO-d$_6$) δ 12.62 (br s, 1H), 9.33 (br s, 1H), 8.87 (br s, 1H), 8.64-8.58 (m, 3H), 8.34 (m, 2H), 8.17 (d, 2H), 8.10 (d, 2H), 7.34 (br s, 1H), 4.09 (br s, 1H), 3.06 (m, 2H), 2.02 (d, 2H), 1.78-1.70 (m, 2H), 3-[1-(4-piperazin-1-yl-phenyl)-1H-[1,2,3]triazol-4-yl]-1H-quinolin-2-one ("A52")

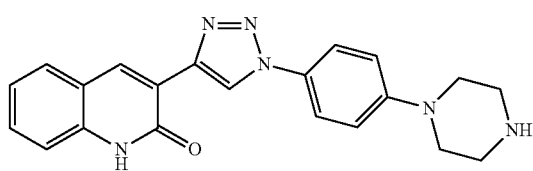 [SMILES: O=c1[nH]c2ccccc2cc1-c1cn(-c2ccc(N3CCNCC3)cc2)nn1]

light brown crystals; HPLC/MS 1.10 min (B), [M+H]+ 373; 1H NMR (500 MHz, DMSO-d$_6$, TFA-d$_1$) δ 9.11 (s, 1H), 8.83 (s, 1H), 7.91-7.86 (m, 3H), 7.55 (ddd, J=8.5, 7.1, 1.4

Hz, 1H), 7.45 (d, J=8.2 Hz, 1H), 7.28-7.19 (m, 3H), 3.53-3.49 (m, 4H), 3.34-3.30 (m, 4H).

6-fluoro-3-{1-[4-(piperazine-1-carbonyl)-phenyl]-1H-[1,2,3]triazol-4-yl}-1H-quinolin-2-one ("A53")

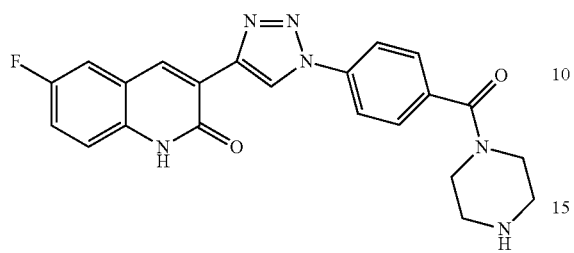

hydrochloride: light brown solid; HPLC/MS 1.07 min (B), [M+H]+ 419; 1H NMR (500 MHz, DMSO-d6) δ 12.30 (s, 1H), 9.31 (s, 1H), 9.22 (bs, 2H), 8.86 (s, 1H), 8.13 (d, J=8.6 Hz, 2H), 7.81 (dd, J=9.2, 2.7 Hz, 1H), 7.72 (d, J=8.6 Hz, 2H), 7.51-7.38 (m, 2H), 3.72 (bs, 4H), 3.20 (bs, 4H).

3-[1-(2-piperazin-1-yl-pyrimidin-5-yl)-1H-[1,2,3]triazol-4-yl]-1H-quinolin-2-one ("A54")

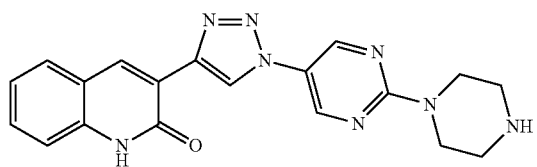 [SMILES: O=c1[nH]c2ccccc2cc1-c1cn(-c2cnc(N3CCNCC3)nc2)nn1]

hydrochloride: brown solid; HPLC/MS 1.14 min (A), [M+H]+ 375; 1H NMR (400 MHz, DMSO-d6) δ 12.20 (s, 1H), 9.18 (m, 3H), 8.99 (s, 2H), 8.82 (s, 1H), 7.90 (d, J=7.8 Hz, 1H), 7.56 (ddd, J=8.4, 7.1, 1.4 Hz, 1H), 7.41 (d, J=8.2 Hz, 1H), 7.30-7.21 (m, 1H), 4.06 (t, J=5.3 Hz, 4H), 3.26-3.19 (m, 4H).

3-[1-(4-[1,4]diazepan-1-yl-phenyl)-1H-[1,2,3]triazol-4-yl]-1H-quinolin-2-one ("A55")

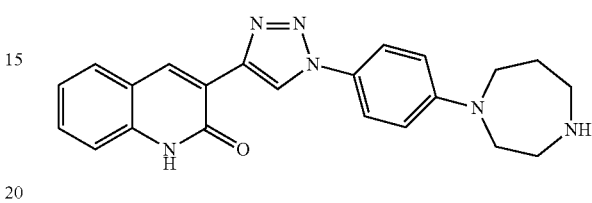

brown solid; HPLC/MS 1.22 min (A), [M+H]+ 387; 1H NMR (500 MHz, DMSO-d6) δ 12.13 (s, 1H), 8.95 (s, 1H), 8.79 (s, 1H), 7.88 (dd, J=8.0, 1.4 Hz, 1H), 7.68 (d, J=9.1 Hz, 2H), 7.54 (ddd, J=8.5, 7.2, 1.4 Hz, 1H), 7.40 (dd, J=8.2, 1.0 Hz, 1H), 7.24 (ddd, J=8.1, 7.2, 1.1 Hz, 1H), 6.85 (d, J=9.1 Hz, 2H), 3.60 (t, J=6.1 Hz, 2H), 3.52 (t, J=5.3 Hz, 2H), 2.95-2.85 (m, 2H), 2.70-2.61 (m, 2H), 1.80 (p, J=6.1 Hz, 2H).

EXAMPLE 4

6-fluoro-3-{1-[4-(4-methyl-piperazine-1-carbonyl)-phenyl]-1H-[1,2,3]triazol-4-yl}-1H-quinolin-2-one ("A56")

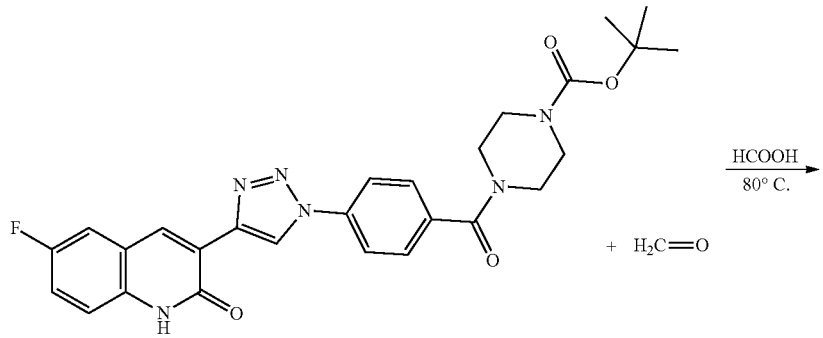

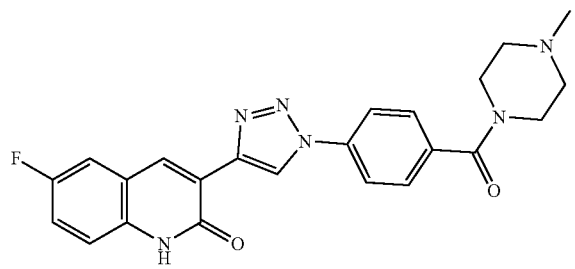

To a solution of 4-{4-[4-(6-fluoro-2-oxo-1,2-dihydro-quinolin-3-yl)-[1,2,3]triazol-1-yl]-benzoyl}-piperazine-1-carboxylic acid tert-butyl ester (52 mg, 0.10 mmol; prepared in analogy to example 1) in formic acid (0.5 ml) is added formaldehyde (37% aqueous solution, 22.5 μl, 0.30 mmol) and the reaction mixture is stirred for 1 hour at 80° C. The reaction mixture is evaporated and the residue is purified by preparative HPLC to afford 6-fluoro-3-{1-[4-(4-methyl-piperazine-1-carbonyl)-phenyl]-1H-[1,2,3]triazol-4-yl}-1H-quinolin-2-one as white powder; HPLC/MS 1.07 min (B), [M+H]+ 433.

$^1$H NMR (500 MHz, DMSO-d$_6$) δ 12.28 (s, 1H), 9.29 (s, 1H), 8.86 (s, 1H), 8.10 (d, J=8.5 Hz, 2H), 7.81 (dd, J=9.2, 2.7 Hz, 1H), 7.66-7.60 (m, 2H), 7.50-7.40 (m, 2H), 3.78-3.50 (m, 4H), 2.47-2.26 (m, 4H), 2.22 (s, 3H).

The following compounds are prepared similarly:

3-{1-[4-(4-methyl-piperazine-1-carbonyl)-phenyl]-1H-[1,2,3]triazol-4-yl}-1H-quinolin-2-one ("A57")

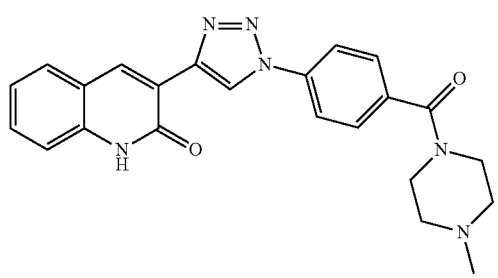 [SMILES: CN1CCN(C(=O)c2ccc(-n3cc(-c4cc5ccccc5[nH]c4=O)nn3)cc2)CC1]

white powder; HPLC/MS 1.08 min (B), [M+H]+ 415; $^1$H NMR (400 MHz, DMSO-d$_6$) δ 12.20 (s, 1H), 9.89 (s, 1H), 9.28 (s, 1H), 8.84 (s, 1H), 8.28-8.07 (m, 2H), 7.90 (d, J=7.3 Hz, 1H), 7.72-7.68 (m, 2H), 7.56 (ddd, J=8.5, 7.1, 1.4 Hz, 1H), 7.41 (d, J=8.2 Hz, 1H), 7.26 (ddd, J=8.1, 7.2, 1.1 Hz, 1H), 3.7-3.0 (m, 8H), 2.81 (s, 3H).

N-(1-Methyl-piperidin-4-yl)-4-[4-(2-oxo-1,2-dihydro-quinolin-3-yl)-[1,2,3]triazol-1-yl]-benzamide ("A58")

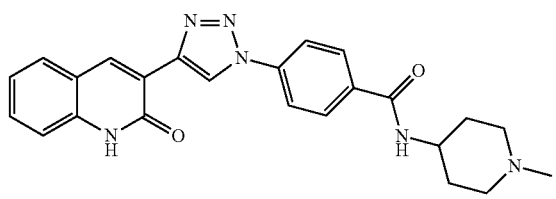 [SMILES: CN1CCC(NC(=O)c2ccc(-n3cc(-c4cc5ccccc5[nH]c4=O)nn3)cc2)CC1]

formate: white solid; HPLC/MS 1.10 min (B), [M+H]+ 429; $^1$H NMR (500 MHz, DMSO-d$_6$) δ 12.22 (s, 1H), 9.30 (s, 1H), 8.86 (s, 1H), 8.43 (d, J=7.7 Hz, 1H), 8.20 (s, 2H), 8.14 (d, J=8.7 Hz, 2H), 8.11-8.07 (m, 2H), 7.92 (dd, J=8.0, 1.3 Hz, 1H), 7.57 (ddd, J=8.4, 7.1, 1.4 Hz, 1H), 7.42 (d, J=8.3 Hz, 1H), 7.27 (td, J=7.6, 1.1 Hz, 1H), 3.79 (tdt, J=11.7, 8.3, 4.4 Hz, 1H), 2.87-2.78 (m, 2H), 2.21 (s, 3H), 2.02 (td, J=11.8, 2.5 Hz, 2H), 1.88-1.77 (m, 2H), 1.63 (qd, J=12.1, 3.8 Hz, 2H).

N-methyl-N-(1-methyl-piperidin-4-yl)-4-[4-(2-oxo-1,2-dihydro-quinolin-3-yl)-[1,2,3]triazol-1-yl]-benzamide ("A59")

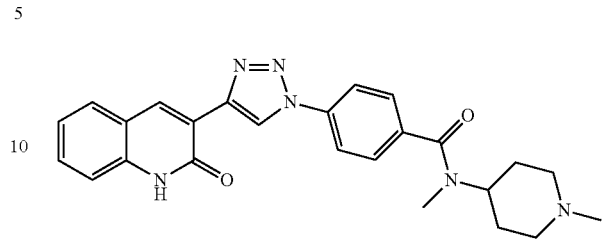

beige solid; HPLC/MS 1.09 min (B), [M+H]+ 443; $^1$H NMR (400 MHz, DMSO-d$_6$) δ 12.20 (s, 1H), 9.26 (s, 1H), 8.84 (s, 1H), 8.12-8.04 (m, 2H), 7.90 (dd, J=8.0, 1.4 Hz, 1H), 7.60 (d, J=8.2 Hz, 2H), 7.56 (ddd, J=8.5, 7.1, 1.4 Hz, 1H), 7.41 (d, J=8.2 Hz, 1H), 7.32-7.22 (m, 1H), 4.4-4.2 (m, 1H), 2.85 (s, 6H), 2.25-2.05 (m, 4H), 1.90-1.78 (m, 2H), 1.67-1.58 (m, 2H).

3-{1-[4-(1-methyl-piperidin-4-ylmethoxy)-phenyl]-1H-[1,2,3]triazol-4-yl}-1H-quinolin-2-one ("A60")

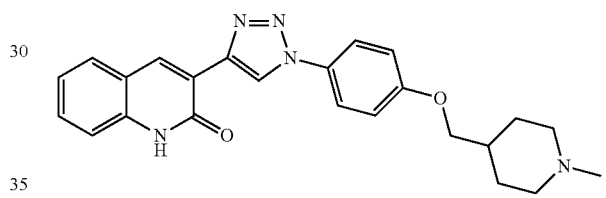

white solid; HPLC/MS 1.12 min (B), [M+H]+ 416; $^1$H NMR (400 MHz, DMSO-d$_6$) δ 12.16 (s, 1H), 9.08 (s, 1H), 8.81 (s, 1H), 7.91-7.84 (m, 3H), 7.55 (ddd, J=8.5, 7.1, 1.4 Hz, 1H), 7.40 (d, J=8.2 Hz, 1H), 7.33-7.22 (m, 1H), 7.19-7.07 (m, 2H), 3.92 (d, J=6.0 Hz, 2H), 2.82-2.76 (m, 2H), 2.17 (s, 3H), 1.92-1.84 (m, 2H), 1.81-1.70 (m, 3H), 1.45-1.26 (m, 2H).

3-{1-[4-(4-dimethylamino-piperidine-1-carbonyl)-phenyl]-1H-[1,2,3]triazol-4-yl}-1H-quinolin-2-one ("A61")

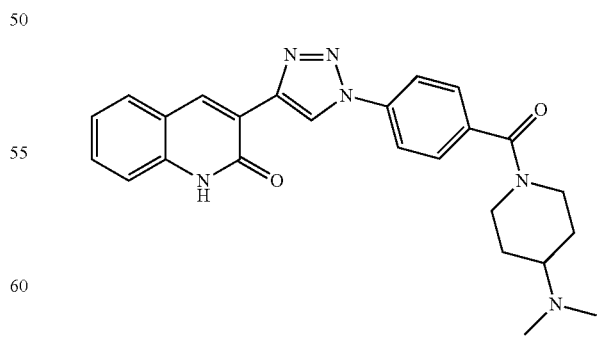

light yellow solid; HPLC/MS 1.06 min (B), [M+H]+ 443; $^1$H NMR (400 MHz, DMSO-d$_6$) δ 12.19 (s, 1H), 9.25 (s, 1H), 8.84 (s, 1H), 8.11-8.03 (m, 2H), 7.90 (dd, J=8.0, 1.4 Hz, 1H), 7.66-7.60 (m, 2H), 7.56 (ddd, J=8.5, 7.2, 1.4 Hz, 1H), 7.41 (d, J=8.3 Hz, 1H), 7.26 (ddd, J=8.1, 7.1, 1.1 Hz, 1H), 4.45 (bs, 1H), 3.64 (bs, 1H), 3.06 (bs, 1H), 2.89 (bs, 1H), 2.36 (tt, J=11.0, 3.6 Hz, 1H), 2.19 (s, 6H), 1.90-1.65 (m, 2H), 1.45-1.30 (m, 2H).

3-{1-[4-(4-methyl-piperazine-1-carbonyl)-phenyl]-1H-[1,2,3]triazol-4-yl}-1H-[1,6]naphthyridin-2-one ("A62")

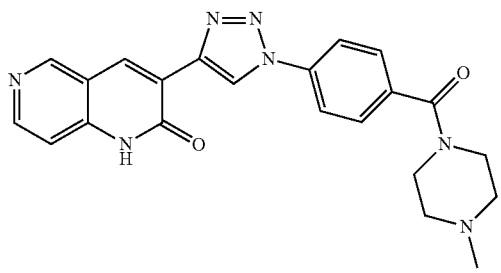 [SMILES: CN1CCN(C(=O)c2ccc(-n3cc(-c4cc5cnccc5[nH]c4=O)nn3)cc2)CC1]

white solid; HPLC/MS 0.87 min (A), [M+H]$^+$ 416; $^1$H NMR (400 MHz, DMSO-d$_6$) δ 12.48 (s, 1H), 9.27 (s, 1H), 9.09 (bs, 1H), 8.92 (s, 1H), 8.52 (bs, 1H), 8.15-8.04 (m, 2H), 7.70-7.56 (m, 2H), 7.29 (d, J=5.6 Hz, 1H), 3.72-3.54 (m, 4H), 2.44-2.26 (m, 4H), 2.21 (s, 3H).

3-{1-[4-(4-methyl-piperazine-1-carbonyl)-phenyl]-1H-[1,2,3]triazol-4-yl}-1H-[1,7]naphthyridin-2-one ("A63")

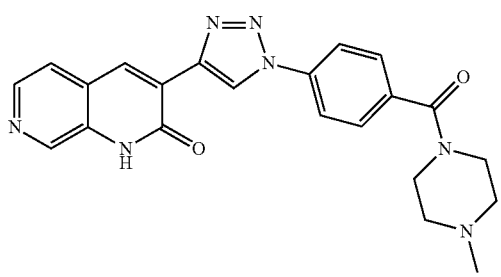 [SMILES: CN1CCN(C(=O)c2ccc(-n3cc(-c4cc5ccncc5[nH]c4=O)nn3)cc2)CC1]

light brown solid; HPLC/MS 0.98 min (A), [M+H]$^+$ 416; $^1$H NMR (300 MHz, DMSO-d$_6$) δ 12.47 (bs, 1H), 9.34 (s, 1H), 8.86 (s, 1H), 8.75 (s, 1H), 8.39 (d, J=5.2 Hz, 1H), 8.10 (d, J=8.6 Hz, 1H), 7.86 (d, J=5.2 Hz, 1H), 7.63 (d, J=8.6 Hz, 1H), 3.5-3.2 (m, 4H), 2.42-2.29 (m, 4H), 2.21 (s, 3H).

3-{1-[4-(4-methyl-piperazine-1-carbonyl)-phenyl]-1H-[1,2,3]triazol-4-yl}-1H-[1,8]naphthyridin-2-one ("A64")

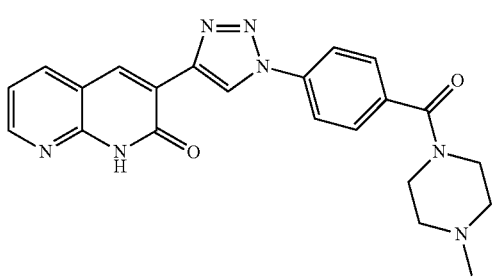

beige solid; HPLC/MS 1.06 min (A), [M+H]$^+$ 416; $^1$H NMR (400 MHz, DMSO-d$_6$) δ 12.59 (s, 1H), 9.28 (s, 1H), 8.87 (s, 1H), 8.59 (dd, J=4.7, 1.8 Hz, 1H), 8.38 (dd, J=7.9, 1.8 Hz, 1H), 8.10 (d, J=8.5 Hz, 1H), 7.64 (d, J=8.5 Hz, 1H), 7.34 (dd, J=7.7, 4.7 Hz, 1H), 3.7-3.3 (m, 4H), 2.45-2.25 (m, 4H), 2.23 (s, 3H).

7-methyl-3-{1-[4-(4-methyl-piperazine-1-carbonyl)-phenyl]-1H-[1,2,3]triazol-4-yl}-1H-[1,8]naphthyridin-2-one ("A65")

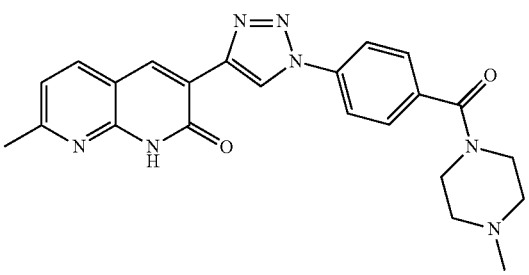 [SMILES: Cc1ccc2cc(-c3cn(-c4ccc(C(=O)N5CCN(C)CC5)cc4)nn3)c(=O)[nH]c2n1]

light yellow solid; HPLC/MS 1.11 min (A), [M+H]$^+$ 430.

3-{1-[2-(4-methyl-piperazin-1-yl)-pyrimidin-5-yl]-1H-[1,2,3]triazol-4-yl}-1H-quinolin-2-one ("A66")

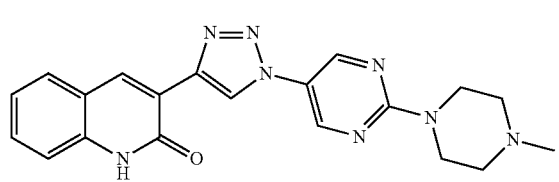 [SMILES: CN1CCN(c2ncc(-n3cc(-c4cc5ccccc5[nH]c4=O)nn3)cn2)CC1]

beige solid; HPLC/MS 1.16 min (A), [M+H]$^+$ 389; $^1$H NMR (400 MHz, DMSO-d$_6$) δ 12.17 (s, 1H), 9.12 (s, 1H), 8.88 (s, 2H), 8.81 (s, 1H), 7.89 (dd, J=8.1, 1.3 Hz, 1H), 7.55 (ddd, J=8.4, 7.1, 1.4 Hz, 1H), 7.40 (d, J=8.3 Hz, 1H), 7.28-7.23 (m, 1H), 3.88-3.77 (m, 4H), 2.45-2.35 (m, 4H), 2.24 (s, 3H).

6-fluoro-3-{1-[4-(4-methyl-piperazine-1-carbonyl)-phenyl]-1H-[1,2,3]triazol-4-yl}-1H-[1,8]naphthyridin-2-one ("A67")

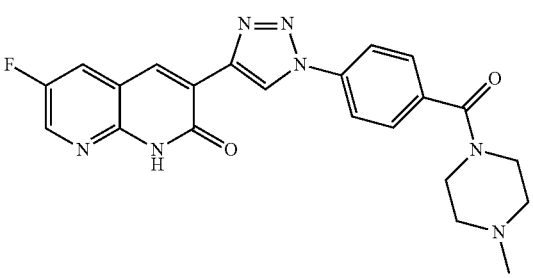 [SMILES: CN1CCN(C(=O)c2ccc(-n3cc(-c4cc5cc(F)cnc5[nH]c4=O)nn3)cc2)CC1]

white solid; HPLC/MS 1.09 min (A), [M+H]$^+$ 434; $^1$H NMR (400 MHz, DMSO-d$_6$) δ 12.73 (s, 1H), 9.30 (s, 1H), 8.87 (s, 1H), 8.61 (d, J=2.9 Hz, 1H), 8.35 (dd, J=8.7, 2.9 Hz,

3-{1-[4-(4-methyl-2-oxo-piperazin-1-yl)-phenyl]-1H-[1,2,3]triazol-4-yl}-1H-quinolin-2-one ("A68")

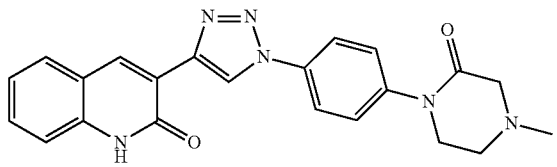 [SMILES: CN1CCN(c2ccc(-n3cc(-c4cc5ccccc5[nH]c4=O)nn3)cc2)C(=O)C1]

white solid; HPLC/MS 1.19 min (A), [M+H]+ 401; $^1$H NMR (400 MHz, DMSO-d$_6$) δ 12.18 (s, 1H), 9.21 (s, 1H), 8.83 (s, 1H), 8.02 (d, J=8.9 Hz, 2H), 7.90 (dd, J=8.1, 1.4 Hz, 1H), 7.67-7.58 (m, 2H), 7.55 (ddd, J=8.5, 7.1, 1.4 Hz, 1H), 7.41 (d, J=8.2 Hz, 1H), 7.25 (td, J=7.5, 1.1 Hz, 1H), 3.76-3.72 (m, 2H), 3.16 (s, 2H), 2.84-2.70 (m, 2H), 2.31 (s, 3H).

3-{1-[4-(4-methyl-[1,4]diazepan-1-yl)-phenyl]-1H-[1,2,3]triazol-4-yl}-1H-quinolin-2-one ("A69")

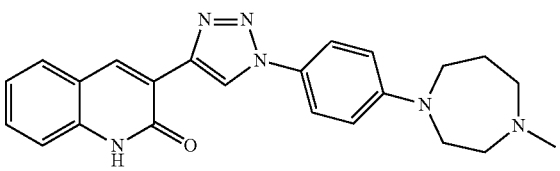 [SMILES: CN1CCCN(c2ccc(-n3cc(-c4cc5ccccc5[nH]c4=O)nn3)cc2)CC1]

beige solid; HPLC/MS 1.23 min (A), [M+H]+ 401; $^1$H NMR (400 MHz, DMSO-d$_6$) δ 12.15 (s, 1H), 8.97 (s, 1H), 8.77 (s, 1H), 7.86 (dd, J=8.0, 1.4 Hz, 1H), 7.68 (d, J=9.1 Hz, 2H), 7.52 (ddd, J=8.5, 7.1, 1.4 Hz, 1H), 7.39 (d, J=8.2 Hz, 1H), 7.22 (ddd, J=8.1, 7.1, 1.2 Hz, 1H), 6.85 (d, J=9.2 Hz, 2H), 3.65-3.55 (m, 2H), 3.50 (t, J=6.2 Hz, 2H), 2.70-2.58 (m, 2H), 2.49-2.45 (m, 2H), 2.27 (s, 3H), 1.92 (p, J=5.9 Hz, 2H).

6-fluoro-3-{1-[4-(4-methyl-piperazin-1-yl)-phenyl]-1H-[1,2,3]triazol-4-yl}-1H-quinolin-2-one ("A70")

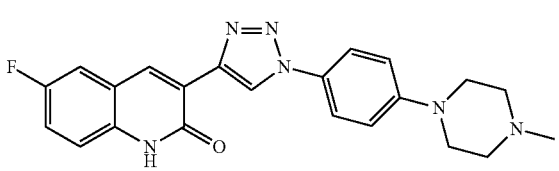 [SMILES: CN1CCN(c2ccc(-n3cc(-c4cc5cc(F)ccc5[nH]c4=O)nn3)cc2)CC1]

off-white solid; HPLC/MS 1.24 min (A), [M+H]+ 405; $^1$H NMR (500 MHz, DMSO-d$_6$) δ 12.23 (s, 1H), 9.05 (s, 1H), 8.81 (s, 1H), 7.92-7.66 (m, 3H), 7.49-7.37 (m, 2H), 7.11 (d, J=9.2 Hz, 2H), 3.24 (t, J=5.0 Hz, 4H), 2.47 (t, J=5.0 Hz, 4H), 2.24 (s, 3H).

6-fluoro-3-{1-[4-(4-methyl-2-oxo-piperazin-1-yl)-phenyl]-1H-[1,2,3]triazol-4-yl}-1H-quinolin-2-one ("A71")

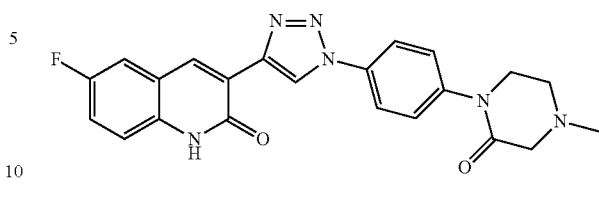

beige solid; HPLC/MS 1.19 min (A), [M+H]+ 419; $^1$H NMR (500 MHz, DMSO-d$_6$) δ 12.26 (s, 1H), 9.23 (s, 1H), 8.84 (s, 1H), 8.03 (d, J=8.9 Hz, 2H), 7.80 (dd, J=9.2, 2.6 Hz, 1H), 7.60 (d, J=8.9 Hz, 2H), 7.48-7.40 (m, 2H), 3.74 (t, J=5.3 Hz, 2H), 3.16 (s, 2H), 2.76 (t, J=5.4 Hz, 2H), 2.31 (s, 3H).

3-(1-{4-[2-(4-methyl-piperazin-1-yl)-ethoxy]-phenyl}-1H-[1,2,3]triazol-4-yl)-1H-quinolin-2-one ("A72")

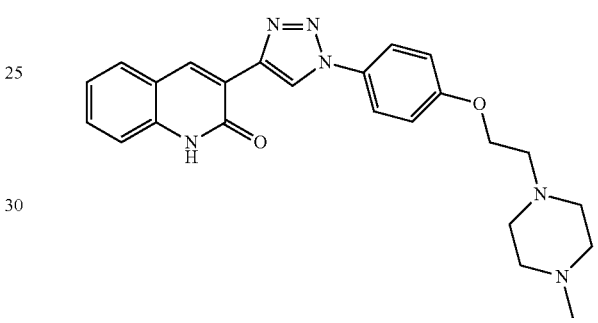

white solid; HPLC/MS 1.20 min (A), [M+H]+ 431; $^1$H NMR (400 MHz, DMSO-d$_6$) δ 12.16 (s, 1H), 9.08 (s, 1H), 8.81 (s, 1H), 7.92-7.85 (m, 3H), 7.55 (ddd, J=8.4, 7.1, 1.4 Hz, 1H), 7.40 (d, J=8.1 Hz, 1H), 7.25 (ddd, J=8.1, 7.1, 1.1 Hz, 1H), 7.20-7.12 (m, 2H), 4.16 (t, J=5.8 Hz, 2H), 2.72 (t, J=5.8 Hz, 2H), 2.54-2.50 (m, 4H), 2.33 (bs, 4H), 2.15 (s, 3H).

EXAMPLE 5

3-{1-[4-(piperazine-1-carbonyl)-phenyl]-1H-pyrazol-4-yl}-1H-quinolin-2-one ("A73") and 3-{1-[4-(4-methyl-piperazine-1-carbonyl)-phenyl]-1H-pyrazol-4-yl}-1H-quinolin-2-one ("A74")

a) Synthesis of 4-{4-[4-(4,4,5,5-tetramethyl-[1,3,2]dioxaborolan-2-yl)-pyrazol-1-yl]-benzoyl}-piperazine-1-carboxylic Acid Tert-Butyl Ester

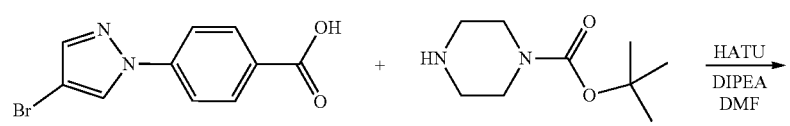

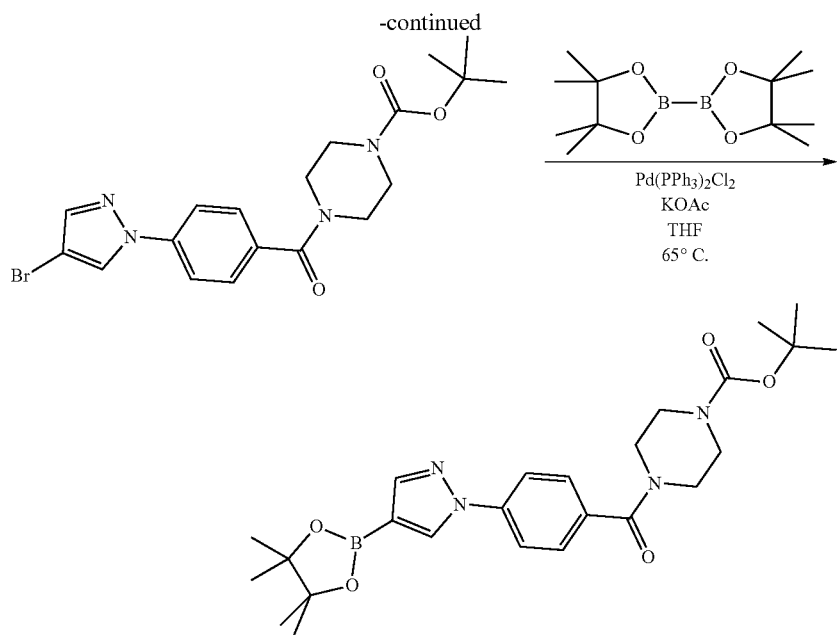
b) Suzuki Reaction—Synthesis of 4-{4-[4-(2-oxo-1,2-dihydro-quinolin-3-yl)-pyrazol-1-yl]-benzoyl}-piperazine-1-carboxylic Acid Tert-Butyl Ester
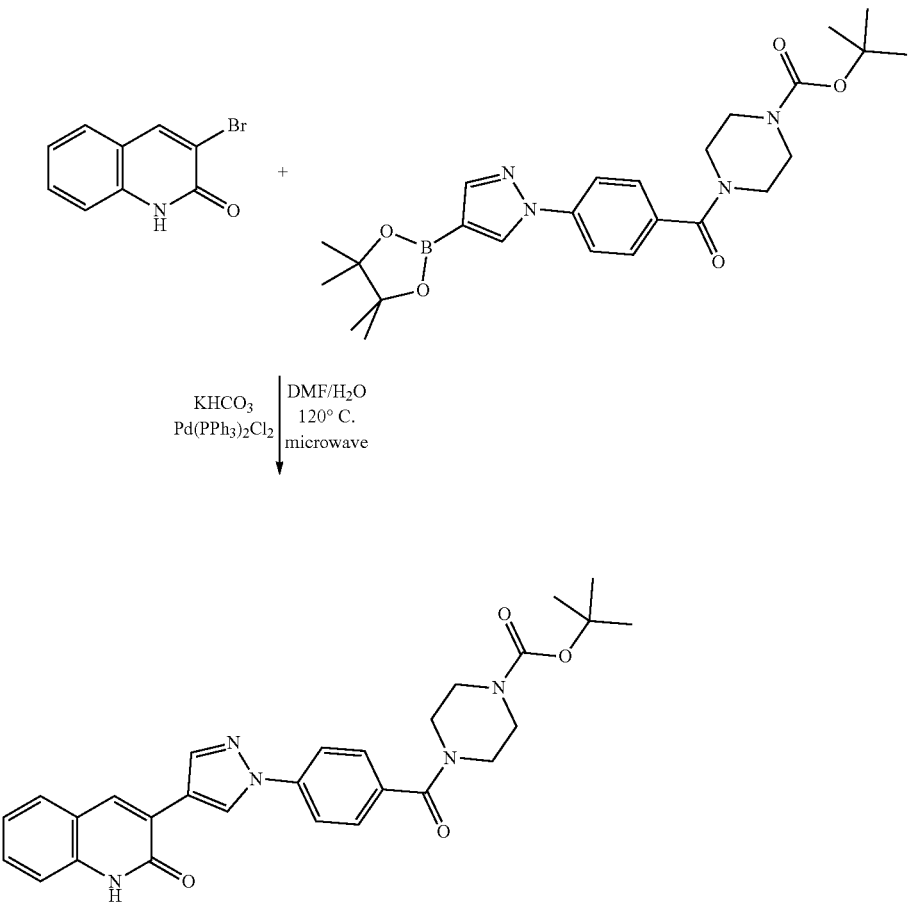

3-(1-phenyl-1H-pyrazol-4-yl)-1H-quinolin-2-one ("A75") is prepared similarly:
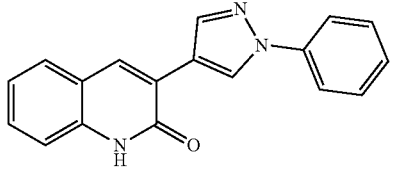 [SMILES: O=c1[nH]c2ccccc2cc1-c1cnn(-c2ccccc2)c1]
white powder; HPLC/MS 1.45 min (B), [M+H]+ 288; ¹H NMR (400 MHz, DMSO-d$_6$) δ 12.00 (s, 1H), 9.11 (s, 1H), 8.45 (s, 1H), 8.42 (s, 1H), 7.91-7.85 (m, 2H), 7.68 (dd, J=7.9, 1.3 Hz, 1H), 7.56-7.51 (m, 2H), 7.49 (ddd, J=8.4, 7.1, 1.5 Hz, 1H), 7.39-7.31 (m, 2H), 7.22 (ddd, J=8.2, 7.2, 1.2 Hz, 1H).
c) Synthesis of 3-{1-[4-(piperazine-1-carbonyl)-phenyl]-1H-pyrazol-4-yl}-1H-quinolin-2-one ("A73") and 3-{1-[4-(4-methyl-piperazine-1-carbonyl)-phenyl]-1H-pyrazol-4-yl}-1H-quinolin-2-one ("A74")
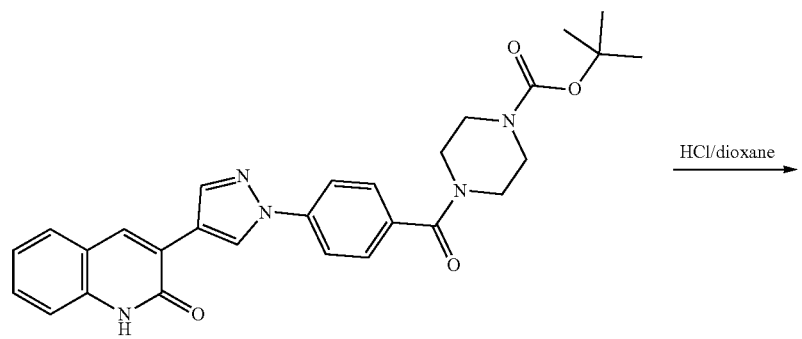
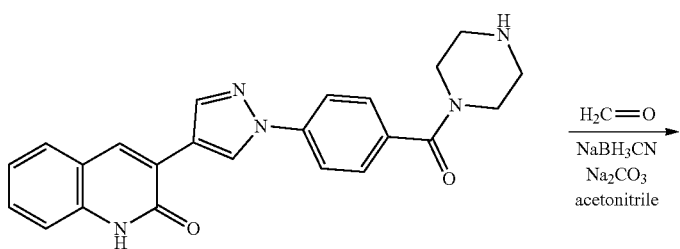
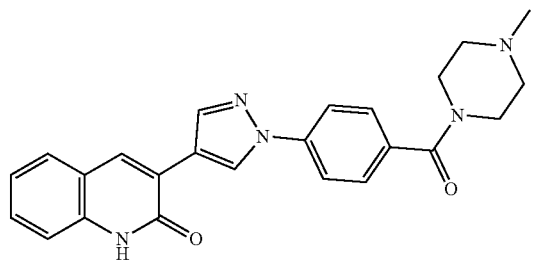

"A73": white solid; HPLC/MS 1.06 min (B), [M+H]⁺ 400; ¹H NMR (400 MHz, DMSO-$d_6$) δ 12.03 (s, 1H), 9.18 (s, 1H), 8.50 (s, 1H), 8.44 (s, 1H), 8.18 (s, 1H), 7.99-7.93 (m, 2H), 7.70 (dd, J=8.0, 1.3 Hz, 1H), 7.59-7.54 (m, 2H), 7.51 (ddd, J=8.5, 7.2, 1.5 Hz, 1H), 7.38 (d, J=8.2 Hz, 1H), 7.24 (ddd, J=8.1, 7.2, 1.1 Hz, 1H), 3.46 (bs, 4H), 2.78 (bs, 4H).

"A74" formate: white solid; HPLC/MS 1.17 min (A), [M+H]⁺ 400; ¹H NMR (700 MHz, DMSO-$d_6$) δ 12.05 (s, 1H), 9.19 (s, 1H), 8.50 (s, 1H), 8.45 (s, 1H), 8.00-7.93 (m, 2H), 7.69 (dd, J=8.0, 1.3 Hz, 1H), 7.60-7.53 (m, 2H), 7.53-7.48 (m, 1H), 7.37 (d, J=8.1 Hz, 1H), 7.23 (t, J=7.4 Hz, 1H), 3.65 (bs, 2H), 3.40 (bs, 2H), 2.34 (bs, 4H), 2.21 (s, 3H).

EXAMPLE 6

3-{1-[3-(morpholine-4-carbonyl)-phenyl]-1H-[1,2,3]triazol-4-yl}-1H-quinolin-2-one ("A76")

a) Synthesis of 3-[4-(2-oxo-1,2-dihydro-quinolin-3-yl)-[1,2,3]triazol-1-yl]-benzoic Acid

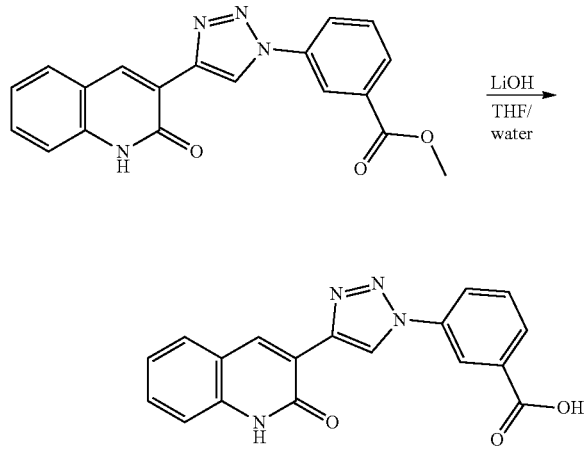

To a suspension of 3-[4-(2-oxo-1,2-dihydro-quinolin-3-yl)-[1,2,3]triazol-1-yl]-benzoic acid methyl ester (346 mg, 1.0 mmol) in THF/water (1:1, 4 ml) is added lithium hydroxide (211 mg, 8.8 mmol) and the reaction mixture is stirred for 2 hours at 65° C. After cooling to room temperature, 1 N aqueous hydrochloric acid is added until a pH of 1 is reached. The resultant precipitate is filtered off, washed with water and dried under vacuum to afford 3-[4-(2-oxo-1,2-dihydro-quinolin-3-yl)-[1,2,3]triazol-1-yl]-benzoic acid as olive green solid; HPLC/MS 1.31 min (B), [M+H]⁺ 333; ¹H NMR (400 MHz, DMSO-$d_6$) δ 13.40 (s, 1H), 12.22 (s, 1H), 9.29 (s, 1H), 8.85 (s, 1H), 8.47 (d, J=1.9 Hz, 1H), 8.31-8.24 (m, 2H), 8.06 (dt, J=7.6, 1.3 Hz, 1H), 7.91 (d, J=7.5 Hz, 1H), 7.76 (t, J=7.9 Hz, 1H), 7.56 (ddd, J=8.5, 7.1, 1.4 Hz, 1H), 7.41 (d, J=8.2 Hz, 1H), 7.29-7.23 (m, 1H).

4-[4-(2-Oxo-1,2-dihydro-[1,8]naphthyridin-3-yl)-[1,2,3]triazol-1-yl]-benzoic acid ("A77") is prepared similarly

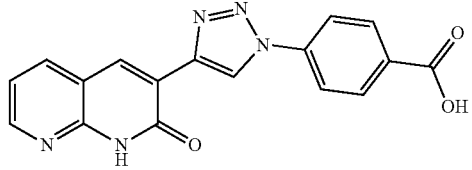 [SMILES: O=C(O)c1ccc(-n2cc(-c3cc4cccnc4[nH]c3=O)nn2)cc1]

¹H NMR (400 MHz, DMSO-$d_6$, TFA-$d_1$) δ 9.31 (d, 1H), 8.86 (br s, 1H), 8.54-8.53 (m, 3H), 8.34 (dd, 2H), 8.16 (m, 4H), 7.30 (m, 1H).

b) Synthesis of "A76"

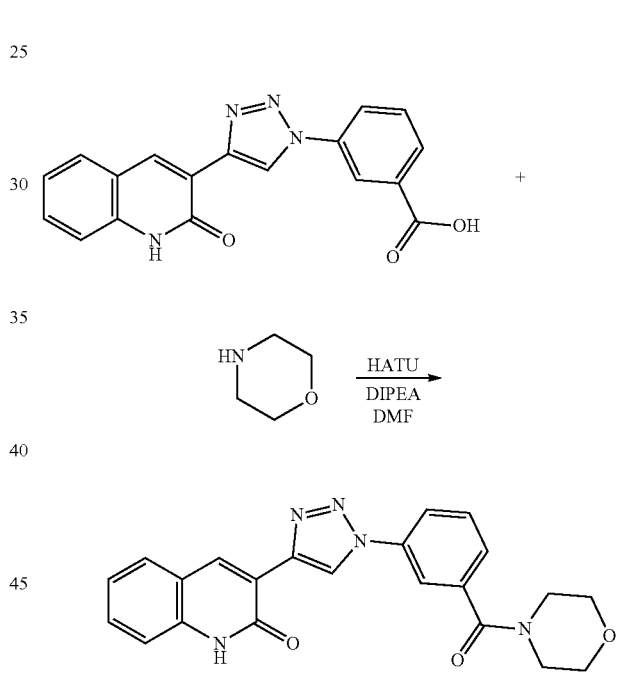

To a solution of 3-[4-(2-oxo-1,2-dihydro-quinolin-3-yl)-[1,2,3]triazol-1-yl]-benzoic acid (99.7 mg, 0.30 mmol), morpholine (26 μl, 0.39 mmol) and [dimethylamino(triazolo[4,5-b]pyridin-3-yloxy)methylene]-dimethyl-ammonium hexafluorophosphate (HATU; 114 mg, 0.30 mmol) in DMF (0.6 ml) is added ethyl-diisopropyl-amine (153 μl, 0.90 mmol) and the reaction mixture is stirred for 16 hours at room temperature. The reaction mixture is treated with saturated aqueous $Na_2CO_3$ solution and water. The resultant precipitate is filtered off, washed with water and dried under vacuum to afford 3-{1-[3-(morpholine-4-carbonyl)-phenyl]-1H-[1,2,3]triazol-4-yl}-1H-quinolin-2-one as off-white solid; HPLC/MS 1.28 min (B), [M+H]⁺ 402.

¹H NMR (500 MHz, DMSO-$d_6$) δ 12.20 (s, 1H), 9.28 (s, 1H), 8.84 (s, 1H), 8.11 (ddd, J=8.1, 2.3, 1.0 Hz, 1H), 8.05 (t, J=1.9 Hz, 1H), 7.90 (dd, J=8.0, 1.3 Hz, 1H), 7.69 (t, J=7.9 Hz, 1H), 7.59-7.50 (m, 2H), 7.41 (d, J=8.2 Hz, 1H), 7.26 (td, J=7.5, 1.1 Hz, 1H), 3.74-3.34 (m, 8H).

EXAMPLE 7

3-{1-[3-(piperazine-1-carbonyl)-phenyl]-1H-[1,2,3]triazol-4-yl}-1H-quinolin-2-one ("A78") and 3-{1-[3-(4-methyl-piperazine-1-carbonyl)-phenyl]-1H-[1,2,3]triazol-4-yl}-1H-quinolin-2-one ("A79")

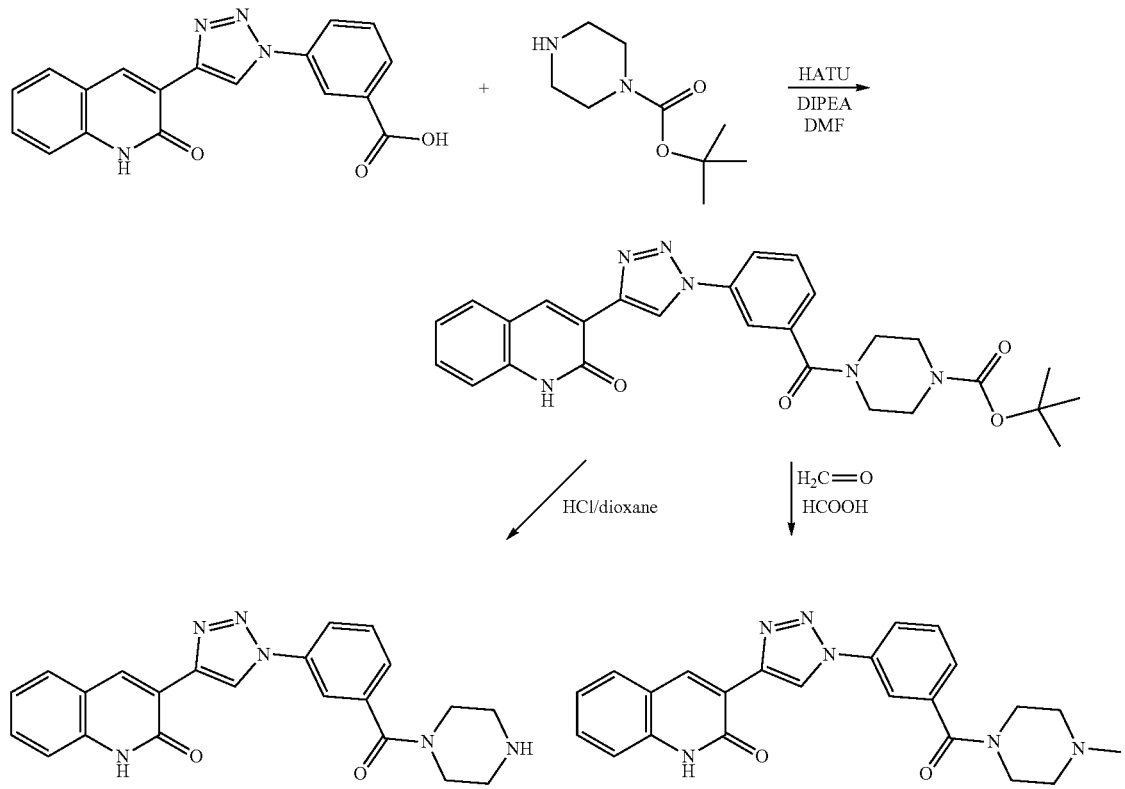

"A78": light yellow solid; HPLC/MS 1.15 min (A), [M+H]+ 401.
$^1$H NMR (400 MHz, DMSO-d$_6$) δ 12.20 (s, 1H), 9.27 (s, 1H), 8.83 (s, 1H), 8.12-8.05 (m, 1H), 8.01 (t, J=1.8 Hz, 1H), 7.89 (dd, J=8.0, 1.4 Hz, 1H), 7.68 (t, J=7.9 Hz, 1H), 7.55 (ddd, J=8.4, 7.1, 1.4 Hz, 1H), 7.49 (dt, J=7.7, 1.3 Hz, 1H), 7.40 (d, J=8.2 Hz, 1H), 7.32-7.21 (m, 1H), 3.58 (bs, 2H), 3.29 (bs, 2H), 2.81-2.62 (m, 4H).

"A79": white solid; HPLC/MS 1.15 min (A), [M+H]+ 415.
$^1$H NMR (400 MHz, DMSO-d$_6$) δ 12.19 (s, 1H), 9.27 (s, 1H), 8.83 (s, 1H), 8.10 (ddd, J=8.1, 2.3, 1.0 Hz, 1H), 8.02 (t, J=1.8 Hz, 1H), 7.90 (dd, J=8.0, 1.4 Hz, 1H), 7.68 (t, J=7.9 Hz, 1H), 7.56 (ddd, J=8.5, 7.1, 1.4 Hz, 1H), 7.50 (dt, J=7.7, 1.2 Hz, 1H), 7.41 (d, J=8.2 Hz, 1H), 7.25 (ddd, J=8.2, 7.2, 1.1 Hz, 1H), 3.66 (bs, 2H), 3.38 (bs, 2H), 2.45-2.25 (m, 4), 2.21 (s, 3H).

EXAMPLE 8

3-[1-(4-isopropenyl-phenyl)-1H-[1,2,3]triazol-4-yl]-1H-quinolin-2-one ("A80") and 3-{1-[4-(1-methanesulfonyl-methyl-ethyl)-phenyl]-1H-[1,2,3]triazol-4-yl}-1H-quinolin-2-one ("A81")

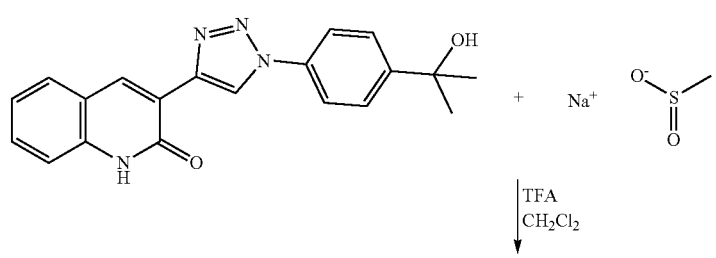

-continued

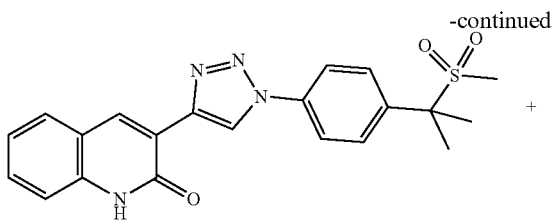 + 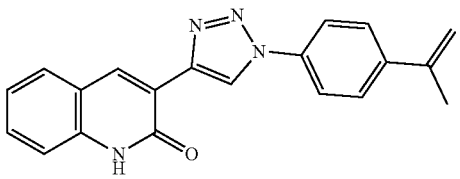

To a solution of 3-{1-[4-(1-hydroxy-1-methyl-ethyl)-phenyl]-1H-[1,2,3]triazol-4-yl}-1H-quinolin-2-one (97.0 mg, 0.28 mmol) in dichloromethane (0.5 ml) is added sodium methanesulfinate (62.6 mg, 0.61 mmol), followed by a solution of trifluoroacetic acid (176 μl, 2.28 mmol) in dichloromethane (0.4 ml). The reaction mixture is stirred for 19 hours at room temperature. The reaction mixture is diluted with dichloromethane and water. The organic phase is separated and the organic phase is extracted twice with water. The combined organic phases are dried over sodium sulfate and evaporated. The residue is chromatographed on a silica gel column with dichloromethane/methanol as eluent to afford two products:

"A80": 3-[1-(4-isopropenyl-phenyl)-1H-[1,2,3]triazol-4-yl]-1H-quinolin-2-one, white crystals; HPLC/MS 1.80 min (A), [M+H]+ 329;

$^{1}$H NMR (400 MHz, DMSO-d$_{6}$) δ 12.18 (s, 1H), 9.20 (s, 1H), 8.83 (s, 1H), 8.03-7.95 (m, 2H), 7.90 (dd, J=8.0, 1.3 Hz, 1H), 7.78-7.70 (m, 2H), 7.56 (ddd, J=8.4, 7.1, 1.4 Hz, 1H), 7.41 (d, J=8.1 Hz, 1H), 7.25 (ddd, J=8.1, 7.1, 1.1 Hz, 1H), 5.56 (s, 1H), 5.23-5.20 (m, 1H), 2.18 (d, J=1.1 Hz, 3H).

"A81": 3-{1-[4-(1-methanesulfonyl-methyl-ethyl)-phenyl]-1H-[1,2,3]triazol-4-yl}-1H-quinolin-2-one, white platelets; HPLC/MS 1.50 min (A), [M+H]+ 409;

$^{1}$H NMR (400 MHz, DMSO-d$_{6}$) δ 12.18 (s, 1H), 9.24 (s, 1H), 8.83 (s, 1H), 8.12-8.02 (m, 2H), 7.90 (dd, J=8.1, 1.4 Hz, 1H), 7.87-7.81 (m, 2H), 7.56 (ddd, J=8.4, 7.1, 1.4 Hz, 1H), 7.41 (d, J=8.2 Hz, 1H), 7.26 (ddd, J=8.1, 7.2, 1.1 Hz, 1H), 2.77 (s, 3H), 1.83 (s, 6H).

EXAMPLE 9

7-chloro-3-{1-[4-(morpholine-4-carbonyl)-phenyl]-1H-[1,2,3]triazol-4-yl}-1H-quinolin-2-one ("A82")

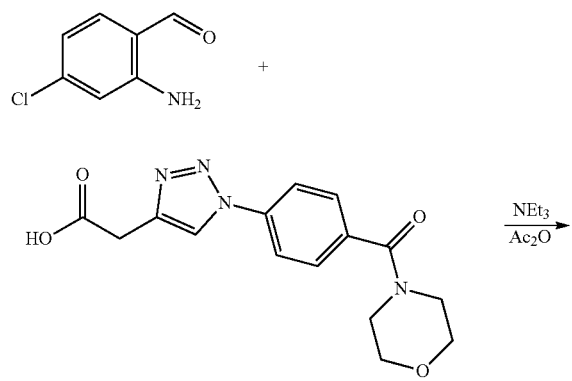

-continued

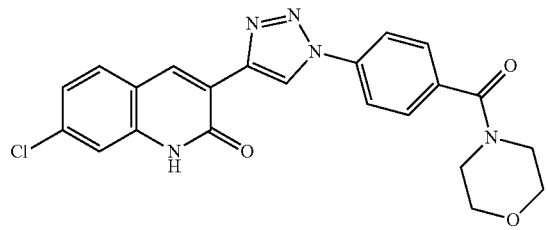

To a suspension of {1-[4-(morpholine-4-carbonyl)-phenyl]-1H-[1,2,3]triazol-4-yl}-acetic acid (158 mg, 0.50 mmol) and 2-amino-4-chlorobenzaldehyde (77.8 mg, 0.5 mmol) in acetic acid anhydride (0.5 ml) is added triethylamine (277 μl, 2.0 mmol) and the reaction mixture is stirred for 18 hours at room temperature. The reaction mixture is diluted with ethyl acetate. The solid is filtered off and dried. The residue is treated with water. The solid is filtered off, washed with water and dried under vacuum to afford 7-chloro-3-{1-[4-(morpholine-4-carbonyl)-phenyl]-1H-[1,2,3]triazol-4-yl}-1H-quinolin-2-one as beige powder; HPLC/MS 1.53 min (A), [M+H]+436.

$^{1}$H NMR (400 MHz, DMSO-d$_{6}$) δ 12.27 (s, 1H), 9.26 (s, 1H), 8.85 (s, 1H), 8.15-8.04 (m, 2H), 7.95 (d, J=8.5 Hz, 1H), 7.75-7.59 (m, 2H), 7.42 (d, J=2.1 Hz, 1H), 7.30 (dd, J=8.5, 2.0 Hz, 1H), 3.85-3.33 (m, 8H).

The following compounds are prepared similarly:

7-fluoro-3-{1-[4-(morpholine-4-carbonyl)-phenyl]-1H-[1,2,3]triazol-4-yl}-1H-quinolin-2-one ("A83")

off-white crystals; HPLC/MS 1.44 min (A), [M+H]+ 420;
$^{1}$H NMR (400 MHz, DMSO-d$_{6}$) δ 12.27 (s, 1H), 9.24 (s, 1H), 8.86 (s, 1H), 8.17-8.04 (m, 2H), 8.00 (dd, J=9.6, 6.1 Hz, 1H), 7.69-7.62 (m, 2H), 7.17-7.10 (m, 2H), 3.80-3.35 (m, 8H).

7-methyl-3-{1-[4-(morpholine-4-carbonyl)-phenyl]-1H-[1,2,3]triazol-4-yl}-1H-quinolin-2-one ("A84")

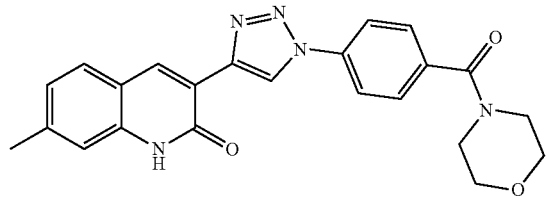 [SMILES: Cc1ccc2cc(-c3cn(-c4ccc(C(=O)N5CCOCC5)cc4)nn3)c(=O)[nH]c2c1]

beige solid; HPLC/MS 1.47 min (A), [M+H]⁺ 416; H NMR (500 MHz, DMSO-d₆) δ 12.13 (s, 1H), 9.24 (s, 1H), 8.80 (s, 1H), 8.13-8.07 (m, 2H), 7.79 (d, J=8.1 Hz, 1H), 7.70-7.63 (m, 2H), 7.20 (s, 1H), 7.11 (dd, J=8.1, 1.5 Hz, 1H), 3.75-3.35 (m, 8H), 2.43 (s, 3H).

3-{1-[4-(morpholine-4-carbonyl)-phenyl]-1H-[1,2,3]triazol-4-yl}-1H-[1,5]naphthyridin-2-one ("A85")

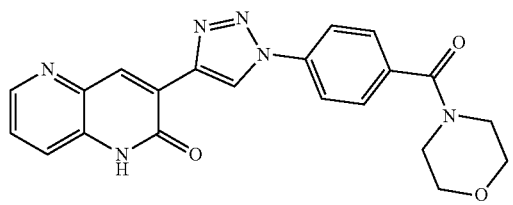 [SMILES: O=C(c1ccc(-n2cc(-c3cc4ncccc4[nH]c3=O)nn2)cc1)N1CCOCC1]

light yellow crystals; HPLC/MS 1.20 min (A), [M+H]⁺ 403; ¹H NMR (700 MHz, DMSO-d₆) δ 12.40 (s, 1H), 9.34 (s, 1H), 8.76 (s, 1H), 8.58 (dd, J=4.5, 1.4 Hz, 1H), 8.11 (d, J=8.6 Hz, 2H), 7.78 (dd, J=8.3, 1.4 Hz, 1H), 7.66 (d, J=8.5 Hz, 2H), 7.58 (dd, J=8.3, 4.4 Hz, 1H), 3.65 (bs, 4H), 3.40 (bs, 4H).

6-fluoro-3-(1-{4-[4-(3-methoxy-propyl)-piperazine-1-carbonyl]-phenyl}-1H-[1,2,3]triazol-4-yl)-1H-quinolin-2-one ("A86")

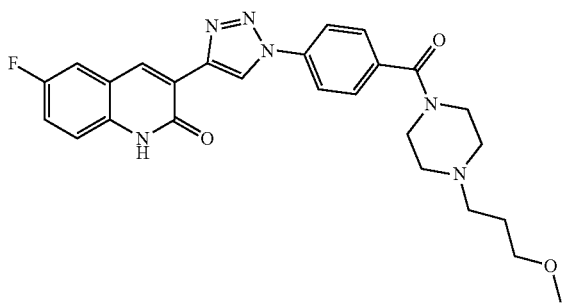 [SMILES: COCCCN1CCN(C(=O)c2ccc(-n3cc(-c4cc5cc(F)ccc5[nH]c4=O)nn3)cc2)CC1]

beige solid; HPLC/MS 1.23 min (A), [M+H]⁺ 491; ¹H NMR (400 MHz, DMSO-d₆) δ 12.27 (s, 1H), 9.28 (s, 1H), 8.85 (s, 1H), 8.08 (d, J=8.6 Hz, 2H), 7.80 (dd, J=9.1, 2.6 Hz, 1H), 7.62 (d, J=8.6 Hz, 2H), 7.50-7.37 (m, 2H), 3.75-3.30 (m, 4H), 3.35 (t, J=6.4 Hz, 2H), 3.22 (s, 3H), 2.47-2.32 (m, 6H), 1.67 (p, J=6.7 Hz, 2H).

5-fluoro-3-(1-{4-[4-(3-methoxy-propyl)-piperazine-1-carbonyl]-phenyl}-1H-[1,2,3]triazol-4-yl)-1H-quinolin-2-one ("A87")

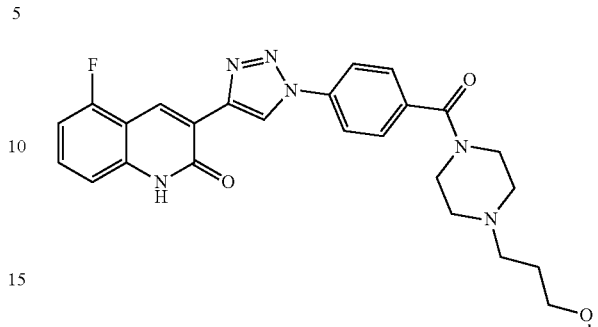

off-white solid; HPLC/MS 1.25 min (A), [M+H]⁺ 491; ¹H NMR (400 MHz, DMSO-d₆) δ 12.43 (s, 1H), 9.28 (s, 1H), 8.82 (s, 1H), 8.09 (d, J=8.6 Hz, 2H), 7.62 (d, J=8.6 Hz, 2H), 7.57 (td, J=8.2, 6.1 Hz, 1H), 7.24 (d, J=8.4 Hz, 1H), 7.11 (ddd, J=10.1, 8.1, 0.9 Hz, 1H), 3.70-3.30 (m, 4H), 3.35 (t, J=6.4 Hz, 2H), 3.22 (s, 3H), 2.40 (bs, 4H), 2.36 (t, J=7.3 Hz, 2H), 1.78-1.57 (m, 2H).

6-fluoro-3-(1-{4-[4-(3-methoxy-propyl)-piperazine-1-carbonyl]-phenyl}-1H-[1,2,3]triazol-4-yl)-1H-[1,8]naphthyridin-2-one ("A88")

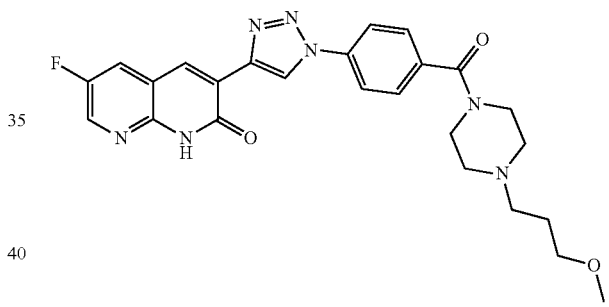

beige solid; HPLC/MS 1.14 min (A), [M+H]⁺ 492; ¹H NMR (400 MHz, DMSO-d₆) δ 12.70 (s, 1H), 9.29 (s, 1H), 8.86 (s, 1H), 8.61 (d, J=2.9 Hz, 1H), 8.35 (dd, J=8.7, 3.0 Hz, 1H), 8.09 (d, J=8.6 Hz, 2H), 7.63 (d, J=8.6 Hz, 2H), 3.75-3.30 (m, 4H), 3.35 (t, J=6.4 Hz, 2H), 3.22 (s, 3H), 2.39 (bs, 4H) 2.36 (t, J=7.3 Hz, 2H), 1.67 (p, J=6.6 Hz, 2H).

3-(1-{4-[4-(3-methoxy-propyl)-piperazine-1-carbonyl]-phenyl}-1H-[1,2,3]triazol-4-yl)-1H-[1,8]naphthyridin-2-one ("A89")

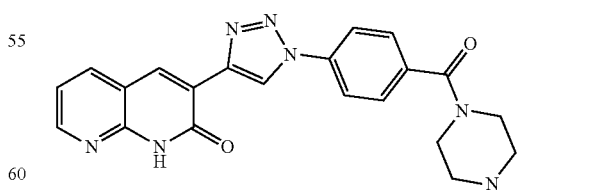

white solid; HPLC/MS 1.08 min (A), [M+H]⁺ 474; ¹H NMR (500 MHz, DMSO-d₆) δ 12.58 (s, 1H), 9.27 (s, 1H), 8.86 (s, 1H), 8.57 (dd, J=4.7, 1.8 Hz, 1H), 8.36 (dd, J=7.8, 1.8 Hz, 1H), 8.08 (d, J=8.5 Hz, 2H), 7.63 (d, J=8.5 Hz, 2H), 7.33 (dd, J=7.7, 4.7 Hz, 1H), 3.70-3.32 (m, 4H), 3.35 (t, J=6.4 Hz, 2H), 3.22 (s, 3H), 2.40 (bs, 4H), 2.36 (t, J=7.3 Hz, 2H), 1.67 (m, 2H).

5,7-difluoro-3-{1-[4-(morpholine-4-carbonyl)-phenyl]-1H-[1,2,3]triazol-4-yl}-1H-quinolin-2-one ("A90")

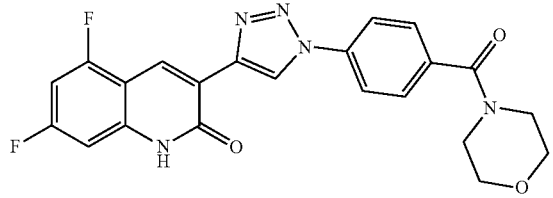 [SMILES: O=C(c1ccc(-n2cc(-c3cc4c(F)cc(F)cc4[nH]c3=O)nn2)cc1)N1CCOCC1]

beige solid; HPLC/MS 1.51 min (A), [M+H]⁺ 438; ¹H NMR (500 MHz, DMSO-d₆) δ 12.54 (s, 1H), 9.28 (s, 1H), 8.77 (s, 1H), 8.11 (d, J=8.6 Hz, 2H), 7.67 (d, J=8.6 Hz, 2H), 7.24 (td, J=9.9, 2.4 Hz, 1H), 7.03 (dd, J=9.9, 2.1 Hz, 1H), 3.75-3.35 (m, 8H).

7-bromo-3-{1-[4-(morpholine-4-carbonyl)-phenyl]-1H-[1,2,3]triazol-4-yl}-1H-quinolin-2-one ("A91")

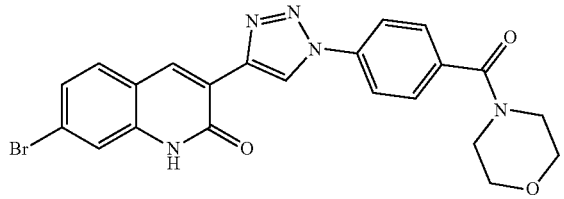 [SMILES: O=C(c1ccc(-n2cc(-c3cc4ccc(Br)cc4[nH]c3=O)nn2)cc1)N1CCOCC1]

beige solid; HPLC/MS 1.56 min (A), [M+H]⁺ 482; ¹H NMR (400 MHz, DMSO-d₆) δ 12.27 (s, 1H), 9.28 (s, 1H), 8.85 (s, 1H), 8.15-8.07 (m, 2H), 7.89 (d, J=8.5 Hz, 1H), 7.72-7.63 (m, 2H), 7.59 (d, J=1.9 Hz, 1H), 7.44 (dd, J=8.4, 1.9 Hz, 1H), 3.74-3.38 (m, 8H).

6-fluoro-3-{1-[4-(4-methyl-3-oxo-piperazine-1-carbonyl)-phenyl]-1H-[1,2,3]triazol-4-yl}-1H-quinolin-2-one ("A92")

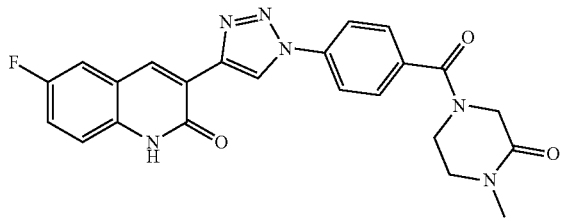 [SMILES: CN1CCN(C(=O)c2ccc(-n3cc(-c4cc5cc(F)ccc5[nH]c4=O)nn3)cc2)CC1=O]

off-white powder; UPLC/MS 0.62 min, [M+H]⁺ 447; ¹H NMR (400 MHz, DMSO-d₆) δ 12.27 (s, 1H), 9.30 (s, 1H), 8.85 (s, 1H), 8.15-8.07 (m, 2H), 7.80 (dd, J=9.2, 2.7 Hz, 1H), 7.75-7.66 (m, 2H), 7.52-7.38 (m, 2H), 4.12 (bs, 2H), 3.94-3.58 (m, 2H), 3.40 (t, J=5.5 Hz, 2H), 2.89 (s, 3H).

7-methoxy-3-{1-[4-(morpholine-4-carbonyl)-phenyl]-1H-[1,2,3]triazol-4-yl}-1H-quinolin-2-one ("A93")

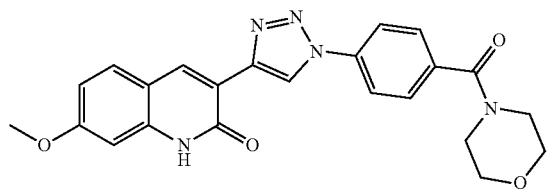 [SMILES: COc1ccc2cc(-c3cn(-c4ccc(C(=O)N5CCOCC5)cc4)nn3)c(=O)[nH]c2c1]

beige powder; UPLC/MS 0.66 min, [M+H]⁺ 432; ¹H NMR (400 MHz, DMSO-d₆) δ 12.06 (s, 1H), 9.19 (s, 1H), 8.76 (s, 1H), 8.13-8.04 (m, 2H), 7.82 (d, J=8.3 Hz, 1H), 7.73-7.62 (m, 2H), 6.96-6.83 (m, 2H), 3.85 (s, 3H), 3.72-3.38 (m, 8H).

6-{1-[4-(Morpholine-4-carbonyl)-phenyl]-1H-[1,2,3]triazol-4-yl}-8H-pyrido[2,3-d]pyrimidin-7-one ("A94")

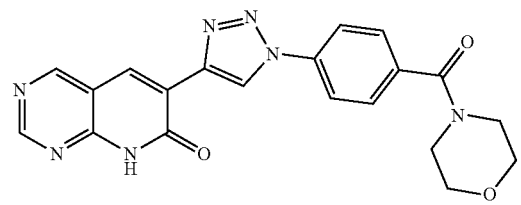 [SMILES: O=C(c1ccc(-n2cc(-c3cc4cncnc4[nH]c3=O)nn2)cc1)N1CCOCC1]

yellow solid; HPLC/MS 1.15 min (A), [M+H]⁺ 404; ¹H NMR (400 MHz, DMSO-d₆) δ 12.97 (s, 1H), 9.30 (s, 1H), 9.29 (s, 1H), 9.03 (s, 1H), 8.91 (s, 1H), 8.15-8.10 (m, 2H), 7.71-7.66 (m, 3H), 3.64 (s, 16H).

6-fluoro-3-{1-[3-(2-morpholin-4-yl-ethoxy)-phenyl]-1H-[1,2,3]triazol-4-yl}-1H-quinolin-2-one ("A94a")

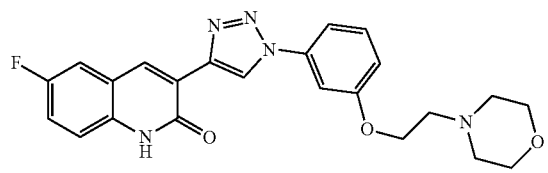 [SMILES: O=c1[nH]c2ccc(F)cc2cc1-c1cn(-c2cccc(OCCN3CCOCC3)c2)nn1]

light beige solid; HPLC/MS 1.24 min (A), [M+H]⁺ 436; ¹H NMR (400 MHz, DMSO-d₆) δ 12.25 (s, 1H), 9.25 (s, 1H), 8.83 (s, 1H), 7.79 (dd, J=9.2, 2.6 Hz, 1H), 7.59-7.54 (m, 2H), 7.50 (t, J=8.4 Hz, 1H), 7.46-7.39 (m, 2H), 7.08 (ddd, J=8.2, 2.4, 1.2 Hz, 1H), 4.24 (t, J=5.7 Hz, 2H), 3.64-3.55 (m, 4H), 2.74 (t, J=5.7 Hz, 2H), 2.53-2.49 (m, 4H).

5,7-difluoro-3-{1-[4-(4-methyl-3-oxo-piperazine-1-carbonyl)-phenyl]-1H-[1,2,3]triazol-4-yl}-1H-quinolin-2-one ("A95")

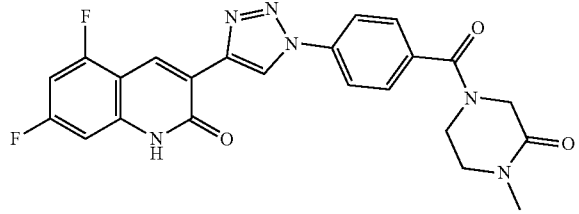 [SMILES: CN1CCN(C(=O)c2ccc(-n3cc(-c4cc5c(F)cc(F)cc5[nH]c4=O)nn3)cc2)CC1=O]

off-white powder; UPLC/MS 0.66 min, [M+H]$^+$ 465; $^1$H NMR (400 MHz, DMSO-d$_6$) δ 12.50 (s, 1H), 9.28 (s, 1H), 8.75 (s, 1H), 8.27-8.03 (m, 2H), 7.81-7.59 (m, 2H), 7.21 (td, J=9.9, 2.4 Hz, 1H), 7.01 (dd, J=9.9, 2.3 Hz, 1H), 4.13 (bs, 2H), 3.94-3.60 (m, 2H), 3.44-3.36 (m, 2H), 2.89 (s, 3H).

6-chloro-3-{1-[4-(4-methyl-3-oxo-piperazine-1-carbonyl)-phenyl]-1H-[1,2,3]triazol-4-yl}-1H-quinolin-2-one ("A96")

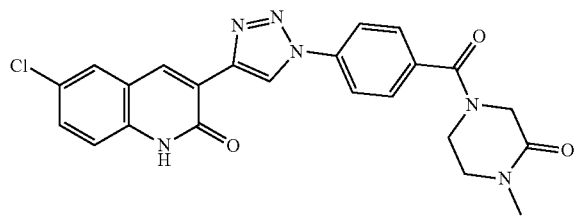 [SMILES: CN1CCN(C(=O)c2ccc(-n3cc(-c4cc5cc(Cl)ccc5[nH]c4=O)nn3)cc2)CC1=O]

off-white powder; UPLC/MS 0.67 min, [M+H]$^+$ 463; $^1$H NMR (400 MHz, DMSO-d$_6$) δ 12.32 (s, 1H), 9.29 (s, 1H), 8.84 (s, 1H), 8.16-8.08 (m, 2H), 8.05 (d, J=2.3 Hz, 1H), 7.74-7.67 (m, 2H), 7.59 (dd, J=8.8, 2.4 Hz, 1H), 7.41 (d, J=8.8 Hz, 1H), 4.13 (bs, 2H), 3.94-3.60 (m, 2H), 3.40 (t, J=5.4 Hz, 2H), 2.89 (s, 3H).

7-chloro-3-{1-[4-(4-methyl-3-oxo-piperazine-1-carbonyl)-phenyl]-1H-[1,2,3]triazol-4-yl}-1H-quinolin-2-one ("A97")

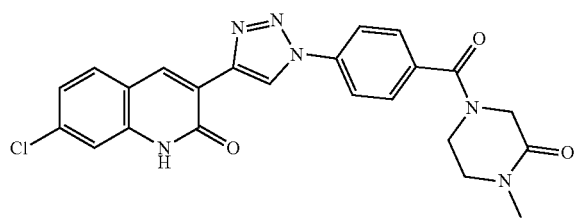 [SMILES: CN1CCN(C(=O)c2ccc(-n3cc(-c4cc5ccc(Cl)cc5[nH]c4=O)nn3)cc2)CC1=O]

off-white powder; UPLC/MS 0.67 min, [M+H]$^+$ 463; $^1$H NMR (400 MHz, DMSO-d$_6$) δ 12.28 (s, 1H), 9.27 (s, 1H), 8.86 (s, 1H), 8.16-8.08 (m, 2H), 7.95 (d, J=8.5 Hz, 1H), 7.77-7.66 (m, 2H), 7.42 (d, J=2.0 Hz, 1H), 7.30 (dd, J=8.4, 2.1 Hz, 1H), 4.12 (bs, 2H), 3.94-3.60 (m, 2H), 3.40 (t, J=5.5 Hz, 2H), 2.89 (s, 3H).

6-fluoro-3-{1-[4-(2-oxo-oxazolidin-3-yl)-phenyl]-1H-[1,2,3]triazol-4-yl}-1H-quinolin-2-one ("A98")

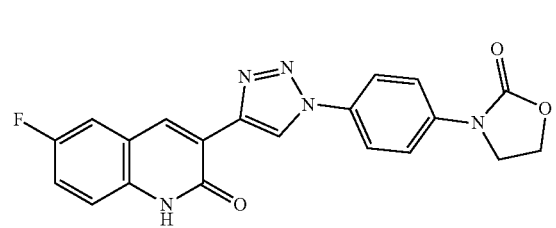 [SMILES: O=C1OCCN1c1ccc(-n2cc(-c3cc4cc(F)ccc4[nH]c3=O)nn2)cc1]

off-white powder; HPLC/MS 1.51 min (A), [M+H]$^+$ 392; $^1$H NMR (400 MHz, DMSO-d$_6$) δ 12.26 (s, 1H), 9.19 (s, 1H), 8.83 (s, 1H), 8.23-7.95 (m, 2H), 7.90-7.77 (m, 3H), 7.51-7.34 (m, 2H), 4.49 (m, 2H), 4.15 (m, 2H).

3-{1-[4-(1,1-dioxo-1l6-isothiazolidin-2-yl)-phenyl]-1H-[1,2,3]triazol-4-yl}-6-fluoro-1H-quinolin-2-one ("A99")

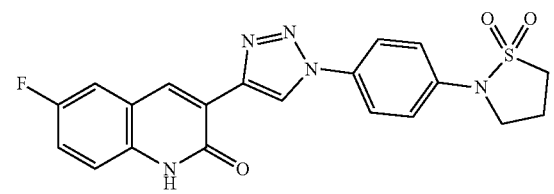 [SMILES: O=c1[nH]c2ccc(F)cc2cc1-c1cn(-c2ccc(N3CCCS3(=O)=O)cc2)nn1]

pale brown powder; HPLC/MS 1.53 min (A), [M+H]$^+$ 426; $^1$H NMR (500 MHz, DMSO-d$_6$) δ 12.26 (s, 1H), 9.18 (s, 1H), 8.84 (s, 1H), 8.13-7.94 (m, 2H), 7.80 (dd, J=9.2, 2.7 Hz, 1H), 7.48-7.37 (m, 4H), 3.84 (t, J=6.5 Hz, 2H), 3.58 (t, J=7.4 Hz, 2H), 2.45 (p, J=6.8 Hz, 2H).

3-{1-[4-([1,3']bipyrrolidinyl-1'-carbonyl)-phenyl]-1H-[1,2,3]triazol-4-yl}-6-fluoro-1H-quinolin-2-one ("A100")

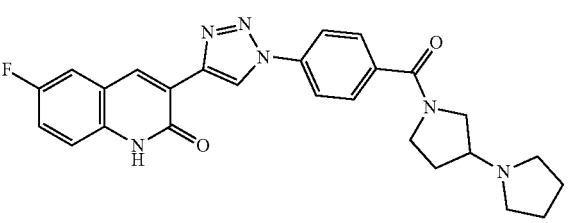 [SMILES: O=C(c1ccc(-n2cc(-c3cc4cc(F)ccc4[nH]c3=O)nn2)cc1)N1CCC(N2CCCC2)C1]

beige solid; HPLC/MS 1.20 min (A), [M+H]$^+$ 473; $^1$H NMR (700 MHz, DMSO-d$_6$, TFA-d$_1$) δ 9.32 (s, 1H), 8.87 (s, 1H), 8.12 (d, J=8.3 Hz, 2H), 7.81 (d, J=8.1 Hz, 2H), 7.65 (dd, J=9.0, 2.8 Hz, 1H), 7.50 (dd, J=9.0, 4.7 Hz, 1H), 7.37 (td, J=8.7, 2.8 Hz, 1H), 4.18-3.46 (m, 7H), 3.33-3.01 (m, 2H), 2.51-1.95 (m, 6H).

3-(1-{4-[2-(4-acetyl-piperazin-1-yl)-ethoxy]-phenyl}-1H-[1,2,3]triazol-4-yl)-6-fluoro-1H-quinolin-2-one ("A100a")

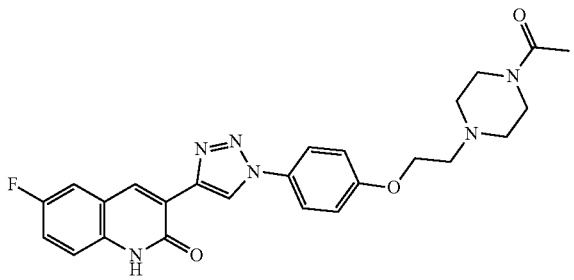 [SMILES: CC(=O)N1CCN(CCOc2ccc(-n3cc(-c4cc5cc(F)ccc5[nH]c4=O)nn3)cc2)CC1]

brown solid; HPLC/MS 1.21 min (A), [M+H]+ 477; 1H NMR (500 MHz, DMSO-d6) δ 12.24 (s, 1H), 9.11 (s, 1H), 8.82 (s, 1H), 7.93-7.85 (m, 2H), 7.79 (dd, J=9.2, 2.7 Hz, 1H), 7.49-7.38 (m, 2H), 7.21-7.12 (m, 2H), 4.19 (t, J=5.7 Hz, 2H), 3.50-3.39 (m, 4H), 2.77 (t, J=5.7 Hz, 2H), 2.52 (m, 2H), 2.45 (m, 2H), 1.99 (s, 3H).

3-(1-{4-[2-(4-acetyl-piperazin-1-yl)-ethoxy]-phenyl}-1H-[1,2,3]triazol-4-yl)-6,7-difluoro-1H-quinolin-2-one ("A101")

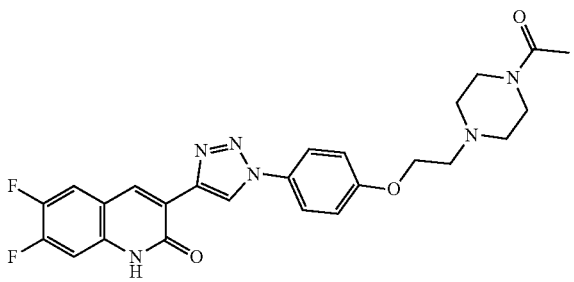 [SMILES: CC(=O)N1CCN(CCOc2ccc(-n3cc(-c4cc5cc(F)c(F)cc5[nH]c4=O)nn3)cc2)CC1]

brown solid; HPLC/MS 1.25 min (A), [M+H]+ 495; 1H NMR (500 MHz, DMSO-d6) δ 12.29 (s, 1H), 9.08 (s, 1H), 8.81 (s, 1H), 8.07 (dd, J=11.0, 8.6 Hz, 1H), 7.96-7.82 (m, 2H), 7.32 (dd, J=11.4, 7.0 Hz, 1H), 7.24-7.10 (m, 2H), 4.19 (t, J=5.7 Hz, 2H), 3.50-3.38 (m, 4H), 2.77 (t, J=5.7 Hz, 2H), 2.52 (m, 2H), 2.45 (t, J=5.2 Hz, 2H), 1.99 (s, 3H).

Acetic Acid 1-{4-[4-(6-fluoro-2-oxo-1,2-dihydro-quinolin-3-yl)-[1,2,3]triazol-1-yl]-benzoyl}-piperidin-4-yl Ester ("A102")

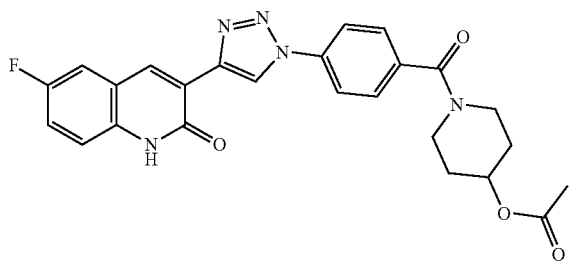 [SMILES: CC(=O)OC1CCN(C(=O)c2ccc(-n3cc(-c4cc5cc(F)ccc5[nH]c4=O)nn3)cc2)CC1]

beige solid; HPLC/MS 1.55 min (A), [M+H]+ 476.

acetic acid 1-{4-[4-(6-fluoro-2-oxo-1,2-dihydro-quinolin-3-yl)-[1,2,3]triazol-1-yl]-benzoyl}-piperidin-3-yl ester ("A103")

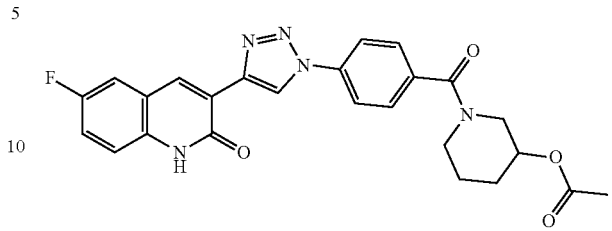

off-white solid; HPLC/MS 1.55 min (A), [M+H]+ 476.

3-{1-[4-([1,3']bipyrrolidinyl-1'-carbonyl)-phenyl]-1H-[1,2,3]triazol-4-yl}-6,7-difluoro-1H-quinolin-2-one ("A104")

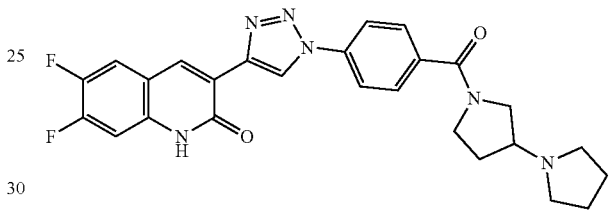

brown solid; HPLC/MS 1.24 min (A), [M+H]+ 491.

3-{1-[4-([1,3']bipyrrolidinyl-1'-carbonyl)-phenyl]-1H-[1,2,3]triazol-4-yl}-5,7-difluoro-1H-quinolin-2-one ("A105")

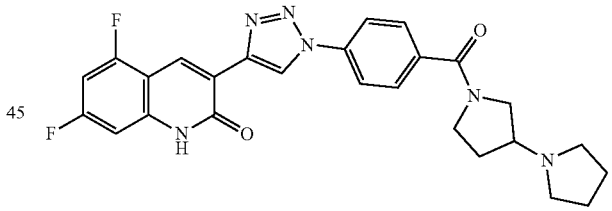

beige solid; HPLC/MS 1.25 min (A), [M+H]+ 491.

6-fluoro-3-{1-[4-(3-methoxymethyl-pyrrolidine-1-carbonyl)-phenyl]-1H-[1,2,3]triazol-4-yl}-1H-quinolin-2-one ("A106")

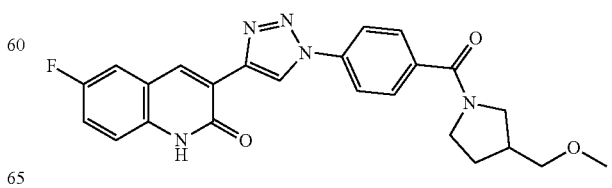

light brown solid; HPLC/MS 1.52 min (A), [M+H]+ 448.

| 101 | 102 |
|---|---|
| 3-{1-[3-([1,3']bipyrrolidinyl-1'-carbonyl)-phenyl]-1H-[1,2,3]triazol-4-yl}-6-fluoro-1H-quinolin-2-one ("A107") | 6-fluoro-3-{1-[4-((R)-3-methoxy-pyrrolidine-1-carbonyl)-phenyl]-1H-[1,2,3]triazol-4-yl}-1H-quinolin-2-one ("A111") |

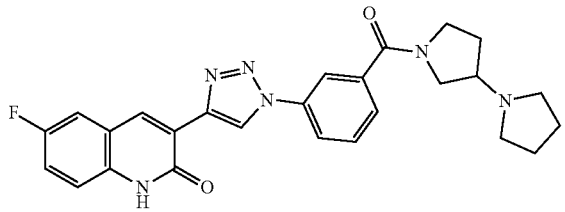 [SMILES: O=C(c1cccc(-n2cc(-c3cc4cc(F)ccc4[nH]c3=O)nn2)c1)N1CCC(N2CCCC2)C1]

brown solid; HPLC/MS 1.20 min (A), [M+H]+ 473.

3-{1-[3-([1,3']bipyrrolidinyl-1'-carbonyl)-phenyl]-1H-[1,2,3]triazol-4-yl}-6,7-difluoro-1H-quinolin-2-one ("A108")

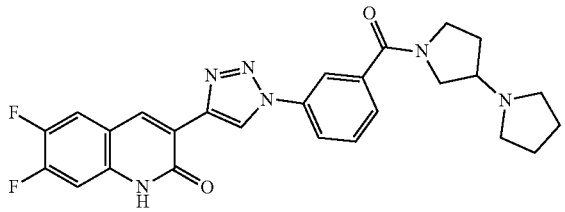 [SMILES: O=C(c1cccc(-n2cc(-c3cc4cc(F)c(F)cc4[nH]c3=O)nn2)c1)N1CCC(N2CCCC2)C1]

brown solid; HPLC/MS 1.24 min (A), [M+H]+ 491.

6,7-difluoro-3-{1-[4-(3-methoxymethyl-pyrrolidine-1-carbonyl)-phenyl]-1H-[1,2,3]triazol-4-yl}-1H-quinolin-2-one ("A109")

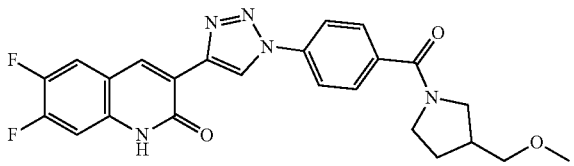 [SMILES: COCC1CCN(C(=O)c2ccc(-n3cc(-c4cc5cc(F)c(F)cc5[nH]c4=O)nn3)cc2)C1]

brown solid; HPLC/MS 1.56 min (A), [M+H]+ 466.

6-fluoro-3-{1-[4-(4-methyl-5-oxo-[1,4]diazepane-1-carbonyl)-phenyl]-1H-[1,2,3]triazol-4-yl}-1H-quinolin-2-one ("A110")

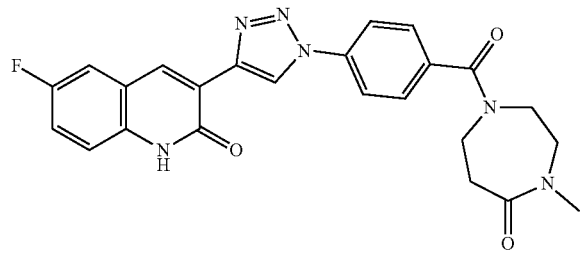 [SMILES: CN1CCN(C(=O)c2ccc(-n3cc(-c4cc5cc(F)ccc5[nH]c4=O)nn3)cc2)CCC1=O]

brown solid; UPLC/MS 0.89 min, [M+H]+ 461.

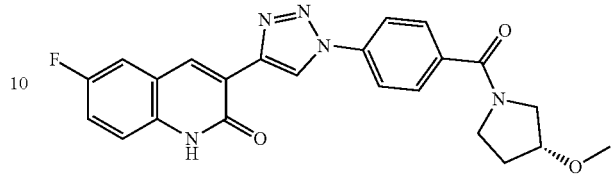

off-white solid; UPLC/MS 0.94 min, [M+H]+ 434.

6-fluoro-3-{1-[4-((S)-3-methoxy-pyrrolidine-1-carbonyl)-phenyl]-1H-[1,2,3]triazol-4-yl}-1H-quinolin-2-one ("A112")

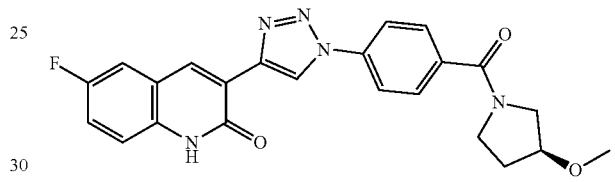

off-white solid; UPLC/MS 0.94 min, [M+H]+ 434.

6,7-difluoro-3-{1-[4-((R)-3-methoxy-pyrrolidine-1-carbonyl)-phenyl]-1H-[1,2,3]triazol-4-yl}-1H-quinolin-2-one ("A113")

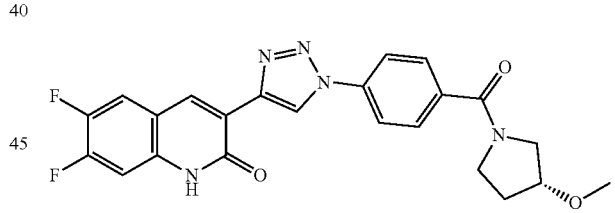

off-white solid; UPLC/MS 0.96 min, [M+H]+ 452.

6,7-difluoro-3-{1-[4-((S)-3-methoxy-pyrrolidine-1-carbonyl)-phenyl]-1H-[1,2,3]triazol-4-yl}-1H-quinolin-2-one ("A114")

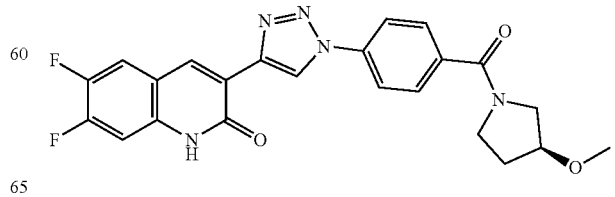

off-white solid; UPLC/MS 0.96 min, [M+H]+ 452.

3-{1-[4-(2-dimethylamino-ethyl)-phenyl]-1H-[1,2,3]
triazol-4-yl}-6,7-difluoro-1H-quinolin-2-one
("A115")

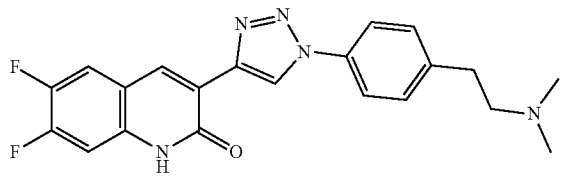 [SMILES: CN(C)CCc1ccc(-n2cc(-c3cc4cc(F)c(F)cc4[nH]c3=O)nn2)cc1]

beige solid; UPLC/MS 0.48 min, [M+H]⁺ 396. ¹H NMR
(300 MHz, DMSO-d₆) δ 12.31 (s, 1H), 9.15 (s, 1H), 8.83 (s,
1H), 8.08 (dd, J=11.1, 8.6 Hz, 1H), 7.93-7.84 (m, 2H),
7.50-7.43 (m, 2H), 7.33 (dd, J=11.5, 7.1 Hz, 1H), 2.81 (t,
J=7.5 Hz, 2H), 2.53 (t, J=7.5 Hz, 2H), 2.21 (s, 6H).

6,7-difluoro-3-{1-[4-(2-pyrrolidin-1-yl-ethyl)-phe-
nyl]-1H-[1,2,3]triazol-4-yl}-1H-quinolin-2-one
("A115a")

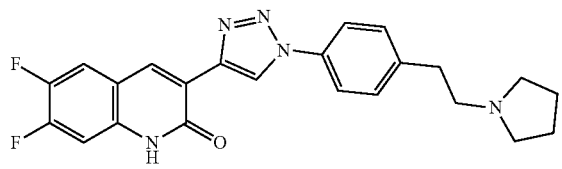 [SMILES: O=c1[nH]c2cc(F)c(F)cc2cc1-c1cn(-c2ccc(CCN3CCCC3)cc2)nn1]

beige solid; UPLC/MS 0.49 min, [M+H]⁺ 396. ¹H NMR
(300 MHz, DMSO-d₆) δ 12.31 (s, 1H), 9.15 (s, 1H), 8.83 (s,
1H), 8.08 (dd, J=11.1, 8.6 Hz, 1H), 7.89 (d, J=8.5 Hz, 2H),
7.47 (d, J=8.5 Hz, 2H), 7.33 (dd, J=11.5, 7.1 Hz, 1H), 2.81
(t, J=7.5 Hz, 2H), 2.56-2.49 (m, 6H), 2.21 (s, 4H).

3-{1-[4-(2-diethylamino-ethoxy)-phenyl]-1H-[1,2,3]
triazol-4-yl}-6,7-difluoro-1H-quinolin-2-one
("A116")

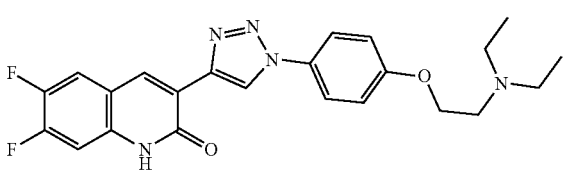 [SMILES: CCN(CC)CCOc1ccc(-n2cc(-c3cc4cc(F)c(F)cc4[nH]c3=O)nn2)cc1]

beige solid; HPLC/MS 1.31 min (A), [M+H]⁺ 440; ¹H
NMR (500 MHz, DMSO-d₆) δ 12.29 (s, 1H), 9.08 (s, 1H),
8.81 (s, 1H), 8.07 (dd, J=11.0, 8.5 Hz, 1H), 7.96-7.82 (m,
2H), 7.31 (dd, J=11.4, 7.0 Hz, 1H), 7.19-7.07 (m, 2H), 4.10
(t, J=6.1 Hz, 2H), 2.81 (t, J=6.1 Hz, 2H), 2.57 (q, J=7.1 Hz,
4H), 0.99 (t, J=7.1 Hz, 6H).

6,7-difluoro-3-{1-[4-(2-pyrrolidin-1-yl-ethoxy)-phe-
nyl]-1H-[1,2,3]triazol-4-yl}-1H-quinolin-2-one
("A186")

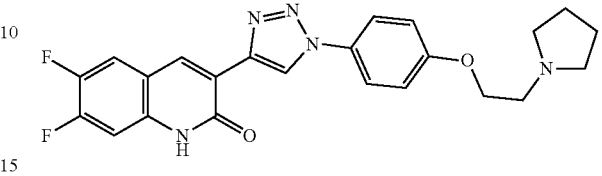

Beige solid; HPLC/MS 1.28 min (A), [M+H]⁺ 438; ¹H
NMR (500 MHz, DMSO-d₆) δ 12.29 (s, 1H), 9.08 (s, 1H),
8.81 (s, 1H), 8.06 (dd, J=11.0, 8.6 Hz, 1H), 7.87 (d, J=9.0
Hz, 2H), 7.31 (dd, J=11.4, 7.1 Hz, 1H), 7.15 (d, J=9.0 Hz,
2H), 4.16 (t, J=5.9 Hz, 2H), 2.83 (t, J=5.8 Hz, 2H), 2.58-2.53
(m, 4H), 1.74-1.66 (m, 4H).

N-{4-[4-(6,7-difluoro-2-oxo-1,2-dihydro-quinolin-3-
yl)-[1,2,3]triazol-1-yl]-phenyl}-N-methyl-acetamide
("A352")

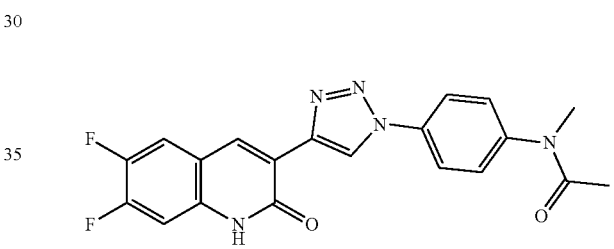

HPLC/MS 1.50 min (A), [M+H]⁺ 396;
¹H NMR (400 MHz, DMSO-d₆) δ 12.32 (s, 1H), 9.24 (s,
1H), 8.84 (s, 1H), 8.12-8.05 (m, 3H), 7.68-7.54 (m, 2H),
7.33 (dd, J=11.5, 7.1 Hz, 1H), 3.24 (bs, 3H), 1.90 (bs, 3H).

N-{4-[4-(6-fluoro-2-oxo-1,2-dihydro-quinolin-3-yl)-
[1,2,3]triazol-1-yl]-phenyl}-N-methyl-acetamide
("A353")

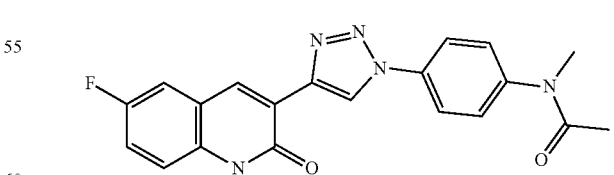

HPLC/MS 1.45 min (A), [M+H]⁺ 378;
¹H NMR (400 MHz, DMSO-d₆) δ 12.27 (s, 1H), 9.26 (s,
1H), 8.84 (s, 1H), 8.07 (d, J=8.2 Hz, 2H), 7.80 (dd, J=9.3,
2.6 Hz, 1H), 7.59 (d, J=8.5 Hz, 2H), 7.53-7.38 (m, 2H), 3.24
(bs, 3H), 1.90 (bs, 3H).

6-fluoro-3-[1-(2-methyl-oxo-2,3-dihydro-1H-isoindol-5-yl)-1H-[1,2,3]triazol-4-yl]-1H-quinolin-2-one ("A354")

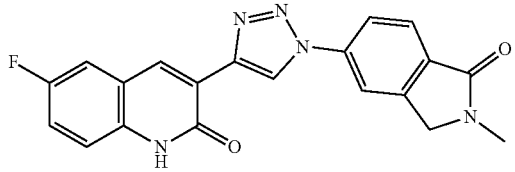 [SMILES: CN1Cc2cc(-n3cc(-c4cc5cc(F)ccc5[nH]c4=O)nn3)ccc2C1=O]

UPLC/MS 0.66 min, [M+H]+ 376;

¹H NMR (400 MHz, DMSO-d₆) δ 12.30 (s, 1H), 9.34 (s, 1H), 8.88 (s, 1H), 8.31 (d, J=1.9 Hz, 1H), 8.15 (dd, J=8.2, 2.0 Hz, 1H), 7.87 (d, J=8.2 Hz, 1H), 7.81 (dd, J=9.3, 2.7 Hz, 1H), 7.54-7.30 (m, 2H), 3.13 (s, 3H), 2.55 (s, 2H).

6-Fluoro-3-{1-[4-((trans)-3-methoxy-cyclopentyloxy)-phenyl]-1H-[1,2,3]triazol-4-yl}-1H-quinolin-2-one ("A355")

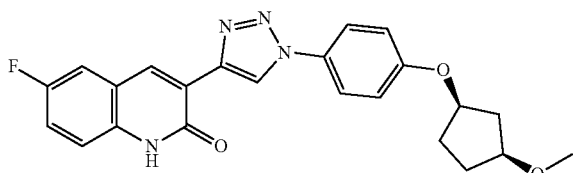

HPLC/MS 1.73 min (A), [M+H]+ 421;

¹H NMR (400 MHz, DMSO-d₆) δ 12.24 (s, 1H), 9.09 (s, 1H), 8.82 (s, 1H), 7.92-7.83 (m, 2H), 7.79 (dd, J=9.1, 2.6 Hz, 1H), 7.51-7.37 (m, 2H), 7.15-7.00 (m, 2H), 4.85 (tt, J=7.2, 3.4 Hz, 1H), 3.83 (p, J=4.7 Hz, 1H), 3.20 (s, 3H), 2.39 (dt, J=14.1, 7.0 Hz, 1H), 2.07-1.96 (m, 1H), 1.90-1.74 (m, 2H), 1.69 (dt, J=14.4, 3.9 Hz, 1H).

6-chloro-3-{1-[4-((1S,3R)-3-methoxy-cyclopentyloxy)-phenyl]-1H-[1,2,3]triazol-4-yl}-1H-quinolin-2-one ("A356")

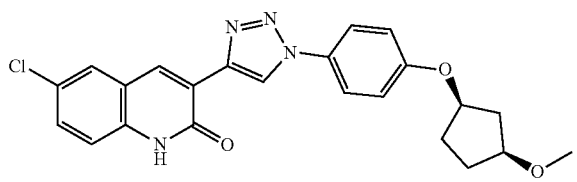 [SMILES: CO[C@H]1CC[C@@H](Oc2ccc(-n3cc(-c4cc5cc(Cl)ccc5[nH]c4=O)nn3)cc2)C1]

HPLC/MS 1.83 min (A), [M+H]+ 437;

¹H NMR (500 MHz, DMSO-d₆) δ 12.30 (s, 1H), 9.10 (s, 1H), 8.82 (s, 1H), 8.05 (d, J=2.4 Hz, 1H), 7.87 (d, J=9.0 Hz, 2H), 7.58 (dd, J=8.8, 2.4 Hz, 1H), 7.41 (d, J=8.7 Hz, 1H), 7.19-6.97 (m, 2H), 4.86 (tt, J=7.1, 3.8 Hz, 1H), 3.84 (dq, J=6.6, 4.7 Hz, 1H), 3.21 (s, 3H), 2.40 (dt, J=14.1, 7.0 Hz, 1H), 2.02 (dtd, J=15.1, 7.6, 5.8 Hz, 1H), 1.89-1.74 (m, 3H), 1.70 (dt, J=14.4, 4.0 Hz, 1H).

6-fluoro-3-[1-(4-methoxy-phenyl)-1H-[1,2,3]triazol-4-yl]-1H-quinolin-2-one ("A357")

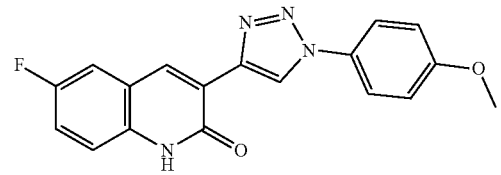 [SMILES: COc1ccc(-n2cc(-c3cc4cc(F)ccc4[nH]c3=O)nn2)cc1]

UPLC/MS 0.77 min, [M+H]+ 337;

¹H NMR (400 MHz, DMSO-d₆) δ 12.25 (s, 1H), 9.11 (s, 1H), 8.82 (s, 1H), 8.09-7.86 (m, 2H), 7.79 (dd, J=9.1, 2.5 Hz, 1H), 7.58-7.36 (m, 2H), 7.23-7.01 (m, 2H), 3.86 (s, 3H).

6-fluoro-3-{1-[4-((R)-3-methoxy-pyrrolidine-1-sulfonyl)-phenyl]-1H-[1,2,3]triazol-4-yl}-1H-quinolin-2-one ("A358")

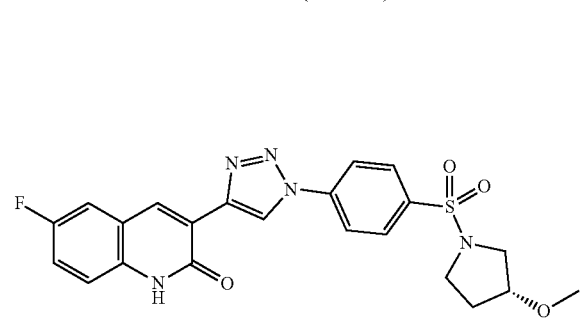

HPLC/MS 1.63 min (A), [M+H]+ 470;

¹H NMR (700 MHz, DMSO-d₆) δ 12.33 (s, 1H), 9.40 (s, 1H), 8.88 (s, 1H), 8.31 (d, J=8.7 Hz, 2H), 8.13-7.97 (m, 2H), 7.82 (dd, J=9.1, 2.8 Hz, 1H), 7.47 (td, J=8.8, 2.9 Hz, 1H), 7.43 (dd, J=9.0, 4.8 Hz, 1H), 3.86 (dq, J=5.7, 3.0 Hz, 1H), 3.37-3.30 (m, 3H), 3.17 (td, J=9.6, 7.2 Hz, 1H), 3.04 (s, 3H), 1.92-1.72 (m, 2H).

6-chloro-3-{1-[4-((R)-3-methoxy-pyrrolidine-1-sulfonyl)-phenyl]-1H-[1,2,3]triazol-4-yl}-1H-quinolin-2-one ("A359")

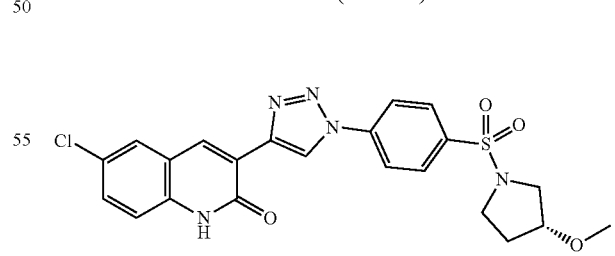

HPLC/MS 1.73 min (A), [M+H]+ 486;

¹H NMR (400 MHz, DMSO-d₆) δ 12.35 (s, 1H), 9.38 (s, 1H), 8.86 (s, 1H), 8.38-8.23 (m, 2H), 8.06 (d, J=2.3 Hz, 1H), 8.05-7.97 (m, 2H), 7.60 (dd, J=8.8, 2.3 Hz, 1H), 7.41 (d, J=8.8 Hz, 1H), 3.87 (p, J=3.2 Hz, 1H), 3.38-3.30 (m, 3H), 3.18 (td, J=9.4, 7.5 Hz, 1H), 1.89-1.70 (m, 2H).

6-fluoro-3-{1-[4-((S)-3-methoxy-pyrrolidine-1-sulfonyl)-phenyl]-1H-[1,2,3]triazol-4-yl}-1H-quinolin-2-one ("A360")

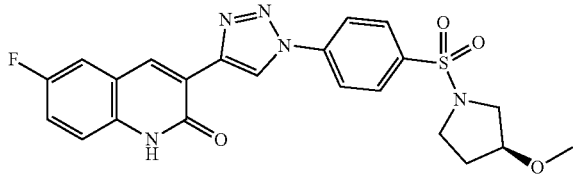 [SMILES: CO[C@H]1CCN(S(=O)(=O)c2ccc(-n3cc(-c4cc5cc(F)ccc5[nH]c4=O)nn3)cc2)C1]

HPLC/MS 1.63 min (A), [M+H]$^+$ 470;

$^1$H NMR (700 MHz, DMSO-d$_6$) δ 12.33 (s, 1H), 9.40 (s, 1H), 8.88 (s, 1H), 8.31 (d, J=8.7 Hz, 2H), 8.13-7.97 (m, 2H), 7.82 (dd, J=9.1, 2.8 Hz, 1H), 7.47 (td, J=8.8, 2.9 Hz, 1H), 7.43 (dd, J=9.0, 4.8 Hz, 1H), 3.86 (dq, J=5.7, 3.0 Hz, 1H), 3.37-3.30 (m, 3H), 3.17 (td, J=9.6, 7.2 Hz, 1H), 3.04 (s, 3H), 1.92-1.72 (m, 2H).

6-chloro-3-{1-[4-((S)-3-methoxy-pyrrolidine-1-sulfonyl)-phenyl]-1H-[1,2,3]triazol-4-yl}-1H-quinolin-2-one ("A361")

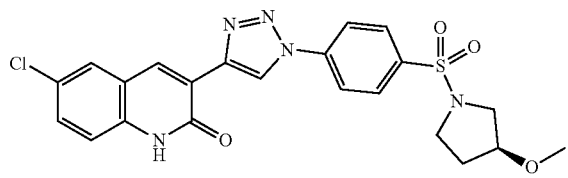 [SMILES: CO[C@H]1CCN(S(=O)(=O)c2ccc(-n3cc(-c4cc5cc(Cl)ccc5[nH]c4=O)nn3)cc2)C1]

HPLC/MS 1.73 min (A), [M+H]$^+$ 486;

$^1$H NMR (400 MHz, DMSO-d$_6$) δ 12.35 (s, 1H), 9.38 (s, 1H), 8.86 (s, 1H), 8.38-8.23 (m, 2H), 8.06 (d, J=2.3 Hz, 1H), 8.05-7.97 (m, 2H), 7.60 (dd, J=8.8, 2.3 Hz, 1H), 7.41 (d, J=8.8 Hz, 1H), 3.87 (p, J=3.2 Hz, 1H), 3.38-3.30 (m, 3H), 3.18 (td, J=9.4, 7.5 Hz, 1H), 1.89-1.70 (m, 2H).

6-fluoro-3-{1-[4-((1S,2S)-2-methoxy-cyclopentyloxy)-phenyl]-1H-[1,2,3]triazol-4-yl}-1H-quinolin-2-one ("A362")

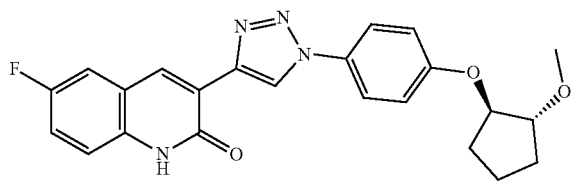 [SMILES: CO[C@@H]1CCC[C@H]1Oc1ccc(-n2cc(-c3cc4cc(F)ccc4[nH]c3=O)nn2)cc1]

HPLC/MS 1.83 min (A), [M+H]$^+$ 421;

$^1$H NMR (500 MHz, DMSO-d$_6$) δ 12.29 (s, 1H), 9.13 (s, 1H), 8.84 (s, 1H), 8.03-7.86 (m, 2H), 7.81 (dd, J=9.2, 2.8 Hz, 1H), 7.46 (td, J=8.8, 2.8 Hz, 1H), 7.42 (dd, J=9.0, 4.9 Hz, 1H), 7.20-7.13 (m, 2H), 4.74 (dt, J=6.0, 2.9 Hz, 1H), 3.85-3.81 (m, 1H), 3.30 (s, 3H), 2.19-2.07 (m, 1H), 2.03-1.90 (m, 1H), 1.75-1.61 (m, 4H).

6-chloro-3-[1-(4-cyclopentyloxy-phenyl)-1H-[1,2,3]triazol-4-yl]-1H-quinolin-2-one ("A363")

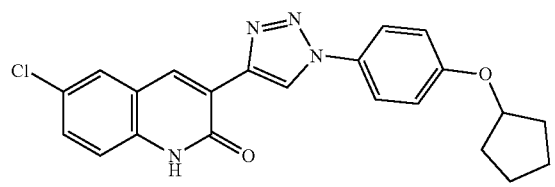 [SMILES: O=c1[nH]c2ccc(Cl)cc2cc1-c1cn(-c2ccc(OC3CCCC3)cc2)nn1]

UPLC/MS 0.97 min, [M+H]$^+$ 407;

$^1$H NMR (500 MHz, DMSO-d$_6$) δ 12.34 (s, 1H), 9.11 (s, 1H), 8.82 (s, 1H), 8.06 (d, J=2.4 Hz, 1H), 7.95-7.82 (m, 2H), 7.59 (dd, J=8.8, 2.4 Hz, 1H), 7.40 (d, J=8.8 Hz, 1H), 7.16-7.06 (m, 2H), 4.95-4.90 (m, 1H), 2.07-1.85 (m, 2H), 1.84-1.68 (m, 4H), 1.67-1.57 (m, 2H).

3-[1-(4-cyclopentyloxy-phenyl)-1H-[1,2,3]triazol-4-yl]-6-fluoro-1H-quinolin-2-one ("A364")

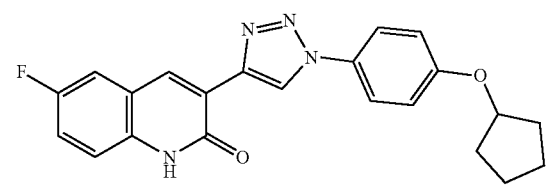 [SMILES: O=c1[nH]c2ccc(F)cc2cc1-c1cn(-c2ccc(OC3CCCC3)cc2)nn1]

UPLC/MS 0.91 min, [M+H]$^+$ 391;

$^1$H NMR (500 MHz, DMSO-d$_6$) δ 12.29 (s, 1H), 9.11 (s, 1H), 8.83 (s, 1H), 7.91-7.85 (m, 2H), 7.81 (dd, J=9.3, 2.8 Hz, 1H), 7.46 (td, J=8.8, 2.8 Hz, 1H), 7.42 (dd, J=9.1, 4.9 Hz, 1H), 7.15-7.09 (m, 2H), 4.95-4.90 (m, 1H), 2.02-1.92 (m, 2H), 1.80-1.68 (m, 4H), 1.68-1.56 (m, 2H).

6-fluoro-3-{1-[4-(tetrahydro-furan-3-yloxy)-phenyl]-1H-[1,2,3]triazol-4-yl}-1H-quinolin-2-one ("A365")

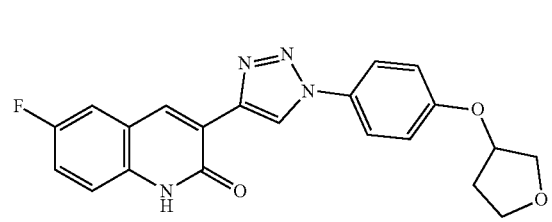 [SMILES: O=c1[nH]c2ccc(F)cc2cc1-c1cn(-c2ccc(OC3CCOC3)cc2)nn1]

UPLC/MS 0.77 min, [M+H]$^+$ 393;

$^1$H NMR (500 MHz, DMSO-d$_6$) δ 12.29 (s, 1H), 9.13 (s, 1H), 8.83 (s, 1H), 8.04-7.87 (m, 2H), 7.81 (dd, J=9.2, 2.8 Hz, 1H), 7.46 (td, J=8.8, 2.8 Hz, 1H), 7.42 (dd, J=9.0, 4.9 Hz, 1H), 7.18-7.11 (m, 2H), 5.15 (ddt, J=6.2, 3.9, 1.7 Hz, 1H), 3.93 (dd, J=10.2, 4.5 Hz, 1H), 3.91-3.82 (m, 2H), 3.79 (td, J=8.4, 4.6 Hz, 1H), 2.28 (dtd, J=16.4, 8.2, 6.2 Hz, 1H), 2.06-1.94 (m, 1H).

6-chloro-3-{1-[4-(tetrahydro-furan-3-yloxy)-phenyl]-1H-[1,2,3]triazol-4-yl}-1H-quinolin-2-one ("A366")

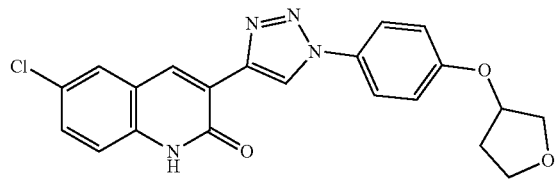 [SMILES: O=c1[nH]c2ccc(Cl)cc2cc1-c1cn(-c2ccc(OC3CCOC3)cc2)nn1]

UPLC/MS 0.82 min, [M+H]+ 409;

$^{1}$H NMR (500 MHz, DMSO-$d_6$) δ 12.34 (s, 1H), 9.12 (s, 1H), 8.82 (s, 1H), 8.06 (d, J=2.3 Hz, 1H), 7.98-7.83 (m, 2H), 7.59 (dd, J=8.8, 2.4 Hz, 1H), 7.40 (d, J=8.8 Hz, 1H), 7.14 (d, J=9.0 Hz, 2H), 5.14 (ddd, J=6.2, 4.2, 1.9 Hz, 1H), 3.93 (dd, J=10.2, 4.5 Hz, 1H), 3.91-3.82 (m, 2H), 3.79 (td, J=8.4, 4.6 Hz, 1H), 2.28 (dtd, J=14.4, 8.2, 6.2 Hz, 1H), 2.07-1.95 (m, 1H).

EXAMPLE 10

7-fluoro-3-{1-[4-(piperazine-1-carbonyl)-phenyl]-1H-[1,2,3]triazol-4-yl}-1H-quinolin-2-one ("A117") and 7-fluoro-3-{1-[4-(4-methyl-piperazine-1-carbonyl)-phenyl]-1H-[1,2,3]triazol-4-yl}-1H-quinolin-2-one ("A118")

added triethylamine (388 µl, 2.80 mmol) and the reaction mixture is stirred for 16 hours at room temperature. The reaction mixture is treated with dichloromethane and water. The organic phase is separated and the aqueous phase is extracted with dichloromethane. The combined organic phases are dried over sodium sulfate and evaporated. The residue is chromatographed on a silica gel column with dichloromethane/methanol as eluent to afford 4-{4-[4-(7-fluoro-2-oxo-1,2-dihydro-quinolin-3-yl)-[1,2,3]triazol-1-yl]-benzoyl}-piperazine-1-carboxylic acid tert-butyl ester as beige solid; HPLC/MS 1.70 min (A), [M+H]+ 519.

EXAMPLE 10A

Synthesis of "A117"

A suspension of 4-{4-[4-(7-fluoro-2-oxo-1,2-dihydro-quinolin-3-yl)-[1,2,3]triazol-1-yl]-benzoyl}-piperazine-1-carboxylic acid tert-butyl ester (83.0 mg, 0.16 mmol) in a 4 M solution of hydrochloric acid in dioxane (362 µl) is heated to 70° C. and stirred at this temperature in a closed reaction vial for 4 hours. The reaction mixture is allowed to reach room temperature and concentrated under vacuum. The residue is treated with saturated $Na_2CO_3$ solution and the mixture is evaporated. The solid residue is extracted with a mixture of dichloromethane and methanol. The extraction solution is evaporated and the residue is chromatographed on a silica gel column with dichloromethane/methanol as eluent to afford 7-fluoro-3-{1-[4-(piperazine-1-carbonyl)-phenyl]-1H-[1,2,3]triazol-4-yl}-1H-quinolin-2-one as off-white solid; HPLC/MS 1.18 min (A), [M+H]+ 419. $^{1}$H NMR

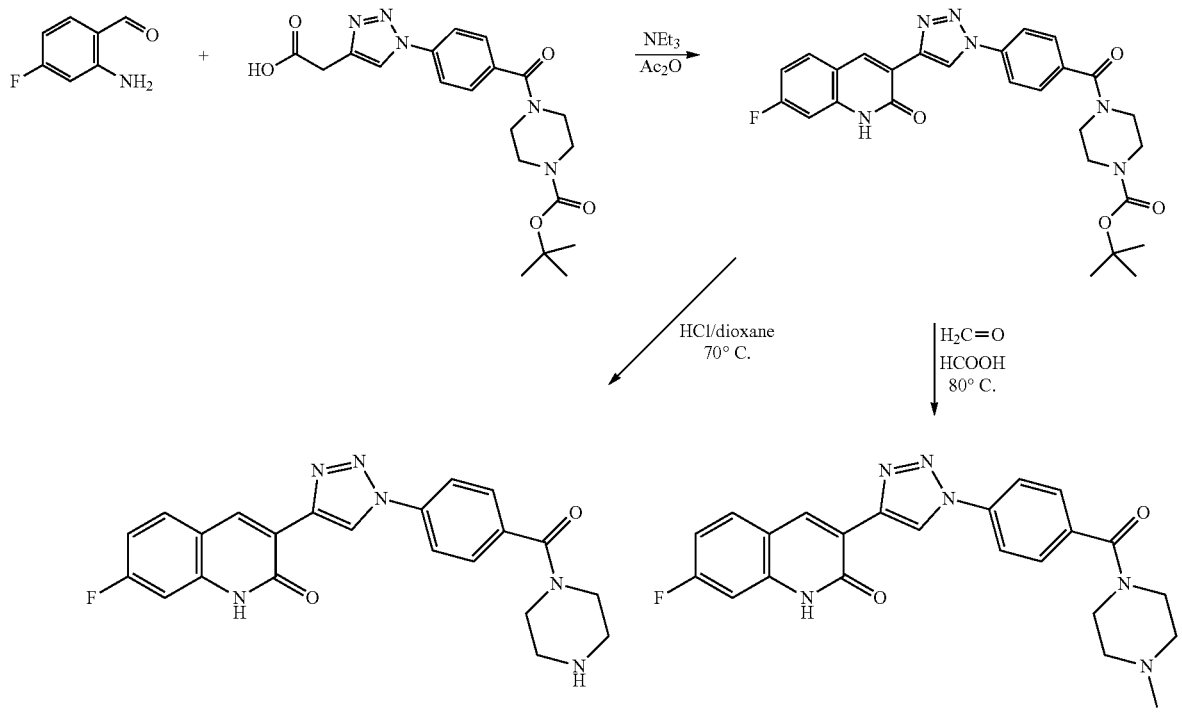

To a suspension of 4-[4-(4-carboxymethyl-[1,2,3]triazol-1-yl)-benzoyl]-piperazine-1-carboxylic acid tert-butyl ester (291 mg, 0.70 mmol) and 2-Amino-4-fluoro-benzaldehyde (97.4 mg, 0.7 mmol) in acetic acid anhydride (1.17 ml) is (400 MHz, DMSO-$d_6$, TFA-$d_1$) δ 9.26 (s, 1H), 8.87 (s, 1H), 8.11 (d, J=8.6 Hz, 2H), 7.90 (dd, J=8.8, 6.0 Hz, 1H), 7.74 (d, J=8.6 Hz, 2H), 7.22 (dd, J=10.2, 2.5 Hz, 1H), 7.06 (td, J=8.8, 2.5 Hz, 1H), 3.83 (bs, 4H), 3.27 (bs, 4H).

The following compounds are prepared similarly:

5-fluoro-3-{1-[4-(piperazine-1-carbonyl)-phenyl]-1H-[1,2,3]triazol-4-yl}-1H-quinolin-2-one ("A119")

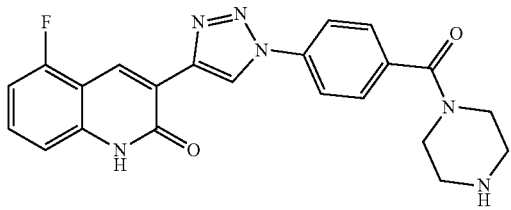 [SMILES: O=C(c1ccc(-n2cc(-c3cc4c(F)cccc4[nH]c3=O)nn2)cc1)N1CCNCC1]

beige solid; HPLC/MS 1.20 min (A), [M+H]⁺ 419; $^1$H NMR (400 MHz, DMSO-d$_6$, TFA-d$_1$) δ 9.17 (s, 1H), 8.84 (s, 1H), 8.00 (d, J=8.7 Hz, 2H), 7.62 (d, J=8.6 Hz, 2H), 7.40 (td, J=8.2, 5.9 Hz, 1H), 7.19 (d, J=8.3 Hz, 1H), 6.95-6.86 (m, 1H), 3.72 (bs, 4H), 3.15 (bs, 4H).

8-fluoro-3-{1-[4-(piperazine-1-carbonyl)-phenyl]-1H-[1,2,3]triazol-4-yl}-1H-quinolin-2-one ("A120")

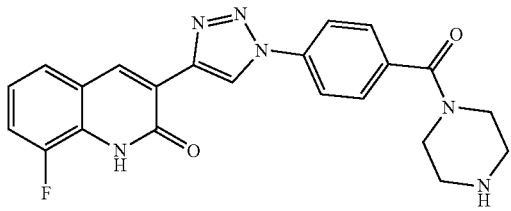 [SMILES: O=C(c1ccc(-n2cc(-c3cc4cccc(F)c4[nH]c3=O)nn2)cc1)N1CCNCC1]

beige solid; HPLC/MS 1.17 min (A), [M+H]⁺ 419; $^1$H NMR (500 MHz, DMSO-d$_6$, TFA-d$_1$) δ 9.27 (s, 1H), 8.90 (d, J=1.5 Hz, 1H), 8.09 (d, J=8.6 Hz, 2H), 7.73 (d, J=8.5 Hz, 2H), 7.66 (d, J=7.8 Hz, 1H), 7.37 (ddd, J=11.0, 8.1, 1.2 Hz, 1H), 7.23 (td, J=8.0, 4.8 Hz, 1H), 3.85 (bs, 4H), 3.27 (bs, 4H).

3-{1-[4-(piperazine-1-carbonyl)-phenyl]-1H-[1,2,3]triazol-4-yl}-1H-[1,8]naphthyridin-2-one ("A121")

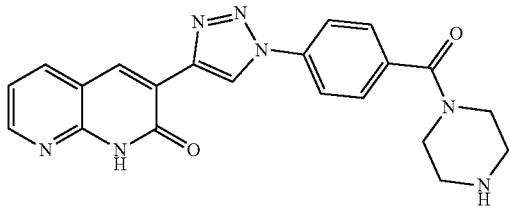 [SMILES: O=C(c1ccc(-n2cc(-c3cc4cccnc4[nH]c3=O)nn2)cc1)N1CCNCC1]

beige solid; HPLC/MS 1.05 min (A), [M+H]⁺ 402; $^1$H NMR (400 MHz, DMSO-d$_6$, TFA-d$_1$) δ 9.21 (s, 1H), 8.83 (s, 1H), 8.52 (dd, J=4.9, 1.8 Hz, 1H), 8.31 (dd, J=7.9, 1.7 Hz, 1H), 8.04 (d, J=8.6 Hz, 2H), 7.66 (d, J=8.6 Hz, 2H), 7.27 (dd, J=7.8, 4.9 Hz, 1H), 3.72 (bs, 4H), 3.18 (bs, 4H).

6-fluoro-3-{1-[4-(piperazine-1-carbonyl)-phenyl]-1H-[1,2,3]triazol-4-yl}-1H-[1,8]naphthyridin-2-one ("A122")

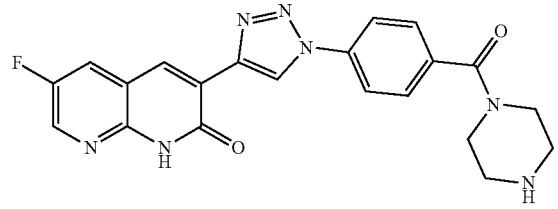 [SMILES: O=C(c1ccc(-n2cc(-c3cc4cc(F)cnc4[nH]c3=O)nn2)cc1)N1CCNCC1]

beige solid; HPLC/MS 1.08 min (A), [M+H]⁺ 420; $^1$H NMR (400 MHz, DMSO-d$_6$) δ 12.74 (s, 1H), 9.32 (s, 1H), 9.30 (bs, 1H), 8.88 (s, 1H), 8.63 (d, J=2.7 Hz, 1H), 8.37 (dd, J=8.7, 2.9 Hz, 1H), 8.13 (d, J=8.6 Hz, 2H), 7.73 (d, J=8.6 Hz, 2H), 3.75 (bs, 4H), 3.19 (s, 4H).

6-chloro-3-{1-[4-(piperazine-1-carbonyl)-phenyl]-1H-[1,2,3]triazol-4-yl}-1H-quinolin-2-one ("A123")

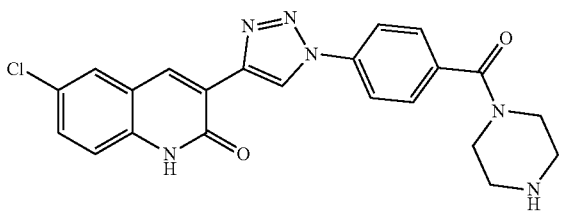 [SMILES: O=C(c1ccc(-n2cc(-c3cc4cc(Cl)ccc4[nH]c3=O)nn2)cc1)N1CCNCC1]

off-white solid; HPLC/MS 1.26 min (A), [M+H]⁺ 435; $^1$H NMR (400 MHz, DMSO-d$_6$) δ 12.35 (s, 1H), 9.30 (s, 1H), 9.28 (bs, 1H), 8.85 (s, 1H), 8.13 (d, J=8.5 Hz, 2H), 8.06 (d, J=2.3 Hz, 1H), 7.73 (d, J=8.6 Hz, 1H), 7.60 (dd, J=8.7, 2.4 Hz, 1H), 7.43 (d, J=8.7 Hz, 1H), 3.75 (bs, 4H), 3.20 (s, 4H).

3-[1-(4-[1,4]diazepan-1-yl-phenyl)-1H-[1,2,3]triazol-4-yl]-6-fluoro-1H-[1,8]naphthyridin-2-one ("A124")

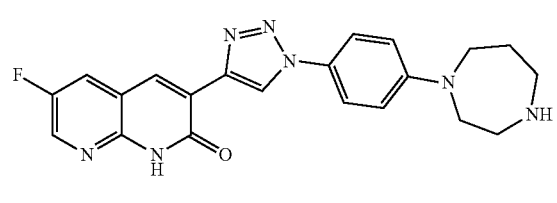 [SMILES: O=c1[nH]c2ncc(F)cc2cc1-c1cn(-c2ccc(N3CCCNCC3)cc2)nn1]

green-brown solid; HPLC/MS 1.17 min (A), [M+H]⁺ 406; $^1$H NMR (400 MHz, DMSO-d$_6$, TFA-d$_1$) δ 9.05 (s, 1H), 8.84 (s, 1H), 8.52 (d, J=2.9 Hz, 1H), 8.18 (dd, J=8.5, 2.9 Hz, 1H), 7.78 (d, J=9.1 Hz, 2H), 6.99 (d, J=9.2 Hz, 2H), 3.85 (t, J=5.2 Hz, 2H), 3.65 (t, J=6.1 Hz, 2H), 3.38 (t, J=5.1 Hz, 2H), 3.29-3.19 (m, 2H), 2.19 (p, J=5.9 Hz, 2H).

6-fluoro-3-{1-[3-(piperazine-1-carbonyl)-phenyl]-
1H-[1,2,3]triazol-4-yl}-1H-quinolin-2-one ("A125")

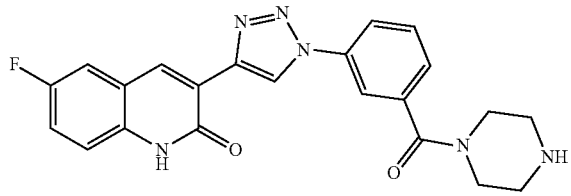 [SMILES: O=C(c1cccc(-n2cc(-c3cc4cc(F)ccc4[nH]c3=O)nn2)c1)N1CCNCC1]

beige solid; HPLC/MS 1.19 min (A), [M+H]+ 419; 1H NMR (400 MHz, DMSO-d6, TFA-d1) δ 9.31 (s, 1H), 8.86 (s, 1H), 8.18-8.10 (m, 2H), 7.75-7.64 (m, 2H), 7.59 (d, J=7.6 Hz, 1H), 7.50 (dd, J=9.0, 4.7 Hz, 1H), 7.37 (td, J=8.8, 2.8 Hz, 1H), 3.89 (bs, 4H), 3.27 (s, 4H).

7-chloro-3-{1-[4-(piperazine-1-carbonyl)-phenyl]-
1H-[1,2,3]triazol-4-yl}-1H-quinolin-2-one ("A126")

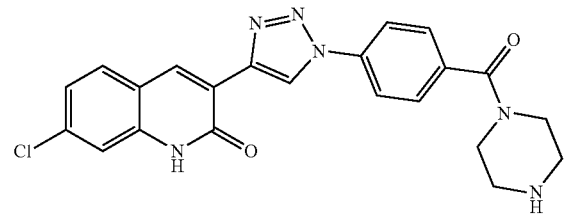 [SMILES: O=C(c1ccc(-n2cc(-c3cc4ccc(Cl)cc4[nH]c3=O)nn2)cc1)N1CCNCC1]

white solid; HPLC/MS 1.27 min (A), [M+H]+ 435; 1H NMR (400 MHz, DMSO-d6) δ 12.28 (bs, 1H), 9.25 (s, 1H), 8.85 (s, 1H), 8.08 (d, J=8.6 Hz, 2H), 7.95 (d, J=8.5 Hz, 1H), 7.62 (d, J=8.6 Hz, 2H), 7.42 (d, J=2.0 Hz, 1H), 7.30 (dd, J=8.4, 2.0 Hz, 1H), 3.65-3.35 (m, 4H), 2.72 (bs, 4H).

5,6-difluoro-3-{1-[4-(piperazine-1-carbonyl)-phe-
nyl]-1H-[1,2,3]triazol-4-yl}-1H-quinolin-2-one
("A127")

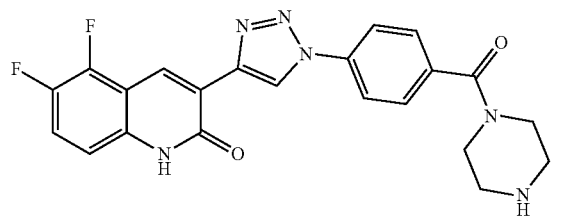 [SMILES: O=C(c1ccc(-n2cc(-c3cc4c(F)c(F)ccc4[nH]c3=O)nn2)cc1)N1CCNCC1]

beige solid; HPLC/MS 1.20 min (A), [M+H]+ 437; 1H NMR (400 MHz, DMSO-d6, TFA-d1) δ 9.27 (s, 1H), 8.83 (s, 1H), 8.13-8.04 (m, 2H), 7.69 (d, J=8.2 Hz, 2H), 7.51 (q, J=9.3, 8.9 Hz, 1H), 7.22 (dd, J=9.4, 3.6 Hz, 1H), 3.73 (bs, 4H), 3.20 (bs, 4H).

6,7-difluoro-3-{1-[4-(piperazine-1-carbonyl)-phe-
nyl]-1H-[1,2,3]triazol-4-yl}-1H-quinolin-2-one
("A128")

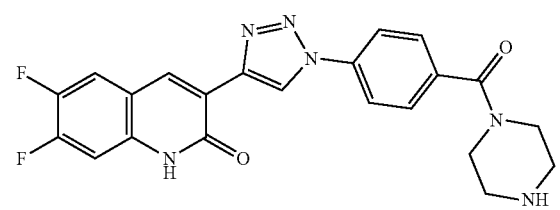 [SMILES: O=C(c1ccc(-n2cc(-c3cc4cc(F)c(F)cc4[nH]c3=O)nn2)cc1)N1CCNCC1]

hydrochloride: beige solid; UPLC/MS 0.48 min, [M+H]+ 437; 1H NMR (500 MHz, DMSO-d6) δ 12.35 (s, 1H), 9.29 (s, 1H), 8.97 (bs, 2H), 8.85 (s, 1H), 8.23-8.02 (m, 3H), 7.71 (d, J=8.5 Hz, 2H), 7.35 (dd, J=11.4, 7.0 Hz, 1H), 3.71 (bs, 4H), 3.16 (bs, 4H).

6-fluoro-3-{1-[4-(piperazine-1-sulfonyl)-phenyl]-
1H-[1,2,3]triazol-4-yl}-1H-quinolin-2-one ("A129")

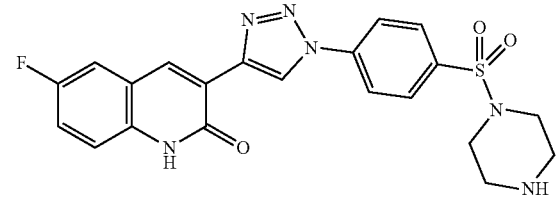 [SMILES: O=c1[nH]c2ccc(F)cc2cc1-c1cn(-c2ccc(S(=O)(=O)N3CCNCC3)cc2)nn1]

hydrochloride: beige powder; UPLC/MS 0.50 min, [M+H]+ 455; 1H NMR (500 MHz, DMSO-d6) δ 12.32 (s, 1H), 9.42 (s, 1H), 9.07 (s, 2H), 8.87 (s, 1H), 8.58-8.28 (m, 2H), 8.17-7.95 (m, 2H), 7.81 (dd, J=9.2, 2.7 Hz, 1H), 7.56-7.37 (m, 2H), 3.26-3.19 (m, 8H).

6,7-difluoro-3-{1-[4-(2-piperazin-1-yl-ethoxy)-phe-
nyl]-1H-[1,2,3]triazol-4-yl}-1H-quinolin-2-one
("A130")

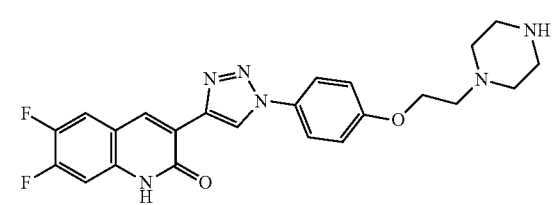 [SMILES: O=c1[nH]c2cc(F)c(F)cc2cc1-c1cn(-c2ccc(OCCN3CCNCC3)cc2)nn1]

light brown solid; HPLC/MS 1.20 min (A), [M+H]+ 453.

115

6-fluoro-3-{1-[4-(3-piperazin-1-yl-propoxy)-phenyl]-1H-[1,2,3]triazol-4-yl}-1H-quinolin-2-one ("A131")

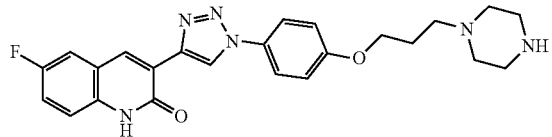 [SMILES: O=c1[nH]c2ccc(F)cc2cc1-c1cn(-c2ccc(OCCCN3CCNCC3)cc2)nn1]

off-white powder; HPLC/MS 1.15 min (A), [M+H]+ 449.

6-fluoro-3-{1-[4-(piperidine-4-carbonyl)-phenyl]-1H-[1,2,3]triazol-4-yl}-1H-quinolin-2-one ("A132")

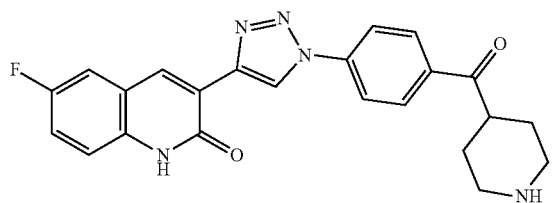 [SMILES: O=C(c1ccc(-n2cc(-c3cc4cc(F)ccc4[nH]c3=O)nn2)cc1)C1CCNCC1]

hydrochloride: beige solid; HPLC/MS 1.25 min (A), [M+H]+ 418. $^1$H NMR (500 MHz, DMSO-d$_6$) δ 12.31 (s, 1H), 9.40 (s, 1H), 8.88 (s, 1H), 8.64 (d, J=11.5 Hz, 1H), 8.45-8.33 (m, 1H), 8.25 (m, 4H), 7.83 (dd, J=9.2, 2.7 Hz, 1H), 7.48 (td, J=8.7, 2.8 Hz, 1H), 7.44 (dd, J=9.1, 5.0 Hz, 1H), 3.86 (tt, J=11.2, 3.6 Hz, 1H), 3.37 (d, J=13.0 Hz, 2H), 3.15-3.02 (m, 2H), 2.06-1.96 (m, 2H), 1.79 (dtd, J=14.5, 11.4, 10.9, 4.0 Hz, 2H).

6-fluoro-3-{1-[4-(2-piperidin-4-yl-ethoxy)-phenyl]-1H-[1,2,3]triazol-4-yl}-1H-quinolin-2-one ("A133")

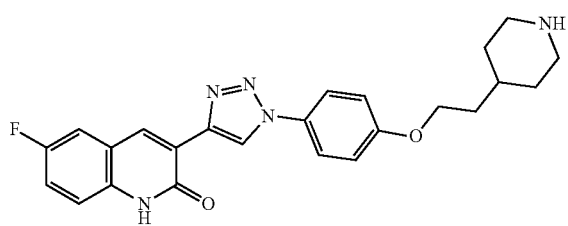 [SMILES: O=c1[nH]c2ccc(F)cc2cc1-c1cn(-c2ccc(OCCC3CCNCC3)cc2)nn1]

beige solid; HPLC/MS 1.31 min (A), [M+H]+ 434.

6,7-difluoro-3-{1-[4-(2-piperidin-4-yl-ethoxy)-phenyl]-1H-[1,2,3]triazol-4-yl}-1H-quinolin-2-one ("A134")

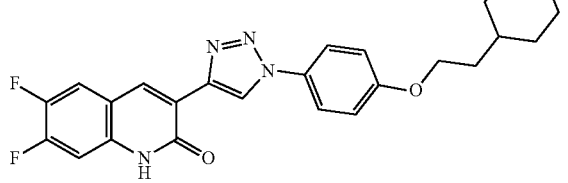

off-white solid; HPLC/MS 1.34 min (A), [M+H]+ 452.

116

6,7-difluoro-3-{1-[4-(3-piperazin-1-yl-propoxy)-phenyl]-1H-[1,2,3]triazol-4-yl}-1H-quinolin-2-one ("A135")

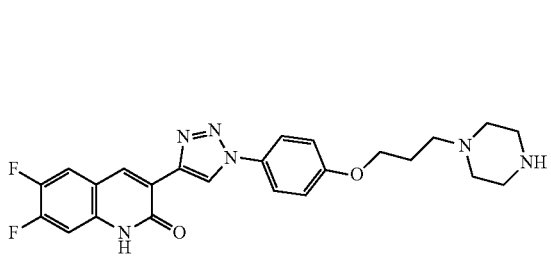 [SMILES: O=c1[nH]c2cc(F)c(F)cc2cc1-c1cn(-c2ccc(OCCCN3CCNCC3)cc2)nn1]

off-white powder; HPLC/MS 1.19 min (A), [M+H]+ 467.

6,7-difluoro-3-{1-[4-(piperidine-4-carbonyl)-phenyl]-1H-[1,2,3]triazol-4-yl}-1H-quinolin-2-one ("A136")

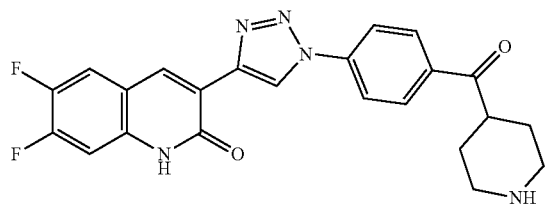 [SMILES: O=C(c1ccc(-n2cc(-c3cc4cc(F)c(F)cc4[nH]c3=O)nn2)cc1)C1CCNCC1]

hydrochloride; beige solid; UPLC/MS 0.76 min, [M+H]+ 436. $^1$H NMR (400 MHz, DMSO-d$_6$) δ 12.36 (s, 1H), 9.37 (s, 1H), 8.86 (s, 1H), 8.83 (bs, 1H), 8.55 (bs, 1H), 8.24 (s, 4H), 8.10 (dd, J=11.0, 8.6 Hz, 1H), 7.35 (dd, J=11.5, 7.1 Hz, 1H), 3.86 (ddd, J=11.2, 7.7, 3.5 Hz, 1H), 3.33 (m, 2H), 3.08 (q, J=11.8 Hz, 2H), 2.01 (d, J=14.0 Hz, 2H), 1.89-1.68 (m, 2H).

6-methyl-3-{1-[4-(piperazine-1-carbonyl)-phenyl]-1H-[1,2,3]triazol-4-yl}-1H-quinolin-2-one ("A137")

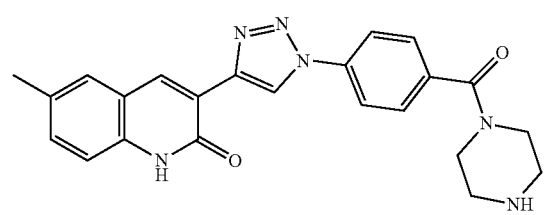 [SMILES: Cc1ccc2[nH]c(=O)c(-c3cn(-c4ccc(C(=O)N5CCNCC5)cc4)nn3)cc2c1]

hydrochloride: beige solid; UPLC/MS 0.72 min, [M+H]+ 415. $^1$H NMR (500 MHz, DMSO-d$_6$) δ 12.14 (s, 1H), 9.28 (s, 1H), 9.14 (bs, 2H), 8.77 (s, 1H), 8.29-8.00 (m, 2H), 7.75-7.70 (m, 2H), 7.69 (bs, 1H), 7.41 (dd, J=8.4, 1.9 Hz, 1H), 7.33 (d, J=8.3 Hz, 1H), 3.74 (bs, 4H), 3.20 (bs, 4H), 2.40 (s, 3H).

5,7-difluoro-3-{1-[1-(2-oxo-2-piperazin-1-yl-ethyl)-1H-indol-5-yl]-1H-[1,2,3]triazol-4-yl}-1H-quinolin-2-one ("A138")

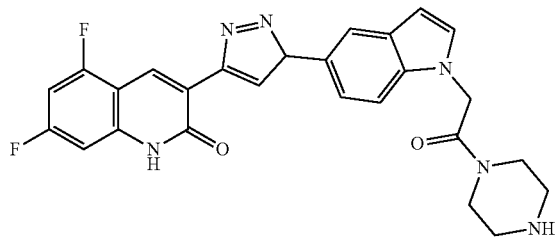 [SMILES: O=C(Cn1ccc2cc(C3C=C(c4cc5c(F)cc(F)cc5[nH]c4=O)N=N3)ccc21)N1CCNCC1]

hydrochloride: beige solid; UPLC/MS 0.92 min, [M+H]$^+$ 490. $^1$H NMR (400 MHz, DMSO-d$_6$) δ 12.33 (s, 1H), 9.29 (bs, 2H), 9.11 (s, 1H), 8.84 (s, 1H), 8.12 (d, J=2.1 Hz, 1H), 8.09 (dd, J=11.1, 8.7 Hz, 1H), 7.69 (dd, J=8.8, 2.1 Hz, 1H), 7.62 (d, J=8.9 Hz, 1H), 7.41 (d, J=3.1 Hz, 1H), 7.35 (dd, J=11.5, 7.1 Hz, 1H), 5.34 (s, 2H), 3.84 (bs, 2H), 3.71 (bs, 2H), 3.26 (bs, 2H), 3.12 (bs, 2H).

6,7-difluoro-3-{1-[1-(2-oxo-2-piperazin-1-yl-ethyl)-1H-indol-5-yl]-1H-[1,2,3]triazol-4-yl}-1H-quinolin-2-one ("A139")

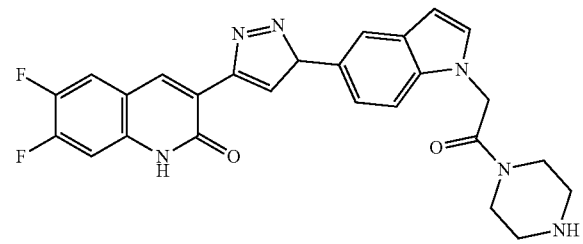 [SMILES: O=C(Cn1ccc2cc(C3C=C(c4cc5cc(F)c(F)cc5[nH]c4=O)N=N3)ccc21)N1CCNCC1]

hydrochloride: light yellow solid; UPLC/MS 0.93 min, [M+H]$^+$ 490.

6,7-difluoro-3-{1-[4-(2-oxo-2-piperazin-1-yl-ethoxy)-phenyl]-1H-[1,2,3]triazol-4-yl}-1H-quinolin-2-one ("A140")

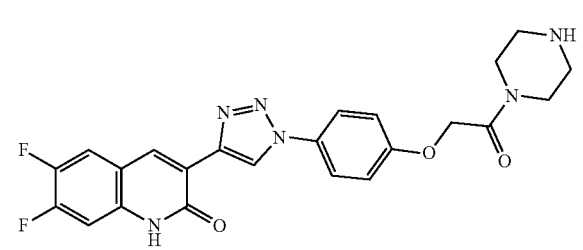 [SMILES: O=C(COc1ccc(-n2cc(-c3cc4cc(F)c(F)cc4[nH]c3=O)nn2)cc1)N1CCNCC1]

hydrochloride: beige solid; UPLC/MS 0.87 min, [M+H]$^+$ 467. $^1$H NMR (400 MHz, DMSO-d$_6$) δ 12.32 (s, 1H), 9.15 (bs, 2H), 9.10 (s, 1H), 8.82 (s, 1H), 8.08 (dd, J=11.0, 8.6 Hz, 1H), 7.93-7.83 (m, 2H), 7.34 (dd, J=11.5, 7.1 Hz, 1H), 7.24-7.11 (m, 2H), 5.01 (s, 2H), 3.71 (bs, 4H), 3.20 (bs, 2H), 3.11 (bs, 2H).

6-fluoro-3-{1-[4-(2-oxo-2-piperazin-1-yl-ethoxy)-phenyl]-1H-[1,2,3]triazol-4-yl}-1H-quinolin-2-one ("A141")

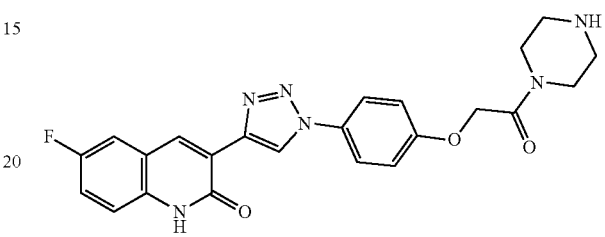

hydrochloride: beige solid; UPLC/MS 0.84 min, [M+H]$^+$ 449.

3-{1-[4-(piperazine-1-carbonyl)-phenyl]-1H-[1,2,3]triazol-4-yl}-7-trifluoromethyl-1H-quinolin-2-one ("A142")

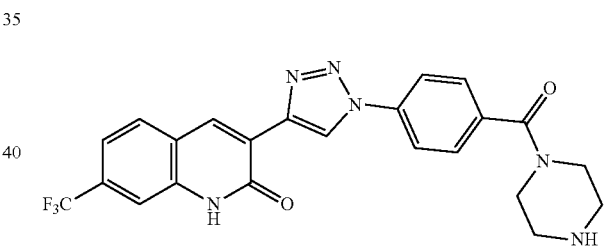

hydrochloride: beige solid; UPLC/MS 0.92 min, [M+H]$^+$ 469.

3-{1-[4-(4-amino-piperidine-1-carbonyl)-phenyl]-1H-[1,2,3]triazol-4-yl}-6,7-difluoro-1H-quinolin-2-one ("A143")

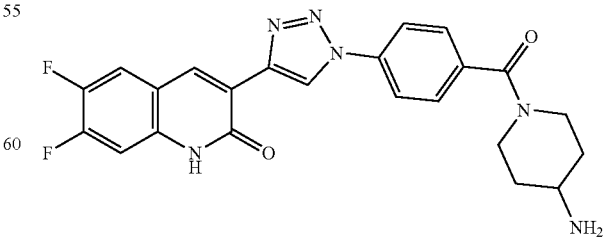

hydrochloride: light beige solid; UPLC/MS 0.85 min, [M+H]$^+$ 451.

3-{1-[4-(4-amino-piperidine-1-carbonyl)-phenyl]-1H-[1,2,3]triazol-4-yl}-6-fluoro-1H-quinolin-2-one ("A144")

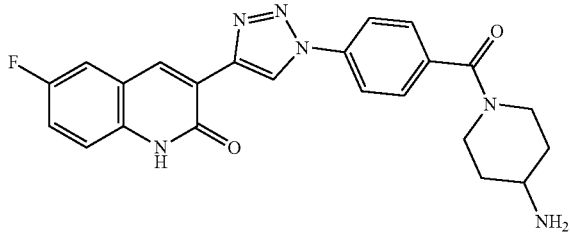 [SMILES: NC1CCN(C(=O)c2ccc(-n3cc(-c4cc5cc(F)ccc5[nH]c4=O)nn3)cc2)CC1]

hydrochloride: beige solid; UPLC/MS 0.81 min, [M+H]+ 433.

6,7-difluoro-3-{1-[4-(2-oxo-piperazin-1-yl)-phenyl]-1H-[1,2,3]triazol-4-yl}-1H-quinolin-2-one ("A145")

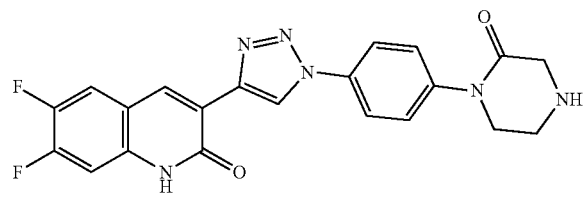 [SMILES: O=C1CNCCN1c1ccc(-n2cc(-c3cc4cc(F)c(F)cc4[nH]c3=O)nn2)cc1]

hydrochloride: light brown solid; HPLC/MS 1.20 min (A), [M+H]+ 423. $^1$H NMR (400 MHz, DMSO-$d_6$) δ 12.34 (s, 1H), 9.72 (s, 2H), 9.23 (s, 1H), 8.84 (s, 1H), 8.13-8.03 (m, 3H), 7.64-7.55 (m, 2H), 7.34 (dd, J=11.5, 7.1 Hz, 1H), 3.96 (bs, 2H), 3.91 (s, 2H), 3.57 (bs, 2H).

6,7-difluoro-3-{1-[1-(2-oxo-2-piperazin-1-yl-ethyl)-1H-indazol-5-yl]-1H-[1,2,3]triazol-4-yl}-1H-quinolin-2-one ("A146")

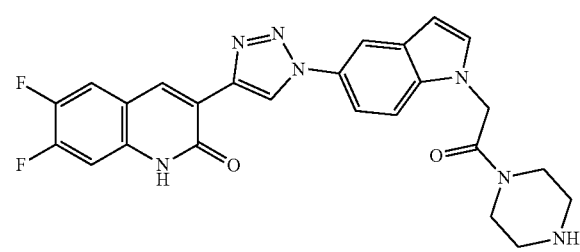 [SMILES: O=C(Cn1ccc2cc(-n3cc(-c4cc5cc(F)c(F)cc5[nH]c4=O)nn3)ccc21)N1CCNCC1]

trifluoroacetate: brown solid; UPLC/MS 0.48 min, [M+H]+ 491. $^1$H NMR (400 MHz, DMSO-$d_6$) δ 12.33 (s, 1H), 9.21 (s, 1H), 8.85 (s, 1H), 8.76 (s, 2H), 8.39 (d, J=2.0 Hz, 1H), 8.24 (d, J=0.9 Hz, 1H), 8.09 (dd, J=11.0, 8.6 Hz, 1H), 8.02 (d, J=9.0, 2.1 Hz, 1H), 7.80 (d, J=9.0 Hz, 1H), 7.33 (dd, J=11.4, 7.1 Hz, 1H), 5.61 (s, 2H), 3.80 (bs, 2H), 3.65 (bs, 2H), 3.26 (bs, 2H), 3.12 (bs, 2H).

6-fluoro-7-methoxy-3-{1-[4-(piperazine-1-carbonyl)-phenyl]-1H-[1,2,3]triazol-4-yl}-1H-quinolin-2-one ("A147")

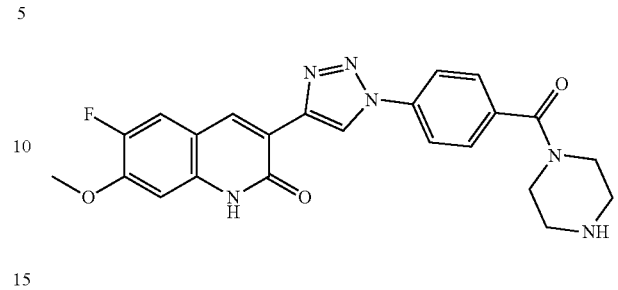

light beige solid; HPLC/MS 1.20 min (A), [M+H]+ 449. $^1$H NMR (400 MHz, DMSO-$d_6$) δ 12.18 (s, 1H), 9.24 (s, 1H), 9.09 (s, 2H), 8.77 (s, 1H), 8.12 (d, J=8.6 Hz, 2H), 7.83 (d, J=11.6 Hz, 1H), 7.77-7.66 (m, 2H), 7.08 (d, J=7.6 Hz, 1H), 3.93 (s, 3H), 3.74 (bs, 4H), 3.20 (b, 4H).

6-chloro-7-fluoro-3-{1-[4-(piperazine-1-carbonyl)-phenyl]-1H-[1,2,3]triazol-4-yl}-1H-quinolin-2-one ("A148")

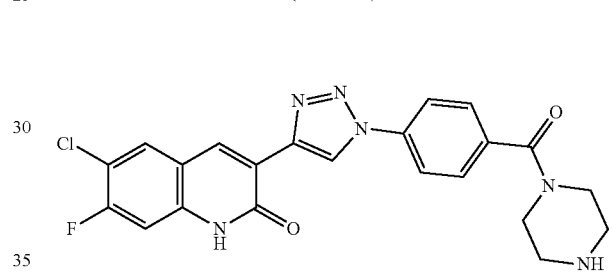

hydrochloride: beige solid; UPLC/MS 0.49 min, [M+H]+ 453. $^1$H NMR (400 MHz, DMSO-$d_6$) δ 12.41 (s, 1H), 9.28 (s, 1H), 9.21 (bs, 2H), 8.85 (s, 1H), 8.27 (d, J=8.0 Hz, 1H), 8.13 (d, J=8.6 Hz, 2H), 7.72 (d, J=8.6 Hz, 2H), 7.33 (d, J=10.3 Hz, 1H), 3.36 (bs, 4H), 3.19 (bs, 4H).

EXAMPLE 10b

Synthesis of "A118"

To a solution of 4-{4-[4-(7-fluoro-2-oxo-1,2-dihydro-quinolin-3-yl)-[1,2,3]triazol-1-yl]-benzoyl}-piperazine-1-carboxylic acid tert-butyl ester (83.0 mg, 0.16 mmol) in formic acid (0.9 ml) is added formaldehyde (37% aqueous solution, 36.5 μl, 0.49 mmol) and the reaction mixture is stirred for 2 hours at 80° C. The reaction mixture is concentrated under reduced pressure and treated with saturated NaHCO$_3$ solution. The resultant precipitate is filtered off, washed with water and dried under vacuum. The residue is chromatographed on a silica gel column with dichloromethane/methanol as eluent to afford 7-fluoro-3-{1-[4-(4-methyl-piperazine-1-carbonyl)-phenyl]-1H-[1,2,3]triazol-4-yl}-1H-quinolin-2-one ("A118") as off-white solid; HPLC/MS 1.19 min (A), [M+H]+ 433.

$^1$H NMR (400 MHz, DMSO-$d_6$) δ 12.27 (s, 1H), 9.23 (s, 1H), 8.85 (s, 1H), 8.08 (d, J=8.6 Hz, 2H), 7.99 (dd, J=9.5, 6.1 Hz, 1H), 7.62 (d, J=8.6 Hz, 2H), 7.18-7.09 (m, 2H), 3.86-3.32 (m, 4H), 2.35 (bs, 4H), 2.21 (s, 3H).

The following compounds are prepared similarly:

5-fluoro-3-{1-[4-(4-methyl-piperazine-1-carbonyl)-phenyl]-1H-[1,2,3]triazol-4-yl}-1H-quinolin-2-one ("A149")

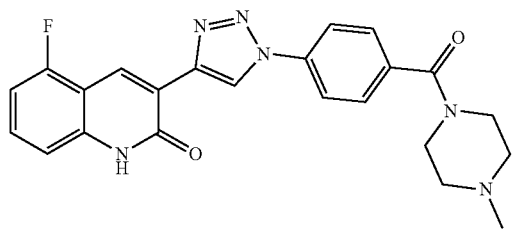 [SMILES: CN1CCN(C(=O)c2ccc(-n3cc(-c4cc5c(F)cccc5[nH]c4=O)nn3)cc2)CC1]

beige solid; HPLC/MS 1.22 min (A), [M+H]+ 433; 1H NMR (400 MHz, DMSO-d6) δ 12.46 (s, 1H), 9.30 (s, 1H), 8.83 (s, 1H), 8.10 (d, J=8.6 Hz, 2H), 7.64 (d, J=8.5 Hz, 2H), 7.58 (td, J=8.2, 6.0 Hz, 1H), 7.26 (d, J=8.3 Hz, 1H), 7.17-7.08 (m, 1H), 3.75-3.30 (m, 4H), 2.35 (bs, 4H), 2.23 (s, 3H).

8-fluoro-3-{1-[4-(4-methyl-piperazine-1-carbonyl)-phenyl]-1H-[1,2,3]triazol-4-yl}-1H-quinolin-2-one ("A150")

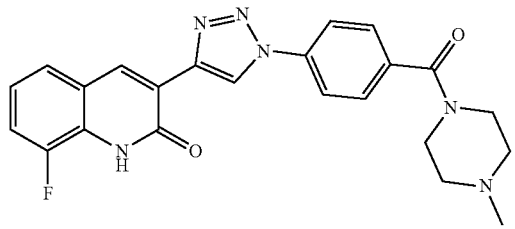 [SMILES: CN1CCN(C(=O)c2ccc(-n3cc(-c4cc5cccc(F)c5[nH]c4=O)nn3)cc2)CC1]

off-white solid; HPLC/MS 1.17 min (A), [M+H]+ 433; 1H NMR (500 MHz, DMSO-d6) (12.24 (s, 1H), 9.28 (s, 1H), 8.88 (d, J=1.5 Hz, 1H), 8.13-8.05 (m, 2H), 7.75 (dd, J=8.0, 1.1 Hz, 1H), 7.66-7.59 (m, 2H), 7.46 (ddd, J=11.1, 8.1, 1.2 Hz, 1H), 7.24 (td, J=8.0, 4.9 Hz, 1H), 3.78-3.30 (m, 4H), 2.44-2.27 (m, 4H), 2.21 (s, 3H).

6-chloro-3-{1-[4-(4-methyl-piperazine-1-carbonyl)-phenyl]-1H-[1,2,3]triazol-4-yl}-1H-quinolin-2-one ("A151")

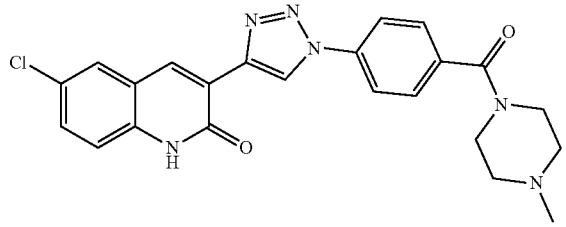 [SMILES: CN1CCN(C(=O)c2ccc(-n3cc(-c4cc5cc(Cl)ccc5[nH]c4=O)nn3)cc2)CC1]

off-white solid; HPLC/MS 1.31 min (A), [M+H]+ 449; 1H NMR (400 MHz, DMSO-d6) δ 12.32 (s, 1H), 9.29 (s, 1H), 8.85 (s, 1H), 8.10 (d, J=8.5 Hz, 2H), 8.07 (d, J=2.4 Hz, 1H), 7.63 (d, J=8.5 Hz, 2H), 7.60 (dd, J=9.1, 2.7 Hz, 1H), 7.42 (d, J=8.8 Hz, 1H), 3.75-3.30 (m, 4H), 2.36 (bs, 4H), 2.23 (s, 3H).

5,7-difluoro-3-{1-[4-(4-methyl-piperazine-1-carbonyl)-phenyl]-1H-[1,2,3]triazol-4-yl}-1H-quinolin-2-one ("A152")

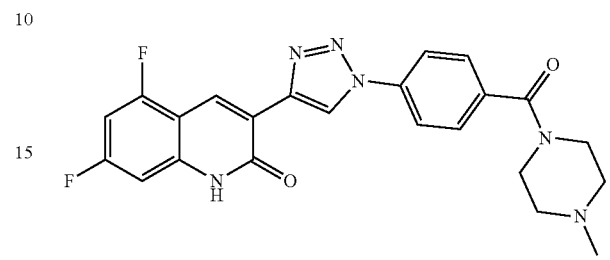

beige solid; HPLC/MS 1.25 min (A), [M+H]+ 451; 1H NMR (500 MHz, DMSO-d6) δ 12.54 (s, 1H), 9.28 (s, 1H), 8.77 (s, 1H), 8.10 (d, J=8.6 Hz, 2H), 7.63 (d, J=8.6 Hz, 2H), 7.24 (td, J=10.0, 2.4 Hz, 1H), 7.03 (dt, J=9.8, 1.7 Hz, 1H), 3.72-3.32 (m, 4H), 2.35 (bs, 4H), 2.22 (s, 3H).

6-Fluoro-3-{1-[3-(4-methyl-piperazine-1-carbonyl)-phenyl]-1H-[1,2,3]triazol-4-yl}-1H-quinolin-2-one ("A153")

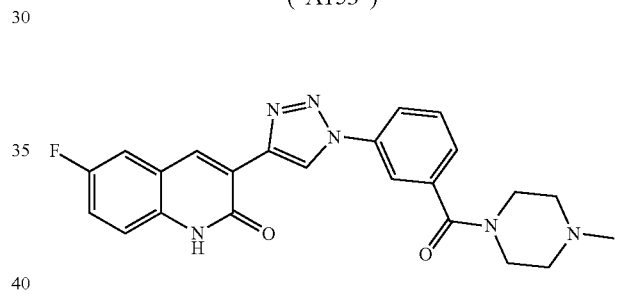

off-white solid; HPLC/MS 1.20 min (A), [M+H]+ 433; 1H NMR (400 MHz, DMSO-d6) δ 12.27 (s, 1H), 9.30 (s, 1H), 8.84 (s, 1H), 8.10 (ddd, J=8.1, 2.3, 1.0 Hz, 1H), 8.02 (t, J=1.8 Hz, 1H), 7.80 (dd, J=9.2, 2.6 Hz, 1H), 7.68 (t, J=7.9 Hz, 1H), 7.50 (dt, J=7.6, 1.3 Hz, 1H), 7.49-7.39 (m, 2H), 3.75-3.30 (m, 4H), 2.45-2.25 (m, 4H), 2.21 (s, 3H).

7-chloro-3-{1-[4-(4-methyl-piperazine-1-carbonyl)-phenyl]-1H-[1,2,3]triazol-4-yl}-1H-quinolin-2-one ("A154")

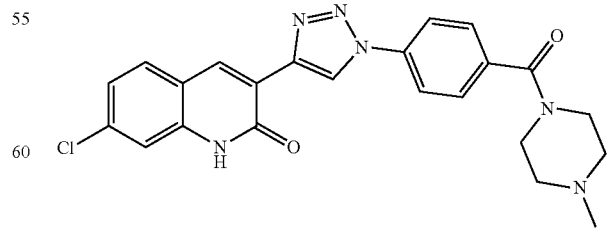

white solid; HPLC/MS 1.27 min (A), [M+H]+ 449; 1H NMR (400 MHz, DMSO-d6) δ 12.28 (s, 1H), 9.26 (s, 1H), 8.86 (s, 1H), 8.09 (d, J=8.4 Hz, 2H), 7.96 (d, J=8.5 Hz, 1H), 7.62 (d, J=8.5 Hz, 2H), 7.42 (d, J=2.0 Hz, 1H), 7.30 (dd, J=8.4, 2.0 Hz, 1H), 3.70-3.30 (m, 4H), 2.35 (bs, 4H), 2.22 (s, 3H).

6-fluoro-3-{1-[4-(4-methyl-[1,4]diazepan-1-yl)-phenyl]-1H-[1,2,3]triazol-4-yl}-1H-[1,8]naphthyridin-2-one ("A155")

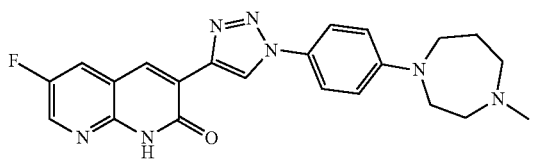 [SMILES: CN1CCCN(c2ccc(-n3cc(-c4cc5cc(F)cnc5[nH]c4=O)nn3)cc2)CC1]

brown solid; HPLC/MS 1.18 min (A), [M+H]$^+$ 420; $^1$H NMR (400 MHz, DMSO-d$_6$) δ 12.64 (s, 1H), 9.02 (s, 1H), 8.74 (s, 1H), 8.55 (d, J=2.9 Hz, 1H), 8.22 (dd, J=8.8, 3.0 Hz, 1H), 7.68 (d, J=9.0 Hz, 2H), 6.86 (d, J=9.2 Hz, 2H), 3.63-3.54 (m, 2H), 3.50 (t, J=6.2 Hz, 2H), 2.71-2.58 (m, 2H), 2.49-2.45 (m, 2H), 2.27 (s, 3H), 1.92 (p, J=5.9 Hz, 3H).

5,6-difluoro-3-{1-[4-(4-methyl-piperazine-1-carbonyl)-phenyl]-1H-[1,2,3]triazol-4-yl}-1H-quinolin-2-one ("A156")

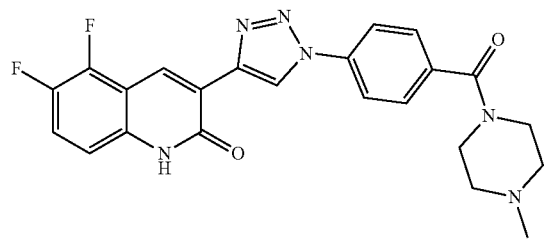 [SMILES: CN1CCN(C(=O)c2ccc(-n3cc(-c4cc5c(F)c(F)ccc5[nH]c4=O)nn3)cc2)CC1]

white solid; HPLC/MS 1.21 min (A), [M+H]$^+$ 451; $^1$H NMR (400 MHz, DMSO-d$_6$) δ 12.48 (s, 1H), 9.31 (s, 1H), 8.81 (s, 1H), 8.13-8.06 (m, 2H), 7.72-7.60 (m, 3H), 7.23 (ddd, J=9.3, 3.9, 1.6 Hz, 1H), 3.64 (bs, 4H), 2.36 (bs, 4H), 2.23 (s, 3H).

6,7-difluoro-3-{1-[4-(4-methyl-piperazine-1-carbonyl)-phenyl]-1H-[1,2,3]triazol-4-yl}-1H-quinolin-2-one ("A157")

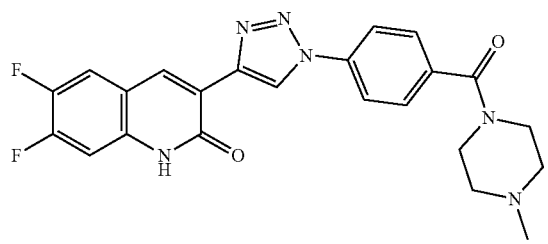 [SMILES: CN1CCN(C(=O)c2ccc(-n3cc(-c4cc5cc(F)c(F)cc5[nH]c4=O)nn3)cc2)CC1]

white solid; UPLC/MS 0.49 min, [M+H]$^+$ 451; $^1$H NMR (500 MHz, DMSO-d$_6$) δ 12.34 (s, 1H), 9.92 (bs, 1H), 9.29 (s, 1H), 8.85 (s, 1H), 8.17-8.12 (m, 2H), 8.09 (dd, J=10.9, 8.6 Hz, 1H), 7.75-7.67 (m, 2H), 7.33 (dd, J=11.4, 7.1 Hz, 1H), 4.44 (bs, 2H), 3.7 (bs, 2H), 3.18 (bs, 4H), 2.81 (s, 3H).

6-fluoro-3-{1-[4-(4-methyl-piperazine-1-sulfonyl)-phenyl]-1H-[1,2,3]triazol-4-yl}-1H-quinolin-2-one ("A158")

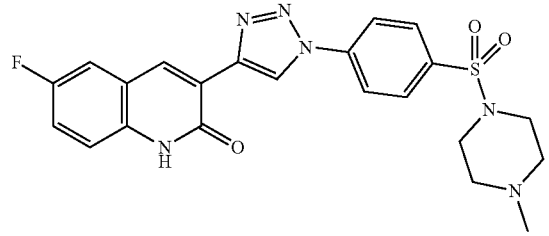 [SMILES: CN1CCN(S(=O)(=O)c2ccc(-n3cc(-c4cc5cc(F)ccc5[nH]c4=O)nn3)cc2)CC1]

beige powder; UPLC/MS 0.50 min, [M+H]$^+$ 469; $^1$H NMR (400 MHz, DMSO-d$_6$) δ 12.31 (s, 1H), 9.39 (s, 1H), 8.87 (s, 1H), 8.51-8.15 (m, 2H), 8.14-7.90 (m, 2H), 7.81 (dd, J=9.3, 2.7 Hz, 1H), 7.62-7.33 (m, 2H), 2.98 (t, J=4.9 Hz, 4H), 2.38 (t, J=4.9 Hz, 4H), 2.15 (s, 3H).

6,7-difluoro-3-(1-{4-[2-(4-methyl-piperazin-1-yl)-ethoxy]-phenyl}-1H-[1,2,3]triazol-4-yl)-1H-quinolin-2-one ("A159")

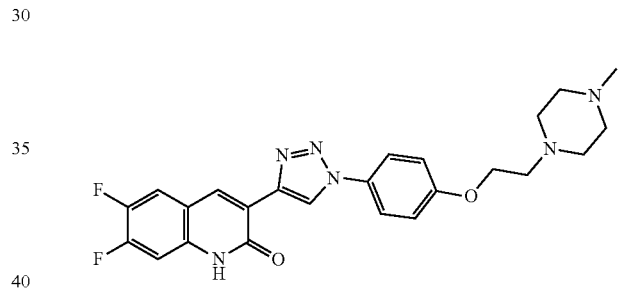

brown solid; HPLC/MS 1.25 min (A), [M+H]$^+$ 467; $^1$H NMR (500 MHz, DMSO-d$_6$) δ 12.30 (s, 1H), 9.09 (s, 1H), 8.78 (s, 1H), 8.03 (dd, J=11.0, 8.6 Hz, 1H), 7.92-7.81 (m, 2H), 7.30 (dd, J=11.5, 7.1 Hz, 1H), 7.21-7.08 (m, 2H), 4.16 (t, J=5.8 Hz, 2H), 2.72 (t, J=5.8 Hz, 2H), 2.50 (m, 4H), 2.32 (m, 4H), 2.15 (s, 3H).

6-fluoro-3-(1-{4-[3-(4-methyl-piperazin-1-yl)-propoxy]-phenyl}-1H-[1,2,3]triazol-4-yl)-1H-quinolin-2-one ("A160")

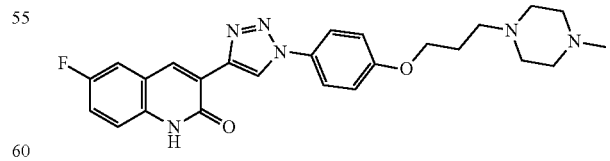

off-white powder; HPLC/MS 1.20 min (A), [M+H]$^+$ 463; $^1$H NMR (500 MHz, DMSO-d$_6$) δ 12.26 (s, 1H), 9.10 (s, 1H), 8.81 (s, 1H), 7.91-7.84 (m, 2H), 7.78 (dd, J=9.3, 2.6 Hz, 1H), 7.48-7.38 (m, 2H), 7.18-7.06 (m, 2H), 4.09 (t, J=6.4 Hz, 2H), 2.43 (t, J=7.1 Hz, 2H), 2.42-2.26 (m, 8H), 2.15 (s, 3H), 1.89 (p, J=6.7 Hz, 2H).

6-fluoro-3-{1-[4-(1-methyl-piperidine-4-carbonyl)-phenyl]-1H-[1,2,3]triazol-4-yl}-1H-quinolin-2-one ("A161")

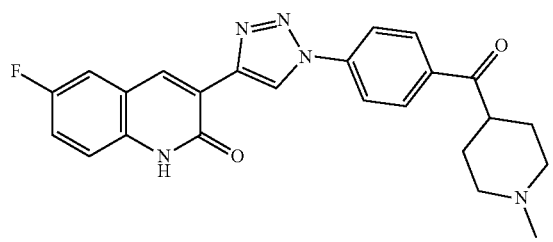 [SMILES: CN1CCC(C(=O)c2ccc(-n3cc(-c4cc5cc(F)ccc5[nH]c4=O)nn3)cc2)CC1]

light beige solid; HPLC/MS 1.24 min (A), [M+H]⁺ 432.

6,7-difluoro-3-(1-{4-[3-(4-methyl-piperazin-1-yl)-propoxy]-phenyl}-1H-[1,2,3]triazol-4-yl)-1H-quinolin-2-one ("A162")

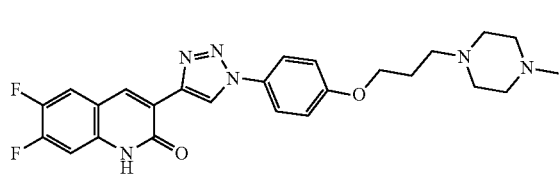 [SMILES: CN1CCN(CCCOc2ccc(-n3cc(-c4cc5cc(F)c(F)cc5[nH]c4=O)nn3)cc2)CC1]

light brown powder; HPLC/MS 1.23 min (A), [M+H]⁺ 481. ¹H NMR (500 MHz, DMSO-d₆) δ 12.30 (s, 1H), 9.09 (s, 1H), 8.79 (s, 1H), 8.04 (dd, J=11.0, 8.6 Hz, 1H), 7.87 (d, J=9.0 Hz, 2H), 7.30 (dd, J=11.5, 7.1 Hz, 1H), 7.13 (d, J=9.0 Hz, 2H), 4.09 (t, J=6.4 Hz, 2H), 2.43 (t, J=7.1 Hz, 2H), 2.45-2.24 (m, 8H), 2.15 (s, 3H), 1.89 (p, J=6.7 Hz, 2H).

6-fluoro-3-(1-{4-[2-(1-methyl-piperidin-4-yl)-ethoxy]-phenyl}-1H-[1,2,3]triazol-4-yl)-1H-quinolin-2-one ("A163")

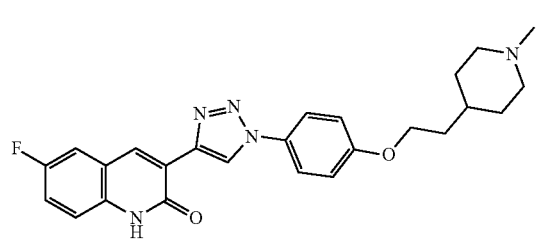 [SMILES: CN1CCC(CCOc2ccc(-n3cc(-c4cc5cc(F)ccc5[nH]c4=O)nn3)cc2)CC1]

off-white solid; HPLC/MS 1.72 min (A), [M+H]⁺ 448.

6,7-difluoro-3-{1-[4-(1-methyl-piperidine-4-carbonyl)-phenyl]-1H-[1,2,3]triazol-4-yl}-1H-quinolin-2-one ("A164")

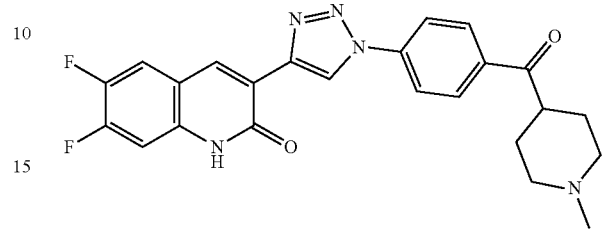

formate; brown solid; UPLC/MS 0.77 min, [M+H]⁺ 450.

6-fluoro-3-(1-{4-[2-(4-methyl-piperazin-1-yl)-2-oxo-ethoxy]-phenyl}-1H-[1,2,3]triazol-4-yl)-1H-quinolin-2-one ("A165")

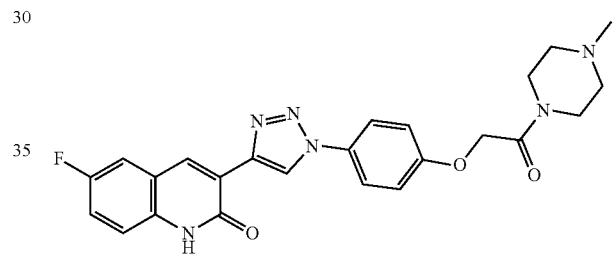

beige solid; UPLC/MS 0.84 min, [M+H]⁺ 463.

6,7-difluoro-3-(1-{4-[2-(1-methyl-piperidin-4-yl)-ethoxy]-phenyl}-1H-[1,2,3]triazol-4-yl)-1H-quinolin-2-one ("A166")

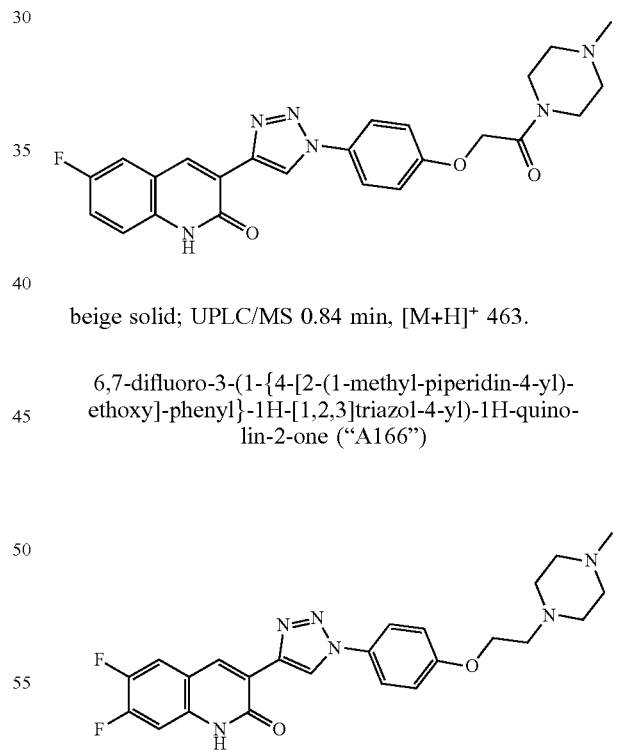

formate: beige solid; HPLC/MS 1.35 min (A), [M+H]⁺ 466. ¹H NMR (400 MHz, DMSO-d₆) δ 12.33 (s, 1H), 9.08 (s, 1H), 8.81 (s, 1H), 8.30 (s, 1H, formate), 8.07 (dd, J=11.0, 8.6 Hz, 1H), 7.95-7.73 (m, 2H), 7.32 (dd, J=11.5, 7.1 Hz, 1H), 7.20-7.03 (m, 2H), 4.09 (t, J=6.6 Hz, 2H), 2.82-2.76 (m, 2H), 2.18 (s, 3H), 1.92 (td, J=11.7, 2.6 Hz, 2H), 1.65-1.72 (m, 4H), 1.50-1.40 (m, 1H), 1.25 (qd, J=12.1, 3.8 Hz, 2H).

127

6,7-difluoro-3-(1-{4-[2-(4-methyl-piperazin-1-yl)-2-oxo-ethoxy]-phenyl}-1H-[1,2,3]triazol-4-yl)-1H-quinolin-2-one ("A167")

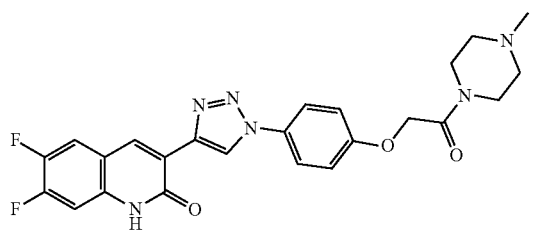 [SMILES: CN1CCN(C(=O)COc2ccc(-n3cc(-c4cc5cc(F)c(F)cc5[nH]c4=O)nn3)cc2)CC1]

formate: beige solid; UPLC/MS 0.86 min, [M+H]⁺ 481.

6-methyl-3-{1-[4-(4-methyl-piperazine-1-carbonyl)-phenyl]-1H-[1,2,3]triazol-4-yl}-1H-quinolin-2-one ("A168")

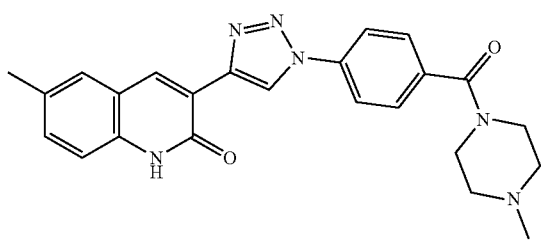 [SMILES: Cc1ccc2[nH]c(=O)c(-c3cn(-c4ccc(C(=O)N5CCN(C)CC5)cc4)nn3)cc2c1]

off-white solid; HPLC/MS 1.22 min (A), [M+H]⁺ 429. $^1$H NMR (400 MHz, DMSO-d$_6$) δ 12.14 (s, 1H), 9.25 (s, 1H), 8.77 (s, 1H), 8.09 (d, J=8.6 Hz, 2H), 7.69 (s, 1H), 7.63 (d, J=8.6 Hz, 2H), 7.40 (dd, J=8.4, 1.9 Hz, 1H), 7.32 (d, J=8.4 Hz, 1H), 3.64 (bs, 2H), 3.40 (bs, 2H), 2.39 (s, 3H), 2.36 (bs, 4H), 2.22 (s, 3H).

6,7-difluoro-3-(1-{4-[2-(4-methyl-piperazin-1-yl)-2-oxo-ethyl]-phenyl}-1H-[1,2,3]triazol-4-yl)-1H-quinolin-2-one ("A169")

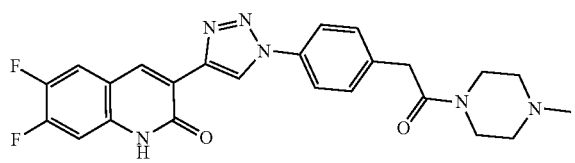 [SMILES: CN1CCN(C(=O)Cc2ccc(-n3cc(-c4cc5cc(F)c(F)cc5[nH]c4=O)nn3)cc2)CC1]

beige solid; UPLC/MS 0.97 min, [M+H]⁺ 465. $^1$H NMR (400 MHz, DMSO-d$_6$) δ 12.32 (s, 1H), 9.17 (s, 1H), 8.84 (s, 1H), 8.08 (dd, J=11.0, 8.5 Hz, 1H), 8.00-7.87 (m, 2H), 7.57-7.41 (m, 2H), 7.33 (dd, J=11.4, 7.1 Hz, 1H), 3.83 (s, 2H), 3.51 (dt, J=15.5, 5.0 Hz, 4H), 2.27 (t, J=5.1 Hz, 4H), 2.18 (s, 3H).

128

3-{1-[4-(4-methyl-piperazine-1-carbonyl)-phenyl]-1H-[1,2,3]triazol-4-yl}-7-trifluoromethyl-1H-quinolin-2-one ("A170")

beige solid; UPLC/MS 0.92 min, [M+H]⁺ 483. $^1$H NMR (400 MHz, DMSO-d$_6$) δ 12.48 (s, 1H), 9.32 (s, 1H), 8.95 (s, 1H), 8.17 (d, J=8.2 Hz, 1H), 8.13-8.07 (m, 2H), 7.72 (s, 1H), 7.66-7.61 (m, 2H), 7.57 (dd, J=8.3, 1.7 Hz, 1H), 3.73-3.34 (m, 4H), 2.34 (bs, 4H), 2.23 (s, 3H).

3-{1-[4-(4-dimethylamino-piperidine-1-carbonyl)-phenyl]-1H-[1,2,3]triazol-4-yl}-6,7-difluoro-1H-quinolin-2-one ("A171")

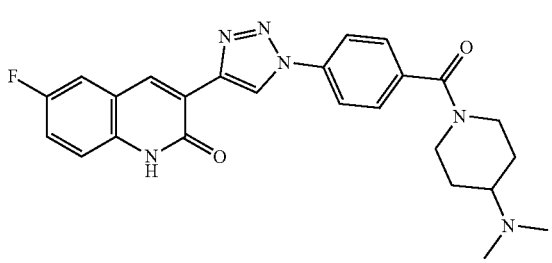 [SMILES: CN(C)C1CCN(C(=O)c2ccc(-n3cc(-c4cc5cc(F)ccc5[nH]c4=O)nn3)cc2)CC1]

beige solid; UPLC/MS 0.86 min, [M+H]⁺ 479.

3-{1-[4-(4-dimethylamino-piperidine-1-carbonyl)-phenyl]-1H-[1,2,3]triazol-4-yl}-6-fluoro-1H-quinolin-2-one ("A172")

beige solid; UPLC/MS 0.83 min, [M+H]⁺ 461.

6,7-difluoro-3-(1-{1-[2-(4-methyl-piperazin-1-yl)-2-oxo-ethyl]-1H-indazol-5-yl}-1H-[1,2,3]triazol-4-yl)-1H-quinolin-2-one ("A173")

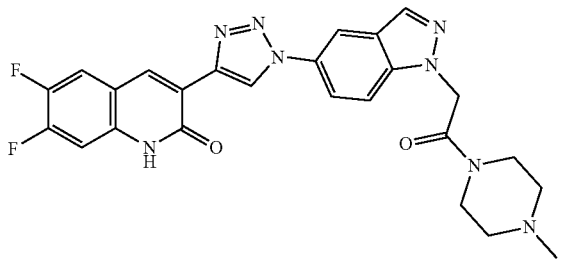 [SMILES: CN1CCN(C(=O)Cn2ncc3cc(-n4cc(-c5cc6cc(F)c(F)cc6[nH]c5=O)nn4)ccc32)CC1]

trifluoroacetate: brown solid; UPLC/MS 0.48 min, [M+H]+ 505. 1H NMR (400 MHz, DMSO-d6) δ 12.33 (s, 1H), 9.87 (s, 1H), 9.21 (s, 1H), 8.85 (s, 1H), 8.39 (d, J=1.9 Hz, 1H), 8.24 (d, J=0.8 Hz, 1H), 8.09 (dd, J=11.0, 8.6 Hz, 1H), 8.02 (dd, J=9.0, 2.1 Hz, 1H), 7.78 (d, J=9.0 Hz, 1H), 7.33 (dd, J=11.4, 7.1 Hz, 1H), 5.63 (bs, 2H), 4.5-4.1 (m, 2H), 3.6-2.9 (m, 6H), 2.86 (s, 3H).

6,7-difluoro-3-{1-[4-(4-methyl-2-oxo-piperazin-1-yl)-phenyl]-1H-[1,2,3]triazol-4-yl}-1H-quinolin-2-one ("A174")

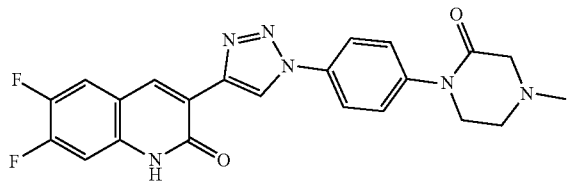 [SMILES: CN1CCN(c2ccc(-n3cc(-c4cc5cc(F)c(F)cc5[nH]c4=O)nn3)cc2)C(=O)C1]

beige solid; HPLC/MS 1.22 min (A), [M+H]+ 437. 1H NMR (400 MHz, DMSO-d6) δ 12.30 (s, 1H), 9.21 (s, 1H), 8.83 (s, 1H), 8.08 (dd, J=11.0, 8.6 Hz, 1H), 8.05-8.00 (m, 2H), 7.62-7.55 (m, 2H), 7.33 (dd, J=11.5, 7.0 Hz, 1H), 3.78-3.71 (m, 2H), 3.16 (s, 2H), 2.77 (t, J=5.4 Hz, 2H), 2.31 (s, 3H).

6-fluoro-3-{1-[4-((R)-1-methyl-pyrrolidin-3-yloxy)-phenyl]-1H-[1,2,3]triazol-4-yl}-1H-quinolin-2-one ("A367")

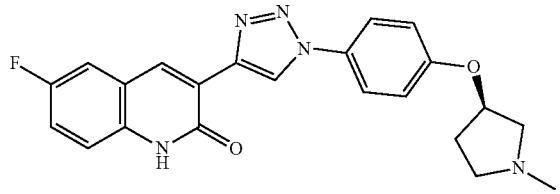 [SMILES: CN1CC[C@@H](Oc2ccc(-n3cc(-c4cc5cc(F)ccc5[nH]c4=O)nn3)cc2)C1]

HPLC/MS 1.23 min (A), [M+H]+ 406;
1H NMR (400 MHz, DMSO-d6) δ 12.24 (s, 1H), 9.10 (s, 1H), 8.82 (s, 1H), 7.98-7.85 (m, 2H), 7.80 (dd, J=9.3, 2.6 Hz, 1H), 7.53-7.36 (m, 2H), 7.17-7.02 (m, 2H), 5.05-4.93 (m, 1H), 2.81 (dd, J=10.4, 6.0 Hz, 1H), 2.74-2.63 (m, 2H), 2.42-2.30 (m, 2H), 2.28 (s, 3H), 1.87-1.76 (m, 1H).

6-chloro-3-{1-[4-((S)-1-methyl-pyrrolidin-3-yloxy)-phenyl]-1H-[1,2,3]triazol-4-yl}-1H-quinolin-2-one ("A368")

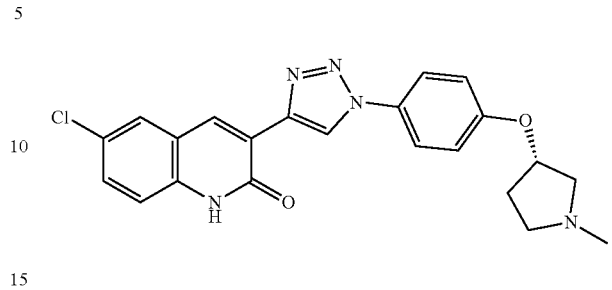

HPLC/MS 1.31 min (A), [M+H]+ 422;
1H NMR (400 MHz, DMSO-d6) δ 12.30 (s, 1H), 9.10 (s, 1H), 8.81 (s, 1H), 8.05 (d, J=2.3 Hz, 1H), 7.87 (d, J=8.9 Hz, 2H), 7.59 (dd, J=8.8, 2.4 Hz, 1H), 7.41 (d, J=8.8 Hz, 1H), 7.09 (d, J=8.9 Hz, 2H), 5.01-4.93 (m, 1H), 2.81 (dd, J=10.5, 6.0 Hz, 1H), 2.76-2.63 (m, 2H), 2.43-2.29 (m, 2H), 2.29 (s, 3H), 1.90-1.74 (m, 1H).

6-chloro-3-{1-[4-((R)-1-methyl-pyrrolidin-3-yloxy)-phenyl]-1H-[1,2,3]triazol-4-yl}-1H-quinolin-2-one ("A369")

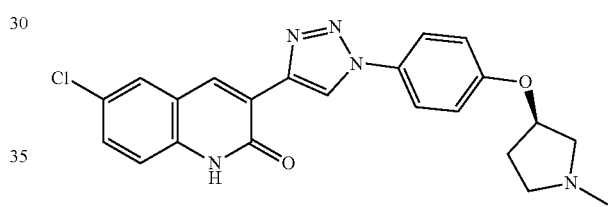

HPLC/MS 1.30 min (A), [M+H]+ 422;
1H NMR (400 MHz, DMSO-d6) δ 12.30 (s, 1H), 9.10 (s, 1H), 8.82 (s, 1H), 8.16 (s, 1H, formate-H), 8.05 (d, J=2.4 Hz, 1H), 7.87 (d, J=9.0 Hz, 2H), 7.59 (dd, J=8.8, 2.3 Hz, 1H), 7.41 (d, J=8.8 Hz, 1H), 7.15-7.04 (m, 2H), 5.06-4.91 (m, 1H), 2.90-2.65 (m, 3H), 2.47-2.26 (m, 5H), 1.88-1.77 (m, 1H).

6-fluoro-3-{1-[4-((S)-1-methyl-pyrrolidin-3-yloxy)-phenyl]-1H-[1,2,3]triazol-4-yl}-1H-quinolin-2-one ("A370")

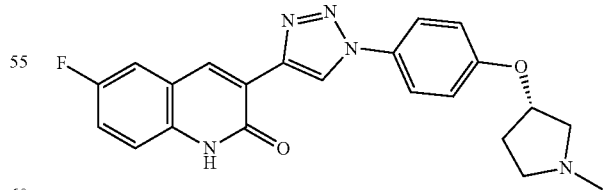

HPLC/MS 1.22 min (A), [M+H]+ 406;
1H NMR (400 MHz, DMSO-d6) δ 12.24 (s, 1H), 9.11 (s, 1H), 8.82 (s, 1H), 8.16 (s, 1H, formate-H), 7.92-7.85 (m, 2H), 7.80 (dd, J=9.3, 2.6 Hz, 1H), 7.50-7.38 (m, 2H), 7.14-7.06 (m, 2H), 5.03-4.92 (m, 1H), 2.93-2.63 (m, 3H), 2.45-2.23 (m, 5H), 1.88-1.77 (m, 1H).

131

6-fluoro-3-{1-[4-(1-methyl-piperidin-4-ylmethyl)-phenyl]-1H-[1,2,3]triazol-4-yl}-1H-quinolin-2-one ("A371")

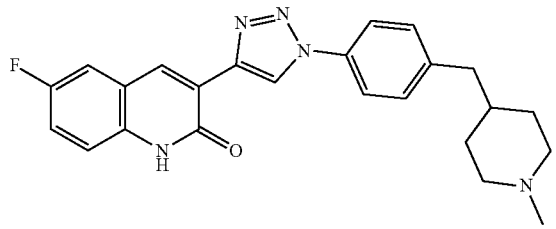 [SMILES: CN1CCC(Cc2ccc(-n3cc(-c4cc5cc(F)ccc5[nH]c4=O)nn3)cc2)CC1]

UPLC/MS 0.52 min, [M+H]+ 418;
$^1$H NMR (400 MHz, DMSO-d$_6$, TFA-d$_1$) δ 9.11 (s, 1H), 8.76 (s, 1H), 7.89-7.78 (m, 2H), 7.60 (dd, J=9.1, 2.8 Hz, 1H), 7.41 (dd, J=9.0, 4.7 Hz, 1H), 7.35 (d, J=8.6 Hz, 2H), 7.29 (td, J=8.8, 2.9 Hz, 1H), 3.38 (d, J=12.2 Hz, 2H), 2.90-3.74 (m, 2H), 2.70 (s, 3H), 2.61 (d, J=6.6 Hz, 2H), 1.85-1.73 (m, 3H), 1.41 (q, J=12.3, 11.9 Hz, 2H).

6,7-difluoro-3-{1-[4-((S)-1-methyl-pyrrolidin-3-yloxy)-phenyl]-1H-[1,2,3]triazol-4-yl}-1H-quinolin-2-one ("A372")

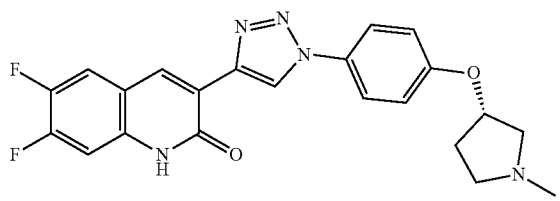 [SMILES: CN1CC[C@H](Oc2ccc(-n3cc(-c4cc5cc(F)c(F)cc5[nH]c4=O)nn3)cc2)C1]

UPLC/MS 0.50 min, [M+H]+ 424;
$^1$H NMR (700 MHz, DMSO-d$_6$) δ 12.33 (s, 1H), 10.25 (s, 1H, NH+), 9.13 (s, 1H), 8.82 (s, 1H), 8.08 (dd, J=10.8, 8.5 Hz, 1H), 7.98-7.90 (m, 2H), 7.33 (dd, J=11.3, 7.0 Hz, 1H), 7.25-7.12 (m, 2H), 5.28 (bs, 1H), 4.2-3.1 (m, 4H), 2.93 (s, 3H), 2.8-2.0 (m, 2H).

6,7-difluoro-3-{1-[4-((R)-1-methyl-pyrrolidin-3-yloxy)-phenyl]-1H-[1,2,3]triazol-4-yl}-1H-quinolin-2-one ("A373")

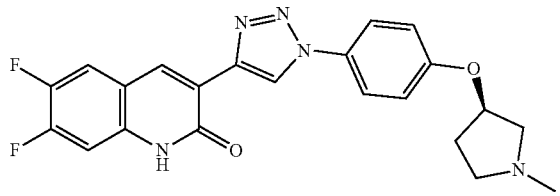 [SMILES: CN1CC[C@@H](Oc2ccc(-n3cc(-c4cc5cc(F)c(F)cc5[nH]c4=O)nn3)cc2)C1]

UPLC/MS 0.50 min, [M+H]+ 424;
$^1$H NMR (700 MHz, DMSO-d$_6$) δ 12.33 (s, 1H), 10.25 (s, 1H, NH+), 9.13 (s, 1H), 8.82 (s, 1H), 8.08 (dd, J=10.8, 8.5 Hz, 1H), 7.98-7.90 (m, 2H), 7.33 (dd, J=11.3, 7.0 Hz, 1H), 7.25-7.12 (m, 2H), 5.28 (bs, 1H), 4.2-3.1 (m, 4H), 2.93 (s, 3H), 2.8-2.0 (m, 2H).

132

6-chloro-3-{1-[4-(1-methyl-piperidin-4-ylmethyl)-phenyl]-1H-[1,2,3]triazol-4-yl}-1H-quinolin-2-one ("A374")

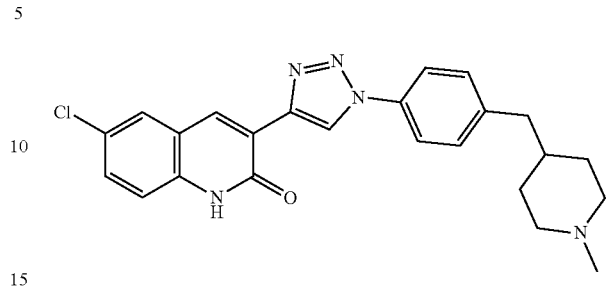

UPLC/MS 0.55 min, [M+H]+ 434;
$^1$H NMR (400 MHz, DMSO-d$_6$) δ 12.32 (s, 1H), 9.18 (s, 1H), 8.83 (s, 1H), 8.06 (d, J=2.4 Hz, 1H), 8.03-7.89 (m, 2H), 7.59 (dd, J=8.8, 2.4 Hz, 1H), 7.47-7.39 (m, 3H), 3.44-3.26 (m, 2H), 2.96-2.81 (m, 2H), 2.74 (s, 3H), 2.71-2.61 (m, 2H), 1.87-1.73 (m, 3H), 1.49-1.30 (m, 2H).

6-fluoro-3-{1-[4-(1-methyl-piperidin-4-yloxy)-phenyl]-1H-[1,2,3]triazol-4-yl}-1H-quinolin-2-one ("A375")

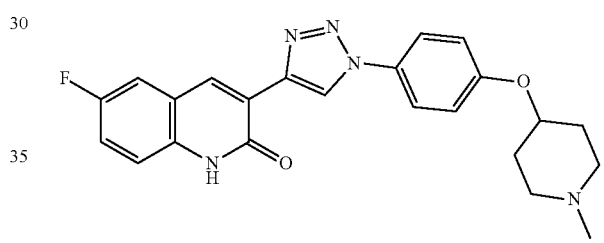

HPLC/MS 1.28 min (A), [M+H]+ 420;
$^1$H NMR (400 MHz, DMSO-d$_6$) δ 12.24 (s, 1H), 9.10 (s, 1H), 8.82 (s, 1H), 7.93-7.83 (m, 2H), 7.79 (dd, J=9.2, 2.6 Hz, 1H), 7.51-7.38 (m, 2H), 7.16 (d, J=9.0 Hz, 1H), 4.48 (tt, J=8.2, 4.0 Hz, 1H), 2.67-2.58 (m, 2H), 2.31-2.14 (m, 5H), 2.04-1.92 (m, 2H), 1.74-1.62 (m, 2H).

6-chloro-3-{1-[4-(1-methyl-piperidin-4-yloxy)-phenyl]-1H-[1,2,3]triazol-4-yl}-1H-quinolin-2-one "A376")

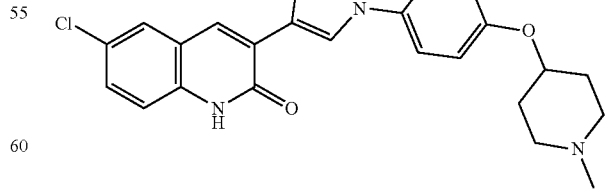

HPLC/MS 1.36 min (A), [M+H]+ 436;
$^1$H NMR (700 MHz, DMSO-d$_6$) δ 12.32 (s, 1H), 9.10 (s, 1H), 8.81 (s, 1H), 8.05 (d, J=2.4 Hz, 1H), 7.91-7.74 (m, 2H), 7.58 (dd, J=8.8, 2.4 Hz, 1H), 7.40 (d, J=8.7 Hz, 1H), 7.22-7.00 (m, 2H), 4.48 (tt, J=8.3, 3.9 Hz, 1H), 2.71-2.58 (m, 2H), 2.22-2.17 (m, 5H), 2.00-1.94 (m, 2H), 1.71-1.64 (m, 2H).

EXAMPLE 11

6-Fluoro-3-(1-{4-[4-(2-methoxy-ethyl)-piperazine-1-carbonyl]-phenyl}-1H-[1,2,3]triazol-4-yl)-1H-[1,8]naphthyridin-2-one ("A175")

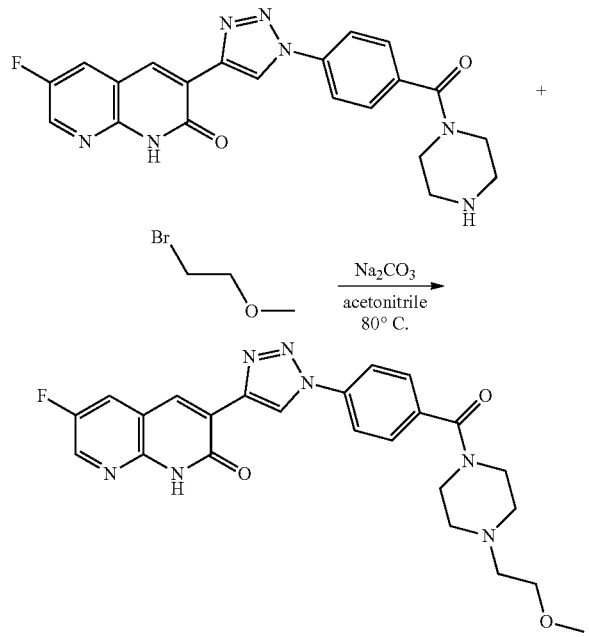

beige solid; HPLC/MS 1.12 min (A), [M+H]+ 478; 1H NMR (400 MHz, DMSO-d6) δ 12.72 (s, 1H), 9.29 (s, 1H), 8.86 (s, 1H), 8.61 (d, J=2.9 Hz, 1H), 8.35 (dd, J=8.7, 3.0 Hz, 1H), 8.09 (d, J=8.5 Hz, 2H), 7.62 (d, J=8.6 Hz, 2H), 3.62 (bs, 2H), 3.45 (t, J=5.7 Hz, 2H), 3.36 (bs, 2H), 3.24 (s, 3H), 2.55-2.40 (m, 6H).

EXAMPLE 12

6-fluoro-3-(1-{4-[2-(4-methyl-piperazin-1-yl)-ethoxy]-phenyl}-1H-[1,2,3]triazol-4-yl)-1H-quinolin-2-one ("A176")

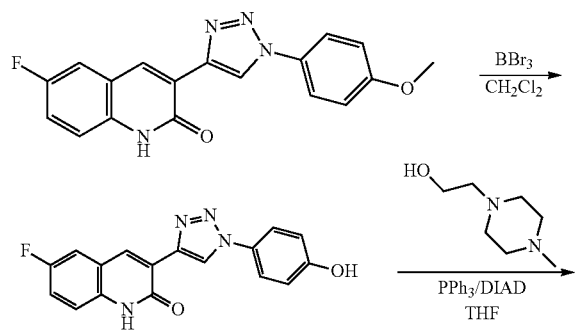

-continued

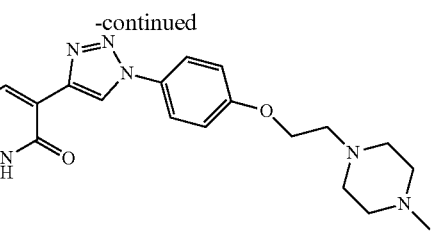

A suspension of 6-fluoro-3-[1-(4-methoxy-phenyl)-1H-[1,2,3]triazol-4-yl]-1H-quinolin-2-one (211 mg, 0.63 mmol, prepared in analogy to example 1) in dichloromethane (6 ml) is cooled to −78° C. and boron tribromide (9.38 ml of a 1 M solution in dichloromethane, 9.38 mmol) is added. The mixture is allowed to reach room temperature and is stirred for 18 hours. To the reaction mixture is added saturated aqueous NaHCO3 solution. The insoluble solid that has formed is filtered off, washed with dichloromethane and water and dried under vacuum to afford 6-fluoro-3-[1-(4-hydroxy-phenyl)-1H-[1,2,3]triazol-4-yl]-1H-quinolin-2-one as grey solid; UPLC/MS 0.68 min, [M+H]+ 323.

To a suspension of 6-fluoro-3-[1-(4-hydroxy-phenyl)-1H-[1,2,3]triazol-4-yl]-1H-quinolin-2-one (203 mg, 0.63 mmol) in THF (2 ml) are added sequentially triphenylphosphine (198 mg, 0.76 mmol), 2-(4-methyl-piperazin-1-yl)-ethanol (109 mg, 0.76 mmol) and diisopropylazodicarboxylate (148 μl, 0.76 mmol). The reaction mixture is stirred for 18 hours at room temperature. Triphenylphosphine (198 mg, 0.76 mmol) and diisopropylazodicarboxylate (148 μl, 0.76 mmol) are added and the reaction mixture is stirred for 55 hours at room temperature. The reaction mixture is evaporated and treated with methanol. The insoluble solid is collected and purified by preparative HPLC to afford 6-fluoro-3-(1-{4-[2-(4-methyl-piperazin-1-yl)-ethoxy]-phenyl}-1H-[1,2,3]triazol-4-yl)-1H-quinolin-2-one as white solid. UPLC/MS 0.49 min, [M+H]+ 449.

1H NMR (400 MHz, DMSO-d6) δ 12.25 (s, 1H), 9.11 (s, 1H), 8.82 (s, 1H), 7.93-7.85 (m, 2H), 7.79 (dd, J=9.2, 2.6 Hz, 1H), 7.51-7.38 (m, 2H), 7.20-7.10 (m, 2H), 4.16 (t, J=5.8 Hz, 2H), 2.72 (t, J=5.8 Hz, 2H), 2.50 (bs, 4H), 2.33 (bs, 4H), 2.15 (s, 3H).

EXAMPLE 13

3-{1-[4-(morpholine-4-carbonyl)-phenyl]-1H-[1,2,3]triazol-4-yl}-2-oxo-1,2-dihydro-quinoline-7-carbonitrile ("A177")

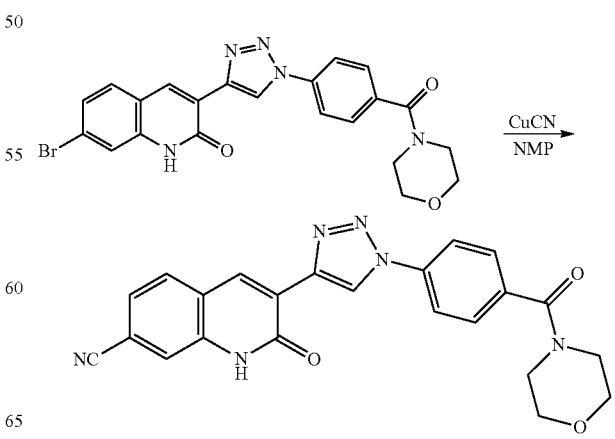

A reaction vial is charged with 7-bromo-3-{1-[4-(morpholine-4-carbonyl)-phenyl]-1H-[1,2,3]triazol-4-yl}-1H-quinolin-2-one (250 mg, 0.52 mmol), N-methyl-pyrrolidone (2.5 ml) and copper(I) cyanide (56.1 mg, 0.63 mmol). The reaction vial is flushed with nitrogen, closed and heated to 170°. The reaction mixture is stirred in the closed reaction vial at this temperature for 8 hours. The reaction mixture is allowed to reach room temperature and treated with water. The insoluble solids are filtered off, washed with water and dried under vacuum. The residue is purified by preparative HPLC to afford 3-{1-[4-(morpholine-4-carbonyl)-phenyl]-1H-[1,2,3]triazol-4-yl}-2-oxo-1,2-dihydro-quinoline-7-carbonitrile as beige solid. HPLC/MS 1.42 min (A), [M+H]$^+$ 427; $^1$H NMR (400 MHz, DMSO-d$_6$) δ 12.48 (s, 1H), 9.34 (s, 1H), 8.94 (s, 1H), 8.18-8.08 (m, 3H), 7.76-7.73 (m, 1H), 7.71-7.63 (m, 3H), 3.74-3.34 (m, 6H).

EXAMPLE 14

6-fluoro-3-(1-{1-[2-(4-methyl-piperazin-1-yl)-2-oxo-ethyl]-1H-indol-5-yl}-1H-[1,2,3]triazol-4-yl)-1H-quinolin-2-one ("A178")

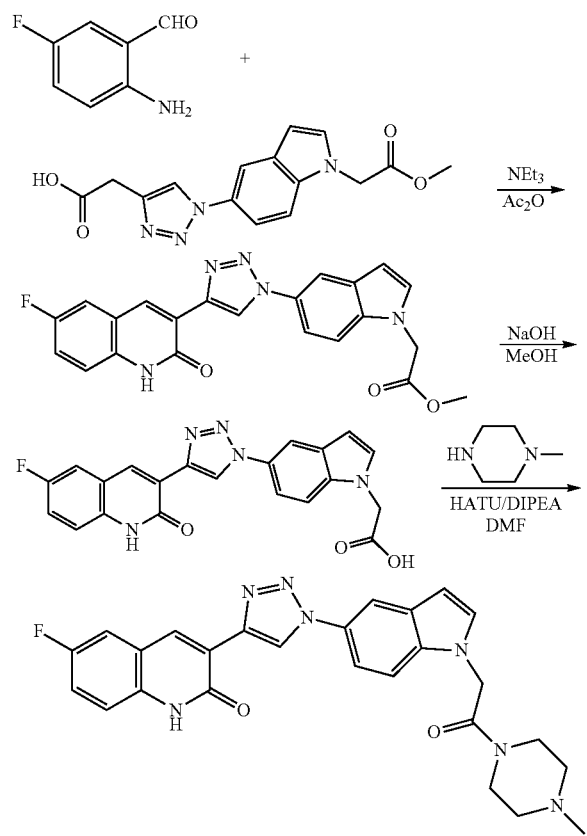

beige solid; HPLC/MS 1.23 min (A), [M+H]$^+$ 486; $^1$H NMR (400 MHz, DMSO-d$_6$) δ 12.25 (s, 1H), 9.13 (s, 1H), 8.85 (s, 1H), 8.12 (d, J=2.1 Hz, 1H), 7.81 (dd, J=9.2, 2.4 Hz, 1H), 7.69 (dd, J=8.7, 2.1 Hz, 1H), 7.58 (d, J=8.8 Hz, 1H), 7.52-7.38 (m, 3H), 6.62 (d, J=3.2 Hz, 1H), 5.29 (bs, 2H), 3.64 (bs, 2H), 3.52 (bs, 2H), 2.57 (bs, 2H), 2.45 (bs, 2H), 2.33 (s, 3H).

EXAMPLE 15

Acetic Acid (R)-1-{4-[4-(6-fluoro-2-oxo-1,2-dihydro-quinolin-3-yl)-[1,2,3]triazol-1-yl]-benzoyl}-pyrrolidin-3-yl ester ("A179")

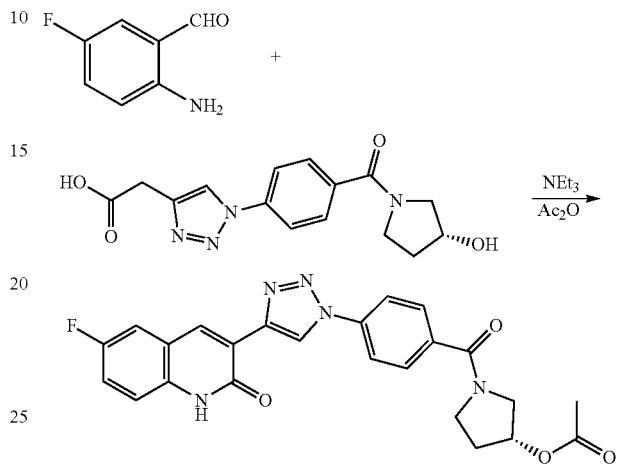

To a suspension of {1-[4-((R)-3-hydroxy-pyrrolidine-1-carbonyl)-phenyl]-1H-[1,2,3]triazol-4-yl}-acetic acid (94.9 mg, 0.30 mmol) and 2-amino-5-fluoro-benzaldehyde (41.7 mg, 0.3 mmol) in acetic acid anhydride (1 ml) is added triethylamine (166 µl, 1.2 mmol) and the reaction mixture is stirred for 30 minutes at 80° C. The reaction mixture is allowed to reach room temperature and concentrated under vacuum. The residue is chromatographed on a silica gel column with dichloromethane/methanol as eluent to afford acetic acid (R)-1-{4-[4-(6-fluoro-2-oxo-1,2-dihydro-quinolin-3-yl)-[1,2,3]triazol-1-yl]-benzoyl}-pyrrolidin-3-yl ester as off-white solid; HPLC/MS 1.49 min (A), [M+H]$^+$ 462. $^1$H NMR (400 MHz, DMSO-d$_6$): 1:1 mixture of rotamers, selection of peaks: δ 12.27 (s, 1H), 9.29 (s, 1H), 8.85 (s, 1H), 8.09 (d, J=8.4 Hz, 2H), 7.86-7.73 (m, 3H), 7.51-7.39 (m, 2H), 2.06 (s, rotamer1), 1.99 (s, rotamer2).

Acetic Acid (S)-1-{4-[4-(6-fluoro-2-oxo-1,2-dihydro-quinolin-3-yl)-[1,2,3]triazol-1-yl]-benzoyl}-pyrrolidin-3-yl ester ("A180")

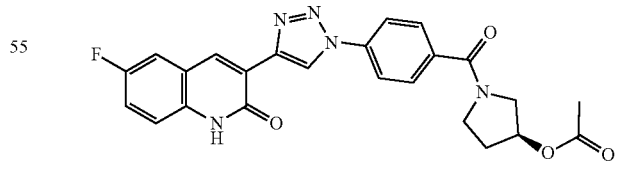

is prepared similarly: off-white solid; HPLC/MS 1.49 min (A), [M+H]$^+$ 462. $^1$H NMR (400 MHz, DMSO-d$_6$): 1:1 mixture of rotamers, selection of peaks: δ 12.27 (s, 1H), 9.29 (s, 1H), 8.85 (s, 1H), 8.09 (d, J=8.4 Hz, 2H), 7.86-7.73 (m, 3H), 7.51-7.39 (m, 2H), 2.06 (s, rotamer1), 1.99 (s, rotamer2).

EXAMPLE 16

6-fluoro-3-{1-[4-((R)-3-hydroxy-pyrrolidine-1-carbonyl)-phenyl]-1H-[1,2,3]triazol-4-yl}-1H-quinolin-2-one ("A181")

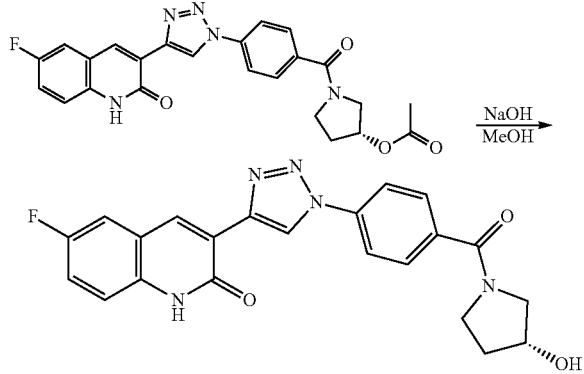

To a solution of acetic acid (R)-1-{4-[4-(6-fluoro-2-oxo-1,2-dihydro-quinolin-3-yl)-[1,2,3]triazol-1-yl]-benzoyl}-pyrrolidin-3-yl ester (94.9 mg, 0.30 mmol) and 2-amino-5-fluorobenzaldehyde (21.9 mg, 0.05 mmol) in methanol (1 ml) is added 1 M sodium hydroxide solution (1 ml) and the reaction mixture is stirred for 3 hours at room temperature. The reaction mixture is concentrated under vacuum and the residue is treated with water. The resultant precipitate is filtered off, washed with water and dried under vacuum to afford 6-fluoro-3-{1-[4-((R)-3-hydroxy-pyrrolidine-1-carbonyl)-phenyl]-1H-[1,2,3]triazol-4-yl}-1H-quinolin-2-one as off-white solid; HPLC/MS 1.34 min (A), [M+H]$^+$ 420.

$^1$H NMR (400 MHz, DMSO-d$_6$): 1:1 mixture of rotamers, selection of peaks: δ 12.26 (s, 1H), 9.29 (s, 1H), 8.85 (s, 1H), 8.15-8.03 (m, 2H), 7.80 (dd, J=9.2, 2.6 Hz, 1H), 7.75 (m, 2H), 7.52-7.37 (m, 2H), 5.02 (d, J=3 Hz, rotamer1), 4.96 (d, J=3.1 Hz, rotamer2), 4.35 (bs, rotamer1), 4.27 (bs, rotamer2).

The following compounds are prepared similarly:

6-fluoro-3-{1-[4-((S)-3-hydroxy-pyrrolidine-1-carbonyl)-phenyl]-1H-[1,2,3]triazol-4-yl}-1H-quinolin-2-one ("A182")

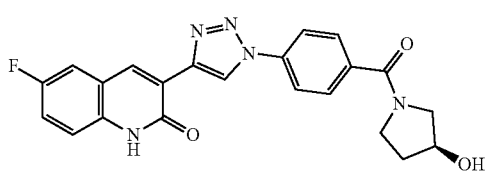 [SMILES: O=C(c1ccc(-n2cc(-c3cc4cc(F)ccc4[nH]c3=O)nn2)cc1)N1CC[C@H](O)C1]

off-white solid; HPLC/MS 1.34 min (A), [M+H]$^+$ 420; $^1$H NMR (400 MHz, DMSO-d$_6$): 1:1 mixture of rotamers, selection of peaks: δ 12.26 (s, 1H), 9.29 (s, 1H), 8.85 (s, 1H), 8.15-8.03 (m, 2H), 7.80 (dd, J=9.2, 2.6 Hz, 1H), 7.75 (m, 2H), 7.52-7.37 (m, 2H), 5.02 (d, J=3 Hz, rotamer1), 4.96 (d, J=3.1 Hz, rotamer2), 4.35 (bs, rotamer1), 4.27 (bs, rotamer2).

6-fluoro-3-{1-[4-(4-hydroxy-piperidine-1-carbonyl)-phenyl]-1H-[1,2,3]triazol-4-yl}-1H-quinolin-2-one ("A183")

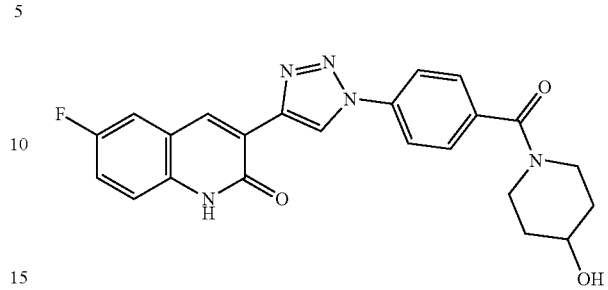

off-white solid; HPLC/MS 1.36 min (A), [M+H]$^+$ 434; $^1$H NMR (500 MHz, DMSO-d$_6$) δ 12.34 (s, 1H), 9.34 (s, 1H), 8.91 (s, 1H), 8.21-8.00 (m, 2H), 7.86 (dd, J=9.3, 2.8 Hz, 1H), 7.74-7.60 (m, 2H), 7.59-7.39 (m, 2H), 4.85 (d, J=3.9 Hz, 1H), 4.08 (bs, 1H), 3.83 (tq, J=8.0, 3.8 Hz, 1H), 3.59 (bs, 1H), 3.29 (bs, 2H), 1.84 (m, 2H), 1.46 (m, 2H).

6-fluoro-3-{1-[4-(3-hydroxy-piperidine-1-carbonyl)-phenyl]-1H-[1,2,3]triazol-4-yl}-1H-quinolin-2-one ("A184")

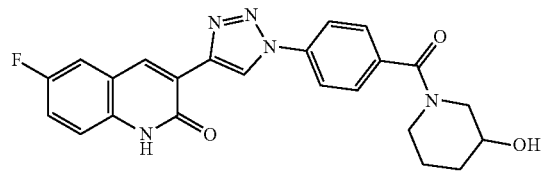 [SMILES: O=C(c1ccc(-n2cc(-c3cc4cc(F)ccc4[nH]c3=O)nn2)cc1)N1CCCC(O)C1]

beige solid; HPLC/MS 1.40 min (A), [M+H]$^+$ 434.

EXAMPLE 17

4-methyl-3-{1-[4-(morpholine-4-carbonyl)-phenyl]-1H-[1,2,3]triazol-4-yl}-1H-quinolin-2-one ("A185")

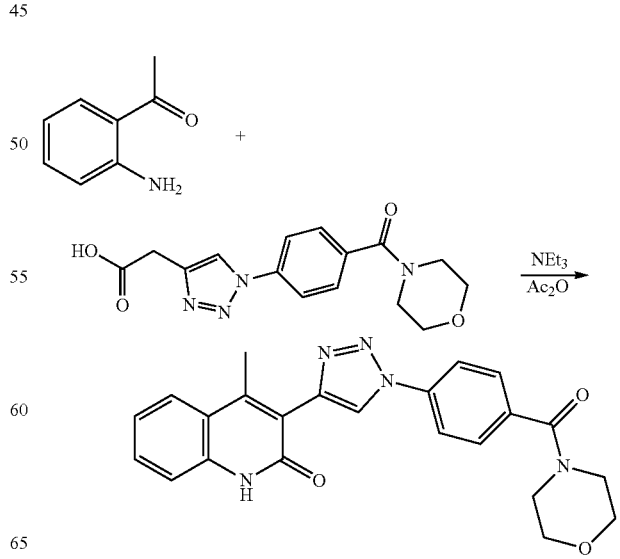

To a suspension of {1-[4-(morpholine-4-carbonyl)-phenyl]-1H-[1,2,3]triazol-4-yl}-acetic acid (94.9 mg, 0.30 mmol) and 1-(2-amino-phenyl)-ethanone (40.6 mg, 0.3 mmol) in acetic acid anhydride (1 ml) is added triethylamine (166 µl, 1.2 mmol) and the reaction mixture is stirred for 5 hours at 100° C. The reaction mixture is allowed to reach room temperature and water is added. The solids are filtered off and partially dissolved in a small amount of DMSO. Methanol is added. The solid is filtered off, washed with methanol and dried under vacuum to afford 4-methyl-3-{1-[4-(morpholine-4-carbonyl)-phenyl]-1H-[1,2,3]triazol-4-yl}-1H-quinolin-2-one as brown powder; UPLC/MS 0.87 min, [M+H]+ 416.

$^1$H NMR (400 MHz, DMSO-$d_6$) δ 11.98 (s, 1H), 9.10 (s, 1H), 8.20-8.03 (m, 2H), 7.91 (dd, J=8.3, 1.3 Hz, 1H), 7.76-7.63 (m, 2H), 7.57 (ddd, J=8.3, 7.1, 1.3 Hz, 1H), 7.38 (dd, J=8.2, 1.2 Hz, 1H), 7.27 (ddd, J=8.3, 7.1, 1.2 Hz, 1H), 3.70-3.35 (m, 8H), 2.65 (s, 3H).

EXAMPLE 18

6-fluoro-3-{1-[4-((R)-2-methyl-pyrrolidine-1-carbonyl)-phenyl]-1H-[1,2,3]triazol-4-yl}-1H-quinolin-2-one ("A186")

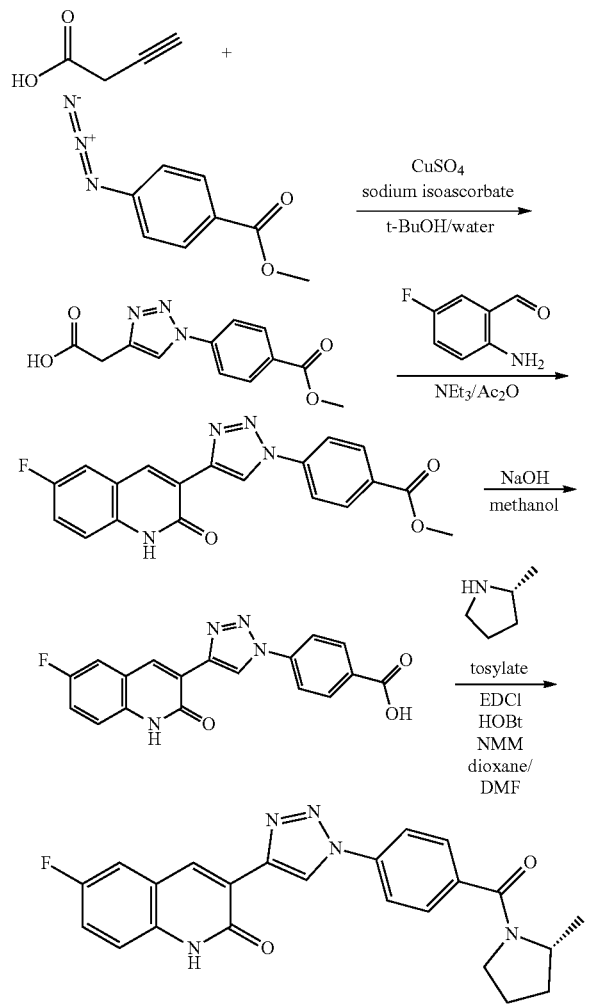

To a suspension of copper(II) sulfate pentahydrate (449 mg, 1.80 mmol) and sodium (2R)-2-[(2R)-3,4-dihydroxy-5-oxo-2H-furan-2-yl]-2-hydroxy-ethanolate hydrate (389 mg, 1.80 mmol) in a mixture of tert-butanol (20 ml) and water (20 ml) are added 3-butynoic acid (1.51 g, 18.0 mmol) and 4-azido-benzoic acid methyl ester (3.19 g, 18.0 mmol). The reaction mixture is stirred at 80° C. for 3 hours. The reaction mixture is allowed to reach room temperature and poured into water. The resultant precipitate is filtered off, washed with water and dried under vacuum to afford 4-(4-carboxymethyl-[1,2,3]triazol-1-yl)-benzoic acid methyl ester as beige solid; UPLC/MS 0.55 min, [M+H]+ 262.

To a suspension of 4-(4-carboxymethyl-[1,2,3]triazol-1-yl)-benzoic acid methyl ester (1.23 g, 4.70 mmol) and 2-amino-5-fluoro-benzaldehyde (654 mg, 4.70 mmol) in acetic acid anhydride (4 ml) is added triethylamine (2.61 ml, 18.8 mmol) and the reaction mixture is stirred for 30 minutes at 80° C. The reaction mixture is diluted cautiously with methanol. The solid is filtered off, washed with tert-butyl methyl ether and dried under vacuum to afford 4-[4-(6-fluoro-2-oxo-1,2-dihydro-quinolin-3-yl)-[1,2,3]triazol-1-yl]-benzoic acid methyl ester as beige solid; UPLC/MS 0.80 min, [M+H]+ 365.

To a suspension of 4-[4-(6-fluoro-2-oxo-1,2-dihydro-quinolin-3-yl)-[1,2,3]triazol-1-yl]-benzoic acid methyl ester (1.24 g, 3.30 mmol) in methanol (30 ml) is added aqueous 2 M sodium hydroxide solution (8.25 ml, 16.5 mmol) and the reaction mixture is stirred for 2 hours at 80° C. The reaction mixture is allowed to reach room temperature and is filtered. The solid residue is triturated with excess 0.5 N hydrochloric acid. The solid is filtered off, washed with water and acetonitrile and dried under vacuum to afford 4-[4-(6-fluoro-2-oxo-1,2-dihydro-quinolin-3-yl)-[1,2,3]triazol-1-yl]-benzoic acid as beige solid; UPLC/MS 0.70 min, [M+H]+ 351.

To a suspension of 4-[4-(6-fluoro-2-oxo-1,2-dihydro-quinolin-3-yl)-[1,2,3]triazol-1-yl]-benzoic acid (35.0 mg, 0.10 mmol) in a mixture of 1,4-dioxane (0.5 ml) and DMF (0.5 ml) are added (R)-2-methylpyrrolidine p-toluenesulfonate (30.9 mg, 0.12 mmol), N-(3-dimethylaminopropyl)-N'-ethylcarbodiimide hydrochloride (28.8 mg, 0.15 mmol), 1-hydroxybenotriazole hydrate (13.5 mg, 0.10 mmol) and 4-methylmorpholine (16.5 µl, 0.15 mmol). The resultant suspension is stirred at room temperature for 5 hours. The reaction mixture is poured into water. The resultant precipitate is filtered off, washed with water and dried. The residue is chromatographed on a silica gel column with dichloromethane/methanol as eluent to afford 6-fluoro-3-{1-[4-((R)-2-methyl-pyrrolidine-1-carbonyl)-phenyl]-1H-[1,2,3]triazol-4-yl}-1H-quinolin-2-one as white crystals; HPLC/MS 1.59 min (A), [M+H]+ 418.

$^1$H NMR (500 MHz, DMSO-$d_6$), mixture of rotamers; main rotamer: δ 12.31 (s, 1H), 9.30 (s, 1H), 8.86 (s, 1H), 8.26-7.95 (m, 2H), 7.82 (dd, J=9.2, 2.8 Hz, 1H), 7.73 (d, J=8.1 Hz, 2H), 7.47 (td, J=8.8, 2.8 Hz, 1H), 7.43 (dd, J=9.0, 4.9 Hz, 1H), 4.25-4.14 (m, 1H), 3.57-3.51 (m, 1H), 3.37-3.32 (m, 1H), 2.10 (dq, J=13.4, 6.8 Hz, 1H), 1.99-1.84 (m, 1H), 1.79-1.68 (m, 1H), 1.64-1.53 (m, 1H), 1.29 (d, J=6.2 Hz, 3H).

The following compounds are prepared similarly:

N-(2-diethylamino-ethyl)-4-[4-(6,7-difluoro-2-oxo-1,2-dihydro-quinolin-3-yl)-[1,2,3]triazol-1-yl]-benzamide ("A187")

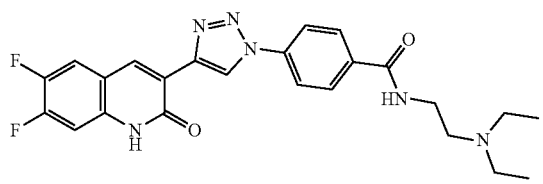

HPLC/MS 1.27 min (A), [M+H]$^+$ 467;
$^1$H NMR (400 MHz, DMSO-d$_6$, TFA-d$_1$) δ 9.33 (s, 1H), 8.86 (s, 1H), 8.20 (d, J=8.9 Hz, 2H), 8.15 (d, J=8.8 Hz, 2H), 7.95 (dd, J=10.8, 8.5 Hz, 1H), 7.37 (dd, J=11.4, 7.0 Hz, 1H), 3.73 (t, J=6.3 Hz, 2H), 3.36 (t, J=6.3 Hz, 2H), 3.30 (qd, J=7.0, 3.8 Hz, 4H), 1.29 (t, J=7.3 Hz, 6H).

4-[4-(7-chloro-6-fluoro-2-oxo-1,2-dihydro-quinolin-3-yl)-[1,2,3]triazol-1-yl]-N-(2-diethylamino-ethyl)-benzamide ("A188")

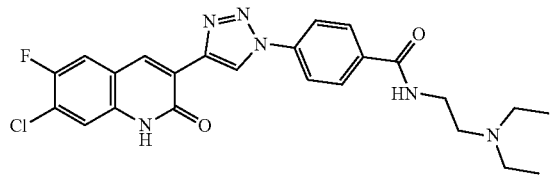 [SMILES: CCN(CC)CCNC(=O)c1ccc(-n2cc(-c3cc4cc(F)c(Cl)cc4[nH]c3=O)nn2)cc1]

HPLC/MS 1.36 min (A), [M+H]$^+$ 483;
$^1$H NMR (400 MHz, DMSO-d$_6$, TFA-d$_1$) δ 9.28 (s, 1H), 8.81 (s, 1H), 8.14 (d, J=8.8 Hz, 2H), 8.08 (d, J=8.8 Hz, 2H), 7.87 (d, J=9.6 Hz, 1H), 7.52 (d, J=6.5 Hz, 1H), 3.65 (t, J=6.3 Hz, 2H), 3.29 (t, J=6.5 Hz, 2H), 3.22 (qd, J=6.9, 3.5 Hz, 3H), 1.22 (t, J=7.2 Hz, 6H).

3-(1-{4-[4-(2-diethylamino-ethyl)-piperazine-1-carbonyl]-phenyl}-1H-[1,2,3]triazol-4-yl)-6,7-difluoro-1H-quinolin-2-one ("A189")

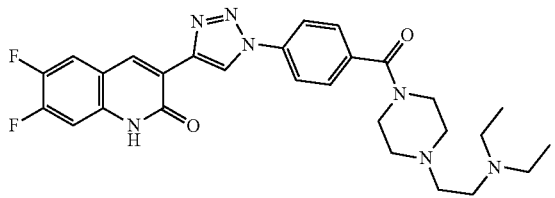 [SMILES: CCN(CC)CCN1CCN(C(=O)c2ccc(-n3cc(-c4cc5cc(F)c(F)cc5[nH]c4=O)nn3)cc2)CC1]

UPLC/MS 0.48 min, [M+H]$^+$ 534;
$^1$H NMR (500 MHz, DMSO-d$_6$, TFA-d$_1$) δ 9.24 (s, 1H), 8.80 (s, 1H), 8.10 (d, J=8.6 Hz, 2H), 7.90 (dd, J=10.8, 8.4 Hz, 1H), 7.69 (d, J=8.6 Hz, 2H), 7.31 (dd, J=11.3, 7.1 Hz, 1H), 4.0-3.6 (m, 4H), 3.63-3.55 (m, 2H), 3.52 (dt, J=10.0, 3.3 Hz, 2H), 3.5-3.35 (m, 4H), 3.20 (q, J=7.2 Hz, 4H), 1.22 (t, J=7.3 Hz, 6H).

6-fluoro-3-{1-[4-(4-methoxy-piperidine-1-carbonyl)-phenyl]-1H-[1,2,3]triazol-4-yl}-1H-quinolin-2-one ("A190")

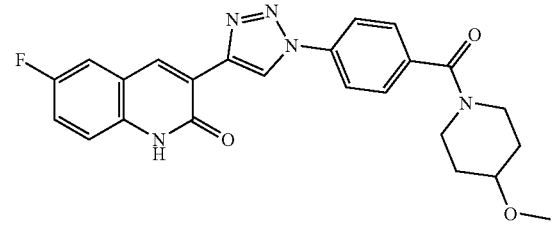 [SMILES: COC1CCN(C(=O)c2ccc(-n3cc(-c4cc5cc(F)ccc5[nH]c4=O)nn3)cc2)CC1]

UPLC/MS 0.70 min, [M+H]$^+$ 448;
1H NMR (400 MHz, DMSO-d$_6$) δ 12.28 (s, 1H), 9.28 (s, 1H), 8.85 (s, 1H), 8.13-8.01 (m, 2H), 7.80 (dd, J=9.2, 2.7 Hz, 1H), 7.69-7.58 (m, 2H), 7.47 (dd, J=9.0, 2.7 Hz, 1H), 7.45-7.39 (m, 1H), 4.1-3.8 (m, 1H), 3.65-3.41 (m, 2H), 3.27 (s, 3H), 3.4-3.1 (m, 2H), 1.87 (bs, 2H), 1.48 (bs, 2H).

6,7-difluoro-3-{1-[4-(4-methoxy-piperidine-1-carbonyl)-phenyl]-1H-[1,2,3]triazol-4-yl}-1H-quinolin-2-one ("A191")

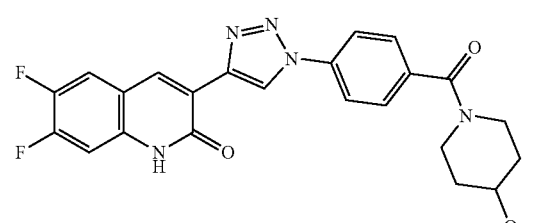

UPLC/MS 0.73 min, [M+H]$^+$ 466;
$^1$H NMR (400 MHz, DMSO-d$_6$) δ 12.32 (s, 1H), 9.25 (s, 1H), 8.84 (s, 1H), 8.29-7.99 (m, 3H), 7.76-7.58 (m, 2H), 7.32 (dd, J=11.4, 7.1 Hz, 1H), 4.1-3.8 (m, 1H), 3.65-3.41 (m, 2H), 3.27 (s, 3H), 3.4-3.1 (m, 2H), 1.87 (bs, 2H), 1.48 (bs, 2H).

6,7-difluoro-3-{1-[4-((R)-3-methoxy-piperidine-1-carbonyl)-phenyl]-1H-[1,2,3]triazol-4-yl}-1H-quinolin-2-one ("A1192")

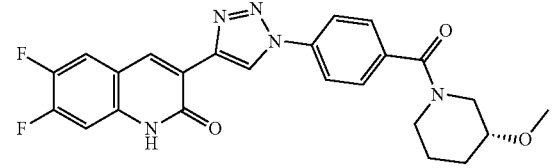 [SMILES: CO[C@@H]1CCCN(C(=O)c2ccc(-n3cc(-c4cc5cc(F)c(F)cc5[nH]c4=O)nn3)cc2)C1]

HPLC/MS 1.56 min (A), [M+H]$^+$ 466;
$^1$H NMR (400 MHz, DMSO-d$_6$) δ 12.33 (s, 1H), 9.26 (s, 1H), 8.84 (s, 1H), 8.13-8.04 (m, 3H), 7.61 (d, J=8.0 Hz, 2H), 7.32 (dd, J=11.4, 7.1 Hz, 1H), 4.0-3.6 (m, 1H), 3.5-3.0 (m, 7H), 2.0-1.35 (m, 4H).

6,7-difluoro-3-{1-[4-((S)-3-methoxy-piperidine-1-carbonyl)-phenyl]-1H-[1,2,3]triazol-4-yl}-1H-quinolin-2-one ("A193")

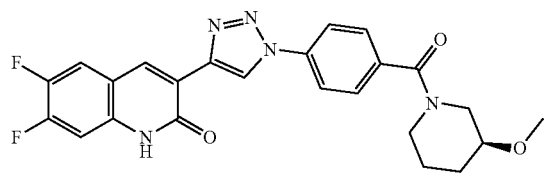 [SMILES: CO[C@H]1CCCN(C(=O)c2ccc(-n3cc(-c4cc5cc(F)c(F)cc5[nH]c4=O)nn3)cc2)C1]

HPLC/MS 1.56 min (A), [M+H]⁺ 466;

¹H NMR (400 MHz, DMSO-d₆) δ 12.33 (s, 1H), 9.26 (s, 1H), 8.84 (s, 1H), 8.13-8.04 (m, 3H), 7.61 (d, J=8.0 Hz, 2H), 7.32 (dd, J=11.4, 7.1 Hz, 1H), 4.0-3.6 (m, 1H), 3.5-3.0 (m, 7H), 2.0-1.35 (m, 4H).

6-fluoro-3-{1-[4-((R)-3-methoxy-piperidine-1-carbonyl)-phenyl]-1H-[1,2,3]triazol-4-yl}-1H-quinolin-2-one ("A194")

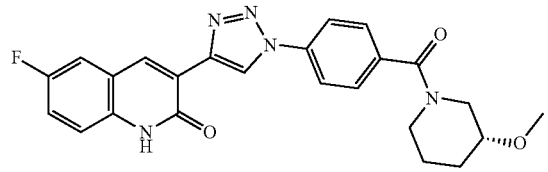 [SMILES: CO[C@@H]1CCCN(C(=O)c2ccc(-n3cc(-c4cc5cc(F)ccc5[nH]c4=O)nn3)cc2)C1]

HPLC/MS 1.52 min (A), [M+H]⁺ 448.

¹H NMR (500 MHz, DMSO-d₆) δ 12.28 (s, 1H), 9.28 (s, 1H), 8.85 (s, 1H), 8.18-8.04 (m, 2H), 7.80 (dd, J=9.2, 2.7 Hz, 1H), 7.65-7.55 (m, 2H), 7.52-7.37 (m, 2H), 4.0-3.6 (m, 1H), 3.5-3.0 (m, 7H), 2.01-1.34 (m, 4H).

6-fluoro-3-{1-[4-((S)-3-methoxy-piperidine-1-carbonyl)-phenyl]-1H-[1,2,3]triazol-4-yl}-1H-quinolin-2-one ("A195")

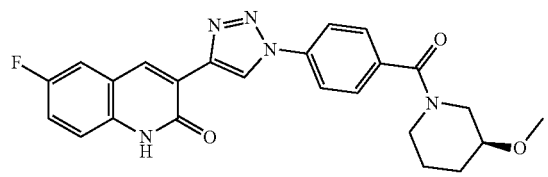 [SMILES: CO[C@H]1CCCN(C(=O)c2ccc(-n3cc(-c4cc5cc(F)ccc5[nH]c4=O)nn3)cc2)C1]

HPLC/MS 1.52 min (A), [M+H]⁺ 448;

¹H NMR (500 MHz, DMSO-d₆) δ 12.28 (s, 1H), 9.28 (s, 1H), 8.85 (s, 1H), 8.18-8.04 (m, 2H), 7.80 (dd, J=9.2, 2.7 Hz, 1H), 7.65-7.55 (m, 2H), 7.52-7.37 (m, 2H), 4.0-3.6 (m, 1H), 3.5-3.0 (m, 7H), 2.01-1.34 (m, 4H).

N-(2-diethylamino-ethyl)-4-[4-(6-fluoro-2-oxo-1,2-dihydro-quinolin-3-yl)-[1,2,3]triazol-1-yl]-benzamide ("A196")

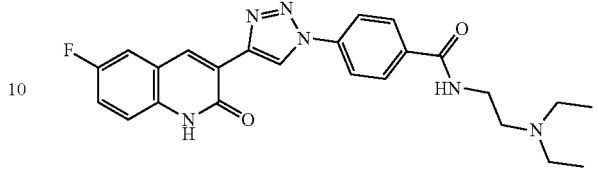

HPLC/MS 1.23 min (A), [M+H]⁺ 449;

¹H NMR (400 MHz, DMSO-d₆) δ 12.29 (s, 1H), 9.31 (s, 1H), 8.86 (s, 1H), 8.55 (t, J=5.7 Hz, 1H), 8.14 (d, J=8.8 Hz, 2H), 8.06 (d, J=8.8 Hz, 2H), 7.81 (dd, J=9.2, 2.6 Hz, 1H), 7.56-7.36 (m, 2H), 3.38-3.32 (m, 2H), 2.61-2.50 (m, 6H), 0.98 (t, J=7.1 Hz, 6H).

6-fluoro-3-{1-[4-((S)-2-hydroxymethyl-pyrrolidine-1-carbonyl)-phenyl]-1H-[1,2,3]triazol-4-yl}-1H-quinolin-2-one ("A197")

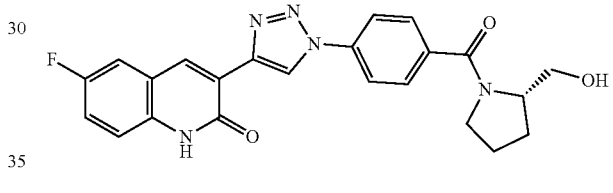

MS [M+H]⁺ 434;

¹H NMR (400 MHz, DMSO-d₆) mixture of 2 rotamers δ 12.29 (s, 1H), 9.30 (s, 1H), 8.86 (s, 1H), 8.09 (d, J=8.4 Hz, 2H), 7.81 (dd, J=9.2, 2.6 Hz, 1H), 7.75 (d, J=8.1 Hz, 2H), 7.51-7.39 (m, 2H), 4.88-4.68 (m, 1H), 4.18 (br. s, 0,7H), 3.91 (br. s, 0,3H), 3.71-3.54 (m, 2H), 3.54-3.43 (m, 1H), 3.37 (br. s, 0,7H), 3.11 (br. s, 0,3H), 2.04-1.84 (m, 3H), 1.80-1.65 (m, 1H).

6-fluoro-3-{1-[4-((R)-2-methoxymethyl-pyrrolidine-1-carbonyl)-phenyl]-1H-[1,2,3]triazol-4-yl}-1H-quinolin-2-one ("A198")

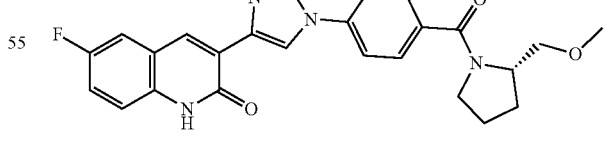

MS [M+H]⁺ 448:

¹H NMR (400 MHz, DMSO-d₆) δ 12.29 (s, 1H), 9.29 (s, 1H), 8.86 (s, 1H), 8.09 (d, J=8.2 Hz, 2H), 7.81 (dd, J=9.3, 2.7 Hz, 1H), 7.72 (d, J=8.2 Hz, 2H), 7.53-7.35 (m, 2H), 4.37-4.23 (m, 1H), 3.68-3.56 (m, 1H), 3.48 (t, J=8.5 Hz, 2H), 3.33 (s, 3H), 3.11-2.97 (m, 1H), 2.09-1.96 (m, 1H), 1.96-1.82 (m, 2H), 1.81-1.68 (m, 1H).

6-fluoro-3-{1-[4-((R)-3-methoxymethyl-pyrrolidine-1-carbonyl)-phenyl]-1H-[1,2,3]triazol-4-yl}-1H-quinolin-2-one ("A199")

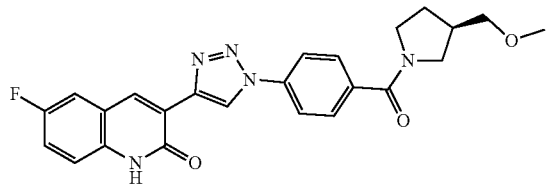 [SMILES: COC[C@@H]1CCN(C(=O)c2ccc(-n3cc(-c4cc5cc(F)ccc5[nH]c4=O)nn3)cc2)C1]

HPLC/MS 1.51 min (A), [M+H]+ 448;
1H NMR (500 MHz, DMSO-d6) δ 12.28 (s, 1H), 9.28 (s, 1H), 8.85 (s, 1H), 8.11-8.05 (m, 2H), 7.80 (dd, J=9.2, 2.7 Hz, 1H), 7.78-7.70 (m, 2H), 7.51-7.37 (m, 2H), 3.69-3.57 (m, 1H), 3.58-3.44 (m, 2H), 3.41-3.17 (m, 6H), 2.55-2.40 (m, 1H), 2.05-1.90 (m, 1H), 1.72-1.60 (m, 1H).

6,7-difluoro-3-{1-[4-((R)-3-methoxymethyl-pyrrolidine-1-carbonyl)-phenyl]-1H-[1,2,3]triazol-4-yl}-1H-quinolin-2-one ("A200")

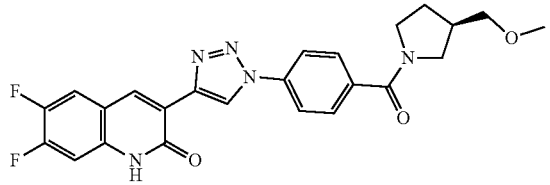 [SMILES: COC[C@@H]1CCN(C(=O)c2ccc(-n3cc(-c4cc5cc(F)c(F)cc5[nH]c4=O)nn3)cc2)C1]

HPLC/MS 1.55 min (A), [M+H]+ 466;
1H NMR (500 MHz, DMSO-d6) δ 12.32 (s, 1H), 9.25 (s, 1H), 8.83 (s, 1H), 8.10-8.04 (m, 3H), 7.77-7.72 (m, 2H), 7.32 (dd, J=11.4, 7.0 Hz, 1H), 3.69-3.57 (m, 1H), 3.58-3.44 (m, 2H), 3.42-3.46 (m, 1H), 3.36-3.19 (m, 5H), 2.55-2.40 (m, 1H), 2.05-1.90 (m, 1H), 1.72-1.60 (m, 1H).

6,7-difluoro-3-{1-[4-((S)-3-methoxymethyl-pyrrolidine-1-carbonyl)-phenyl]-1H-[1,2,3]triazol-4-yl}-1H-quinolin-2-one ("A201")

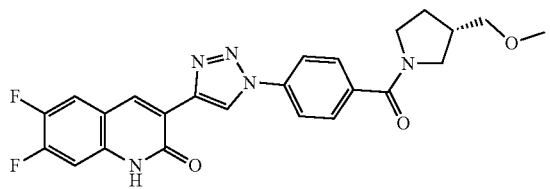 [SMILES: COC[C@H]1CCN(C(=O)c2ccc(-n3cc(-c4cc5cc(F)c(F)cc5[nH]c4=O)nn3)cc2)C1]

HPLC/MS 1.55 min (A), [M+H]+ 466;
1H NMR (500 MHz, DMSO-d6) δ 12.32 (s, 1H), 9.25 (s, 1H), 8.83 (s, 1H), 8.10-8.04 (m, 3H), 7.77-7.72 (m, 2H), 7.32 (dd, J=11.4, 7.0 Hz, 1H), 3.69-3.57 (m, 1H), 3.58-3.44 (m, 2H), 3.42-3.46 (m, 1H), 3.36-3.19 (m, 5H), 2.55-2.40 (m, 1H), 2.05-1.90 (m, 1H), 1.72-1.60 (m, 1H).

6-fluoro-3-{1-[4-((S)-3-methoxymethyl-pyrrolidine-1-carbonyl)-phenyl]-1H-[1,2,3]triazol-4-yl}-1H-quinolin-2-one ("A202")

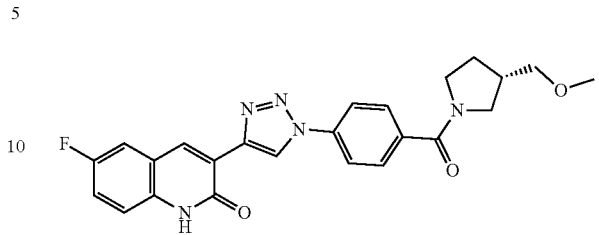

HPLC/MS 1.51 min (A), [M+H]+ 448.
1H NMR (500 MHz, DMSO-d6) δ 12.28 (s, 1H), 9.28 (s, 1H), 8.85 (s, 1H), 8.11-8.05 (m, 2H), 7.80 (dd, J=9.2, 2.7 Hz, 1H), 7.78-7.70 (m, 2H), 7.51-7.37 (m, 2H), 3.69-3.57 (m, 1H), 3.58-3.44 (m, 2H), 3.41-3.17 (m, 6H), 2.55-2.40 (m, 1H), 2.05-1.90 (m, 1H), 1.72-1.60 (m, 1H).

3-(1-{4-[3-(2-diethylamino-ethoxy)-pyrrolidine-1-carbonyl]-phenyl}-1H-[1,2,3]triazol-4-yl)-6-fluoro-1H-quinolin-2-one ("A203")

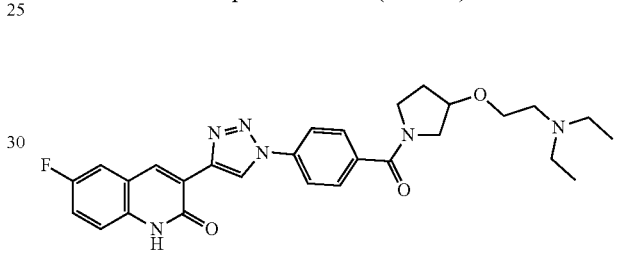

MS [M+H]+ 519;
1H NMR (400 MHz, DMSO-d6)) mixture of 2 rotamers δ 12.27 (s, 1H), 9.29 (s, 1H), 8.85 (s, 1H), 8.09 (d, J=8.3 Hz, 2H), 7.80 (dd, J=9.2, 2.6 Hz, 1H), 7.75 (d, J=8.6 Hz, 2H), 7.51-7.39 (m, 2H), 4.16 (s, 0,4H), 4.07 (s, 0,6H), 3.64 (td, J=13.1, 12.2, 4.6 Hz, 1H), 3.53 (dt, J=23.1, 6.6 Hz, 2H), 3.44-3.37 (m, 3H), 2.57 (t, J=6.2 Hz, 1H), 2.42 (q, J=7.1 Hz, 2H), 2.05-1.91 (m, 2H), 0.96 (t, J=7.1 Hz, 3H), 0.88 (t, J=7.1 Hz, 3H).

6-fluoro-3-{1-[4-(2-oxa-7-aza-spiro[4.4]nonane-7-carbonyl)-phenyl]-1H-[1,2,3]triazol-4-yl}-1H-quinolin-2-one ("A204")

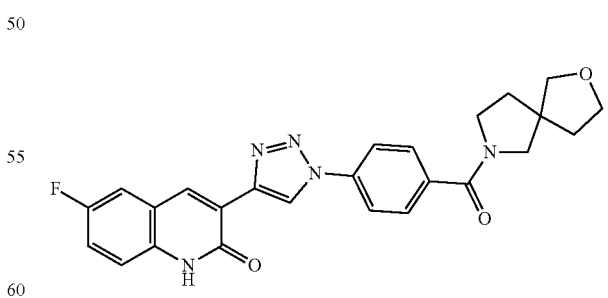

MS [M+H]+ 460;
1H NMR (500 MHz, DMSO-d6) δ 12.27 (s, 1H), 9.29 (d, J=3.0 Hz, 1H), 8.85 (s, 1H), 8.08 (d, J=8.5 Hz, 2H), 7.84-7.72 (m, 3H), 7.51-7.38 (m, 2H), 3.81 (t, J=7.1 Hz, 1H), 3.78-3.47 (m, 6H), 3.43 (s, 1H), 2.03-1.85 (m, 3H), 1.82 (t, J=7.1 Hz, 1H).

6-fluoro-3-{1-[4-(2-oxa-6-aza-spiro[3.4]octane-6-carbonyl)-phenyl]-1H-[1,2,3]triazol-4-yl}-1H-quinolin-2-one ("A205")

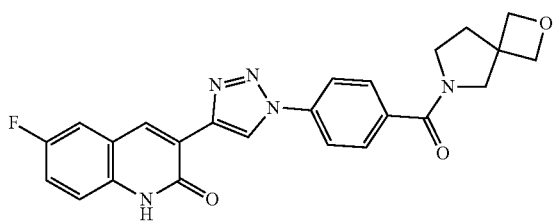 [SMILES: O=C(c1ccc(-n2cc(-c3cc4cc(F)ccc4[nH]c3=O)nn2)cc1)N1CCC2(COC2)C1]

MS [M+H]⁺ 446;
¹H NMR (500 MHz, DMSO-d₆) δ 12.29 (s, 1H), 9.30 (d, J=4.0 Hz, 1H), 8.86 (s, 1H), 8.10 (t, J=8.7 Hz, 2H), 7.81 (dd, J=9.2, 2.7 Hz, 1H), 7.76 (dd, J=8.2, 6.1 Hz, 2H), 7.50-7.41 (m, 2H), 4.65 (d, J=5.9 Hz, 1H), 4.55-4.44 (m, 3H), 3.74 (d, J=17.9 Hz, 2H), 3.51 (dt, J=20.1, 7.0 Hz, 2H), 2.26-2.12 (m, 2H).

6-fluoro-3-{1-[4-(3-hydroxymethyl-pyrrolidine-1-carbonyl)-phenyl]-1H-[1,2,3]triazol-4-yl}-1H-quinolin-2-one ("A206")

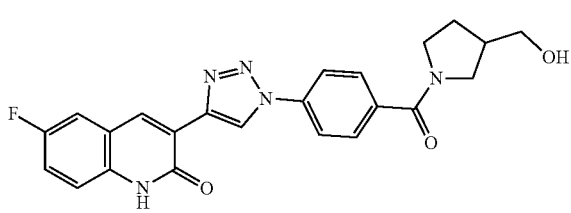 [SMILES: O=C(c1ccc(-n2cc(-c3cc4cc(F)ccc4[nH]c3=O)nn2)cc1)N1CCC(CO)C1]

MS [M+H]⁺ 434;
¹H NMR (500 MHz, DMSO-d₆) mixture of 2 rotamers δ 12.28 (s, 1H), 9.29 (s, 1H), 8.86 (s, 1H), 8.09 (dd, J=8.6, 3.4 Hz, 2H), 7.81 (dd, J=9.2, 2.7 Hz, 1H), 7.76 (d, J=8.3 Hz, 2H), 7.50-7.41 (m, 2H), 4.72 (t, J=5.3 Hz, 0,4H), 4.65 (t, J=5.2 Hz, 0,6H), 3.69-3.57 (m, 1H), 3.57-3.37 (m, 3H), 3.30-3.23 (m, 2H), 2.45-2.24 (m, 1H), 2.03-1.87 (m, 1H), 1.75-1.60 (m, 1H).

3-{1-[4-(3-dimethylamino-pyrrolidine-1-carbonyl)-phenyl]-1H-[1,2,3]triazol-4-yl}-6-fluoro-1H-quinolin-2-one ("A207")

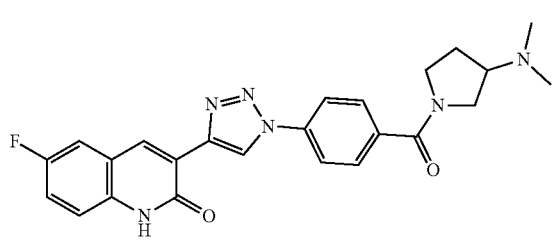 [SMILES: CN(C)C1CCN(C(=O)c2ccc(-n3cc(-c4cc5cc(F)ccc5[nH]c4=O)nn3)cc2)C1]

MS [M+H]⁺ 447;
¹H NMR (500 MHz, DMSO-d₆) mixture of 2 rotamers δ 12.29 (s, 1H), 9.29 (s, 1H), 8.86 (s, 1H), 8.09 (d, J=8.6 Hz, 2H), 7.81 (dd, J=9.2, 2.6 Hz, 1H), 7.77 (t, J=8.9 Hz, 2H), 7.50-7.40 (m, 2H), 3.81-3.72 (m, 0,5H), 3.71-3.63 (m, 0,5H), 3.62-3.44 (m, 2H), 3.41-3.17 (m, 1H), 2.81-2.75 (m, 0,5H), 2.74-2.64 (m, 0,5H), 2.22 (s, 3H), 2.11 (s, 3H), 2.09-2.00 (m, 1H), 1.84-1.69 (m, 1H).

6-fluoro-3-(1-{4-[3-(4-hydroxy-piperidin-1-yl)-pyrrolidine-1-carbonyl]-phenyl}-1H-[1,2,3]triazol-4-yl)-1H-quinolin-2-one ("A208")

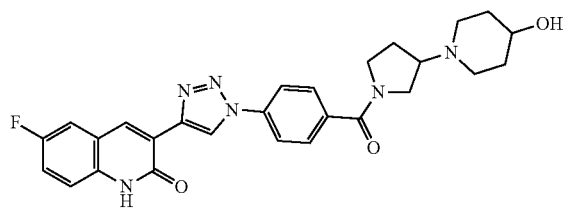 [SMILES: O=C(c1ccc(-n2cc(-c3cc4cc(F)ccc4[nH]c3=O)nn2)cc1)N1CCC(N2CCC(O)CC2)C1]

MS [M+H]⁺ 503;
¹H NMR (500 MHz, DMSO-d₆) mixture of 2 rotamers δ 12.29 (s, 1H), 9.29 (s, 1H), 8.86 (s, 1H), 8.08 (d, J=7.7 Hz, 2H), 7.81 (dd, J=9.2, 2.6 Hz, 1H), 7.79-7.72 (m, 2H), 7.51-7.40 (m, 2H), 3.84-3.39 (m, 5H), 3.32 (s, 1H), 2.94-2.68 (m, 2H), 2.22-1.94 (m, 3H), 1.84-1.58 (m, 3H), 1.51-1.29 (m, 2H).

6-fluoro-3-(1-{4-[3-(2-morpholin-4-yl-ethoxy)-pyrrolidine-1-carbonyl]-phenyl}-1H-[1,2,3]triazol-4-yl)-1H-quinolin-2-one ("A209")

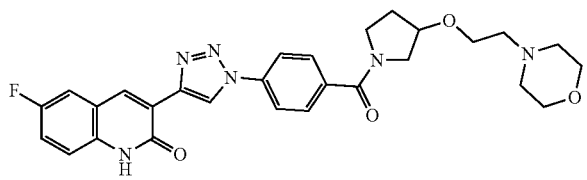 [SMILES: O=C(c1ccc(-n2cc(-c3cc4cc(F)ccc4[nH]c3=O)nn2)cc1)N1CCC(OCCN2CCOCC2)C1]

UPLC/MS 0.48 min, [M+H]⁺ 533;
¹H NMR (500 MHz, DMSO-d₆) δ 12.29 (s, 1H), 9.30 (s, 1H), 8.86 (s, 1H), 8.13-8.08 (m, 2H), 7.81 (dd, J=9.2, 2.7 Hz, 1H), 7.78-7.73 (m, 2H), 7.51-7.39 (m, 2H), 4.20-4.50 (m, 1H), 3.74-3.37 (m, 12H), 2.46-2.32 (m, 4H), 2.05-1.95 (m, 2H).

6-fluoro-3-(1-{4-[(R)-3-(2-methoxy-ethoxymethyl)-pyrrolidine-1-carbonyl]-phenyl}-1H-[1,2,3]triazol-4-yl)-1H-quinolin-2-one ("A210")

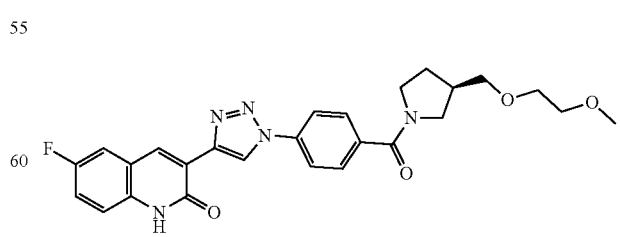

UPLC/MS 0.69 min, [M+H]⁺ 492;
¹H NMR (500 MHz, DMSO-d₆) δ 12.29 (s, 1H), 9.30 (s, 1H), 8.86 (s, 1H), 8.11-8.07 (m, 2H), 7.81 (dd, J=9.2, 2.7 Hz, 1H), 7.78-7.73 (m, 2H), 7.49-7.40 (m, 2H), 3.73-3.14 (m, 13H), 2.54-2.42 (m, 1H), 2.08-1.90 (m, 1H), 1.73-1.62 (m, 1H).

4-[4-(6-fluoro-2-oxo-1,2-dihydro-quinolin-3-yl)-[1,2,3]triazol-1-yl]-N-(2-methoxy-ethyl)-N-methyl-benzamide ("A211")

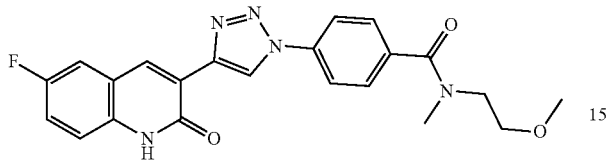

HPLC/MS 1.47 min (A), [M+H]$^+$ 422;
$^1$H NMR (400 MHz, DMSO-d$_6$) δ 12.28 (s, 1H), 9.28 (s, 1H), 8.85 (s, 1H), 8.07 (d, J=8.1 Hz, 2H), 7.80 (dd, J=9.3, 2.6 Hz, 1H), 7.69-7.60 (m, 2H), 7.50-7.39 (m, 2H), 3.72-3.55 (m, 2H), 3.45 (bs, 2H), 3.36-3.16 (m, 3H), 3.00 (s, 3H).

4-[4-(6,7-difluoro-2-oxo-1,2-dihydro-quinolin-3-yl)-[1,2,3]triazol-1-yl]-N-(2-methoxy-ethyl)-N-methyl-benzamide ("A212")

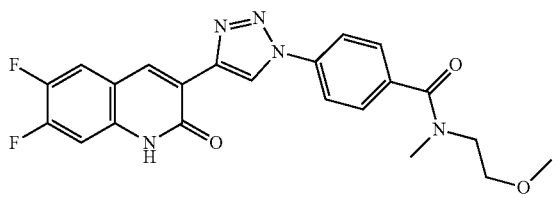 [SMILES: COCCN(C)C(=O)c1ccc(-n2cc(-c3cc4cc(F)c(F)cc4[nH]c3=O)nn2)cc1]

HPLC/MS 1.51 min (A), [M+H]$^+$ 440;
$^1$H NMR (400 MHz, DMSO-d$_6$) δ 12.32 (s, 1H), 9.25 (s, 1H), 8.84 (s, 1H), 8.14-8.01 (m, 3H), 7.67-7.59 (m, 2H), 7.32 (dd, J=11.4, 7.0 Hz, 1H), 3.72-3.55 (m, 2H), 3.45 (bs, 2H), 3.36-3.16 (m, 3H), 3.00 (s, 3H).

6-fluoro-3-{1-[4-((R)-3-hydroxymethyl-morpholine-4-carbonyl)-phenyl]-1H-[1,2,3]triazol-4-yl}-1H-quinolin-2-one ("A213")

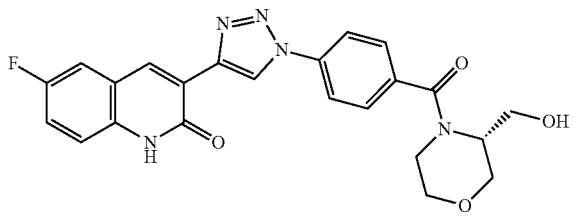 [SMILES: O=C(c1ccc(-n2cc(-c3cc4cc(F)ccc4[nH]c3=O)nn2)cc1)N1CCOC[C@H]1CO]

MS [M+H]$^+$ 450;
$^1$H NMR (400 MHz, DMSO-d$_6$) δ 12.28 (s, 1H), 9.28 (s, 1H), 8.86 (s, 1H), 8.09 (d, J=8.5 Hz, 2H), 7.81 (dd, J=9.3, 2.7 Hz, 1H), 7.67 (d, J=8.5 Hz, 2H), 7.51-7.39 (m, 2H), 4.94 (t, J=5.5 Hz, 1H), 4.52-3.35 (m, 8H), 3.30-2.94 (m, 1H).

6-fluoro-3-{1-[4-(2-hydroxymethyl-piperidine-1-carbonyl)-phenyl]-1H-[1,2,3]triazol-4-yl}-1H-quinolin-2-one ("A214")

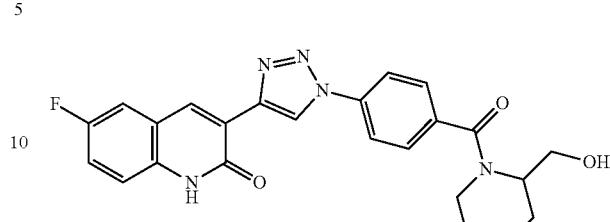

MS [M+H]$^+$ 448;
$^1$H NMR (400 MHz, DMSO-d$_6$) δ 12.26 (s, 1H), 9.26 (s, 1H), 8.84 (s, 1H), 8.05 (d, J=8.5 Hz, 2H), 7.79 (dd, J=9.2, 2.5 Hz, 1H), 7.60 (d, J=8.5 Hz, 2H), 7.51-7.38 (m, 2H), 4.79 (t, J=5.5 Hz, 1H), 4.34 (s, 1H), 3.81-3.60 (m, 2H), 3.61-3.34 (m, 1H), 3.14-2.71 (m, 1H), 1.90-1.49 (m, 6H), 1.50-1.30 (m, 1H).

6-fluoro-3-{1-[4-((S)-2-methoxymethyl-pyrrolidine-1-carbonyl)-phenyl]-1H-[1,2,3]triazol-4-yl}-1H-quinolin-2-one ("A215")

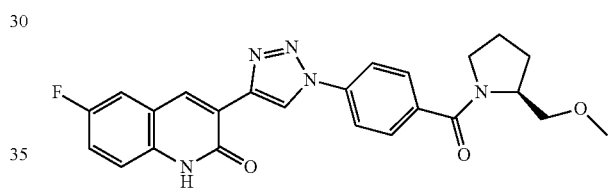

MS [M+H]$^+$ 448;
$^1$H NMR (400 MHz, DMSO-d$_6$) δ 12.28 (s, 1H), 9.29 (s, 1H), 8.85 (s, 1H), 8.08 (d, J=8.7 Hz, 2H), 7.80 (dd, J=9.2, 2.7 Hz, 1H), 7.71 (d, J=8.2 Hz, 2H), 7.50-7.39 (m, 2H), 4.29 (br. s, 1H), 3.61 (br. s, 1H), 3.53-3.42 (m, 2H), 3.04 (br. s, 1H), 2.11-1.96 (m, 1H), 1.96-1.83 (m, 2H), 1.81-1.64 (m, 1H).

6-fluoro-3-{1-[4-((S)-3-hydroxymethyl-morpholine-4-carbonyl)-phenyl]-1H-[1,2,3]triazol-4-yl}-1H-quinolin-2-one ("A216")

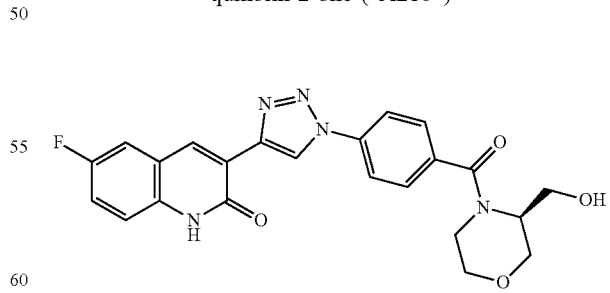

MS [M+H]$^+$ 450;
$^1$H NMR (400 MHz, DMSO-d$_6$) δ 12.28 (s, 1H), 9.28 (s, 1H), 8.86 (s, 1H), 8.09 (d, J=8.5 Hz, 2H), 7.81 (dd, J=9.3, 2.7 Hz, 1H), 7.67 (d, J=8.5 Hz, 2H), 7.51-7.39 (m, 2H), 4.94 (t, J=5.5 Hz, 1H), 4.52-3.35 (m, 8H), 3.30-2.94 (m, 1H).

3-{1-[4-((2S,5S)-2,5-bis-methoxymethyl-pyrrolidine-1-carbonyl)-phenyl]-1H-[1,2,3]triazol-4-yl}-6-fluoro-1H-quinolin-2-one ("A217")

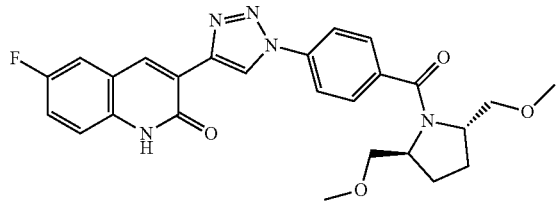 [SMILES: COC[C@@H]1CC[C@@H](COC)N1C(=O)c1ccc(-n2cc(-c3cc4cc(F)ccc4[nH]c3=O)nn2)cc1]

UPLC/MS 0.75 min, [M+H]+ 492;
¹H NMR (400 MHz, DMSO-d₆) δ 12.29 (s, 1H), 9.30 (s, 1H), 8.86 (s, 1H), 8.27-8.03 (m, 2H), 7.82 (dd, J=9.2, 2.7 Hz, 1H), 7.71 (d, J=8.6 Hz, 2H), 7.59-7.36 (m, 2H), 4.38-4.27 (m, 1H), 4.20-4.12 (m, 1H), 3.58-3.51 (m, 1H), 3.40 (t, J=8.4 Hz, 1H), 3.32 (s, 3H), 3.05-2.88 (m, 5H), 2.26-2.13 (m, 1H), 2.10-1.96 m, 1H), 1.90-1.75 (m, 2H).

3-{1-[4-((2R,5R)-2,5-bis-methoxymethyl-pyrrolidine-1-carbonyl)-phenyl]-1H-[1,2,3]triazol-4-yl}-6-fluoro-1H-quinolin-2-one ("A218")

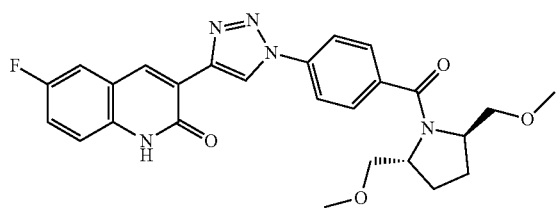 [SMILES: COC[C@H]1CC[C@H](COC)N1C(=O)c1ccc(-n2cc(-c3cc4cc(F)ccc4[nH]c3=O)nn2)cc1]

UPLC/MS 0.74 min, [M+H]+ 492;
¹H NMR (400 MHz, DMSO-d₆) δ 12.29 (s, 1H), 9.30 (s, 1H), 8.86 (s, 1H), 8.27-8.03 (m, 2H), 7.82 (dd, J=9.2, 2.7 Hz, 1H), 7.71 (d, J=8.6 Hz, 2H), 7.59-7.36 (m, 2H), 4.38-4.27 (m, 1H), 4.20-4.12 (m, 1H), 3.58-3.51 (m, 1H), 3.40 (t, J=8.4 Hz, 1H), 3.32 (s, 3H), 3.05-2.88 (m, 5H), 2.26-2.13 (m, 1H), 2.10-1.96 m, 1H), 1.90-1.75 (m, 2H).

3-{1-[4-((2S,5S)-2,5-bis-methoxymethyl-pyrrolidine-1-carbonyl)-phenyl]-1H-[1,2,3]triazol-4-yl}-6,7-difluoro-1H-quinolin-2-one ("A219")

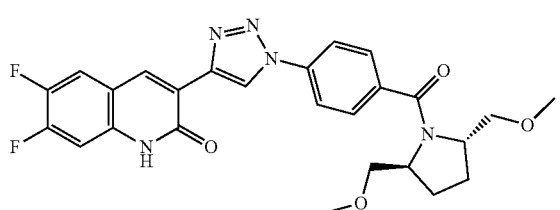

UPLC/MS 0.75 min, [M+H]+ 510;
¹H NMR (300 MHz, DMSO-d₆) δ 12.34 (s, 1H), 9.28 (s, 1H), 8.86 (s, 1H), 8.22-7.99 (m, 3H), 7.78-7.66 (m, 2H), 7.33 (dd, J=11.5, 7.1 Hz, 1H), 4.38-4.27 (m, 1H), 4.20-4.12 (m, 1H), 3.58-3.51 (m, 1H), 3.40 (t, J=8.4 Hz, 1H), 3.32 (s, 3H), 3.05-2.88 (m, 5H), 2.26-2.13 (m, 1H), 2.10-1.96 m, 1H), 1.90-1.75 (m, 2H).

3-{1-[4-((2R,5R)-2,5-bis-methoxymethyl-pyrrolidine-1-carbonyl)-phenyl]-1H-[1,2,3]triazol-4-yl}-6,7-difluoro-1H-quinolin-2-one ("A220")

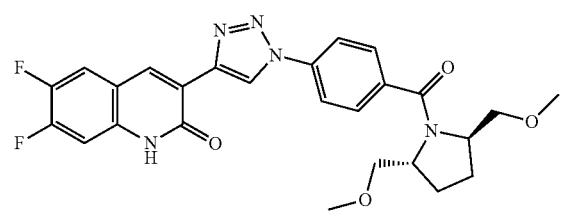 [SMILES: COC[C@H]1CC[C@H](COC)N1C(=O)c1ccc(-n2cc(-c3cc4cc(F)c(F)cc4[nH]c3=O)nn2)cc1]

UPLC/MS 0.76 min, [M+H]+ 510;
¹H NMR (300 MHz, DMSO-d₆) δ 12.34 (s, 1H), 9.28 (s, 1H), 8.86 (s, 1H), 8.22-7.99 (m, 3H), 7.78-7.66 (m, 2H), 7.33 (dd, J=11.5, 7.1 Hz, 1H), 4.38-4.27 (m, 1H), 4.20-4.12 (m, 1H), 3.58-3.51 (m, 1H), 3.40 (t, J=8.4 Hz, 1H), 3.32 (s, 3H), 3.05-2.88 (m, 5H), 2.26-2.13 (m, 1H), 2.10-1.96 m, 1H), 1.90-1.75 (m, 2H).

6,7-difluoro-3-(1-{4-[3-(2-morpholin-4-yl-ethoxy)-pyrrolidine-1-carbonyl]-phenyl}-1H-[1,2,3]triazol-4-yl)-1H-quinolin-2-one ("A221")

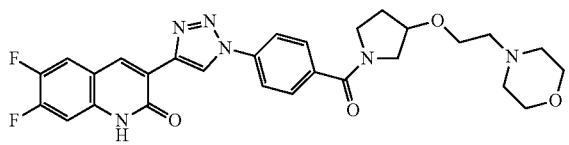 [SMILES: O=C(c1ccc(-n2cc(-c3cc4cc(F)c(F)cc4[nH]c3=O)nn2)cc1)N1CCC(OCCN2CCOCC2)C1]

UPLC/MS 0.49 min, [M+H]+ 551;
¹H NMR (400 MHz, DMSO-d₆) δ 12.34 (s, 1H), 9.28 (s, 1H), 8.13-8.06 (m, 3H), 7.78-7.73 (m, 2H), 7.33 (dd, J=11.4, 7.1 Hz, 1H), 4.23-3.93 (m, 1H), 3.73-3.36 (m, 10H), 2.47-2.30 (m, 6H), 2.06-1.94 (m, 2H).

6-fluoro-7-methyl-3-{1-[4-(4-methyl-piperazine-1-carbonyl)-phenyl]-1H-[1,2,3]triazol-4-yl}-1H-quinolin-2-one ("A222")

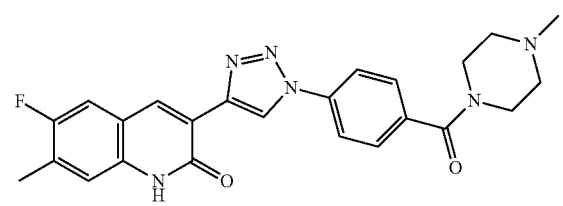 [SMILES: Cc1cc2[nH]c(=O)c(-c3cn(-c4ccc(C(=O)N5CCN(C)CC5)cc4)nn3)cc2cc1F]

6,7-difluoro-3-(1-{4-[(R)-3-(2-methoxy-ethoxymethyl)-pyrrolidine-1-carbonyl]-phenyl}-1H-[1,2,3]triazol-4-yl)-1H-quinolin-2-one ("A223")

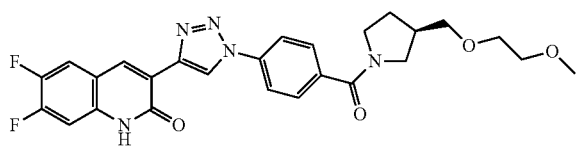 [SMILES: COCCOC[C@@H]1CCN(C(=O)c2ccc(-n3cc(-c4cc5cc(F)c(F)cc5[nH]c4=O)nn3)cc2)C1]

HPLC/MS 1.54 min (A), [M+H]+ 510;

¹H NMR (400 MHz, DMSO-d₆) δ 12.33 (s, 1H), 9.27 (s, 1H), 8.85 (s, 1H), 8.17-8.04 (m, 3H), 7.78-7.72 (m, 2H), 7.33 (dd, J=11.4, 7.1 Hz, 1H), 3.73-3.37 (m, 9H), 3.36-3.18 (m, 5H), 2.56-2.41 (m, 1H), 2.06-1.90 (m, 1H), 1.76-1.58 (m, 1H).

6-fluoro-3-(1-{4-[3-(2-pyrrolidin-1-yl-ethoxy)-pyrrolidine-1-carbonyl]-phenyl}-1H-[1,2,3]triazol-4-yl)-1H-quinolin-2-one ("A224")

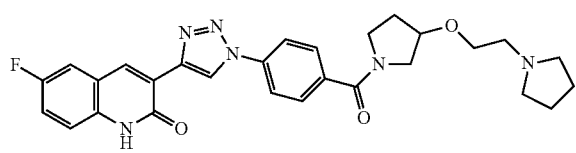 [SMILES: O=C(c1ccc(-n2cc(-c3cc4cc(F)ccc4[nH]c3=O)nn2)cc1)N1CCC(OCCN2CCCC2)C1]

UPLC/MS 0.49 min, [M+H]+ 517;

¹H NMR (500 MHz, DMSO-d₆, TFA-d₁) δ 9.32 (s, 1H), 8.88 (s, 1H), 8.17-8.11 (m, 2H), 7.84-7.72 (m, 3H), 7.48 (dd, J=9.0, 4.9 Hz, 1H), 7.43 (td, J=8.7, 2.8 Hz, 1H), 4.32-4.12 (m, 1H), 3.83-3.31 (m, 10H), 3.21-2.98 (m, 3H), 2.21-1.76 (m, 5H).

6,7-difluoro-3-(1-{4-[3-(2-pyrrolidin-1-yl-ethoxy)-pyrrolidine-1-carbonyl]-phenyl}-1H-[1,2,3]triazol-4-yl)-1H-quinolin-2-one ("A225")

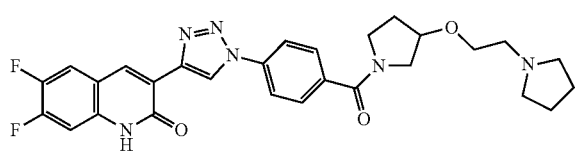 [SMILES: O=C(c1ccc(-n2cc(-c3cc4cc(F)c(F)cc4[nH]c3=O)nn2)cc1)N1CCC(OCCN2CCCC2)C1]

UPLC/MS 0.50 min, [M+H]+ 535;

¹H NMR (500 MHz, DMSO-d₆, TFA-d₁) δ 9.30 (s, 1H), 8.87 (s, 1H), 8.17-8.06 (m, 2H), 8.02 (dd, J=10.9, 8.5 Hz, 1H), 7.82-7.76 m, 2H), 7.37 (dd, J=11.4, 7.1 Hz, 1H), 4.32-4.12 (m, 1H), 3.83-3.31 (m, 10H), 3.21-2.98 (m, 3H), 2.21-1.76 (m, 5H).

(R)-1-{4-[4-(6-fluoro-2-oxo-1,2-dihydro-quinolin-3-yl)-[1,2,3]triazol-1-yl]-benzoyl}-pyrrolidine-3-carboxylic Acid Amide ("A226")

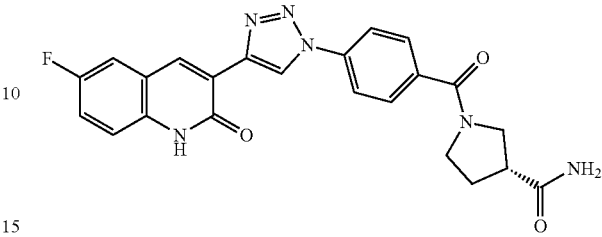

UPLC/MS 0.59 min, [M+H]+ 447.

¹H NMR (500 MHz, DMSO-d₆) δ 12.27 (s, 1H), 9.29 (s, 1H), 8.85 (s, 1H), 8.11-8.06 (m, 2H), 7.80 (dd, J=9.2, 2.7 Hz, 1H), 7.78-7.72 (m, 2H), 7.53-7.34 (m, 3H), 6.99-6.91 (m, 1H), 3.77-3.45 (m, 4H), 3.05-2.91 (m, 1H), 2.20-1.93 (m, 2H).

6-fluoro-3-{1-[4-((2S,4R)-4-hydroxy-2-hydroxymethyl-pyrrolidine-1-carbonyl)-phenyl]-1H-[1,2,3]triazol-4-yl}-1H-quinolin-2-one ("A227")

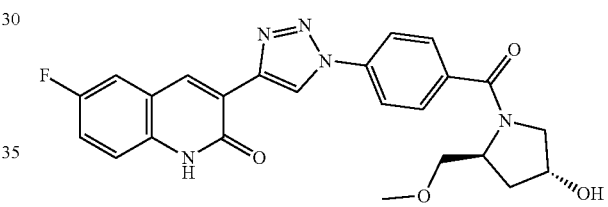

MS [M+H]+ 450;

¹H NMR (500 MHz, DMSO-d₆) δ 12.29 (s, 1H), 9.31 (s, 1H), 8.87 (s, 1H), 8.10 (d, J=8.5 Hz, 2H), 7.82 (dd, J=9.2, 2.7 Hz, 1H), 7.76 (d, J=8.5 Hz, 2H), 7.53-7.37 (m, 2H), 4.83 (d, J=3.1 Hz, 1H), 4.78 (t, J=5.9 Hz, 1H), 4.31 (q, J=6.2, 5.2 Hz, 1H), 4.23 (br. s, 1H), 3.79-3.69 (m, 1H), 3.67-3.52 (m, 2H), 3.26 (d, J=11.1 Hz, 1H), 2.14-2.01 (m, 1H), 1.98-1.85 (m, 1H).

6-fluoro-3-{1-[4-(2-oxa-6-aza-spiro[3.5]nonane-6-carbonyl)-phenyl]-1H-[1,2,3]triazol-4-yl}-1H-quinolin-2-one ("A228")

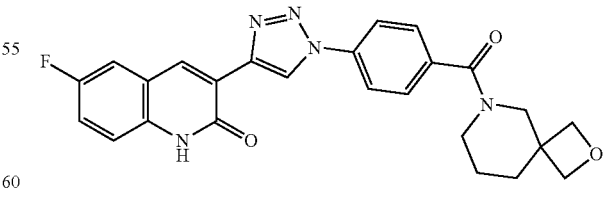

MS [M+H]+ 460;

¹H NMR (400 MHz, DMSO-d₆) δ 12.27 (s, 1H), 9.29 (s, 1H), 8.85 (s, 1H), 8.10 (d, J=8.4 Hz, 2H), 7.80 (dd, J=9.2, 2.6 Hz, 1H), 7.61 (d, J=7.4 Hz, 2H), 7.50-7.37 (m, 2H), 4.49-3.98 (m, 4H), 3.88 (br. s, 1H), 3.60 (br. s, 2H), 3.33 (br. s, 1H), 1.94-1.79 (m, 2H), 1.58-1.37 (m, 2H).

6-fluoro-3-{1-[4-(2-oxa-7-aza-spiro[3.5]nonane-7-carbonyl)-phenyl]-1H-[1,2,3]triazol-4-yl}-1H-quinolin-2-one ("A229")

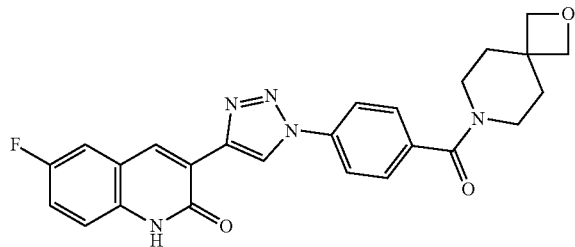 [SMILES: O=C(c1ccc(-n2cc(-c3cc4cc(F)ccc4[nH]c3=O)nn2)cc1)N1CCC2(CC1)COC2]

MS [M+H]⁺ 460;
¹H NMR (400 MHz, DMSO-d₆) δ 12.27 (s, 1H), 9.28 (s, 1H), 8.85 (s, 1H), 8.08 (d, J=8.6 Hz, 2H), 7.80 (dd, J=9.3, 2.6 Hz, 1H), 7.60 (d, J=8.6 Hz, 2H), 7.50-7.37 (m, 2H), 4.35 (s, 4H), 3.55 (br. s, 2H), 3.32 (br. s, 2H), 1.83 (br. s, 4H).

6-fluoro-3-{1-[4-(4-oxetan-3-yl-piperazine-1-carbonyl)-phenyl]-1H-[1,2,3]triazol-4-yl}-1H-quinolin-2-one ("A230")

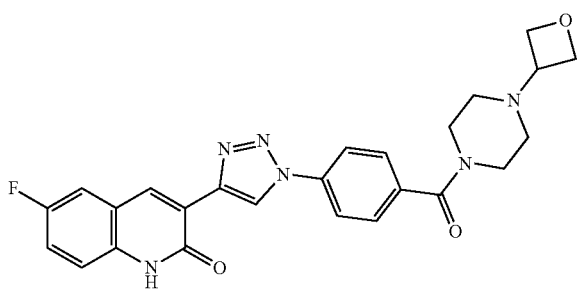 [SMILES: O=C(c1ccc(-n2cc(-c3cc4cc(F)ccc4[nH]c3=O)nn2)cc1)N1CCN(C2COC2)CC1]

MS [M+H]⁺ 475;
¹H NMR (400 MHz, DMSO-d₆) δ 12.27 (s, 1H), 9.32-9.23 (m, 1H), 8.85 (s, 1H), 8.09 (d, J=8.6 Hz, 2H), 7.79 (dd, J=9.2, 2.6 Hz, 1H), 7.63 (d, J=8.6 Hz, 2H), 7.55-7.30 (m, 2H), 4.55 (t, J=6.5 Hz, 2H), 4.46 (t, J=6.1 Hz, 2H), 3.66 (br. s, 2H), 3.47 (p, J=6.3 Hz, 1H), 3.42 (br. s, 2H), 2.32 (br. s, 4H).

3-{1-[4-(2,5-dioxa-8-aza-spiro[3.5]nonane-8-carbonyl)-phenyl]-1H-[1,2,3]triazol-4-yl}-6-fluoro-1H-quinolin-2-one ("A231")

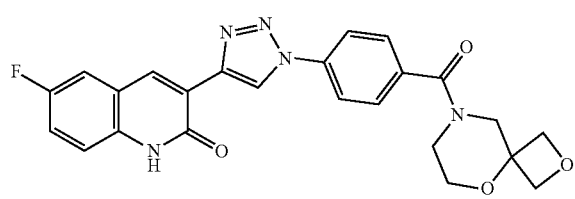 [SMILES: O=C(c1ccc(-n2cc(-c3cc4cc(F)ccc4[nH]c3=O)nn2)cc1)N1CCOC2(COC2)C1]

MS [M+H]⁺ 462;
¹H NMR (500 MHz, DMSO-d₆) δ 12.27 (s, 1H), 9.30 (s, 1H), 8.85 (s, 1H), 8.12 (d, J=8.1 Hz, 2H), 7.80 (dd, J=9.2, 2.7 Hz, 1H), 7.67 (d, J=8.4 Hz, 2H), 7.53-7.33 (m, 2H), 4.60-4.12 (m, 4H), 4.03-3.32 (m, 6H).

4-[4-(6-fluoro-2-oxo-1,2-dihydro-quinolin-3-yl)-[1,2,3]triazol-1-yl]-N-oxetan-3-yl-benzamide ("A232")

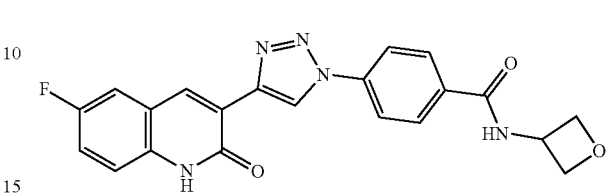

MS [M+H]⁺ 406;
¹H NMR (500 MHz, DMSO-d₆) δ 12.28 (s, 1H), 9.33 (s, 1H), 9.26 (d, J=6.4 Hz, 1H), 8.86 (s, 1H), 8.17 (d, J=8.8 Hz, 2H), 8.12 (d, J=8.8 Hz, 2H), 7.80 (dd, J=9.2, 2.7 Hz, 1H), 7.52-7.37 (m, 2H), 5.04 (ddt, J=14.0, 7.5, 6.5 Hz, 1H), 4.80 (dd, J=7.5, 6.4 Hz, 2H), 4.63 (t, J=6.4 Hz, 2H).

6,7-difluoro-3-(1-{4-[(S)-3-(2-methoxy-ethoxymethyl)-pyrrolidine-1-carbonyl]-phenyl}-1H-[1,2,3]triazol-4-yl)-1H-quinolin-2-one ("A233")

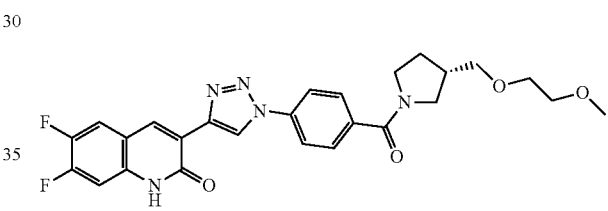

HPLC/MS 1.54 min (A), [M+H]⁺ 510;
¹H NMR (400 MHz, DMSO-d₆) δ 12.33 (s, 1H), 9.27 (s, 1H), 8.85 (s, 1H), 8.17-8.04 (m, 3H), 7.78-7.72 (m, 2H), 7.33 (dd, J=11.4, 7.1 Hz, 1H), 3.73-3.37 (m, 8H), 3.36-3.18 (m, 5H), 2.56-2.41 (m, 1H), 2.06-1.90 (m, 1H), 1.76-1.58 (m, 1H).

6-fluoro-3-{1-[4-(2-oxa-5-aza-spiro[3.4]octane-5-carbonyl)-phenyl]-1H-[1,2,3]triazol-4-yl}-1H-quinolin-2-one ("A234")

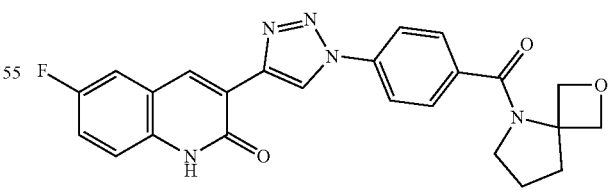

MS [M+H]⁺ 446;
¹H NMR (500 MHz, DMSO-d₆) δ 12.28 (s, 1H), 9.29 (s, 1H), 8.85 (s, 1H), 8.09 (d, J=8.6 Hz, 2H), 7.80 (dd, J=9.2, 2.7 Hz, 1H), 7.75 (d, J=8.6 Hz, 2H), 7.55-7.30 (m, 2H), 5.47 (d, J=5.1 Hz, 2H), 4.33 (d, J=5.2 Hz, 2H), 3.39 (t, J=6.5 Hz, 2H), 2.34 (t, J=6.7 Hz, 2H), 1.71 (p, J=6.6 Hz, 2H).

6-fluoro-3-{1-[4-(2-oxa-6-aza-spiro[3.3]heptane-6-carbonyl)-phenyl]-1H-[1,2,3]triazol-4-yl}-1H-quinolin-2-one ("A235")

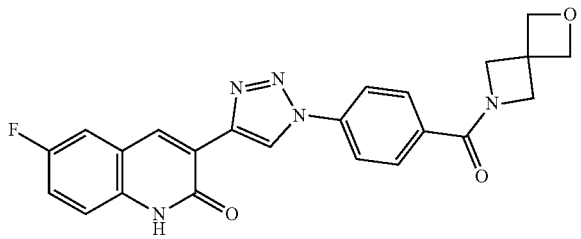 [SMILES: O=C(c1ccc(-n2cc(-c3cc4cc(F)ccc4[nH]c3=O)nn2)cc1)N1CC2(COC2)C1]

MS [M+H]+ 432;
1H NMR (400 MHz, DMSO-d6) δ 12.28 (s, 1H), 9.30 (s, 1H), 8.85 (s, 1H), 8.11 (d, J=8.7 Hz, 2H), 7.84 (d, J=8.7 Hz, 2H), 7.80 (dd, J=9.2, 2.6 Hz, 1H), 7.50-7.38 (m, 2H), 4.70 (s, 4H), 4.55 (s, 2H), 4.25 (s, 2H).

6-fluoro-3-(1-{4-[(S)-3-(2-methoxy-ethoxymethyl)-pyrrolidine-1-carbonyl]-phenyl}-1H-[1,2,3]triazol-4-yl)-1H-quinolin-2-one ("A236")

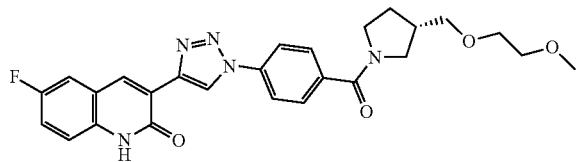 [SMILES: COCCOC[C@H]1CCN(C(=O)c2ccc(-n3cc(-c4cc5cc(F)ccc5[nH]c4=O)nn3)cc2)C1]

HPLC/MS 1.49 min (A), [M+H]+ 492;
1H NMR (400 MHz, DMSO-d6) δ 12.28 (s, 1H), 9.29 (s, 1H), 8.86 (s, 1H), 8.16-8.03 (m, 2H), 7.81 (dd, J=9.3, 2.7 Hz, 1H), 7.78-7.72 (m, 2H), 7.50-7.40 (m, 2H), 3.73-3.37 (m, 8H), 3.36-3.18 (m, 5H), 2.56-2.41 (m, 1H), 2.06-1.90 (m, 1H), 1.76-1.58 (m, 1H).

3-{1-[4-((3R,4S)-3,4-dimethoxy-pyrrolidine-1-carbonyl)-phenyl]-1H-[1,2,3]triazol-4-yl}-6-fluoro-1H-quinolin-2-one ("A237")

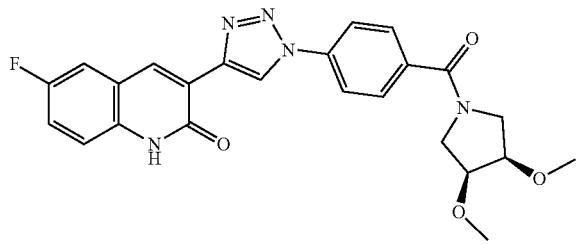 [SMILES: CO[C@H]1CN(C(=O)c2ccc(-n3cc(-c4cc5cc(F)ccc5[nH]c4=O)nn3)cc2)C[C@H]1OC]

UPLC/MS 0.65 min, [M+H]+ 464;
1H NMR (400 MHz, DMSO-d6) δ 12.28 (s, 1H), 9.29 (s, 1H), 8.85 (s, 1H), 8.13-8.05 (m, 2H), 7.80 (dd, J=9.2, 2.7 Hz, 1H), 7.78-7.72 (m, 2H), 7.51-7.39 (m, 2H), 4.03 (q, J=5.1 Hz, 1H), 3.98-3.90 (m, 1H), 3.70-3.61 (m, 2H), 3.53-3.41 (m, 2H), 3.38 (s, 3H), 3.28 (s, 3H).

4-[4-(6-fluoro-2-oxo-1,2-dihydro-quinolin-3-yl)-[1,2,3]triazol-1-yl]-N,N-bis-(2-methoxy-ethyl)-benzamide ("A238")

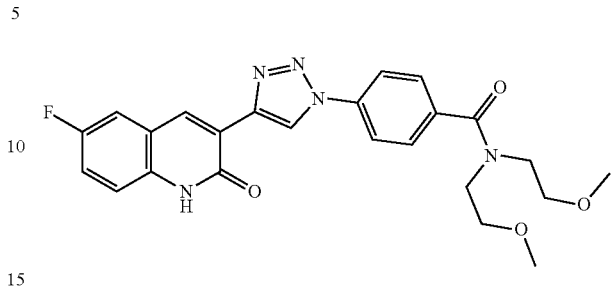

UPLC/MS 0.70 min, [M+H]+ 466;
1H NMR (500 MHz, DMSO-d6) δ 12.28 (s, 1H), 9.28 (s, 1H), 8.85 (s, 1H), 8.12-8.02 (m, 2H), 7.80 (dd, J=9.2, 2.7 Hz, 1H), 7.68-7.56 (m, 2H), 7.51-7.39 (m, 2H), 3.75-3.11 (m, 14H).

3-{1-[4-(3-diethylaminomethyl-pyrrolidine-1-carbonyl)-phenyl]-1H-[1,2,3]triazol-4-yl}-6,7-difluoro-1H-quinolin-2-one ("A239")

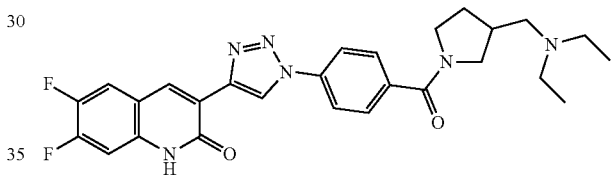

UPLC/MS 0.50 min, [M+H]+ 507;
1H NMR (500 MHz, DMSO-d6, TFA-d1) δ 9.26 (s, 1H), 8.83 (s, 1H), 8.10 (s, 1H, formate-H), 8.12-8.07 (m, 2H), 8.01 (dd, J=10.9, 8.5 Hz, 1H), 7.78-7.72 (m, 2H), 7.33 (dd, J=11.4, 7.1 Hz, 1H), 3.90-3.47 (m, 4H), 3.38-3.04 (m, 6H), 2.72-2.57 (m, 1H), 2.23-2.07 (m, 1H), 1.78-1.66 (m, 1H), 1.28-1.11 (m, 6H).

N-(3-acetyl-3-aza-bicyclo[3.1.0]hex-6-yl)-4-[4-(6-fluoro-2-oxo-1,2-dihydro-quinolin-3-yl)-[1,2,3]triazol-1-yl]-benzamide ("A240")

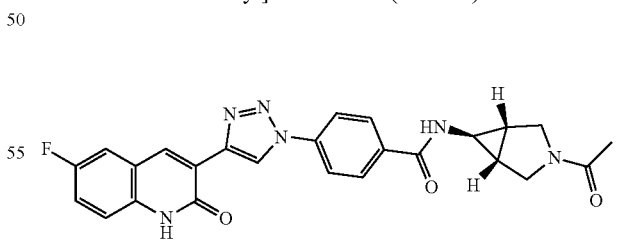

MS [M+H]+ 473;
1H NMR (400 MHz, DMSO-d6) δ 12.29 (s, 1H), 9.32 (s, 1H), 8.87 (s, 1H), 8.72 (d, J=3.9 Hz, 1H), 8.15 (d, J=8.7 Hz, 2H), 8.06 (d, J=8.7 Hz, 2H), 7.81 (dd, J=9.2, 2.7 Hz, 1H), 7.52-7.38 (m, 2H), 3.66 (qd, J=10.2, 4.1 Hz, 2H), 3.44-3.32 (m, 2H), 2.60 (q, J=2.8 Hz, 1H), 1.94 (s, 3H), 1.90-1.80 (m, 1H), 1.10 (t, J=7.0 Hz, 1H).

6-fluoro-3-{1-[4-((2S,4R)-2-hydroxymethyl-4-methoxy-pyrrolidine-1-carbonyl)-phenyl]-1H-[1,2,3]triazol-4-yl}-1H-quinolin-2-one ("A241")

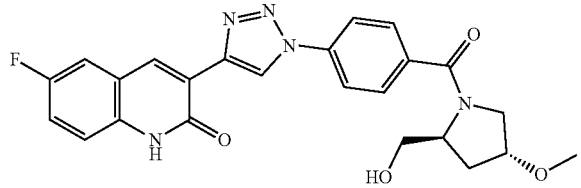 [SMILES: CO[C@@H]1C[C@@H](CO)N(C(=O)c2ccc(-n3cc(-c4cc5cc(F)ccc5[nH]c4=O)nn3)cc2)C1]

MS [M+H]⁺ 464;
¹H NMR (400 MHz, DMSO-d$_6$) δ 12.29 (s, 1H), 9.30 (s, 1H), 8.87 (s, 1H), 8.11 (d, J=8.4 Hz, 2H), 7.81 (dd, J=9.3, 2.7 Hz, 1H), 7.76 (d, J=8.3 Hz, 2H), 7.51-7.40 (m, 2H), 4.81 (t, J=5.8 Hz, 1H), 4.24 (s, 1H), 3.92 (s, 1H), 3.82-3.71 (m, 1H), 3.67-3.50 (m, 2H), 3.40 (d, J=11.8 Hz, 1H), 3.12 (s, 3H), 2.18-2.03 (m, 2H).

(S)-1-{4-[4-(6-fluoro-2-oxo-1,2-dihydro-quinolin-3-yl)-[1,2,3]triazol-1-yl]-benzoyl}-pyrrolidine-2-carboxylic acid amide ("A242")

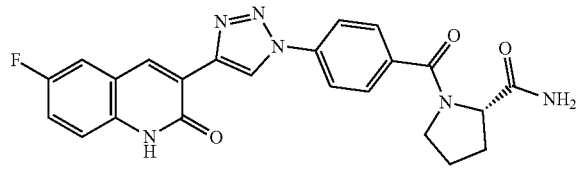 [SMILES: NC(=O)[C@@H]1CCCN1C(=O)c1ccc(-n2cc(-c3cc4cc(F)ccc4[nH]c3=O)nn2)cc1]

UPLC/MS 0.60 min, [M+H]⁺ 447;
mixture of rotamers, some signals of main rotamer: ¹H NMR (400 MHz, DMSO-d$_6$) δ 12.28 (s, 1H), 9.30 (s, 1H), 8.86 (s, 1H), 8.11 (d, J=8.6 Hz, 2H), 7.88-7.73 (m, 3H), 7.53-7.38 (m, 3H), 6.97 (bs, 1H), 4.40 (dd, J=8.3, 5.2 Hz, 1H), 3.75-3.56 (m, 2H), 2.26-2.16 (m, 1H), 1.95-1.75 (m, 3H).

(S)-1-{4-[4-(6-fluoro-2-oxo-1,2-dihydro-quinolin-3-yl)-[1,2,3]triazol-1-yl]-benzoyl}-pyrrolidine-3-carboxylic acid amide ("A243")

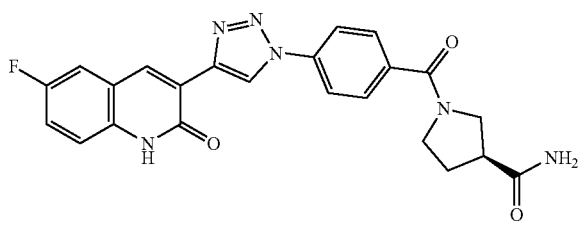 [SMILES: NC(=O)[C@H]1CCN(C(=O)c2ccc(-n3cc(-c4cc5cc(F)ccc5[nH]c4=O)nn3)cc2)C1]

UPLC/MS 0.60 min, [M+H]⁺ 447;
¹H NMR (500 MHz, DMSO-d$_6$) δ 12.27 (s, 1H), 9.29 (s, 1H), 8.85 (s, 1H), 8.11-8.06 (m, 2H), 7.80 (dd, J=9.2, 2.7 Hz, 1H), 7.78-7.72 (m, 2H), 7.53-7.34 (m, 3H), 6.99-6.91 (m, 1H), 3.77-3.45 (m, 4H), 3.05-2.91 (m, 1H), 2.20-1.93 (m, 2H).

6-fluoro-3-{1-[4-((2R,4R)-2-hydroxymethyl-4-methoxy-pyrrolidine-1-carbonyl)-phenyl]-1H-[1,2,3]triazol-4-yl}-1H-quinolin-2-one ("A244")

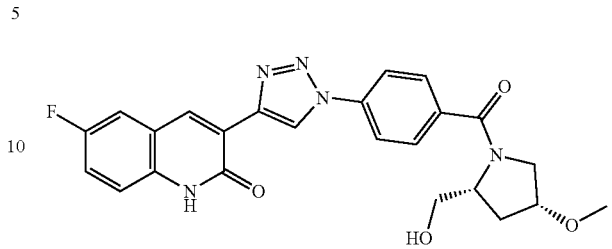

MS [M+H]⁺ 464;
¹H NMR (400 MHz, DMSO-d$_6$) mixture of 2 rotamers δ 12.28 (s, 1H), 9.29 (s, 1H), 8.85 (s, 1H), 8.08 (d, J=8.3 Hz, 2H), 7.80 (dd, J=9.3, 2.7 Hz, 1H), 7.73 (d, J=7.6 Hz, 2H), 7.51-7.37 (m, 2H), 4.83 (s, 0,7H), 4.70 (s, 0,3H), 4.22 (br. s, 0,7H), 4.04 (br. s, 0,3H), 3.91 (br. s, 1H), 3.64 (br. s, 2H), 3.48-3.36 (m, 1H), 3.22 (s, 3H), 2.26-2.11 (m, 1H), 2.10-1.95 (m, 1H).

6-fluoro-3-{1-[4-(2-oxa-5-aza-spiro[3.5]nonane-5-carbonyl)-phenyl]-1H-[1,2,3]triazol-4-yl}-1H-quinolin-2-one ("A245")

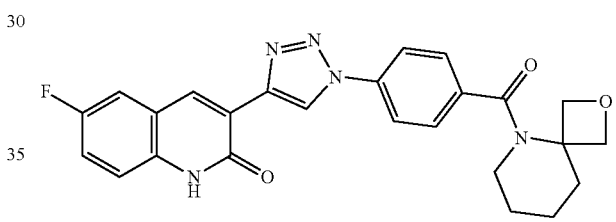

MS [M+H]⁺ 460;
¹H NMR (500 MHz, DMSO-d$_6$) δ 12.27 (s, 1H), 9.30 (s, 1H), 8.85 (s, 1H), 8.12 (d, J=8.6 Hz, 2H), 7.80 (dd, J=9.2, 2.7 Hz, 1H), 7.74 (d, J=8.6 Hz, 2H), 7.52-7.35 (m, 2H), 4.71 (d, J=6.8 Hz, 2H), 4.38 (d, J=6.9 Hz, 2H), 3.23 (t, J=5.5 Hz, 2H), 2.06 (t, J=6.0 Hz, 2H), 1.70 (p, J=6.0 Hz, 2H), 1.26 (p, J=5.7 Hz, 2H).

6-chloro-3-{1-[4-((S)-2-hydroxymethyl-pyrrolidine-1-carbonyl)-phenyl]-1H-[1,2,3]triazol-4-yl}-1H-quinolin-2-one ("A246")

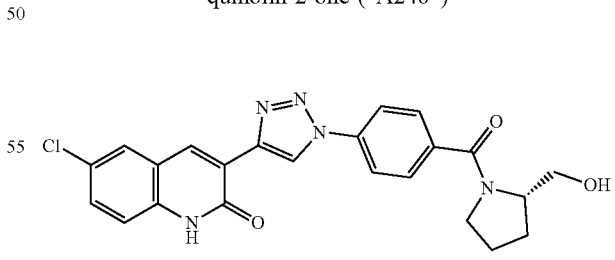

MS [M+H]⁺ 450;
¹H NMR (400 MHz, DMSO-d$_6$) δ 12.33 (s, 1H), 9.28 (s, 1H), 8.84 (s, 1H), 8.08 (d, J=8.4 Hz, 2H), 8.05 (d, J=2.2 Hz, 1H), 7.73 (d, J=8.0 Hz, 2H), 7.58 (dd, J=8.8, 2.4 Hz, 1H), 7.40 (d, J=8.8 Hz, 2H), 4.79 (t, J=5.4 Hz, 1H), 4.17 (s, 1H), 3.60 (s, 2H), 3.48 (dt, J=10.2, 6.7 Hz, 1H), 3.36 (s, 1H), 2.03-1.83 (m, 3H), 1.82-1.60 (m, 1H).

6-chloro-3-{1-[4-((2R,4R)-2-hydroxymethyl-4-methoxy-pyrrolidine-1-carbonyl)-phenyl]-1H-[1,2,3]triazol-4-yl}-1H-quinolin-2-one ("A247")

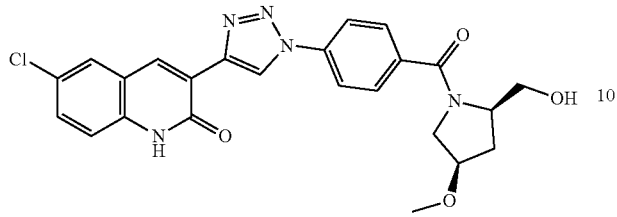

MS [M+H]$^+$ 480;
$^1$H NMR (400 MHz, DMSO-d$_6$) mixture of 2 rotamers δ 12.33 (s, 1H), 9.28 (s, 1H), 8.84 (s, 1H), 8.08 (d, J=8.4 Hz, 2H), 8.05 (d, J=2.3 Hz, 1H), 7.73 (d, J=8.1 Hz, 2H), 7.58 (dd, J=8.8, 2.4 Hz, 1H), 7.40 (d, J=8.8 Hz, 1H), 4.81 (br. s, 0,7H), 4.68 (br. s, 0,3H), 4.22 (br. s, 0,7H), 4.05 (br. s, 0,3H), 3.90 (br. s, 1H), 3.64 (br. s, 2H), 3.49-3.35 (m, 1H), 3.22 (s, 3H), 2.24-2.12 (m, 1H), 2.11-1.94 (m, 1H).

6-chloro-3-{1-[4-((2S,4R)-2-hydroxymethyl-4-methoxy-pyrrolidine-1-carbonyl)-phenyl]-1H-[1,2,3]triazol-4-yl}-1H-quinolin-2-one ("A248")

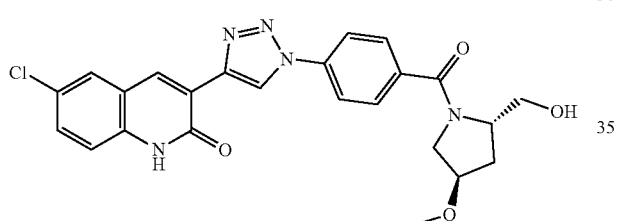

MS [M+H]$^+$ 480;
$^1$H NMR (500 MHz, DMSO-d$_6$) δ 12.33 (s, 1H), 9.29 (s, 1H), 8.84 (s, 1H), 8.10 (d, J=8.4 Hz, 2H), 8.05 (d, J=2.3 Hz, 1H), 7.75 (d, J=8.3 Hz, 2H), 7.58 (dd, J=8.8, 2.4 Hz, 1H), 7.40 (d, J=8.8 Hz, 1H), 4.80 (s, 1H), 4.24 (s, 1H), 3.91 (q, J=4.2 Hz, 1H), 3.74 (d, J=11.2 Hz, 1H), 3.61 (dd, J=11.7, 3.7 Hz, 1H), 3.55 (d, J=11.2 Hz, 1H), 3.40 (d, J=11.7 Hz, 1H), 3.11 (s, 3H), 2.08 (dd, J=8.2, 4.9 Hz, 2H).

6-chloro-3-(1-{4-[3-(4-hydroxy-piperidin-1-yl)-pyrrolidine-1-carbonyl]-phenyl}-1H-[1,2,3]triazol-4-yl)-1H-quinolin-2-one ("A249")

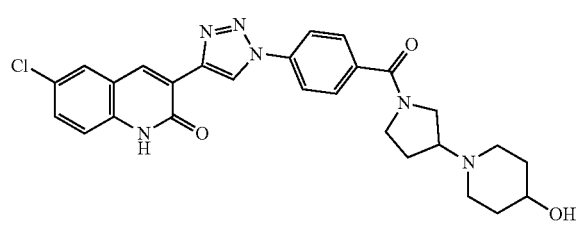 [SMILES: O=C(c1ccc(-n2cc(-c3cc4cc(Cl)ccc4[nH]c3=O)nn2)cc1)N1CCC(N2CCC(O)CC2)C1]

MS [M+H]$^+$ 519;
$^1$H NMR (400 MHz, DMSO-d$_6$) mixture of 2 rotamers δ 12.33 (s, 1H), 9.28 (s, 1H), 8.84 (s, 1H), 8.07 (d, J=8.4 Hz, 2H), 8.05 (d, J=2.3 Hz, 1H), 7.75 (t, J=9.1 Hz, 2H), 7.58 (dd, J=8.8, 2.4 Hz, 1H), 7.40 (d, J=8.8 Hz, 1H), 4.53 (d, J=4.0 Hz, 0.5H), 4.50 (d, J=4.0 Hz, 0.5H), 3.83-3.37 (m, 4H), 3.37-3.18 (m, 1H), 2.94-2.51 (m, 3H), 2.21-1.94 (m, 3H), 1.82-1.60 (m, 3H), 1.47-1.27 (m, 2H).

6-chloro-3-{1-[4-(4-oxetan-3-yl-piperazine-1-carbonyl)-phenyl]-1H-[1,2,3]triazol-4-yl}-1H-quinolin-2-one ("A250")

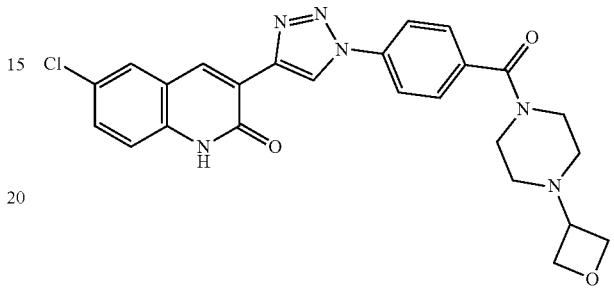

MS [M+H]$^+$ 491;
$^1$H NMR (400 MHz, DMSO-d$_6$) δ 12.32 (s, 1H), 9.27 (s, 1H), 8.84 (s, 1H), 8.09 (d, J=8.6 Hz, 2H), 8.05 (d, J=2.3 Hz, 1H), 7.63 (d, J=8.6 Hz, 2H), 7.58 (dd, J=8.8, 2.4 Hz, 1H), 7.40 (d, J=8.8 Hz, 1H), 4.55 (t, J=6.5 Hz, 2H), 4.46 (t, J=6.1 Hz, 2H), 3.66 (br. s, 2H), 3.54-3.33 (m, 3H), 2.32 (br. s, 4H).

6-fluoro-3-(1-{4-[(S)-3-(2-methoxy-ethoxy)-pyrrolidine-1-carbonyl]-phenyl}-1H-[1,2,3]triazol-4-yl)-1H-quinolin-2-one ("A251")

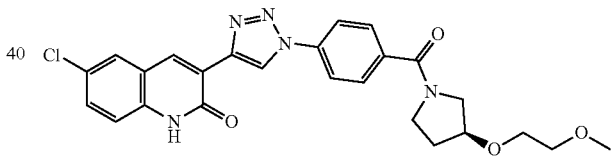

HPLC/MS 1.46 min (A), [M+H]$^+$ 478;
$^1$H NMR (500 MHz, DMSO-d6) mixture of 2 rotamers: δ 12.29 (s, 1H), 9.30 (s, 1H), 8.86 (s, 1H), 8.15-8.05 (m, 2H), 7.81 (dd, J=9.2, 2.7 Hz, 1H), 7.78-7.72 (m, 0.5H), 7.54-7.38 (m, 2H), 4.21-4.17 (m, 0.5H), 4.13-4.08 (m, 0.5H), 3.71-3.37 (m, 8H), 3.28 (s, 1.5H), 3.21 (s, 11.5H), 2.06-1.95 (m, 2H).

6-fluoro-3-(1-{4-[(R)-3-(2-methoxy-ethoxy)-pyrrolidine-1-carbonyl]-phenyl}-1H-[1,2,3]triazol-4-yl)-1H-quinolin-2-one ("A252")

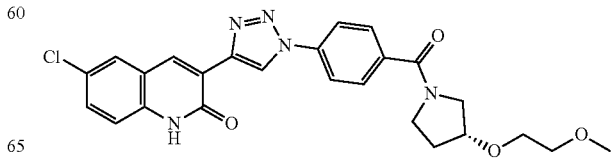

HPLC/MS 1.46 min (A), [M+H]⁺ 478;
¹H NMR (500 MHz, DMSO-d₆) mixture of 2 rotamers: δ 12.29 (s, 1H), 9.30 (s, 1H), 8.86 (s, 1H), 8.15-8.05 (m, 2H), 7.81 (dd, J=9.2, 2.7 Hz, 1H), 7.78-7.72 (m, 0.5H), 7.54-7.38 (m, 2H), 4.21-4.17 (m, 0.5H), 4.13-4.08 (m, 0.5H), 3.71-3.37 (m, 8H), 3.28 (s, 1.5H), 3.21 (s, 11.5H), 2.06-1.95 (m, 2H).

6-chloro-3-{1-[4-((S)-2-methoxymethyl-pyrrolidine-1-carbonyl)-phenyl]-1H-[1,2,3]triazol-4-yl}-1H-quinolin-2-one ("A253")

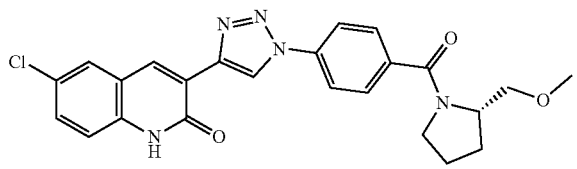 [SMILES: COC[C@@H]1CCCN1C(=O)c1ccc(-n2cc(-c3cc4cc(Cl)ccc4[nH]c3=O)nn2)cc1]

MS [M+H]⁺ 464;
¹H NMR (400 MHz, DMSO-d₆) mixture of 2 rotamers δ 12.33 (s, 1H), 9.28 (s, 1H), 8.84 (s, 1H), 8.08 (d, J=8.6 Hz, 2H), 8.05 (d, J=2.3 Hz, 1H), 7.71 (d, J=8.4 Hz, 2H), 7.58 (dd, J=8.8, 2.4 Hz, 1H), 7.40 (d, J=8.8 Hz, 1H), 4.29 (br.s, 0.7H), 4.07 (br. s, 0.3H), 3.73-3.55 (m, 1H), 3.54-3.42 (m, 2H), 3.32 (s, 3H), 3.16-2.92 (m, 1H), 2.09-1.96 (m, 1H), 1.96-1.81 (m, 2H), 1.81-1.63 (m, 1H).

6-chloro-3-{1-[4-(3-dimethylamino-pyrrolidine-1-carbonyl)-phenyl]-1H-[1,2,3]triazol-4-yl}-1H-quinolin-2-one ("A254")

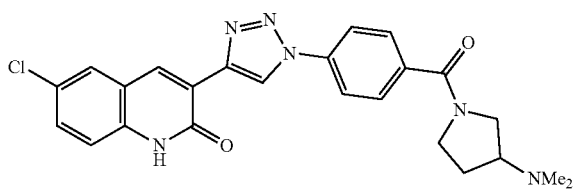 [SMILES: CN(C)C1CCN(C(=O)c2ccc(-n3cc(-c4cc5cc(Cl)ccc5[nH]c4=O)nn3)cc2)C1]

MS [M+H]⁺ 463;
¹H NMR (400 MHz, DMSO-d₆) mixture of 2 rotamers δ 12.33 (s, 1H), 9.28 (s, 1H), 8.84 (s, 1H), 8.08 (d, J=8.6 Hz, 2H), 8.05 (d, J=2.3 Hz, 1H), 7.75 (t, J=8.0 Hz, 2H), 7.58 (dd, J=8.7, 2.4 Hz, 1H), 7.40 (d, J=8.8 Hz, 1H), 3.79-3.71 (m, 0.5H), 3.70-3.61 (m, 0.5H), 3.60-3.43 (m, 2H), 3.38-3.20 (m, 1H), 2.82-2.61 (m, 1H), 2.20 (s, 3H), 2.11 (s, 3H), 2.10-1.97 (m, 1H), 1.84-1.67 (m, 1H).

6-chloro-3-{1-[4-(2-hydroxymethyl-piperidine-1-carbonyl)-phenyl]-1H-[1,2,3]triazol-4-yl}-1H-quinolin-2-one ("A255")

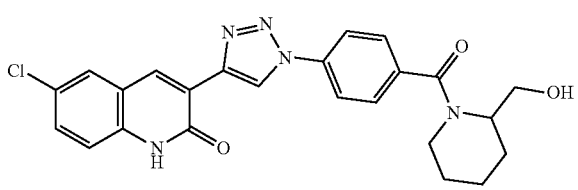 [SMILES: O=C(c1ccc(-n2cc(-c3cc4cc(Cl)ccc4[nH]c3=O)nn2)cc1)N1CCCCC1CO]

MS [M+H]⁺ 464;
¹H NMR (500 MHz, DMSO-d₆) mixture of 2 rotamers δ 12.32 (s, 1H), 9.26 (s, 1H), 8.84 (s, 1H), 8.12-7.99 (m, 3H), 7.65-7.52 (m, 3H), 7.40 (d, J=8.8 Hz, 1H), 4.79 (t, J=5.5 Hz, 1H), 4.73-4.52 (m, 0.3H), 4.52-4.15 (m, 0.7H), 3.95-3.36 (m, 3H), 3.19-2.77 (m, 1H), 1.96-1.29 (m, 6H).

6-chloro-3-{1-[4-(2-oxa-7-aza-spiro[3.5]nonane-7-carbonyl)-phenyl]-1H-[1,2,3]triazol-4-yl}-1H-quinolin-2-one ("A256")

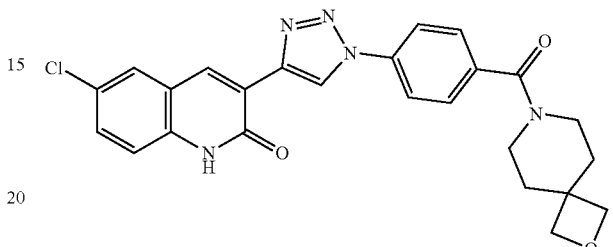

MS [M+H]⁺ 476;
¹H NMR (500 MHz, DMSO-d₆) δ 12.32 (s, 1H), 9.27 (s, 1H), 8.84 (s, 1H), 8.08 (d, J=8.6 Hz, 2H), 8.05 (d, J=2.3 Hz, 1H), 7.60 (d, J=8.5 Hz, 2H), 7.58 (d, J=2.4 Hz, 1H), 7.40 (d, J=8.8 Hz, 1H), 4.35 (br. s, 4H), 3.55 (br. s, 2H), 3.27 (br. s, 2H), 1.83 (br. s, 4H).

6-chloro-3-{1-[4-(2-oxa-6-aza-spiro[3.4]octane-6-carbonyl)-phenyl]-1H-[1,2,3]triazol-4-yl}-1H-quinolin-2-one ("A257")

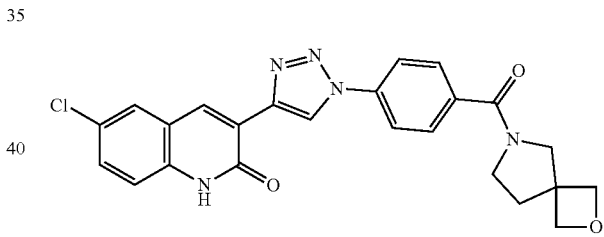

MS [M+H]⁺ 462;
¹H NMR (500 MHz, DMSO-d₆) δ 12.33 (s, 1H), 9.28 (d, J=2.4 Hz, 1H), 8.84 (s, 1H), 8.09 (t, J=7.7 Hz, 2H), 8.05 (d, J=2.0 Hz, 1H), 7.75 (dd, J=8.4, 4.2 Hz, 2H), 7.58 (dd, J=8.8, 2.4 Hz, 1H), 7.41 (d, J=8.8 Hz, 1H), 4.64 (d, J=6.0 Hz, 1H), 4.55-4.42 (m, 3H), 3.73 (d, J=14.1 Hz, 2H), 3.50 (dt, J=14.7, 6.9 Hz, 2H), 2.18 (dt, J=12.8, 7.0 Hz, 2H).

6-chloro-3-{1-[4-(2-oxa-6-aza-spiro[3.3]heptane-6-carbonyl)-phenyl]-1H-[1,2,3]triazol-4-yl}-1H-quinolin-2-one ("A258")

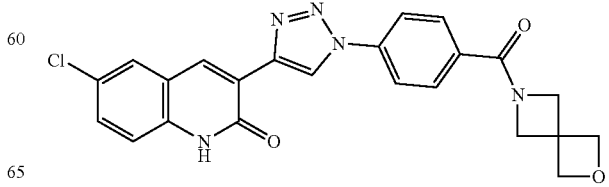

MS [M+H]+ 448;
1H NMR (500 MHz, DMSO-d6) δ 1H NMR (500 MHz, DMSO-d6) δ 12.33 (s, 1H), 9.29 (s, 1H), 8.84 (s, 1H), 8.10 (d, J=8.7 Hz, 2H), 8.05 (d, J=2.3 Hz, 1H), 7.84 (d, J=8.7 Hz, 2H), 7.58 (dd, J=8.7, 2.4 Hz, 1H), 7.40 (d, J=8.8 Hz, 1H), 4.70 (s, 4H), 4.55 (s, 2H), 4.25 (s, 2H).

6-chloro-3-(1-{4-[(S)-3-(2-methoxy-ethoxy)-pyrrolidine-1-carbonyl]-phenyl}-1H-[1,2,3]triazol-4-yl)-1H-quinolin-2-one ("A259")

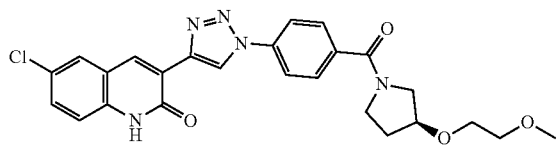 [SMILES: COCCO[C@H]1CCN(C(=O)c2ccc(-n3cc(-c4cc5cc(Cl)ccc5[nH]c4=O)nn3)cc2)C1]

HPLC/MS 1.56 min (A), [M+H]+ 494;
1H NMR (400 MHz, DMSO-d6) mixture of 2 rotamers: δ 12.33 (s, 1H), 9.29 (s, 1H), 8.85 (s, 1H), 8.09 (d, J=8.3 Hz, 2H), 8.06 (d, J=2.4 Hz, 1H), 7.76 (d, J=8.3 Hz, 2H), 7.59 (dd, J=8.8, 2.3 Hz, 1H), 7.41 (d, J=8.8 Hz, 1H), 4.22-4.15 (m, 0.5H), 4.13-4.07 (m, 0.5H), 3.74-3.35 (m, 8H), 3.28 (s, 1.5H), 3.21 (s, 1.5H), 2.12-1.88 (m, 2H).

6-chloro-3-(1-{4-[(R)-3-(2-methoxy-ethoxy)-pyrrolidine-1-carbonyl]-phenyl}-1H-[1,2,3]triazol-4-yl)-1H-quinolin-2-one ("A260")

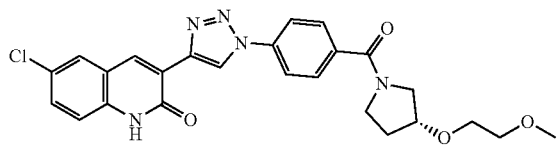 [SMILES: COCCO[C@@H]1CCN(C(=O)c2ccc(-n3cc(-c4cc5cc(Cl)ccc5[nH]c4=O)nn3)cc2)C1]

HPLC/MS 1.56 min (A), [M+H]+ 494;
1H NMR (400 MHz, DMSO-d6) mixture of 2 rotamers: δ 12.33 (s, 1H), 9.29 (s, 1H), 8.85 (s, 1H), 8.09 (d, J=8.3 Hz, 2H), 8.06 (d, J=2.4 Hz, 1H), 7.76 (d, J=8.3 Hz, 2H), 7.59 (dd, J=8.8, 2.3 Hz, 1H), 7.41 (d, J=8.8 Hz, 1H), 4.22-4.15 (m, 0.5H), 4.13-4.07 (m, 0.5H), 3.74-3.35 (m, 8H), 3.28 (s, 1.5H), 3.21 (s, 1.5H), 2.12-1.88 (m, 2H).

6-fluoro-3-(1-{4-[(R)-3-(2-methoxy-ethoxy)-pyrrolidine-1-carbonyl]-phenyl}-1H-pyrazol-4-yl)-1H-quinolin-2-one ("A261")

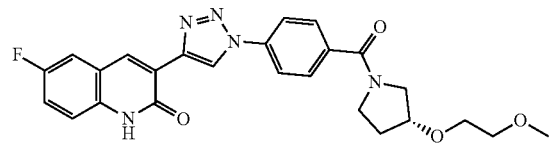 [SMILES: COCCO[C@@H]1CCN(C(=O)c2ccc(-n3cc(-c4cc5cc(F)ccc5[nH]c4=O)nn3)cc2)C1]

HPLC/MS 1.46 min (A), [M+H]+ 477;
1H NMR (400 MHz, DMSO-d6) mixture of 2 rotamers δ 12.12 (s, 1H), 9.20 (s, 1H), 8.47 (s, 1H), 8.42 (s, 1H), 8.01-7.91 (m, 2H), 7.70 (d, J=8.4 Hz, 2H), 7.49 (dt, J=9.3, 1.7 Hz, 1H), 7.44-7.35 (m, 2H), 4.21-4.14 (m, 0.5H), 4.13-4.06 (m, 0.5H), 3.75-3.35 (m, 7H), 3.28 (s, 1.5H), 3.21 (s, 1.5H), 2.05-1.93 (m, 2H).

(R)-1-{4-[4-(6-fluoro-2-oxo-1,2-dihydro-quinolin-3-yl)-[1,2,3]triazol-1-yl]-benzoyl}-pyrrolidine-2-carboxylic acid amide ("A262")

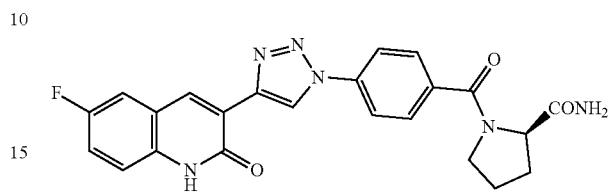

UPLC/MS 0.62 min, [M+H]+ 447;
mixture of rotamers, some signals of main rotamer: 1H NMR (400 MHz, DMSO-d6) δ 12.28 (s, 1H), 9.30 (s, 1H), 8.86 (s, 1H), 8.11 (d, J=8.6 Hz, 2H), 7.88-7.73 (m, 3H), 7.53-7.38 (m, 3H), 6.97 (bs, 1H), 4.40 (dd, J=8.3, 5.2 Hz, 1H), 3.75-3.56 (m, 2H), 2.26-2.16 (m, 1H), 1.95-1.75 (m, 3H).

3-{1-[4-((3R,4R)-3,4-dimethoxy-pyrrolidine-1-carbonyl)-phenyl]-1H-[1,2,3]triazol-4-yl}-6-fluoro-1H-quinolin-2-one ("A263")

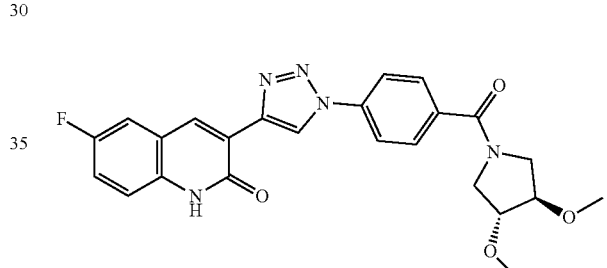

HPLC/MS 1.49 min (A), [M+H]+ 464;
1H NMR (400 MHz, DMSO-d6) δ 12.29 (s, 1H), 9.31 (s, 1H), 8.86 (s, 1H), 8.13-8.06 (m, 2H), 7.81 (dd, J=9.3, 2.7 Hz, 1H), 7.79-7.73 (m, 2H), 7.52-7.39 (m, 2H), 3.97-3.92 (m, 1H), 3.91-3.87 (m, 1H), 3.76-3.62 (m, 2H), 3.56 (d, J=13.4 Hz, 1H), 3.43 (d, J=11.7 Hz, 1H), 3.36 (s, 3H), 3.26 (s, 3H).

3-{1-[4-((3S,4S)-3,4-dimethoxy-pyrrolidine-1-carbonyl)-phenyl]-1H-[1,2,3]triazol-4-yl}-6-fluoro-1H-quinolin-2-one ("A264")

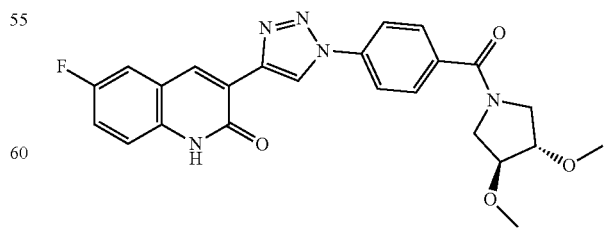

HPLC/MS 1.49 min (A), [M+H]+ 464;
1H NMR (400 MHz, DMSO-d6) δ 12.29 (s, 1H), 9.31 (s, 1H), 8.86 (s, 1H), 8.13-8.06 (m, 2H), 7.81 (dd, J=9.3, 2.7 Hz, 1H), 7.79-7.73 (m, 2H), 7.52-7.39 (m, 2H), 3.97-3.92 (m, 1H), 3.91-3.87 (m, 1H), 3.76-3.62 (m, 2H), 3.56 (d, J=13.4 Hz, 1H), 3.43 (d, J=11.7 Hz, 1H), 3.36 (s, 3H), 3.26 (s, 3H).

6-fluoro-3-{1-[4-((S)-3-fluoro-pyrrolidine-1-carbonyl)-phenyl]-1H-[1,2,3]triazol-4-yl}-1H-quinolin-2-one ("A265")

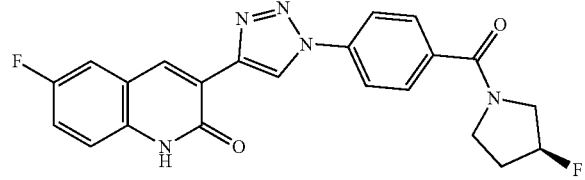 [SMILES: O=C(c1ccc(-n2cc(-c3cc4cc(F)ccc4[nH]c3=O)nn2)cc1)N1CC[C@H](F)C1]

MS [M+H]+ 422;
1H NMR (500 MHz, DMSO-d6) δ 12.28 (s, 1H), 9.30 (s, 1H), 8.86 (s, 1H), 8.11 (d, J=8.6 Hz, 2H), 7.81 (dd, J=9.2, 2.4 Hz, 2H), 7.77 (d, J=8.4 Hz, 1H), 7.50-7.40 (m, 2H), 5.38 (dd, J=52.9, 40.3 Hz, 1H), 3.94-3.52 (m, 4H), 2.30-2.02 (m, 2H).

6-chloro-3-{1-[4-((S)-3-fluoro-pyrrolidine-1-carbonyl)-phenyl]-1H-[1,2,3]triazol-4-yl}-1H-quinolin-2-one ("A266")

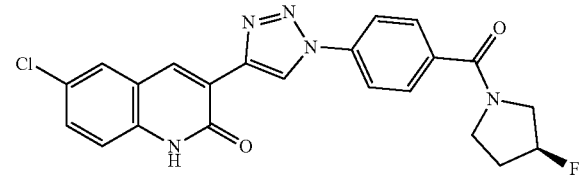 [SMILES: O=C(c1ccc(-n2cc(-c3cc4cc(Cl)ccc4[nH]c3=O)nn2)cc1)N1CC[C@H](F)C1]

MS [M+H]+ 438;
1H NMR (500 MHz, DMSO-d6) δ 12.34 (s, 1H), 9.30 (s, 1H), 8.85 (s, 1H), 8.11 (d, J=8.6 Hz, 2H), 8.06 (d, J=2.3 Hz, 1H), 7.81 (d, J=8.4 Hz, 1H), 7.77 (d, J=8.3 Hz, 1H), 7.60 (dd, J=8.8, 2.4 Hz, 1H), 7.42 (d, J=8.8 Hz, 1H), 5.53-5.23 (m, 1H), 3.94-3.52 (m, 4H), 2.30-2.00 (m, 2H).

3-{1-[4-(3,3-difluoro-pyrrolidine-1-carbonyl)-phenyl]-1H-[1,2,3]triazol-4-yl}-6-fluoro-1H-quinolin-2-one ("A267")

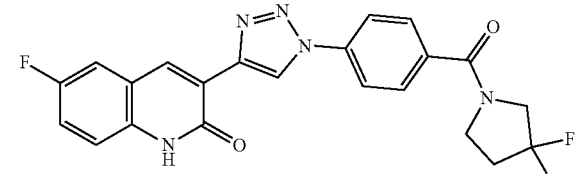

MS [M+H]+ 440;
1H NMR (500 MHz, DMSO-d6) δ 12.29 (s, 1H), 9.31 (s, 1H), 8.86 (s, 1H), 8.12 (d, J=8.6 Hz, 2H), 7.84-7.76 (m, 3H), 7.50-7.40 (m, 2H), 3.96 (t, J=13.2 Hz, 2H), 3.76 (br. s, 2H), 2.48 (br. s, 2H).

6-chloro-3-{1-[4-(3,3-difluoro-pyrrolidine-1-carbonyl)-phenyl]-1H-[1,2,3]triazol-4-yl}-1H-quinolin-2-one ("A268")

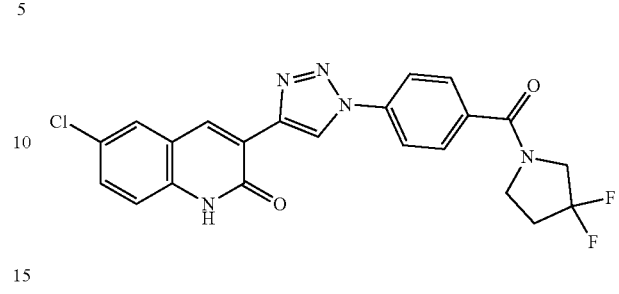

MS [M+H]+ 440;
1H NMR (500 MHz, DMSO-d6) δ 1H NMR (500 MHz, DMSO-d6) δ 12.34 (s, 1H), 9.31 (s, 1H), 8.86 (s, 1H), 8.12 (d, J=8.6 Hz, 2H), 8.07 (d, J=2.4 Hz, 1H), 7.81 (d, J=8.2 Hz, 2H), 7.60 (dd, J=8.8, 2.4 Hz, 1H), 7.42 (d, J=8.8 Hz, 1H), 3.96 (t, J=13.2 Hz, 2H), 3.76 (br. s, 2H), 2.48 (br.s, 2H).

6-fluoro-3-{1-[4-((R)-3-fluoro-pyrrolidine-1-carbonyl)-phenyl]-1H-[1,2,3]triazol-4-yl}-1H-quinolin-2-one ("A269")

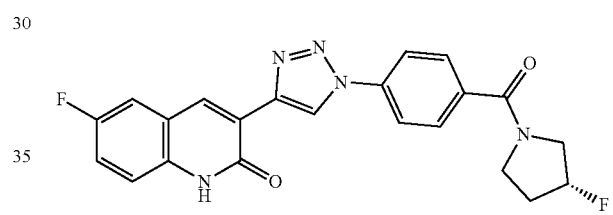

MS [M+H]+ 421;
1H NMR (500 MHz, DMSO-d6) δ 12.27 (s, 1H), 9.28 (s, 1H), 8.85 (s, 1H), 8.09 (d, J=8.6 Hz, 2H), 7.83-7.74 (m, 3H), 7.50-7.41 (m, 2H), 5.52-5.20 (m, 1H), 3.91-3.58 (m, 4H), 2.29-2.02 (m, 2H).

6-chloro-3-{1-[4-((R)-3-fluoro-pyrrolidine-1-carbonyl)-phenyl]-1H-[1,2,3]triazol-4-yl}-1H-quinolin-2-one ("A270")

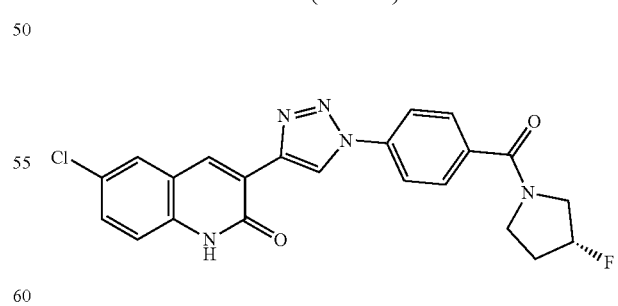

MS [M+H]+ 438;
1H NMR (500 MHz, DMSO-d6) δ 12.34 (s, 1H), 9.30 (s, 1H), 8.85 (s, 1H), 8.11 (d, J=8.6 Hz, 2H), 8.06 (d, J=2.3 Hz, 1H), 7.81 (d, J=8.4 Hz, 1H), 7.77 (d, J=8.3 Hz, 1H), 7.60 (dd, J=8.8, 2.4 Hz, 1H), 7.42 (d, J=8.8 Hz, 1H), 5.53-5.23 (m, 1H), 3.94-3.52 (m, 4H), 2.30-2.00 (m, 2H).

6-chloro-3-{1-[4-((3R,4R)-3,4-dimethoxy-pyrrolidine-1-carbonyl)-phenyl]-1H-[1,2,3]triazol-4-yl}-1H-quinolin-2-one ("A271")

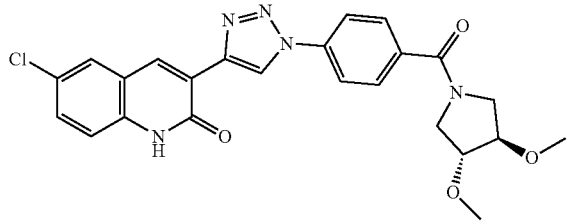 [SMILES: CO[C@@H]1CN(C(=O)c2ccc(-n3cc(-c4cc5cc(Cl)ccc5[nH]c4=O)nn3)cc2)C[C@H]1OC]

HPLC/MS 1.60 min (A), [M+H]⁺ 480;
1H NMR (400 MHz, DMSO-d₆) δ 12.33 (s, 1H), 9.30 (s, 1H), 8.85 (s, 1H), 8.13-8.07 (m, 2H), 8.06 (d, J=2.4 Hz, 1H), 7.81-7.73 (m, 2H), 7.60 (dd, J=8.8, 2.4 Hz, 1H), 7.41 (d, J=8.8 Hz, 1H), 3.94 (bs, 1H), 3.89 (bs, 1H), 3.69 (td, J=14.3, 13.2, 4.5 Hz, 2H), 3.56 (d, J=13.4 Hz, 1H), 3.43 (d, J=11.7 Hz, 1H), 3.37 (s, 3H), 3.26 (s, 3H).

6-chloro-3-{1-[4-((3S,4S)-3,4-di methoxy-pyrrolidine-1-carbonyl)-phenyl]-1H-[1,2,3]triazol-4-yl}-1H-quinolin-2-one ("A272")

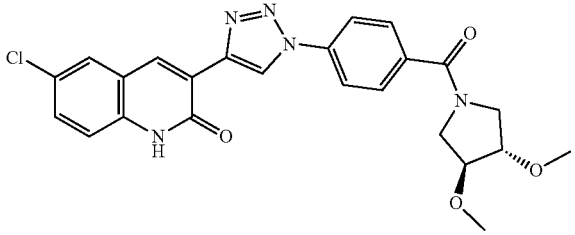 [SMILES: CO[C@H]1CN(C(=O)c2ccc(-n3cc(-c4cc5cc(Cl)ccc5[nH]c4=O)nn3)cc2)C[C@@H]1OC]

HPLC/MS 1.59 min (A), [M+H]⁺ 480;
1H NMR (400 MHz, DMSO-d₆) δ 12.33 (s, 1H), 9.30 (s, 1H), 8.85 (s, 1H), 8.13-8.07 (m, 2H), 8.06 (d, J=2.4 Hz, 1H), 7.81-7.73 (m, 2H), 7.60 (dd, J=8.8, 2.4 Hz, 1H), 7.41 (d, J=8.8 Hz, 1H), 3.94 (bs, 1H), 3.89 (bs, 1H), 3.69 (td, J=14.3, 13.2, 4.5 Hz, 2H), 3.56 (d, J=13.4 Hz, 1H), 3.43 (d, J=11.7 Hz, 1H), 3.37 (s, 3H), 3.26 (s, 3H).

6-fluoro-3-{1-[4-(pyrrolidine-1-carbonyl)-phenyl]-1H-[1,2,3]triazol-4-yl}-1H-quinolin-2-one ("A273")

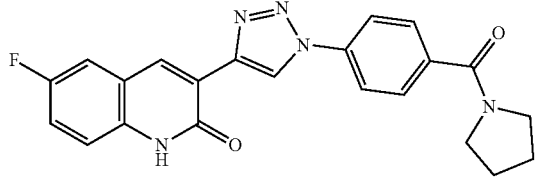 [SMILES: O=C(c1ccc(-n2cc(-c3cc4cc(F)ccc4[nH]c3=O)nn2)cc1)N1CCCC1]

UPLC/MS 0.72 min, [M+H]⁺ 404;
¹H NMR (400 MHz, DMSO-d₆) δ 12.28 (s, 1H), 9.29 (s, 1H), 8.86 (s, 1H), 8.18-8.03 (m, 2H), 7.81 (dd, J=9.3, 2.7 Hz, 1H), 7.79-7.68 (m, 2H), 7.54-7.37 (m, 2H), 3.51 (t, J=6.7 Hz, 2H), 3.46 (t, J=6.3 Hz, 2H), 1.95-1.81 (m, 4H).

6-fluoro-3-{1-[4-((R)-4-hydroxy-isoxazolidine-2-carbonyl)-phenyl]-1H-[1,2,3]triazol-4-yl}-1H-quinolin-2-one ("A274")

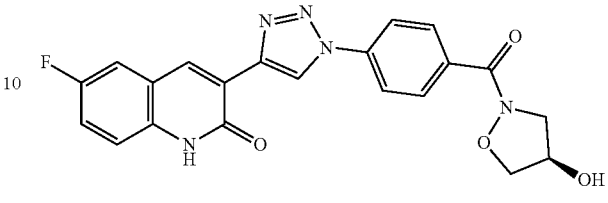

MS [M+H]⁺ 422;
¹H NMR (400 MHz, DMSO-d₆) δ 12.28 (s, 1H), 9.30 (s, 1H), 8.86 (s, 1H), 8.12 (d, J=8.7 Hz, 2H), 7.92 (d, J=8.7 Hz, 2H), 7.80 (dd, J=9.2, 2.6 Hz, 1H), 7.50-7.39 (m, 2H), 5.49 (d, J=4.0 Hz, 1H), 4.71 (dt, J=6.1, 4.1 Hz, 1H), 4.03-3.91 (m, 2H), 3.87 (d, J=1.7 Hz, 1H), 3.66 (dd, J=11.5, 1.6 Hz, 1H).

6-chloro-3-{1-[4-((R)-4-hydroxy-isoxazolidine-2-carbonyl)-phenyl]-1H-[1,2,3]triazol-4-yl}-1H-quinolin-2-one ("A275")

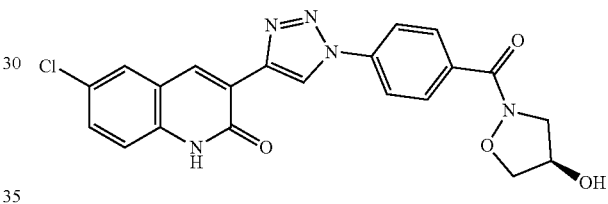

MS [M+H]⁺ 438;
¹H NMR (400 MHz, DMSO-d₆) δ δ 12.33 (s, 1H), 9.30 (s, 1H), 8.85 (s, 1H), 8.12 (d, J=8.8 Hz, 2H), 8.05 (d, J=2.3 Hz, 1H), 7.92 (d, J=8.7 Hz, 2H), 7.59 (dd, J=8.8, 2.4 Hz, 1H), 7.41 (d, J=8.8 Hz, 1H), 5.49 (d, J=4.0 Hz, 1H), 4.77-4.62 (m, 1H), 4.03-3.91 (m, 2H), 3.86 (dd, J=8.6, 1.8 Hz, 1H), 3.66 (dd, J=11.4, 1.6 Hz, 1H).

6-fluoro-3-{1-[4-((S)-4-hydroxy-isoxazolidine-2-carbonyl)-phenyl]-1H-[1,2,3]triazol-4-yl}-1H-quinolin-2-one ("A276")

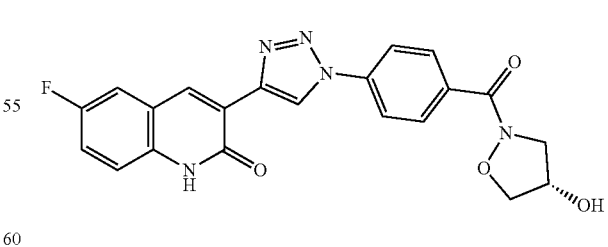

MS [M+H]⁺ 422;
¹H NMR (400 MHz, DMSO-d₆) δ 12.28 (s, 1H), 9.30 (s, 1H), 8.86 (s, 1H), 8.12 (d, J=8.7 Hz, 2H), 7.92 (d, J=8.7 Hz, 2H), 7.80 (dd, J=9.2, 2.6 Hz, 1H), 7.50-7.39 (m, 2H), 5.49 (d, J=4.0 Hz, 1H), 4.71 (dt, J=6.1, 4.1 Hz, 1H), 4.03-3.91 (m, 2H), 3.87 (d, J=1.7 Hz, 1H), 3.66 (dd, J=11.5, 1.6 Hz, 1H).

6-chloro-3-{1-[4-((S)-4-hydroxy-isoxazolidine-2-carbonyl)-phenyl]-1H-[1,2,3]triazol-4-yl}-1H-quinolin-2-one ("A277")

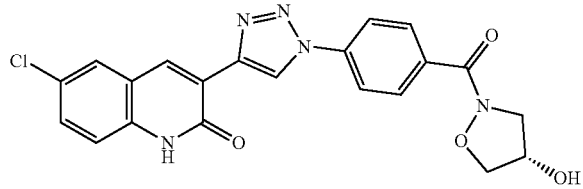 [SMILES: O=C(c1ccc(-n2cc(-c3cc4cc(Cl)ccc4[nH]c3=O)nn2)cc1)N1C[C@H](O)CO1]

MS [M+H]⁺ 438;

¹H NMR (400 MHz, DMSO-d₆) δ δ 12.33 (s, 1H), 9.30 (s, 1H), 8.85 (s, 1H), 8.12 (d, J=8.8 Hz, 2H), 8.05 (d, J=2.3 Hz, 1H), 7.92 (d, J=8.7 Hz, 2H), 7.59 (dd, J=8.8, 2.4 Hz, 1H), 7.41 (d, J=8.8 Hz, 1H), 5.49 (d, J=4.0 Hz, 1H), 4.77-4.62 (m, 1H), 4.03-3.91 (m, 2H), 3.86 (dd, J=8.6, 1.8 Hz, 1H), 3.66 (dd, J=11.4, 1.6 Hz, 1H).

6-fluoro-3-{1-[4-((R)-2-pyrrolidin-1-ylmethyl-pyrrolidine-1-carbonyl)-phenyl]-1H-[1,2,3]triazol-4-yl}-1H-quinolin-2-one ("A278")

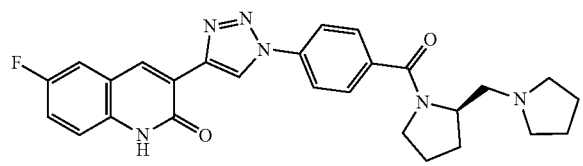 [SMILES: O=C(c1ccc(-n2cc(-c3cc4cc(F)ccc4[nH]c3=O)nn2)cc1)N1CCC[C@@H]1CN1CCCC1]

HPLC/MS 1.28 min (A), [M+H]⁺ 487;

¹H NMR (500 MHz, DMSO-d₆) δ 12.22 (s, 1H), 9.22 (s, 1H), 8.79 (s, 1H), 8.07-7.97 (m, 2H), 7.74 (dd, J=9.2, 2.7 Hz, 1H), 7.70-7.60 (m, 2H), 7.49-7.30 (m, 2H), 4.34-3.88 (m, 1H), 3.61-3.28 (m, 3H), 2.78-2.02 (m, 6H), 2.00-1.90 (m, 1H), 1.90-1.76 (m, 2H), 1.76-1.32 (m, 4H).

6-fluoro-3-{1-[4-((S)-2-pyrrolidin-1-ylmethyl-pyrrolidine-1-carbonyl)-phenyl]-1H-[1,2,3]triazol-4-yl}-1H-quinolin-2-one ("A279")

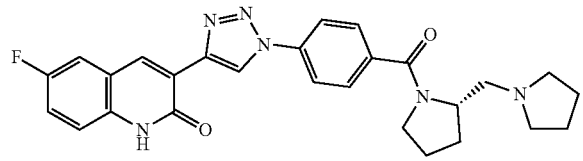 [SMILES: O=C(c1ccc(-n2cc(-c3cc4cc(F)ccc4[nH]c3=O)nn2)cc1)N1CCC[C@H]1CN1CCCC1]

HPLC/MS 1.29 min (A), [M+H]⁺ 487;

¹H NMR (500 MHz, DMSO-d₆) δ 12.22 (s, 1H), 9.22 (s, 1H), 8.79 (s, 1H), 8.07-7.97 (m, 2H), 7.74 (dd, J=9.2, 2.7 Hz, 1H), 7.70-7.60 (m, 2H), 7.49-7.30 (m, 2H), 4.34-3.88 (m, 1H), 3.61-3.28 (m, 3H), 2.78-2.02 (m, 6H), 2.00-1.90 (m, 1H), 1.90-1.76 (m, 2H), 1.76-1.32 (m, 4H).

3-{1-[4-(azetidine-1-carbonyl)-phenyl]-1H-[1,2,3]triazol-4-yl}-6-fluoro-1H-quinolin-2-one ("A280")

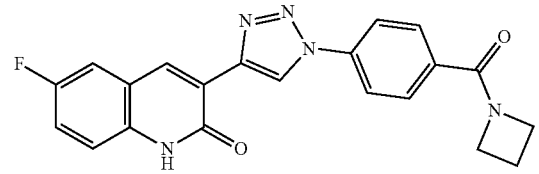 [SMILES: O=C(c1ccc(-n2cc(-c3cc4cc(F)ccc4[nH]c3=O)nn2)cc1)N1CCC1]

UPLC/MS 0.70 min, [M+H]⁺ 390;

¹H NMR (400 MHz, DMSO-d₆) δ 12.26 (s, 1H), 9.30 (s, 1H), 8.86 (s, 1H), 8.22-8.00 (m, 2H), 7.94-7.84 (m, 2H), 7.81 (dd, J=9.3, 2.6 Hz, 1H), 7.54-7.38 (m, 2H), 4.38 (t, J=7.4 Hz, 2H), 4.10 (t, J=7.8 Hz, 2H), 2.38-2.18 (m, 2H).

6-fluoro-3-(1-{4-[2-(4-methyl-piperazine-1-carbonyl)-pyrrolidine-1-carbonyl]-phenyl}-1H-[1,2,3]triazol-4-yl)-1H-quinolin-2-one ("A281")

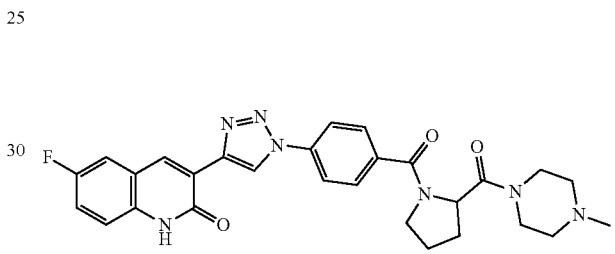

UPLC/MS 0.49 min, [M+H]⁺ 530;

¹H NMR (400 MHz, DMSO-d₆, TFA-d₁) δ 9.20 (s, 1H), 8.76 (s, 1H), 8.00 (d, J=8.6 Hz, 2H), 7.69 (d, J=8.3 Hz, 2H), 7.56 (dd, J=9.1, 2.8 Hz, 1H), 7.39 (dd, J=9.1, 4.7 Hz, 1H), 7.26 (td, J=8.8, 2.8 Hz, 1H), 5.06-4.70 (m, 2H), 4.60-4.19 (m, 3H), 3.78-2.85 (m, 6H), 2.82 (s, 3H), 2.31-2.15 (m, 2H), 2.03-1.70 (m, 2H).

6-fluoro-3-{1-[4-((R)-3-methanesulfonyl-pyrrolidine-1-carbonyl)-phenyl]-1H-[1,2,3]triazol-4-yl}-1H-quinolin-2-one ("A282")

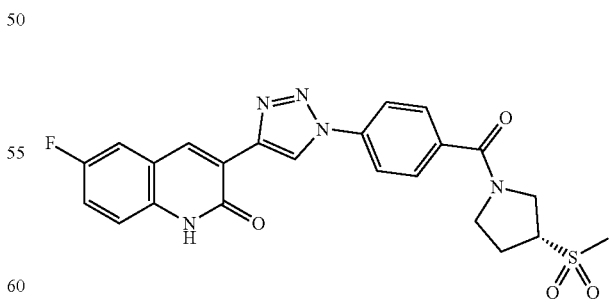

HPLC/MS 1.41 min (A), [M+H]⁺ 482;

¹H NMR (400 MHz, DMSO-d₆) δ 12.29 (s, 1H), 9.31 (s, 1H), 8.86 (s, 1H), 8.12 (d, J=8.4 Hz, 2H), 7.88-7.70 (m, 3H), 7.53-7.40 (m, 2H), 4.15-3.55 (m, 5H), 3.13-2.99 (m, 3H), 2.43-2.20 (m, 2H).

6-fluoro-3-{1-[4-((S)-3-methanesulfonyl-pyrrolidine-1-carbonyl)-phenyl]-1H-[1,2,3]triazol-4-yl}-1H-quinolin-2-one ("A283")

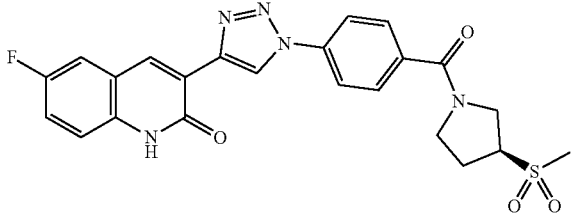 [SMILES: CS(=O)(=O)[C@H]1CCN(C(=O)c2ccc(-n3cc(-c4cc5cc(F)ccc5[nH]c4=O)nn3)cc2)C1]

HPLC/MS 1.40 min (A), [M+H]+ 482;

¹H NMR (400 MHz, DMSO-d₆) δ 12.29 (s, 1H), 9.31 (s, 1H), 8.86 (s, 1H), 8.12 (d, J=8.4 Hz, 2H), 7.88-7.70 (m, 3H), 7.53-7.40 (m, 2H), 4.15-3.55 (m, 5H), 3.13-2.99 (m, 3H), 2.43-2.20 (m, 2H).

6-fluoro-3-{1-[4-(3-methanesulfonylmethyl-pyrrolidine-1-carbonyl)-phenyl]-1H-[1,2,3]triazol-4-yl}-1H-quinolin-2-one ("A284")

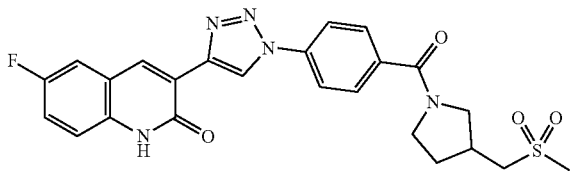 [SMILES: CS(=O)(=O)CC1CCN(C(=O)c2ccc(-n3cc(-c4cc5cc(F)ccc5[nH]c4=O)nn3)cc2)C1]

UPLC/MS 0.65 min, [M+H]+ 496;

¹H NMR (700 MHz, DMSO-d₆) 1:1 mixture of rotamers, selected peaks δ 12.30 (s, 1H), 9.31 (s, 0.5H), 9.30 (s, 0.5H), 8.86 (s, 1H), 8.13-8.08 (m, 2H), 7.81 (dd, J=9.1, 2.9 Hz, 1H), 7.79-7.71 (m, 2H), 7.47 (td, J=8.8, 2.8 Hz, 1H), 7.43 (dd, J=9.0, 4.8 Hz, 1H), 3.05 (s, 1.5H), 2.98 (s, 1.5H).

6-fluoro-3-(1-{4-[2-(1-methyl-1H-pyrazol-4-yl)-pyrrolidine-1-carbonyl]-phenyl}-1H-[1,2,3]triazol-4-yl)-1H-quinolin-2-one ("A285")

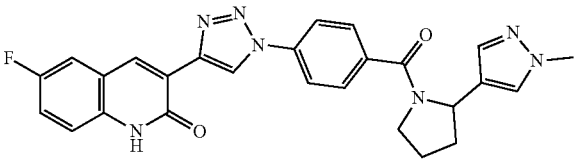 [SMILES: Cn1cc(C2CCCN2C(=O)c2ccc(-n3cc(-c4cc5cc(F)ccc5[nH]c4=O)nn3)cc2)cn1]

MS [M+H]+ 484;

¹H NMR (500 MHz, DMSO-d₆) mixture of 2 rotamers δ 12.32 (s, 1H), 9.31 (s, 0,70H), 9.26 (s, 0,30H), 8.86 (s, 1H), 8.09 (d, J=8.1 Hz, 1,4H), 7.97 (d, J=8.1 Hz, 0,60H), 7.81 (d, J=9.1 Hz, 1H), 7.76 (d, J=8.4 Hz, 2H), 7.68 (s, 1H), 5.26-5.14 (m, 0,70H), 4.99-4.87 (m, 0,30H), 3.80 (s, 2H), 3.72 (s, 1H), 3.71-3.61 (m, 1,40H), 3.46-3.38 (m, 0,6H), 2.29-2.13 (m, 1H), 2.02-1.75 (m, 3H).

6-fluoro-3-{1-[4-(2-pyridin-3-yl-pyrrolidine-1-carbonyl)-phenyl]-1H-[1,2,3]triazol-4-yl}-1H-quinolin-2-one ("A286")

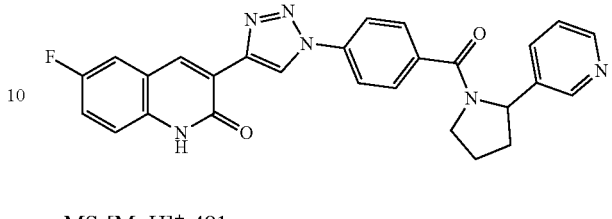

MS [M+H]+ 481;

¹H NMR (500 MHz, DMSO-d₆) mixture of rotamers, signals of major δ 12.32 (s, 1H), 9.32 (s, 1H), 8.87 (s, 1H), 8.57 (d, J=91.1 Hz, 2H), 8.12 (d, J=8.5 Hz, 2H), 7.90-7.85 (m, 2H), 7.84-7.78 (m, 2H), 7.54-7.31 (m, 3H), 5.18 (t, J=6.9 Hz, 1H), 3.98-3.89 (m, 1H), 3.62-3.54 (m, 1H), 2.49-2.39 (m, 1H), 2.03-1.74 (m, 3H).

6-fluoro-3-(1-{4-[2-(4-methyl-piperazin-1-ylmethyl)-pyrrolidine-1-carbonyl]-phenyl}-1H-[1,2,3]triazol-4-yl)-1H-quinolin-2-one ("A287")

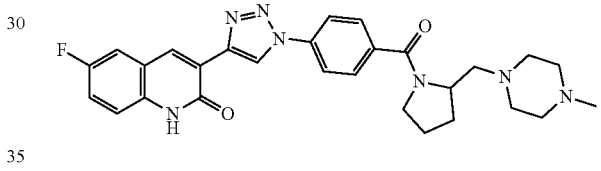

MS [M+H]+ 516;

¹H NMR (400 MHz, DMSO-d₆, TFA-d₁) δ 9.33 (s, 1H), 8.87 (s, 1H), 8.15 (d, J=8.6 Hz, 2H), 7.86 (d, J=8.4 Hz, 2H), 7.78 (dd, J=9.3, 2.7 Hz, 1H), 7.50-7.39 (m, 2H), 4.70-4.60 (m, 1H), 4.35-3.30 (m, 12H), 2.93 (s, 3H), 2.30-2.16 (m, 1H), 2.03-1.73 (m, 3H).

6-fluoro-3-{1-[4-(2-methyl-pyrrolidine-1-carbonyl)-phenyl]-1H-[1,2,3]triazol-4-yl}-1H-quinolin-2-one ("A288")

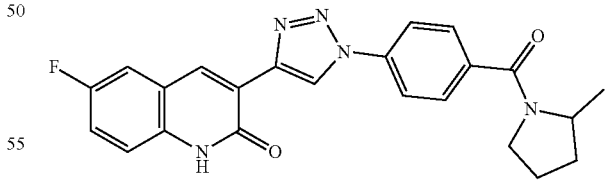

UPLC/MS 0.76 min, [M+H]+ 418;

¹H NMR (500 MHz, DMSO-d₆) mixture of rotamers, signals of major rotamer: δ 12.31 (s, 1H), 9.30 (s, 1H), 8.86 (s, 1H), 8.26-7.95 (m, 2H), 7.82 (dd, J=9.2, 2.8 Hz, 1H), 7.73 (d, J=8.1 Hz, 2H), 7.47 (td, J=8.8, 2.8 Hz, 1H), 7.43 (dd, J=9.0, 4.9 Hz, 1H), 4.25-4.14 (m, 1H), 3.57-3.51 (m, 1H), 3.37-3.32 (m, 1H), 2.10 (dq, J=13.4, 6.8 Hz, 1H), 1.99-1.84 (m, 1H), 1.79-1.68 (m, 1H), 1.64-1.53 (m, 1H), 1.29 (d, J=6.2 Hz, 3H).

6-fluoro-3-{1-[4-(2-methyl-2,6-diaza-spiro[3.4]oc-
tane-6-carbonyl)-phenyl]-1H-[1,2,3]triazol-4-yl}-
1H-quinolin-2-one ("A289")

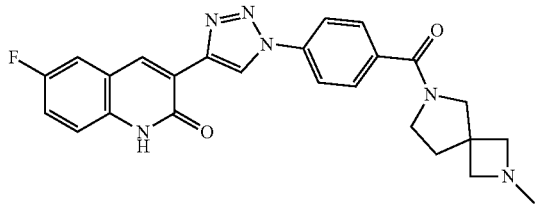 [SMILES: CN1CC2(CCN(C(=O)c3ccc(-n4cc(-c5cc6cc(F)ccc6[nH]c5=O)nn4)cc3)C2)C1]

UPLC/MS 0.47 min, [M+H]+ 459;
¹H NMR (500 MHz, DMSO-d₆) 1:1 mixture of rotamers δ 12.33 (s, 1H), 9.89 (bs, 1H, NH+), 9.32 (s, 0.5H), 9.31 (s, 0.5H), 8.86 (s, 1H), 8.20-8.04 (m, 2H), 7.82 (dd, J=9.2, 2.8 Hz, 1H), 7.79-7.74 (m, 2H), 7.48 (ddd, J=9.2, 6.1, 2.3 Hz, 1H), 7.43 (dd, J=8.8, 4.6 Hz, 1H), 4.26-3.94 (m, 4H), 3.79-3.69 (m, 2H), 3.59-3.48 (m, 2H), 2.87 (s, 1.5H), 2.78 (s, 1.5H), 2.24-2.13 (m, 2H).

6-chloro-3-{1-[4-(2-methyl-2,6-diaza-spiro[3.4]oc-
tane-6-carbonyl)-phenyl]-1H-[1,2,3]triazol-4-yl}-
1H-quinolin-2-one ("A290")

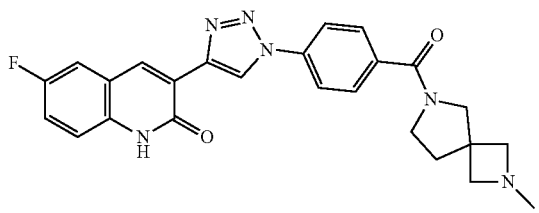 [SMILES: CN1CC2(CCN(C(=O)c3ccc(-n4cc(-c5cc6cc(F)ccc6[nH]c5=O)nn4)cc3)C2)C1]

UPLC/MS 0.50 min, [M+H]+ 475;
¹H NMR (500 MHz, DMSO-d₆) 1:1 mixture of rotamers δ 12.38 (s, 1H), 9.83 (bs, 1H, NH+), 9.32 (s, 0.5H), 9.31 (s, 0.5H), 8.86 (s, 1H), 8.17-8.09 (m, 2H), 8.08 (d, J=2.3 Hz, 0.5H), 7.78-7.74 (m, 2H), 7.61 (dt, J=8.8, 1.8 Hz, 1H), 7.41 (d, J=8.8 Hz, 1H), 4.26-3.94 (m, 4H), 3.79-3.69 (m, 2H), 3.59-3.48 (m, 2H), 2.84 (s, 1.5H), 2.75 (s, 1.5H), 2.24-2.13 (m, 2H).

6-fluoro-3-{1-[4-((3aR,6aR)-5-methyl-hexahydro-
pyrrolo[3,4-b]pyrrole-1-carbonyl)-phenyl]-1H-[1,2,
3]triazol-4-yl}-1H-quinolin-2-one ("A291")

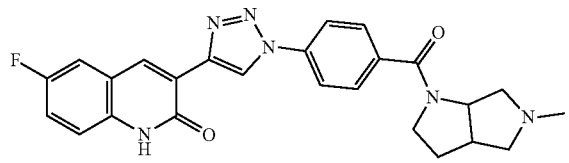 [SMILES: CN1CC2CCN(C(=O)c3ccc(-n4cc(-c5cc6cc(F)ccc6[nH]c5=O)nn4)cc3)C2C1]

HPLC/MS 1.23 min (A), [M+H]+ 459;
¹H NMR (500 MHz, DMSO-d₆) mixture of rotamers, signals of major rotamer: δ 12.33 (s, 1H), 9.30 (s, 1H), 8.86 (s, 1H), 8.18-8.02 (m, 2H), 7.82 (dd, J=9.2, 2.8 Hz, 1H), 7.75-7.70 (m, 1H), 7.47 (td, J=8.8, 2.8 Hz, 1H), 7.42 (dd, J=9.0, 4.9 Hz, 1H), 4.56 (ddd, J=8.1, 5.8, 2.2 Hz, 1H), 3.62 (td, J=10.3, 6.6 Hz, 1H), 3.46 (ddd, J=10.5, 8.0, 2.7 Hz, 1H), 2.95-2.80 (m, 1H), 2.74 (dd, J=9.9, 2.2 Hz, 1H), 2.57-2.51 (m, 2H), 2.47-2.36 (m, 1H), 2.24 (s, 3H), 2.02-1.88 (m, 1H), 1.74 (ddd, J=12.1, 6.0, 2.8 Hz, 1H).

6-chloro-3-{1-[4-((R)-2-methyl-pyrrolidine-1-carbo-
nyl)-phenyl]-1H-[1,2,3]triazol-4-yl}-1H-quinolin-2-
one ("A292")

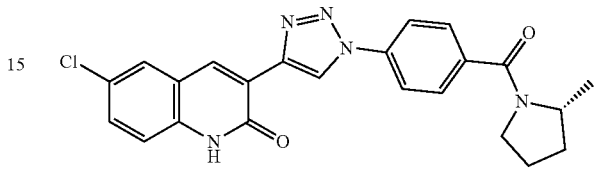

HPLC/MS 1.69 min (A), [M+H]+ 434;
¹H NMR (500 MHz, DMSO-d₆) mixture of rotamers, signals of major rotamer: δ 12.37 (s, 1H), 9.30 (s, 1H), 8.86 (s, 1H), 8.10-8.07 (m, 2H), 8.07 (d, J=2.4 Hz, 1H), 7.73 (d, J=8.3 Hz, 1H), 7.60 (dd, J=8.8, 2.4 Hz, 1H), 7.40 (d, J=8.8 Hz, 1H), 4.18 (h, J=5.9 Hz, 1H), 3.58-3.50 (m, 1H), 3.39-3.32 (m, 1H), 2.10 (dq, J=13.3, 6.8 Hz, 1H), 1.85-1.85 (m, 1H), 1.78-1.67 (m, 1H), 1.57 (dq, J=13.4, 6.8 Hz, 1H), 1.28 (d, J=6.2 Hz, 2H).

3-{1-[4-(2,2-dimethyl-pyrrolidine-1-carbonyl)-phe-
nyl]-1H-[1,2,3]triazol-4-yl}-6-fluoro-1H-quinolin-2-
one ("A293")

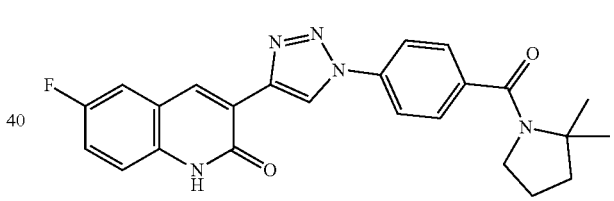

HPLC/MS 1.68 min (A), [M+H]+ 432;
¹H NMR (400 MHz, DMSO-d₆) δ 12.27 (s, 1H), 9.27 (s, 1H), 8.85 (s, 1H), 8.05 (d, J=8.5 Hz, 2H), 7.80 (dd, J=9.2, 2.6 Hz, 1H), 7.64 (d, J=8.3 Hz, 2H), 7.53-7.37 (m, 2H), 3.40 (t, J=6.5 Hz, 2H), 1.90-1.71 (m, 4H), 1.53 (s, 6H).

6-fluoro-3-(1-{4-[3-(4-methyl-piperazine-1-carbo-
nyl)-pyrrolidine-1-carbonyl]-phenyl}-1H-[1,2,3]
triazol-4-yl)-1H-quinolin-2-one ("A294")

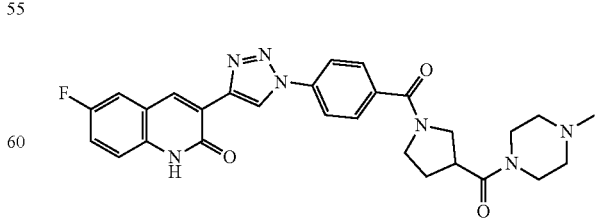

UPLC/MS 0.47 min, [M+H]+ 530;
¹H NMR (500 MHz, DMSO-d₆) 1:1 mixture of rotamers, selection of signals δ 12.31 (s, 1H), 9.32 (s, 1H), 8.84 (s, 1H), 8.15-8.04 (m, 2H), 7.85-7.67 (m, 3H), 7.50-7.34 (m, 2H), 2.20 (s, 1.5H), 2.15 (s, 1.5H).

EXAMPLE 19

6-fluoro-3-{1-[4-((R)-2-methyl-pyrrolidine-1-carbonyl)-phenyl]-1H-pyrazol-4-yl}-1H-quinolin-2-one ("A295")

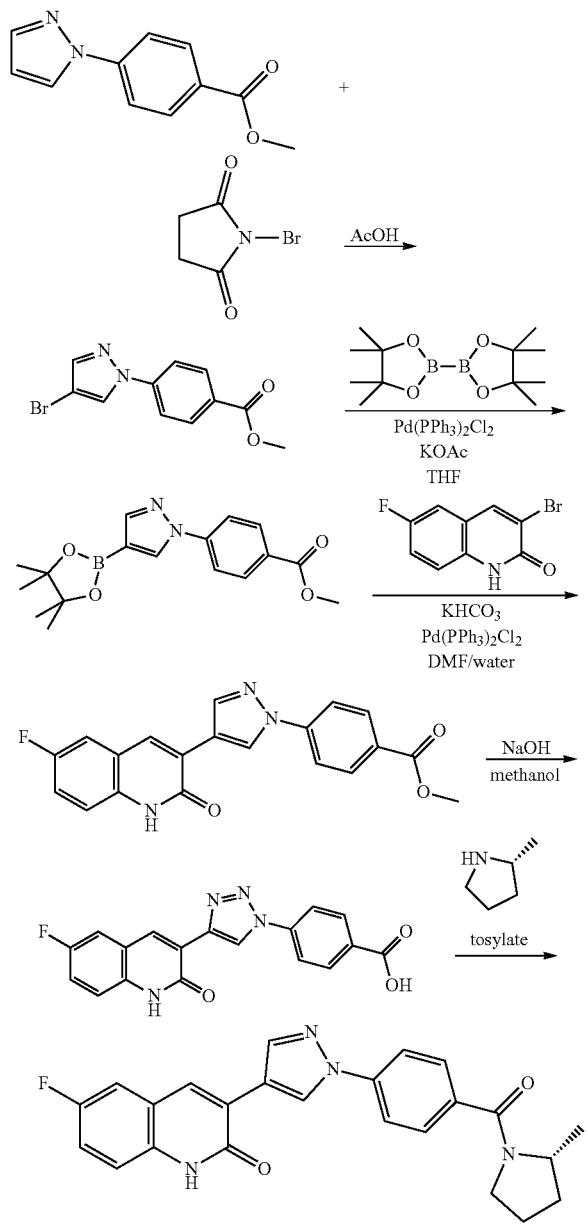

To a solution of methyl 4-(1H-pyrazol)-1-yl)-benzenecarboxylate (9.58 g, 47.4 mmol) in acetic acid (100 ml) is added N-bromosuccinimide (9.00 g, 50.6 mmol). The reaction mixture is heated to 100° C. and stirred at this temperature for 2 hours. The reaction mixture is allowed to reach room temperature. The solid is filtered off, washed with water and dried under vacuum to afford methyl 4-(4-bromo-1H-pyrazol-1-yl)benzoate as white crystalline solid; UPLC/MS 0.82 min, [M+H]$^+$ 281/283.

$^1$H NMR (400 MHz, DMSO-d$_6$) δ 8.94 (s, 1H), 8.17-8.06 (m, 2H), 8.03-7.98 (m, 2H), 7.97 (s, 1H), 3.88 (s, 3H).

A suspension of methyl 4-(4-bromo-1H-pyrazol-1-yl) benzoate (5.12 g, 18.2 mmol), bis(pinacolato)diboron (6.10 g, 24.0 mmol) and dry potassium acetate (5.36 g, 54.6 mmol) in THF (110 ml) is flushed with nitrogen and bis (triphenyl-phosphine)palladium(II)chloride (260 mg, 0.37 mmol) is added. The reaction mixture is heated to 65° C. under nitrogen and stirred at this temperature for 3 days. The reaction mixture is filtered over kieselguhr and washed with dichloromethane. The filtrate is evaporated and chromatographed on a silica gel column with cyclohexane/ethyl acetate as eluent to afford 4-[4-(4,4,5,5-tetramethyl-[1,3,2] dioxaborolan-2-yl)-pyrazol-1-yl]-benzoic acid methyl ester as white solid; UPLC/MS 0.86 min, [M+H]$^+$ 329.

$^1$H NMR (300 MHz, DMSO-d$_6$) δ 8.87 (s, 1H), 8.11-8.03 (m, 4H), 7.93 (s, 1H), 3.88 (s, 3H), 1.30 (s, 12H).

A suspension of 3-bromo-6-fluoro-1H-quinolin-2-one (980 mg, 4.05 mmol), 4-[4-(4,4,5,5-tetramethyl-[1,3,2]dioxaborolan-2-yl)-pyrazol-1-yl]-benzoic acid methyl ester (1.46 g, 4.45 mmol) and 645 mg (6.44 mmol) potassium hydrogen carbonate in DMF (13 ml) and water (6.5 ml) is flushed with nitrogen and bis(triphenylphosphine)palladium (II)chloride (60 mg, 0.085 mmol) is added. The mixture is irradiated in a microwave reactor for 1 hour at 120° C. The reaction mixture is allowed to reach room temperature. The solids are filtered off, washed with water and methanol and dried under vacuum to afford 4-[4-(6-fluoro-2-oxo-1,2-dihydro-quinolin-3-yl)-pyrazol-1-yl]-benzoic acid methyl ester as grey solid; UPLC/MS 0.80 min, [M+H]$^+$ 364.

$^1$H NMR (400 MHz, DMSO-d$_6$) δ 12.14 (s, 1H), 9.25 (s, 1H), 8.51 (s, 1H), 8.44 (s, 1H), 8.14-8.10 (m, 2H), 8.09-8.04 (m, 2H), 7.54-7.47 (m, 1H), 7.45-7.35 (m, 2H), 3.89 (s, 3H).

To a solution of 4-[4-(6-fluoro-2-oxo-1,2-dihydro-quinolin-3-yl)-pyrazol-1-yl]-benzoic acid methyl ester (832 mg, 2.29 mmol) in methanol (18 ml) is added aqueous 2 M sodium hydroxide solution (9.5 ml, 19 mmol) and the reaction mixture is stirred for 1 hour at 80° C. The reaction mixture is allowed to reach room temperature and is acidified with 2 N HCl. The resultant precipitate is filtered off, washed with water and dried under vacuum to afford 4-[4-(6-fluoro-2-oxo-1,2-dihydro-quinolin-3-yl)-pyrazol-1-yl]-benzoic acid as grey solid; UPLC/MS 0.70 min, [M+H]$^+$ 350.

To a suspension of 4-[4-(6-fluoro-2-oxo-1,2-dihydro-quinolin-3-yl)-pyrazol-1-yl]-benzoic acid (28.0.0 mg, 0.08 mmol) in a mixture of 1,4-dioxane (0.4 ml) and DMF (0.4 ml) are added (R)-2-methylpyrrolidine p-toluenesulfonate (25.5 mg, 0.10 mmol), N-(3-dimethylaminopropyl)-N'-ethylcarbodiimide hydrochloride (23.0 mg, 0.12 mmol), 1-hydroxybenzotriazole hydrate (10.8 mg, 0.08 mmol) and 4-methylmorpholine (13.2 µl, 0.12 mmol). The resultant suspension is stirred at room temperature for 2 hours. The reaction mixture is poured into water. The resultant precipitate is filtered off, washed with water and dried. The residue is chromatographed on a silica gel column with dichloromethane/methanol as eluent to afford 6-fluoro-3-{1-[4-((R)-2-methyl-pyrrolidine-1-carbonyl)-phenyl]-1H-pyrazol-4-yl}-1H-quinolin-2-one as white crystals; HPLC/MS 1.60 min (A), [M+H]$^+$ 417.

$^1$H NMR (500 MHz, DMSO-d$_6$), mixture of rotamers; main rotamer: δ 12.15 (s, 1H), 9.20 (s, 1H), 8.47 (s, 1H), 8.42 (s, 1H), 8.00-7.92 (m, 2H), 7.67 (d, J=8.2 Hz, 2H), 7.49 (dd, J=9.0, 2.5 Hz, 1H), 7.43-7.35 (m, 2H), 4.20-4.11 (m, 1H), 3.59-3.50 (m, 1H), 3.42-3.34 (m, 1H), 2.09 (dq, J=12.6, 6.2, 5.7 Hz, 1H), 2.00-1.82 (m, 1H), 1.77-1.66 (m, 1H), 1.63-1.51 (m, 1H), 1.27 (d, J=6.2 Hz, 3H).

The following compounds are prepared similarly:

6-fluoro-3-{1-[4-(4-methyl-piperazine-1-carbonyl)-phenyl]-1H-pyrazol-4-yl}-1H-quinolin-2-one ("A296")

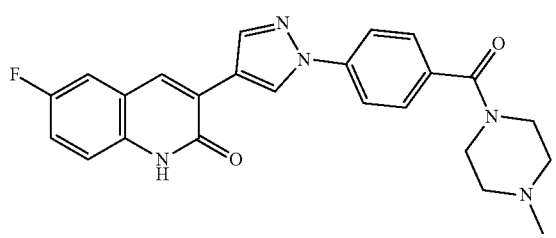 [SMILES: CN1CCN(C(=O)c2ccc(-n3cc(-c4cc5cc(F)ccc5[nH]c4=O)cn3)cc2)CC1]

UPLC/MS 0.47 mm, [M+H]$^+$ 432;
$^1$H NMR (400 MHz, DMSO-d$_6$) δ 12.11 (s, 1H), 9.18 (s, 1H), 8.46 (s, 1H), 8.41 (s, 1H), 8.01-7.90 (m, 2H), 7.61-7.52 (m, 2H), 7.52-7.46 (m, 1H), 7.41-7.37 (m, 2H), 3.5 (bs, 4H), 2.36 (bs, 4H), 2.22 (s, 3H).

6-fluoro-3-{1-[4-((S)-3-methoxy-pyrrolidine-1-carbonyl)-phenyl]-1H-pyrazol-4-yl}-1H-quinolin-2-one ("A297")

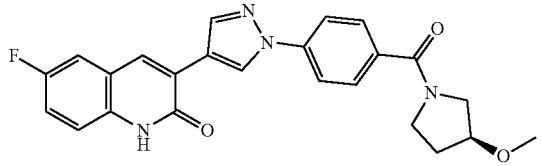 [SMILES: CO[C@H]1CCN(C(=O)c2ccc(-n3cc(-c4cc5cc(F)ccc5[nH]c4=O)cn3)cc2)C1]

UPLC/MS 0.69 min, [M+H]$^+$ 433;
$^1$H NMR (400 MHz, DMSO-d$_6$) mixture of 2 rotamers δ 12.12 (s, 1H), 9.19 (s, 1H), 8.47 (s, 1H), 8.41 (s, 1H), 7.95 (d, J=8.2 Hz, 2H), 7.78-7.62 (m, 2H), 7.49 (dt, J=9.1, 1.7 Hz, 1H), 7.42-7.36 (m, 2H), 4.07-4.00 (m, 0.5H), 3.99-3.93 (m, 0.5H), 3.71-3.40 (m, 4H), 3.29 (s, 1.5H), 3.19 (s, 1.5H), 2.13-1.87 (m, 2H).

6-fluoro-3-{1-[4-((R)-3-methoxy-pyrrolidine-1-carbonyl)-phenyl]-1H-pyrazol-4-yl}-1H-quinolin-2-one ("A298")

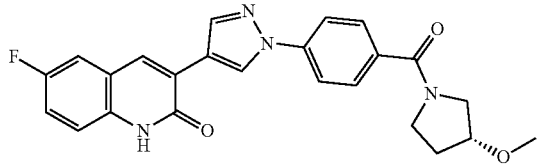 [SMILES: CO[C@@H]1CCN(C(=O)c2ccc(-n3cc(-c4cc5cc(F)ccc5[nH]c4=O)cn3)cc2)C1]

UPLC/MS 0.69 min, [M+H]$^+$ 433;
$^1$H NMR (400 MHz, DMSO-d$_6$) mixture of 2 rotamers δ 12.12 (s, 1H), 9.19 (s, 1H), 8.47 (s, 1H), 8.41 (s, 1H), 7.95 (d, J=8.2 Hz, 2H), 7.78-7.62 (m, 2H), 7.49 (dt, J=9.1, 1.7 Hz, 1H), 7.42-7.36 (m, 2H), 4.07-4.00 (m, 0.5H), 3.99-3.93 (m, 0.5H), 3.71-3.40 (m, 4H), 3.29 (s, 1.5H), 3.19 (s, 1.5H), 2.13-1.87 (m, 2H).

6-fluoro-3-(1-{4-[(S)-3-(2-methoxy-ethoxy)-pyrrolidine-1-carbonyl]-phenyl}-1H-pyrazol-4-yl)-1H-quinolin-2-one ("A299")

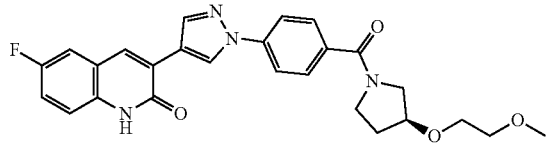 [SMILES: COCCO[C@H]1CCN(C(=O)c2ccc(-n3cc(-c4cc5cc(F)ccc5[nH]c4=O)cn3)cc2)C1]

UPLC/MS 0.69 min, [M+H]$^+$ 477;
$^1$H NMR (400 MHz, DMSO-d$_6$) mixture of 2 rotamers δ 12.12 (s, 1H), 9.19 (s, 1H), 8.47 (s, 1H), 8.42 (s, 1H), 7.95 (d, J=8.5 Hz, 2H), 7.70 (d, J=8.4 Hz, 2H), 7.49 (dt, J=9.1, 1.7 Hz, 1H), 7.44-7.34 (m, 2H), 4.22-4.14 (m, 0.5H), 4.13-4.06 (m, 0.5H), 3.73-3.36 (m, 8H), 3.28 (s, 1.5H), 3.21 (s, 1.5H), 2.06-1.90 (m, 2H).

3-{1-[4-((3R,4R)-3,4-dimethoxy-pyrrolidine-1-carbonyl)-phenyl]-1H-pyrazol-4-yl}-6-fluoro-1H-quinolin-2-one ("A300")

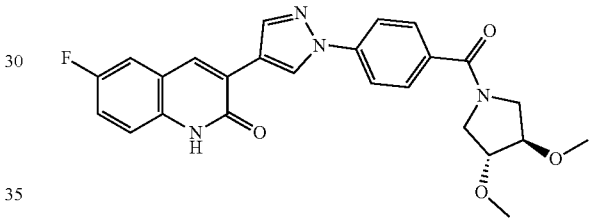

HPLC/MS 1.50 min (A), [M+H]$^+$ 463;
$^1$H NMR (700 MHz, DMSO-d$_6$) δ 12.14 (s, 1H), 9.21 (s, 1H), 8.48 (s, 1H), 8.43 (s, 1H), 8.00-7.93 (m, 2H), 7.74-7.67 (m, 2H), 7.50 (dd, J=9.0, 2.5 Hz, 1H), 7.44-7.34 (m, 2H), 3.94 (d, J=4.7 Hz, 1H), 3.91-3.86 (m, 1H), 3.72 (dd, J=11.8, 4.3 Hz, 1H), 3.65 (dd, J=13.3, 4.9 Hz, 1H), 3.55 (d, J=13.4 Hz, 1H), 3.44 (d, J=11.7 Hz, 1H), 3.36 (s, 3H), 3.25 (s, 3H).

6-fluoro-3-{1-[4-((2S,4R)-2-hydroxymethyl-4-methoxy-pyrrolidine-1-carbonyl)-phenyl]-1H-pyrazol-4-yl}-1H-quinolin-2-one ("A301")

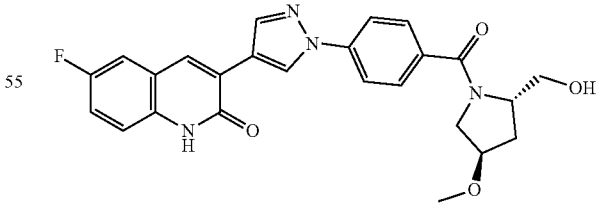

MS [M+H]$^+$ 463;
$^1$H NMR (500 MHz, DMSO-d$_6$) δ 12.11 (s, 1H), 9.19 (s, 1H), 8.46 (s, 1H), 8.41 (s, 1H), 7.96 (d, J=8.4 Hz, 2H), 7.68 (d, J=8.2 Hz, 2H), 7.49 (dt, J=9.2, 1.5 Hz, 1H), 7.39 (dd, J=7.5, 2.0 Hz, 2H), 4.79 (t, J=5.8 Hz, 1H), 4.23 (br. s, 1H), 3.90 (br. s, 1H), 3.78-3.67 (m, 1H), 3.61 (dd, J=11.8, 3.6 Hz,

1H), 3.59-3.50 (m, 1H), 3.42 (d, J=11.7 Hz, 1H), 3.17 (d, J=5.2 Hz, 2H), 3.10 (s, 3H) 2.17-1.99 (m, 2H).

6-fluoro-3-{1-[4-((2R,4R)-2-hydroxymethyl-4-methoxy-pyrrolidine-1-carbonyl)-phenyl]-1H-pyrazol-4-yl}-1H-quinolin-2-one ("A302")

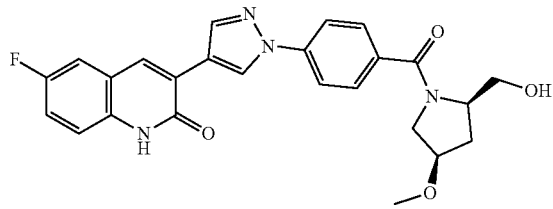 [SMILES: CO[C@@H]1C[C@H](CO)N(C(=O)c2ccc(-n3cc(-c4cc5cc(F)ccc5[nH]c4=O)cn3)cc2)C1]

MS [M+H]+ 463;
1H NMR (500 MHz, DMSO-d6) δ 12.11 (s, 1H), 9.19 (s, 1H), 8.46 (s, 1H), 8.41 (s, 1H), 7.94 (d, J=8.6 Hz, 2H), 7.67 (d, J=8.2 Hz, 2H), 7.49 (dt, J=9.2, 1.5 Hz, 1H), 7.41-7.37 (m, 2H), 4.81 (br. s, 1H), 4.22 (br. s, 1H), 3.90 (br. s, 1H), 3.76-3.48 (m, 2H), 3.41 (dd, J=11.3, 5.0 Hz, 1H), 3.22 (s, 3H), 3.17 (d, J=5.2 Hz, 1H), 2.16 (d, J=8.3 Hz, 1H), 2.02 (s, 1H).

3-{1-[4-((3S,4S)-3,4-dimethoxy-pyrrolidine-1-carbonyl)-phenyl]-1H-pyrazol-4-yl}-6-fluoro-1H-quinolin-2-one ("A303")

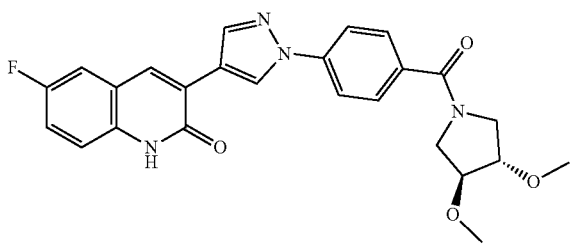 [SMILES: CO[C@H]1CN(C(=O)c2ccc(-n3cc(-c4cc5cc(F)ccc5[nH]c4=O)cn3)cc2)C[C@@H]1OC]

HPLC/MS 1.50 min (A), [M+H]+ 463;
1H NMR (700 MHz, DMSO-d6) δ 12.14 (s, 1H), 9.21 (s, 1H), 8.48 (s, 1H), 8.43 (s, 1H), 8.00-7.93 (m, 2H), 7.74-7.67 (m, 2H), 7.50 (dd, J=9.0, 2.5 Hz, 1H), 7.44-7.34 (m, 2H), 3.94 (d, J=4.7 Hz, 1H), 3.91-3.86 (m, 1H), 3.72 (dd, J=11.8, 4.3 Hz, 1H), 3.65 (dd, J=13.3, 4.9 Hz, 1H), 3.55 (d, J=13.4 Hz, 1H), 3.44 (d, J=11.7 Hz, 1H), 3.36 (s, 3H), 3.25 (s, 3H).

6,7-difluoro-3-{1-[4-(4-methyl-piperazine-1-carbonyl)-phenyl]-1H-pyrazol-4-yl}-1H-quinolin-2-one ("A304")

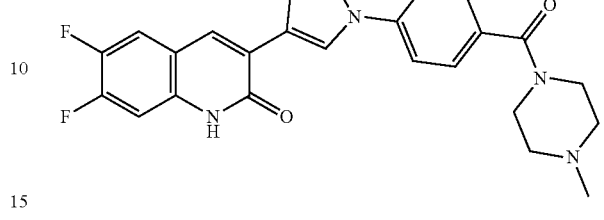

HPLC/MS 1.24 min (A), [M+H]+ 450;
1H NMR (500 MHz, DMSO-d6) δ 12.20 (s, 1H), 9.16 (s, 1H), 8.43 (s, 1H), 8.39 (s, 1H), 8.06-7.91 (m, 2H), 7.74 (dd, J=10.8, 8.4 Hz, 1H), 7.60-7.49 (m, 2H), 7.29 (dd, J=11.4, 7.1 Hz, 1H), 3.70-3.31 (m, 4H), 2.45-2.25 (m, 4H), 2.21 (s, 3H).

6-chloro-3-{1-[4-(4-methyl-piperazine-1-carbonyl)-phenyl]-1H-pyrazol-4-yl}-1H-quinolin-2-one ("A305")

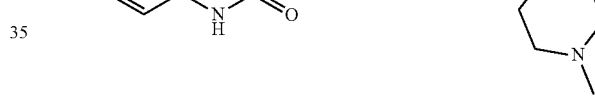

UPLC/MS 0.50 min, [M+H]+ 448;
1H NMR (500 MHz, DMSO-d6) δ 12.13 (bs, 1H), 9.18 (s, 1H), 8.45 (s, 1H), 8.40 (s, 1H), 7.99-7.93 (m, 2H), 7.74 (d, J=2.4 Hz, 1H), 7.59-7.55 (m, 2H), 7.53 (dd, J=8.7, 2.4 Hz, 1H), 7.37 (d, J=8.8 Hz, 1H), 3.8-3.3 (m, 4H), 2.45-2.25 (m, 4H), 2.21 (s, 3H).

EXAMPLE 20

3-{1-[4-((S)-3-amino-pyrrolidine-1-carbonyl)-phenyl]-1H-[1,2,3]triazol-4-yl}-6-fluoro-1H-quinolin-2-one ("A306")

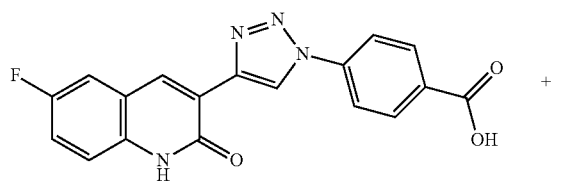

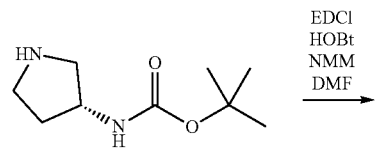

EDCl
HOBt
NMM
DMF

-continued

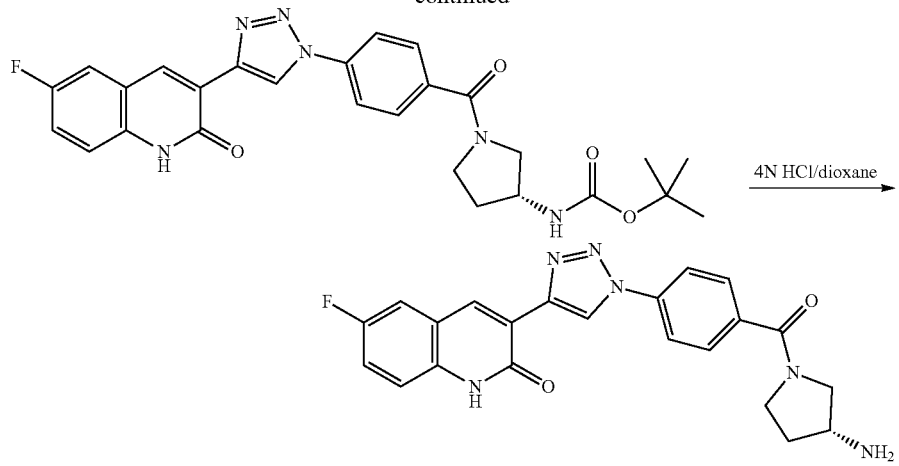

MS [M+H]⁺ 419; HCl salt;
¹H NMR (500 MHz, DMSO-d₆) mixture of 2 rotamers δ 12.30 (s, 1H), 9.31 (s, 1H), 8.86 (s, 1H), 8.30 (br. s, 2H), 8.18 (br. s, 1H), 8.13 (d, J=8.6 Hz, 2H), 7.88-7.70 (m, 3H), 7.54-7.39 (m, 2H), 3.97-3.65 (m, 3H), 3.66-3.45 (m, 2H), 2.25 (br. s, 1H), 2.06 (br. s, 1H).

The following compounds are prepared similarly:

6,7-difluoro-3-{1-[4-((cis)-hexahydro-pyrrolo[3,4-c]pyrrole-2-carbonyl)-phenyl]-1H-[1,2,3]triazol-4-yl}-1H-quinolin-2-one ("A307")

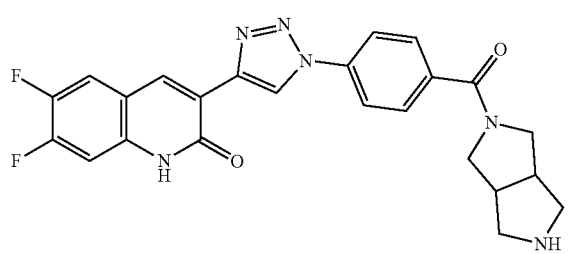 [SMILES: O=C(c1ccc(-n2cc(-c3cc4cc(F)c(F)cc4[nH]c3=O)nn2)cc1)N1CC2CNCC2C1]

UPLC/MS 0.47 min, [M+H]⁺ 463;
¹H NMR (500 MHz, DMSO-d₆, TFA-d₁) δ 9.29 (s, 1H), 8.86 (s, 1H), 8.23-8.09 (m, 2H), 7.98 (dd, J=10.8, 8.5 Hz, 1H), 7.84-7.75 (m, 2H), 7.37 (dd, J=11.3, 7.0 Hz, 1H), 3.85-3.05 (m, 1 0H).

6-fluoro-3-{1-[4-((cis)-hexahydro-pyrrolo[3,4-c]pyrrole-2-carbonyl)-phenyl]-1H-[1,2,3]triazol-4-yl}-1H-quinolin-2-one ("A308")

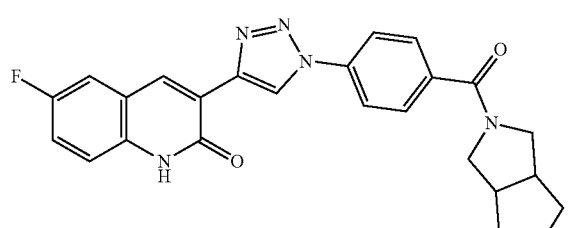

HPLC/MS 1.25 min (A), [M+H]⁺ 445;
¹H NMR (500 MHz, DMSO-d₆, TFA-d₁) δ 9.32 (s, 1H), 8.87 (s, 1H), 8.12 (d, J=8.6 Hz, 2H), 7.79 (d, J=8.6 Hz, 2H), 7.72 (dd, J=9.1, 2.8 Hz, 1H), 7.49 (dd, J=9.0, 4.7 Hz, 1H), 7.40 (td, J=8.8, 2.8 Hz, 1H), 3.90-3.04 (m, 10H).

3-{1-[4-((R)-3-amino-piperidine-1-carbonyl)-phenyl]-1H-[1,2,3]triazol-4-yl}-6,7-difluoro-1H-quinolin-2-one hydrochloride ("A309")

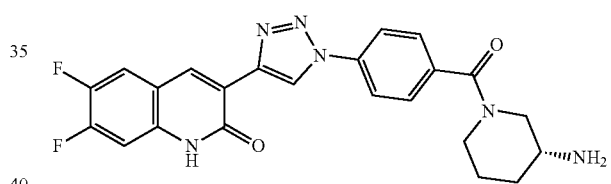

UPLC/MS 0.47 min, [M+H]⁺ 451;
¹H NMR (500 MHz, DMSO-d₆) δ 12.36 (s, 1H), 9.28 (s, 1H), 8.85 (s, 1H), 8.34-8.01 (m, 6H), 7.69 (d, J=8.5 Hz, 2H), 7.36 (dd, J=11.4, 7.0 Hz, 1H), 4.47-3.01 (m, 4H), 2.14-2.01 (m, 1H), 1.86-1.49 (m, 4H).

3-{1-[4-((S)-3-amino-piperidine-1-carbonyl)-phenyl]-1H-[1,2,3]triazol-4-yl}-6,7-difluoro-1H-quinolin-2-one hydrochloride ("A310")

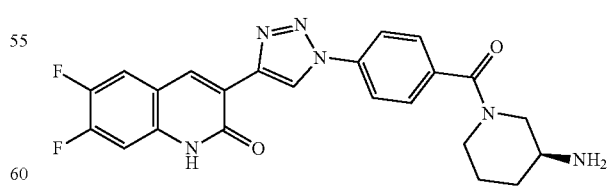

UPLC/MS 0.47 min, [M+H]⁺ 451.
¹H NMR (500 MHz, DMSO-d₆) δ 12.36 (s, 1H), 9.28 (s, 1H), 8.85 (s, 1H), 8.34-8.01 (m, 6H), 7.69 (d, J=8.5 Hz, 2H), 7.36 (dd, J=11.4, 7.0 Hz, 1H), 4.47-3.01 (m, 4H), 2.14-2.01 (m, 1H), 1.86-1.49 (m, 4H).

6-Fluoro-3-{1-[4-((R)-3-methylamino-pyrrolidine-1-
carbonyl)-phenyl]-1H-[1,2,3]triazol-4-yl}-1H-quino-
lin-2-one hydrochloride ("A311")

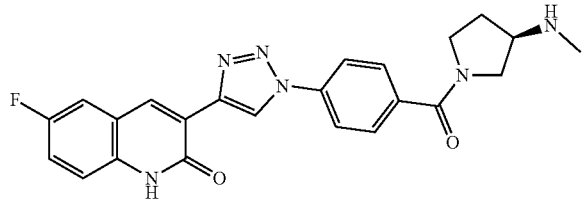 [SMILES: CN[C@@H]1CCN(C(=O)c2ccc(-n3cc(-c4cc5cc(F)ccc5[nH]c4=O)nn3)cc2)C1]

MS [M+H]$^+$ 433; HCl salt;

$^1$H NMR (500 MHz, DMSO-d$_6$) mixture of 2 rotamers δ 12.30 (s, 1H), 9.31 (s, 1H), 9.27-8.91 (m, 2H, NH$_2$$^+$), 8.86 (s, 1H), 8.13 (d, J=8.6 Hz, 2H), 7.85-7.74 (m, 3H), 7.51-7.41 (m, 2H), 3.92-3.68 (m, 3H), 3.68-3.51 (m, 2H), 2.65 (s, 1.8H), 2.56 (s, 1.2H), 2.27 (br. s, 1H), 2.17 (br. s, 1H).

6-fluoro-3-{1-[4-((S)-3-methylamino-pyrrolidine-1-
carbonyl)-phenyl]-1H-[1,2,3]triazol-4-yl}-1H-quino-
lin-2-one hydrochloride ("A312")

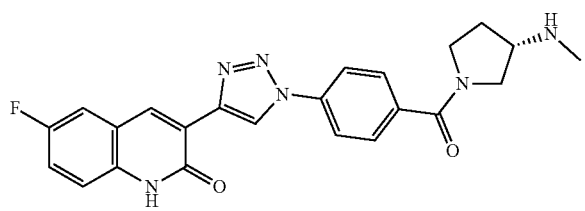 [SMILES: CN[C@H]1CCN(C(=O)c2ccc(-n3cc(-c4cc5cc(F)ccc5[nH]c4=O)nn3)cc2)C1]

MS [M+H]$^+$ 433; HCl salt;

$^1$H NMR (500 MHz, DMSO-d$_6$) mixture of 2 rotamers δ 12.30 (s, 1H), 9.31 (s, 1H), 9.27-8.91 (m, 2H, NH$_2$$^+$), 8.86 (s, 1H), 8.13 (d, J=8.6 Hz, 2H), 7.85-7.74 (m, 3H), 7.51-7.41 (m, 2H), 3.92-3.68 (m, 3H), 3.68-3.51 (m, 2H), 2.65 (s, 1.8H), 2.56 (s, 1.2H), 2.27 (br. s, 1H), 2.17 (br. s, 1H).

3-{1-[4-((R)-3-amino-pyrrolidine-1-carbonyl)-phe-
nyl]-1H-[1,2,3]triazol-4-yl}-6-fluoro-1H-quinolin-2-
one hydrochloride ("A313")

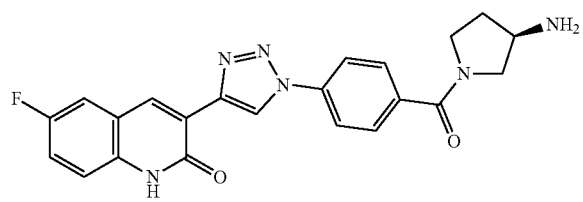 [SMILES: N[C@@H]1CCN(C(=O)c2ccc(-n3cc(-c4cc5cc(F)ccc5[nH]c4=O)nn3)cc2)C1]

MS [M+H]$^+$ 419; HCl salt;

$^1$H NMR (500 MHz, DMSO-d$^6$) mixture of 2 rotamers δ 12.30 (s, 1H), 9.31 (s, 1H), 8.86 (s, 1H), 8.30 (br. s, 2H), 8.18 (br. s, 1H), 8.13 (d, J=8.6 Hz, 2H), 7.88-7.70 (m, 3H), 7.54-7.39 (m, 2H), 3.97-3.65 (m, 3H), 3.66-3.45 (m, 2H), 2.25 (br. s, 1H), 2.06 (br. s, 1H).

6-fluoro-3-{1-[4-((R)-3-hydroxymethyl-piperazine-
1-carbonyl)-phenyl]-1H-[1,2,3]triazol-4-yl}-1H-
quinolin-2-one hydrochloride ("A314")

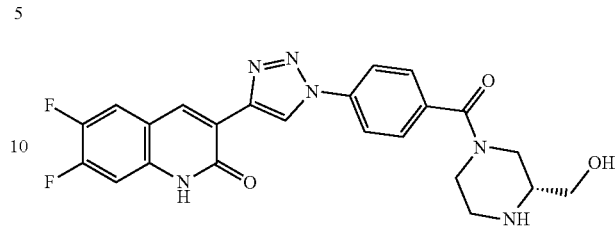

MS [M+H]$^+$ 449; dihydrochloride;

$^1$H NMR (500 MHz, DMSO-d$_6$) δ 12.29 (s, 1H), 9.42 (br. s, 1H), 9.30 (s, 1H), 9.10 (br. s, 1H), 8.85 (s, 1H), 8.12 (d, J=8.6 Hz, 2H), 7.81 (dd, J=9.2, 2.7 Hz, 1H), 7.72 (d, J=8.5 Hz, 2H), 7.50-7.40 (m, 2H), 5.47 (s, 1H), 4.49 (br. s, 1H), 3.64 (br. s, 2H), 3.57 (s, 2H), 3.47-3.33 (m, 2H), 3.22-2.95 (m, 2H).

6-fluoro-3-{1-[4-((S)-2-hydroxymethyl-piperazine-
1-carbonyl)-phenyl]-1H-[1,2,3]triazol-4-yl}-1H-
quinolin-2-one ("A315")

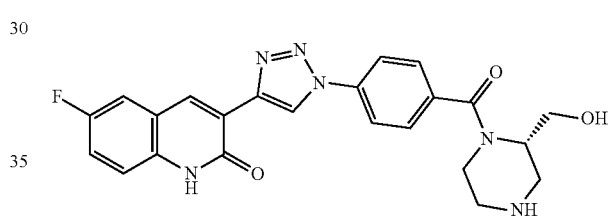

MS [M+H]$^+$ 449;

$^1$H NMR (500 MHz, DMSO-d$_6$) mixture of 2 rotamers δ 12.30 (s, 1H), 9.28 (s, 1H), 8.86 (s, 1H), 8.07 (d, J=8.4 Hz, 2H), 7.81 (dd, J=9.2, 2.6 Hz, 1H), 7.63 (d, J=8.4 Hz, 2H), 7.50-7.40 (m, 2H), 4.91 (br. s, 1H), 4.49-4.04 (m, 1H), 3.93-3.45 (m, 3H), 3.13-2.54 (m, 4H), 2.20-1.95 (m, 1H).

6-fluoro-3-{1-[4-((R)-2-hydroxymethyl-piperazine-
1-carbonyl)-phenyl]-1H-[1,2,3]triazol-4-yl}-1H-
quinolin-2-one ("A316")

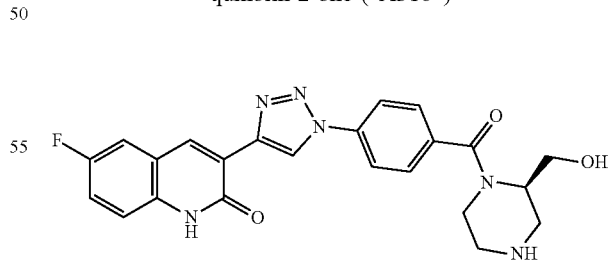

MS [M+H]$^+$ 449;

$^1$H NMR (500 MHz, DMSO-d$_6$) mixture of 2 rotamers δ 12.30 (s, 1H), 9.28 (s, 1H), 8.86 (s, 1H), 8.07 (d, J=8.4 Hz, 2H), 7.81 (dd, J=9.2, 2.6 Hz, 1H), 7.63 (d, J=8.4 Hz, 2H), 7.50-7.40 (m, 2H), 4.91 (br. s, 1H), 4.49-4.04 (m, 1H), 3.93-3.45 (m, 3H), 3.13-2.54 (m, 4H), 2.20-1.95 (m, 1H).

3-{1-[4-(6-amino-3-aza-bicyclo[3.1.0]hexane-3-carbonyl)-phenyl]-1H-[1,2,3]triazol-4-yl}-6-fluoro-1H-quinolin-2-one ("A317")

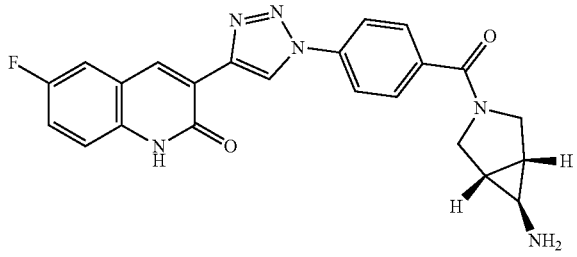 [SMILES: N[C@@H]1[C@H]2CN(C(=O)c3ccc(-n4cc(-c5cc6cc(F)ccc6[nH]c5=O)nn4)cc3)C[C@@H]12]

MS [M+H]+ 431;
¹H NMR (400 MHz, DMSO-d₆) δ 12.33 (s, 1H), 9.29 (s, 1H), 8.86 (s, 1H), 8.07 (d, J=8.7 Hz, 2H), 7.81 (dd, J=9.2, 2.6 Hz, 1H), 7.67 (d, J=8.7 Hz, 2H), 7.51-7.39 (m, 2H), 3.89 (d, J=12.1 Hz, 1H), 3.66 (dd, J=10.6, 4.4 Hz, 1H), 3.45 (dd, J=12.0, 4.4 Hz, 1H), 3.38 (d, J=10.7 Hz, 1H), 2.00 (t, J=2.2 Hz, 1H), 1.56-1.41 (m, 2H).

6-chloro-3-{1-[4-((S)-2-dimethylaminomethyl-pyrrolidine-1-carbonyl)-phenyl]-1H-[1,2,3]triazol-4-yl}-1H-quinolin-2-one ("A318")

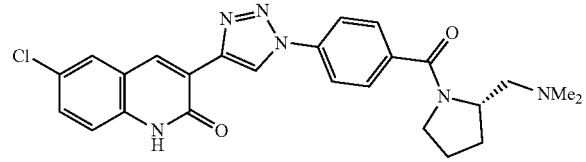 [SMILES: CN(C)C[C@@H]1CCCN1C(=O)c1ccc(-n2cc(-c3cc4cc(Cl)ccc4[nH]c3=O)nn2)cc1]

HPLC/MS 1.35 min (A), [M+H]+ 477;
¹H NMR (500 MHz, DMSO-d₆, TFA-d₁) δ 9.21 (s, 1H), 8.75 (s, 1H), 8.11-8.01 (m, 2H), 7.84 (d, J=2.3 Hz, 1H), 7.78-7.72 (m, 2H), 7.43 (dd, J=8.8, 2.3 Hz, 1H), 7.38 (d, J=8.7 Hz, 1H), 4.55 (qd, J=7.7, 3.4 Hz, 1H), 3.56 (dt, J=10.3, 7.3 Hz, 1H), 3.50-3.38 (m, 2H), 3.18 (dd, J=13.5, 3.5 Hz, 1H), 2.98 (s, 3H), 2.84 (s, 3H), 2.16 (dq, J=13.2, 6.6 Hz, 1H), 1.86 (dq, J=11.3, 5.8 Hz, 1H), 1.80-1.61 (m, 2H).

3-{1-[4-((S)-2-dimethylaminomethyl-pyrrolidine-1-carbonyl)-phenyl]-1H-[1,2,3]triazol-4-yl}-6-fluoro-1H-quinolin-2-one ("A319")

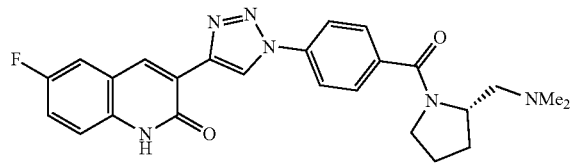 [SMILES: CN(C)C[C@@H]1CCCN1C(=O)c1ccc(-n2cc(-c3cc4cc(F)ccc4[nH]c3=O)nn2)cc1]

UPLC/MS 0.50 min, [M+H]+ 461;
¹H NMR (400 MHz, DMSO-d₆, TFA-d₁) δ 9.19 (s, 1H), 8.75 (s, 1H), 8.00 (d, J=8.2 Hz, 2H), 7.72 (d, J=8.4 Hz, 2H), 7.55-7.48 (m, 1H), 7.39 (dd, J=9.1, 4.7 Hz, 1H), 7.23 (td, J=8.8, 2.8 Hz, 1H), 4.57-4.47 (m, 1H), 3.63-3.49 (m, 1H), 3.49-3.36 (m, 2H), 3.15 (dd, J=13.5, 3.3 Hz, 1H), 2.97 (s, 3H), 2.82 (s, 3H), 2.20-2.10 (m, 1H), 1.97-1.79 (m, 1H), 1.79-1.58 (m, 2H).

3-{1-[4-((R)-2-dimethylaminomethyl-pyrrolidine-1-carbonyl)-phenyl]-1H-[1,2,3]triazol-4-yl}-6,7-difluoro-1H-quinolin-2-one ("A320")

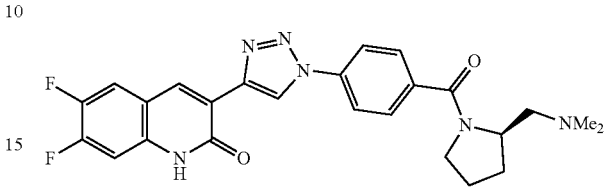

UPLC/MS 0.52 min, [M+H]+ 479;
¹H NMR (400 MHz, DMSO-d₆, TFA-d₁) δ 9.17 (s, 1H), 8.74 (s, 1H), 8.01 (d, J=8.6 Hz, 2H), 7.83-7.71 (m, 3H), 7.27 (dd, J=11.4, 7.0 Hz, 1H), 4.58-4.48 (m, 1H), 3.63-3.50 (m, 1H), 3.49-3.36 (m, 2H), 3.16 (dd, J=13.4, 3.4 Hz, 1H), 2.20-2.10 (m, 1H), 1.92-1.80 (m, 1H), 1.80-1.57 (m, 2H).

3-{1-[4-((R)-2-dimethylaminomethyl-pyrrolidine-1-carbonyl)-phenyl]-1H-[1,2,3]triazol-4-yl}-6-fluoro-1H-quinolin-2-one ("A321")

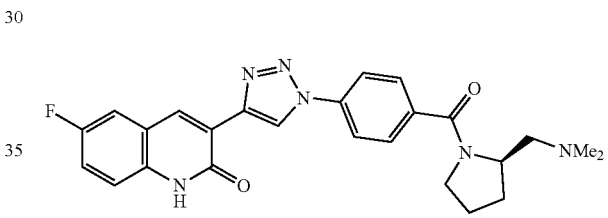

UPLC/MS 0.50 min, [M+H]+ 461;
¹H NMR (500 MHz, DMSO-d₆, TFA-d₁) δ 9.26 (s, 1H), 8.80 (s, 1H), 8.15-8.07 (m, 2H), 7.84-7.76 (m, 2H), 7.64 (dd, J=9.1, 2.8 Hz, 1H), 7.42 (dd, J=9.0, 4.7 Hz, 1H), 7.32 (td, J=8.8, 2.8 Hz, 1H), 4.57 (qd, J=7.5, 3.7 Hz, 1H), 3.58 (dt, J=10.5, 7.3 Hz, 1H), 3.49-3.41 (m, 2H), 3.20 (dd, J=13.4, 3.8 Hz, 1H), 3.00 (s, 3H), 2.86 (s, 3H), 2.21-2.12 (m, 1H), 1.95-1.84 (m, 1H), 1.82-1.64 (m, 2H).

6-chloro-3-{1-[4-((R)-2-dimethylaminomethyl-pyrrolidine-1-carbonyl)-phenyl]-1H-[1,2,3]triazol-4-yl}-1H-quinolin-2-one ("A322")

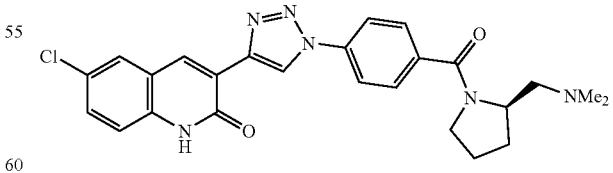

UPLC/MS 0.53 min, [M+H]+ 477;
¹H NMR (500 MHz, DMSO-d₆, TFA-d₁) δ 9.21 (s, 1H), 8.75 (s, 1H), 8.11-8.01 (m, 2H), 7.84 (d, J=2.3 Hz, 1H), 7.78-7.72 (m, 2H), 7.43 (dd, J=8.8, 2.3 Hz, 1H), 7.38 (d, J=8.7 Hz, 1H), 4.55 (qd, J=7.7, 3.4 Hz, 1H), 3.56 (dt, J=10.3, 7.3 Hz, 1H), 3.50-3.38 (m, 2H), 3.18 (dd, J=13.5, 3.5 Hz, 1H), 2.98 (s, 3H), 2.84 (s, 3H), 2.16 (dq, J=13.2, 6.6 Hz, 1H), 1.86 (dq, J=11.3, 5.8 Hz, 1H), 1.80-1.61 (m, 2H).

3-{1-[4-((S)-2-dimethylaminomethyl-pyrrolidine-1-carbonyl)-phenyl]-1H-[1,2,3]triazol-4-yl}-6,7-difluoro-1H-quinolin-2-one ("A323")

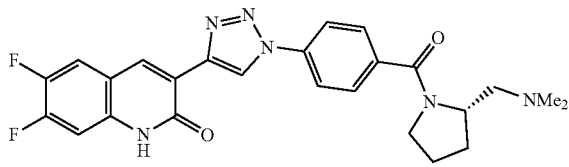 [SMILES: CN(C)C[C@@H]1CCCN1C(=O)c1ccc(-n2cc(-c3cc4cc(F)c(F)cc4[nH]c3=O)nn2)cc1]

UPLC/MS 0.51 min, [M+H]⁺ 479;
¹H NMR (400 MHz, DMSO-d₆) δ 12.35 (s, 1H), 9.30 (s, 1H), 9.11 (bs, 1H, NH⁺), 8.86 (s, 1H), 8.19-8.13 (m, 2H), 8.10 (dd, J=11.0, 8.6 Hz, 1H), 7.86-7.76 (m, 2H), 7.34 (dd, J=11.4, 7.1 Hz, 1H), 4.64-4.54 (m, 1H), 3.64-3.54 (m, 1H), 3.51-3.39 (m, 2H), 3.28-2.16 (m, 1H), 3.08-2.80 (m, 6H), 2.22-2.10 (m, 1H), 2.01-1.88 (m, 1H), 1.86-1.68 (m, 2H).

3-{1-[4-((S)-2-dimethylaminomethyl-pyrrolidine-1-carbonyl)-phenyl]-1H-pyrazol-4-yl}-6-fluoro-1H-quinolin-2-one ("A324")

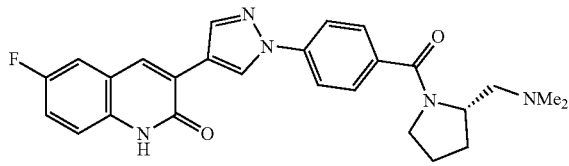 [SMILES: CN(C)C[C@@H]1CCCN1C(=O)c1ccc(-n2cc(-c3cc4cc(F)ccc4[nH]c3=O)cn2)cc1]

UPLC/MS 0.51 min, [M+H]⁺ 460;
¹H NMR (400 MHz, DMSO-d₆) δ 12.12 (s, 1H), 9.21 (s, 1H), 9.12 (bs, 1H, NH⁺), 8.48 (s, 1H), 8.42 (s, 1H), 8.10-7.96 (m, 2H), 7.84-7.66 (m, 2H), 7.50 (dd, J=8.5, 1.9 Hz, 1H), 7.44-7.30 (m, 2H), 4.63-4.54 (m, 1H), 3.66-3.56 (m, 1H), 3.55-3.14 (m, 3H), 3.01 (d, J=4.2 Hz, 3H), 2.88 (d, J=4.2 Hz, 3H), 2.22-2.11 (m, 1H), 2.04-1.87 (m, 1H), 1.85-1.66 (m, 2H).

3-{1-[4-((R)-2-dimethylaminomethyl-pyrrolidine-1-carbonyl)-phenyl]-1H-pyrazol-4-yl}-6-fluoro-1H-quinolin-2-one ("A325")

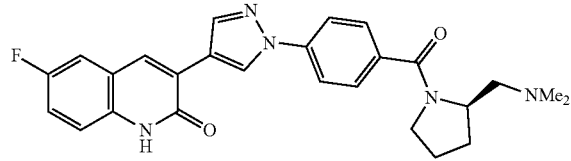 [SMILES: CN(C)C[C@H]1CCCN1C(=O)c1ccc(-n2cc(-c3cc4cc(F)ccc4[nH]c3=O)cn2)cc1]

UPLC/MS 0.51 min, [M+H]⁺ 460;
¹H NMR (400 MHz, DMSO-d₆) δ 12.12 (s, 1H), 9.21 (s, 1H), 9.12 (bs, 1H, NH⁺), 8.48 (s, 1H), 8.42 (s, 1H), 8.10-7.96 (m, 2H), 7.84-7.66 (m, 2H), 7.50 (dd, J=8.5, 1.9 Hz, 1H), 7.44-7.30 (m, 2H), 4.63-4.54 (m, 1H), 3.66-3.56 (m, 1H), 3.55-3.14 (m, 3H), 3.01 (d, J=4.2 Hz, 3H), 2.88 (d, J=4.2 Hz, 3H), 2.22-2.11 (m, 1H), 2.04-1.87 (m, 1H), 1.85-1.66 (m, 2H).

EXAMPLE 21

3-{1-[4-((S)-3-dimethylaminomethyl-pyrrolidine-1-carbonyl)-phenyl]-1H-[1,2,3]triazol-4-yl}-6-fluoro-1H-quinolin-2-one ("A326")

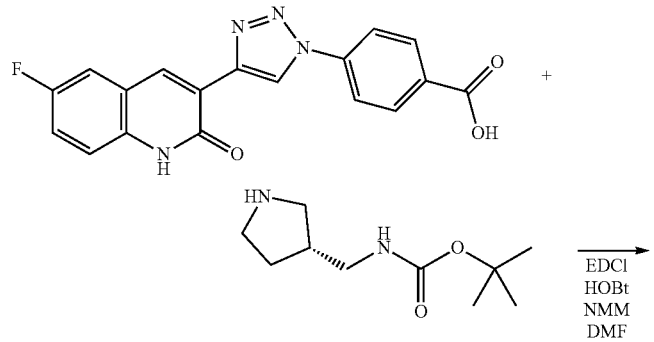

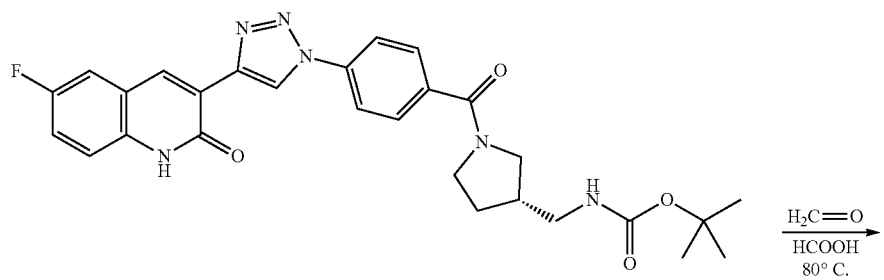

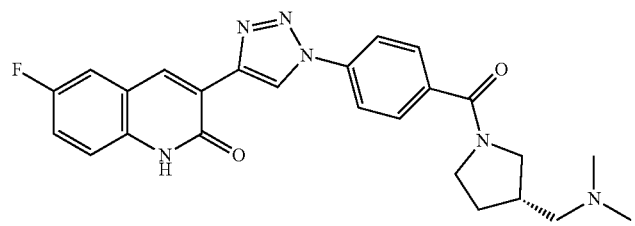

UPLC/MS 0.46 min, [M+H]+ 461;
$^1$H NMR (400 MHz, DMSO-d$_6$, TFA-d$_1$) δ 9.22 (s, 1H), 8.77 (s, 1H), 8.11-7.97 (m, 2H), 7.70 (d, J=8.1 Hz, 2H), 7.59 (dd, J=9.2, 2.8 Hz, 1H), 7.40 (dd, J=9.0, 4.7 Hz, 1H), 7.28 (td, J=8.8, 2.8 Hz, 1H), 3.87-3.07 (m, 6H), 2.87-2.57 (m, 7H), 2.16-2.01 (m, 1H), 1.74-1.59 (m, 1H).

The following compounds are prepared similarly:

6-fluoro-3-{1-[4-((cis)-5-methyl-hexahydro-pyrrolo[3,4-c]pyrrole-2-carbonyl)-phenyl]-1H-[1,2,3]triazol-4-yl}-1H-quinolin-2-one ("A327")

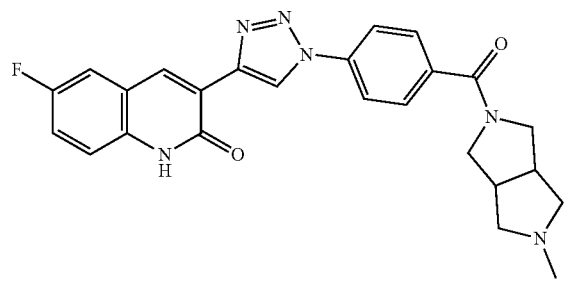 [SMILES: CN1CC2CN(C(=O)c3ccc(-n4cc(-c5cc6cc(F)ccc6[nH]c5=O)nn4)cc3)CC2C1]

HPLC/MS 1.26 min (A), [M+H]+ 459;
$^1$H NMR (500 MHz, DMSO-d$_6$) δ 12.28 (s, 1H), 9.28 (s, 1H), 8.85 (s, 1H), 8.17 (s, 1H), 8.12-8.04 (m, 2H), 7.80 (dd, J=9.2, 2.7 Hz, 1H), 7.75-7.64 (m, 2H), 7.48-7.40 (m, 2H), 3.79 (bs, 1H), 3.67 (bs, 1H), 3.48 (bs, 1H), 3.31 (bs, 1H), 2.82 (bs, 2H), 2.52-2.34 (m, 4H), 2.25 (s, 3H).

3-{1-[4-((R)-3-dimethylamino-piperidine-1-carbonyl)-phenyl]-1H-[1,2,3]triazol-4-yl}-6,7-difluoro-1H-quinolin-2-one ("A328")

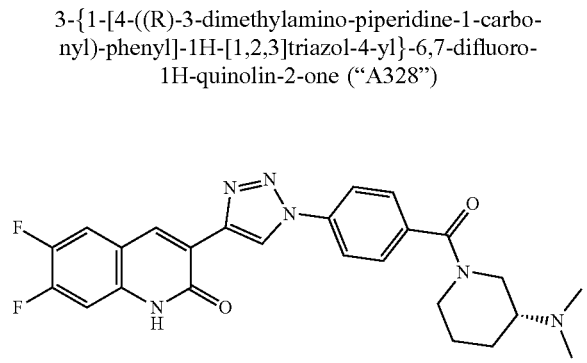

HPLC/MS 1.23 min (A), [M+H]+ 479;
$^1$H NMR (400 MHz, DMSO-d$_6$) δ 12.32 (s, 1H), 9.26 (s, 1H), 8.84 (s, 1H), 8.12-8.05 (m, 3H), 7.60 (d, J=8.1 Hz, 2H), 7.32 (dd, J=11.4, 7.1 Hz, 1H), 4.5-4-2 (m, 1H), 3.77-2.74 (m, 4H), 2.32-2.02 (m, 7H), 1.85-1.62 (m, 1H), 1.73 (d, J=36.7 Hz, 1H), 1.54-1.34 (m, 2H).

3-{1-[4-((S)-3-dimethylamino-piperidine-1-carbonyl)-phenyl]-1H-[1,2,3]triazol-4-yl}-6,7-difluoro-1H-quinolin-2-one ("A329")

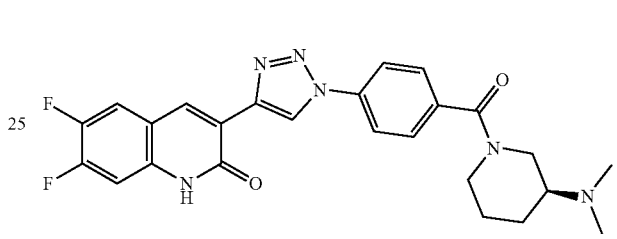

HPLC/MS 1.25 min (A), [M+H]+ 479;
$^1$H NMR (400 MHz, DMSO-d$_6$) δ 12.32 (s, 1H), 9.26 (s, 1H), 8.84 (s, 1H), 8.12-8.05 (m, 3H), 7.60 (d, J=8.1 Hz, 2H), 7.32 (dd, J=11.4, 7.1 Hz, 1H), 4.5-4-2 (m, 1H), 3.77-2.74 (m, 4H), 2.32-2.02 (m, 7H), 1.85-1.62 (m, 1H), 1.73 (d, J=36.7 Hz, 1H), 1.54-1.34 (m, 2H).

3-{1-[4-(6-dimethylamino-3-aza-bicyclo[3.1.0]hexane-3-carbonyl)-phenyl]-1H-[1,2,3]triazol-4-yl}-6-fluoro-1H-quinolin-2-one ("A330")

MS [M+H]+ 459;
$^1$H NMR (500 MHz, DMSO-d$_6$) δ 12.27 (s, 1H), 9.28 (s, 1H), 8.85 (s, 1H), 8.07 (d, J=8.6 Hz, 2H), 7.80 (dd, J=9.2, 2.7 Hz, 1H), 7.68 (d, J=8.7 Hz, 2H), 7.51-7.37 (m, 2H), 3.90 (d, J=12.1 Hz, 1H), 3.70 (dd, J=10.7, 4.4 Hz, 1H), 3.44 (dd, J=12.2, 4.5 Hz, 1H), 3.37 (d, J=10.6 Hz, 1H), 2.21 (s, 6H), 1.70-1.57 (m, 2H), 1.35 (t, J=2.1 Hz, 1H).

3-{1-[4-((R)-3-dimethylamino-piperidine-1-carbonyl)-phenyl]-1H-[1,2,3]triazol-4-yl}-6-fluoro-1H-quinolin-2-one ("A331")

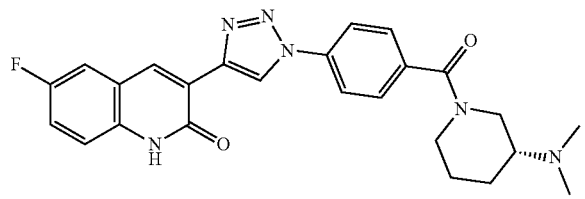 [SMILES: CN(C)[C@@H]1CCCN(C(=O)c2ccc(-n3cc(-c4cc5cc(F)ccc5[nH]c4=O)nn3)cc2)C1]

HPLC/MS 1.21 min (A), [M+H]+ 461;

$^1$H NMR (400 MHz, DMSO-d$_6$) δ 12.28 (s, 1H), 9.29 (s, 1H), 8.86 (s, 1H), 8.09 (d, J=8.4 Hz, 2H), 7.81 (dd, J=9.3, 2.7 Hz, 1H), 7.61 (d, J=8.1 Hz, 2H), 7.53-7.39 (m, 2H), 4.71-0.89 (m, 15H).

3-{1-[4-((S)-3-dimethylamino-piperidine-1-carbonyl)-phenyl]-1H-[1,2,3]triazol-4-yl}-6-fluoro-1H-quinolin-2-one ("A332")

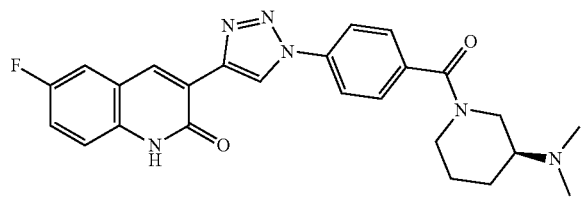 [SMILES: CN(C)[C@H]1CCCN(C(=O)c2ccc(-n3cc(-c4cc5cc(F)ccc5[nH]c4=O)nn3)cc2)C1]

HPLC/MS 1.19 min (A), [M+H]+ 461;

$^1$H NMR (400 MHz, DMSO-d$_6$) δ 12.28 (s, 1H), 9.29 (s, 1H), 8.86 (s, 1H), 8.09 (d, J=8.4 Hz, 2H), 7.81 (dd, J=9.3, 2.7 Hz, 1H), 7.61 (d, J=8.1 Hz, 2H), 7.53-7.39 (m, 2H), 4.71-0.89 (m, 15H).

3-{1-[4-((R)-3-dimethylamino-piperidine-1-carbonyl)-phenyl]-1H-[1,2,3]triazol-4-yl}-7-fluoro-1H-quinolin-2-one ("A333")

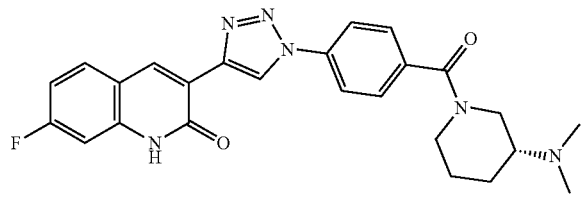 [SMILES: CN(C)[C@@H]1CCCN(C(=O)c2ccc(-n3cc(-c4cc5ccc(F)cc5[nH]c4=O)nn3)cc2)C1]

UPLC/MS 0.46 min, [M+H]+ 461;

$^1$H NMR (400 MHz, DMSO-d$_6$) δ 12.27 (s, 1H), 9.24 (s, 1H), 8.86 (s, 1H), 8.08 (d, J=8.2 Hz, 2H), 8.00 (dd, J=9.6, 6.1 Hz, 1H), 7.60 (d, J=8.1 Hz, 2H), 7.27-6.99 (m, 2H), 4.71-0.89 (m, 15H).

3-{1-[4-((R)-3-dimethylaminomethyl-pyrrolidine-1-carbonyl)-phenyl]-1H-[1,2,3]triazol-4-yl}-6-fluoro-1H-quinolin-2-one ("A334")

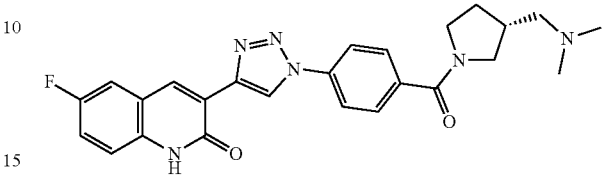

UPLC/MS 0.46 min, [M+H]+ 461;

$^1$H NMR (400 MHz, DMSO-d$_6$, TFA-d$_1$) δ 9.22 (s, 1H), 8.77 (s, 1H), 8.11-7.97 (m, 2H), 7.70 (d, J=8.1 Hz, 2H), 7.59 (dd, J=9.2, 2.8 Hz, 1H), 7.40 (dd, J=9.0, 4.7 Hz, 1H), 7.28 (td, J=8.8, 2.8 Hz, 1H), 3.87-3.07 (m, 6H), 2.87-2.57 (m, 7H), 2.16-2.01 (m, 1H), 1.74-1.59 (m, 1H).

3-{1-[4-((R)-3-dimethylaminomethyl-pyrrolidine-1-carbonyl)-phenyl]-1H-[1,2,3]triazol-4-yl}-6,7-difluoro-1H-quinolin-2-one ("A335")

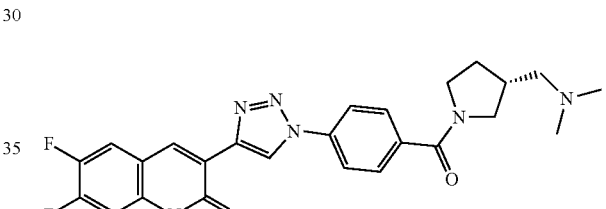

UPLC/MS 0.48 min, [M+H]+ 479;

$^1$H NMR (400 MHz, DMSO-d$_6$, TFA-d$_1$) δ 9.18 (s, 1H), 8.75 (s, 1H), 8.07-7.96 (m, 2H), 7.80 (dd, J=10.8, 8.4 Hz, 1H), 7.69 (d, J=8.1 Hz, 2H), 7.28 (dd, J=11.4, 7.0 Hz, 1H), 3.87-3.07 (m, 6H), 2.87-2.57 (m, 7H), 2.16-2.01 (m, 1H), 1.74-1.59 (m, 1H).

3-{1-[4-((S)-3-dimethylamino-piperidine-1-carbonyl)-phenyl]-1H-[1,2,3]triazol-4-yl}-7-fluoro-1H-quinolin-2-one ("A336")

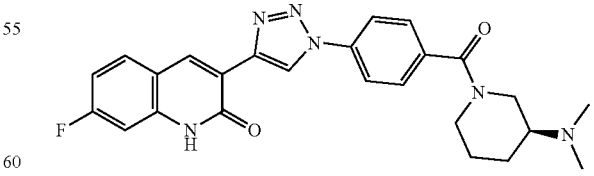

UPLC/MS 0.48 min, [M+H]+ 461;

$^1$H NMR (400 MHz, DMSO-d$_6$) δ 12.27 (s, 1H), 9.24 (s, 1H), 8.86 (s, 1H), 8.08 (d, J=8.2 Hz, 2H), 8.00 (dd, J=9.6, 6.1 Hz, 1H), 7.60 (d, J=8.1 Hz, 2H), 7.27-6.99 (m, 2H), 4.71-0.89 (m, 15H).

3-{1-[4-((S)-3-diethylamino-piperidine-1-carbonyl)-phenyl]-1H-[1,2,3]triazol-4-yl}-6-fluoro-1H-quinolin-2-one ("A337")

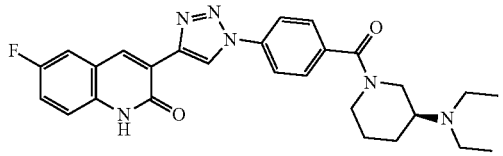 [SMILES: CCN(CC)[C@H]1CCCN(C(=O)c2ccc(-n3cc(-c4cc5cc(F)ccc5[nH]c4=O)nn3)cc2)C1]

HPLC/MS 1.25 min (A), [M+H]⁺ 489;
¹H NMR (500 MHz, DMSO-d₆) δ 12.29 (s, 1H), 9.30 (d, J=2.5 Hz, 1H), 8.86 (s, 1H), 8.10 (d, J=8.0 Hz, 2H), 7.81 (dd, J=9.2, 2.7 Hz, 1H), 7.71-7.58 (m, 2H), 7.55-7.33 (m, 2H), 4.60-4.35 (m, 1H), 3.62-3.46 (m, 1H), 3.08-2.90 (m, 1H), 2.78-2.34 (m, 6H), 2.03-1.38 (m, 4H), 0.94 (d, J=69.7 Hz, 6H).

3-{1-[4-((R)-3-diethylamino-piperidine-1-carbonyl)-phenyl]-1H-[1,2,3]triazol-4-yl}-6-fluoro-1H-quinolin-2-one ("A338")

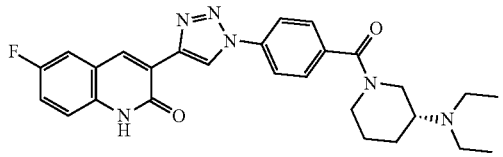 [SMILES: CCN(CC)[C@@H]1CCCN(C(=O)c2ccc(-n3cc(-c4cc5cc(F)ccc5[nH]c4=O)nn3)cc2)C1]

HPLC/MS 1.24 min (A), [M+H]⁺ 489;
¹H NMR (500 MHz, DMSO-d₆) δ 12.29 (s, 1H), 9.30 (d, J=2.5 Hz, 1H), 8.86 (s, 1H), 8.10 (d, J=8.0 Hz, 2H), 7.81 (dd, J=9.2, 2.7 Hz, 1H), 7.71-7.58 (m, 2H), 7.55-7.33 (m, 2H), 4.60-4.35 (m, 1H), 3.62-3.46 (m, 1H), 3.08-2.90 (m, 1H), 2.78-2.34 (m, 6H), 2.03-1.38 (m, 4H), 0.94 (d, J=69.7 Hz, 6H).

3-{1-[4-(4-dimethylamino-3,3-difluoro-pyrrolidine-1-carbonyl)-phenyl]-1H-[1,2,3]triazol-4-yl}-6-fluoro-1H-quinolin-2-one ("A339")

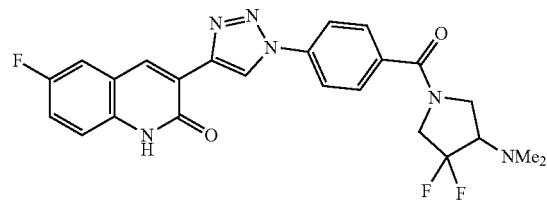 [SMILES: CN(C)C1CN(C(=O)c2ccc(-n3cc(-c4cc5cc(F)ccc5[nH]c4=O)nn3)cc2)CC1(F)F]

HPLC/MS 1.27 min (A), [M+H]⁺ 483;
¹H NMR (700 MHz, DMSO-d₆) 1:1 mixture of rotamers, δ 12.31 (s, 1H), 9.32 (s, 1H), 8.87 (s, 1H), 8.12 (d, J=8.3 Hz, 2H), 7.85-7.78 (m, 3H), 7.47 (td, J=8.7, 2.8 Hz, 1H), 7.43 (dd, J=9.1, 4.8 Hz, 1H), 4.21-3.78 (m, 3H), 3.68 (t, J=10.1 Hz, 0.5H), 3.47 (t, J=10.9 Hz, 0.5H), 3.23 (dq, J=17.7, 9.0 Hz, 1H), 2.33 (s, 3H), 2.24 (s, 3H).

3-{1-[4-((S)-3-dimethylaminomethyl-pyrrolidine-1-carbonyl)-phenyl]-1H-pyrazol-4-yl}-6-fluoro-1H-quinolin-2-one ("A340")

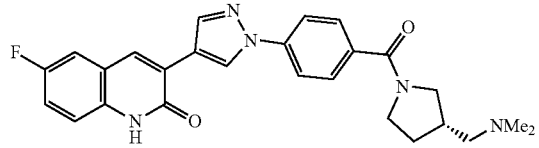 [SMILES: CN(C)C[C@@H]1CCN(C(=O)c2ccc(-n3cc(-c4cc5cc(F)ccc5[nH]c4=O)cn3)cc2)C1]

UPLC/MS 0.48 min, [M+H]⁺ 460;
¹H NMR (500 MHz, DMSO-d₆) 1:1 mixture of rotamers, selection of signals δ 12.16 (s, 1H), 9.20 (s, 1H), 8.47 (s, 1H), 8.43 (s, 1H), 7.99-7.90 (m, 2H), 7.78-7.65 (m, 2H), 7.50 (dd, J=9.0, 2.5 Hz, 1H), 7.45-7.32 (m, 2H), 2.18 (s, 3H), 2.08 (s, 3H).

3-{1-[4-((trans)-3-dimethylamino-4-fluoro-pyrrolidine-1-carbonyl)-phenyl]-1H-[1,2,3]triazol-4-yl}-6-fluoro-1H-quinolin-2-one ("A341")

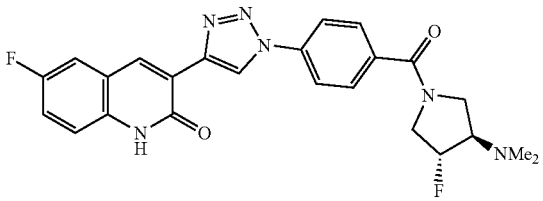

HPLC/MS 1.23 min (A), [M+H]⁺ 465;
¹H NMR (500 MHz, DMSO-d₆) 1:1 mixture of rotamers δ 12.32 (s, 1H), 9.32 (s, 1H), 8.87 (s, 1H), 8.24-7.95 (m, 2H), 7.86-7.76 (m, 3H), 7.47 (td, J=8.8, 2.8 Hz, 1H), 7.43 (dd, J=9.0, 4.9 Hz, 1H), 5.30 (m, 1H), 4.04-3.49 (m, 4H), 3.05-2.92 (m, 1H), 2.26 (s, 3H), 2.16 (s, 3H).

EXAMPLE 22

6-fluoro-3-[1-(4-methylamino-phenyl)-1H-[1,2,3]triazol-4-yl]-1H-quinolin-2-one ("A342") and (R)-tetrahydro-furan-2-carboxylic acid {4-[4-(6-fluoro-2-oxo-1,2-dihydro-quinolin-3-yl)-[1,2,3]triazol-1-yl]-phenyl}-methyl-amide ("A343")

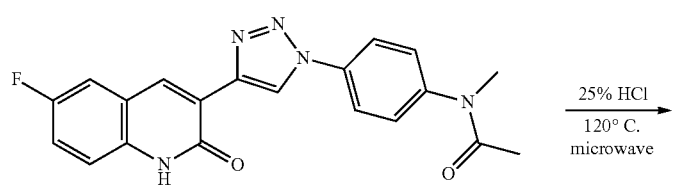

-continued

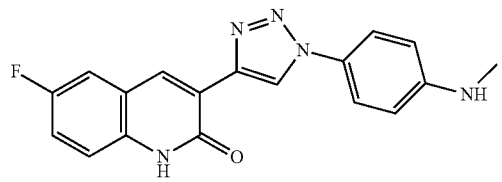 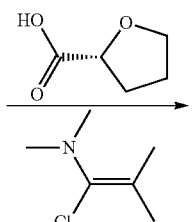

2,6-dimethylpyridine
CH₂C

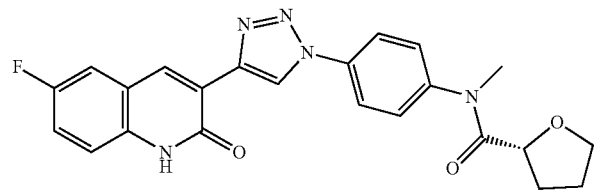

"A342": MS [M+H]⁺ 336;
¹H NMR (400 MHz, DMSO-d₆) δ 12.22 (s, 1H), 8.98 (s, 1H), 8.80 (s, 1H), 7.80-7.74 (m, 1H), 7.69 (d, J=8.8 Hz, 2H), 7.46-7.38 (m, 2H), 6.79 (d, J=8.6 Hz, 2H), 4.07 (br. s, 1H), 2.50 (p, J=1.9 Hz, 3H).

"A343": MS [M+H]⁺ 434;
¹H NMR (400 MHz, DMSO-d₆) δ 12.26 (s, 1H), 9.26 (s, 1H), 8.84 (s, 1H), 8.08 (d, J=8.6 Hz, 2H), 7.79 (dd, J=9.3, 2.6 Hz, 1H), 7.58 (d, J=8.6 Hz, 2H), 7.49-7.39 (m, 2H), 4.29 (br. s, 1H), 3.81 (q, J=7.1 Hz, 1H), 3.69 (br. s, 1H), 3.25 (s, 3H), 2.01 (br. s, 1H), 1.96-1.80 (m, 2H), 1.73 (br. s, 1H).

The following compounds are prepared similarly:

(S)-tetrahydro-furan-2-carboxylic acid {4-[4-(6-fluoro-2-oxo-1,2-dihydro-quinolin-3-yl)-[1,2,3]triazol-1-yl]-phenyl}-methyl-amide ("A344")

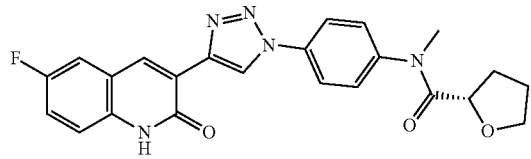 [SMILES: CN(C(=O)[C@@H]1CCCO1)c1ccc(-n2cc(-c3cc4cc(F)ccc4[nH]c3=O)nn2)cc1]

MS [M+H]⁺ 434;
¹H NMR (400 MHz, DMSO-d₆) δ 12.26 (s, 1H), 9.26 (s, 1H), 8.84 (s, 1H), 8.08 (d, J=8.6 Hz, 2H), 7.79 (dd, J=9.3, 2.6 Hz, 1H), 7.58 (d, J=8.6 Hz, 2H), 7.49-7.39 (m, 2H), 4.29 (br. s, 1H), 3.81 (q, J=7.1 Hz, 1H), 3.69 (br. s, 1H), 3.25 (s, 3H), 2.01 (br. s, 1H), 1.96-1.80 (m, 2H), 1.73 (br. s, 1H).

tetrahydro-pyran-4-carboxylic acid {4-[4-(6-fluoro-2-oxo-1,2-dihydro-quinolin-3-yl)-[1,2,3]triazol-1-yl]-phenyl}-methyl-amide ("A345")

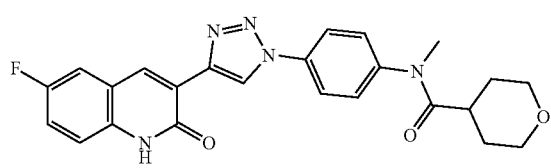 [SMILES: CN(C(=O)C1CCOCC1)c1ccc(-n2cc(-c3cc4cc(F)ccc4[nH]c3=O)nn2)cc1]

MS [M+H]⁺ 448;
¹H NMR (400 MHz, DMSO-d₆) δ 12.27 (s, 1H), 9.27 (s, 1H), 8.85 (s, 1H), 8.09 (d, J=8.6 Hz, 2H), 7.80 (dd, J=9.2, 2.6 Hz, 1H), 7.59 (d, J=8.5 Hz, 2H), 7.50-7.39 (m, 2H), 3.78 (d, J=11.3 Hz, 2H), 3.23 (s, 3H), 3.11 (br. s, 2H), 1.65 (qd, J=12.3, 4.4 Hz, 2H), 1.58-1.43 (m, 2H).

(R)—N-{4-[4-(6-fluoro-2-oxo-1,2-dihydro-quinolin-3-yl)-[1,2,3]triazol-1-yl]-phenyl}-2-methoxy-N-methyl-propionamide ("A346")

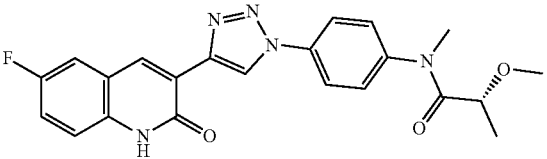 [SMILES: CO[C@H](C)C(=O)N(C)c1ccc(-n2cc(-c3cc4cc(F)ccc4[nH]c3=O)nn2)cc1]

MS [M+H]⁺ 422;
¹H NMR (400 MHz, DMSO-d₆) δ 12.24 (s, 1H), 9.27 (s, 1H), 8.85 (s, 1H), 8.10 (d, J=8.6 Hz, 2H), 7.80 (dd, J=9.2, 2.6 Hz, 1H), 7.59 (d, J=8.7 Hz, 2H), 7.50-7.39 (m, 2H), 3.88 (br. s, 1H), 3.26 (s, 3H), 3.08 (s, 3H), 1.16 (br. s, 3H).

(2S,4S)-4-methoxy-pyrrolidine-2-carboxylic acid {4-[4-(6-fluoro-2-oxo-1,2-dihydro-quinolin-3-yl)-[1,2,3]triazol-1-yl]-phenyl}-methyl-amide ("A347")

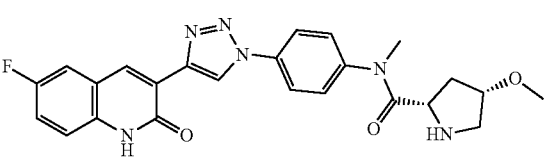 [SMILES: CO[C@@H]1CN[C@H](C(=O)N(C)c2ccc(-n3cc(-c4cc5cc(F)ccc5[nH]c4=O)nn3)cc2)C1]

MS [M+H]⁺ 463; hydrochloride
¹H NMR (700 MHz, DMSO-d₆+CF₃COOD) δ 9.34 (s, 1H), 8.88 (s, 1H), 8.22 (d, J=8.4 Hz, 2H), 7.78 (dd, J=9.1, 2.8 Hz, 1H), 7.73 (d, J=8.3 Hz, 2H), 7.50-7.40 (m, 2H), 4.26 (dd, J=10.3, 6.9 Hz, 1H), 3.94 (br. s, 1H), 3.48-3.38 (m, 1H), 3.34 (s, 3H), 3.22 (s, 3H), 3.13 (dd, J=12.4, 4.7 Hz, 1H), 2.07 (ddd, J=16.0, 10.5, 6.1 Hz, 1H), 1.95-1.84 (m, 1H).

(S)—N-{4-[4-(6-fluoro-2-oxo-1,2-dihydro-quinolin-3-yl)-[1,2,3]triazol-1-yl]-phenyl}-2-methoxy-N-methyl-propionamide ("A348")

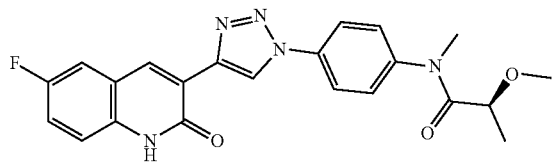 [SMILES: CO[C@@H](C)C(=O)N(C)c1ccc(-n2cc(-c3cc4cc(F)ccc4[nH]c3=O)nn2)cc1]

MS [M+H]⁺ 422;
¹H NMR (400 MHz, DMSO-d₆) δ ¹H NMR (400 MHz, DMSO-d₆) δ 12.24 (s, 1H), 9.27 (s, 1H), 8.85 (s, 1H), 8.10 (d, J=8.6 Hz, 2H), 7.80 (dd, J=9.2, 2.6 Hz, 1H), 7.59 (d, J=8.7 Hz, 2H), 7.50-7.39 (m, 2H), 3.88 (br. s, 1H), 3.26 (s, 3H), 3.08 (s, 3H), 1.16 (br. s, 3H).

1-methyl-piperidine-4-carboxylic acid {4-[4-(6-fluoro-2-oxo-1,2-dihydro-quinolin-3-yl)-[1,2,3]triazol-1-yl]-phenyl}-methyl-amide ("A349")

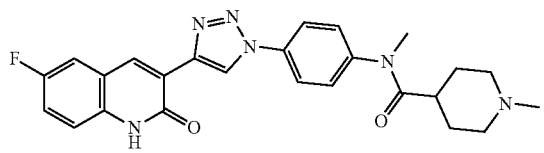 [SMILES: CN1CCC(C(=O)N(C)c2ccc(-n3cc(-c4cc5cc(F)ccc5[nH]c4=O)nn3)cc2)CC1]

MS [M+H]⁺ 461; hydrochloride
¹H NMR (500 MHz, DMSO-d₆) δ 12.34 (s, 1H), 9.76 (s, 1H), 9.30 (s, 1H), 8.86 (s, 1H), 8.15 (d, J=7.5 Hz, 2H), 7.82 (dd, J=9.2, 2.8 Hz, 1H), 7.65 (d, J=6.6 Hz, 2H), 7.52-7.41 (m, 2H), 3.35-3.26 (m, 2H), 3.22 (s, 3H), 2.82-2.67 (m, 2H), 2.61 (s, 3H), 2.44 (br. s, 1H), 1.99-1.74 (m, 4H).

EXAMPLE 23

6-fluoro-3-{1-[5-((S)-3-methoxy-pyrrolidine-1-carbonyl)-thiophen-3-yl]-1H-[1,2,3]triazol-4-yl}-1H-quinolin-2-one ("A350")

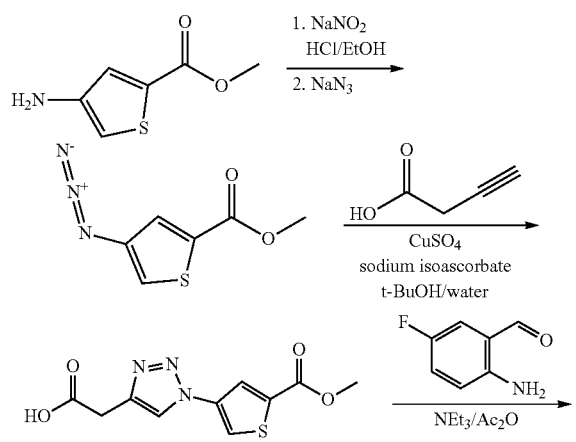

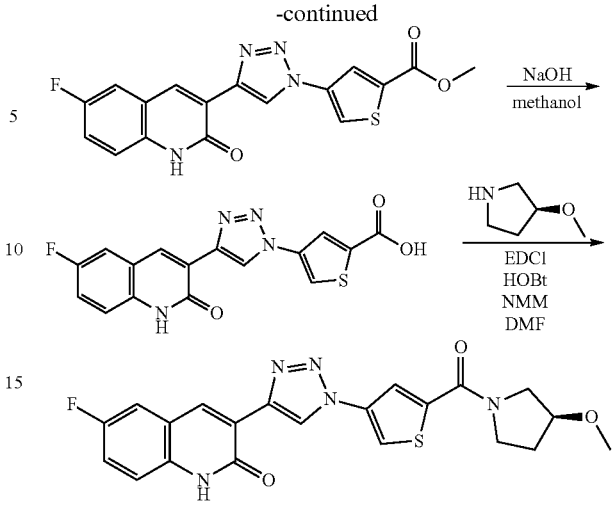

UPLC/MS 0.70 min, [M+H]⁺ 440;
¹H NMR (500 MHz, DMSO-d₆) 1:1 mixture of rotamers δ 12.30 (s, 1H), 9.35 (s, 0.5H), 9.34 (s, 0.5H), 8.85 (s, 1H), 8.42 (d, J=1.4 Hz, 1H), 8.22 (d, J=1.5 Hz, 0.5H), 8.19 (d, J=1.5 Hz, 0.5H), 7.82 (dd, J=9.3, 2.8 Hz, 1H), 7.46 (td, J=8.8, 2.8 Hz, 1H), 7.42 (dd, J=9.1, 4.9 Hz, 1H), 4.20-3.87 (m, 3H), 3.75-3.47 (m, 2H), 3.29 (s, 1.5H), 3.27 (s, 1.5H), 2.25-1.90 (m, 2H).

The following compounds are prepared similarly:

6-fluoro-3-{1-[5-((R)-3-methoxy-pyrrolidine-1-carbonyl)-thiophen-3-yl]-1H-[1,2,3]triazol-4-yl}-1H-quinolin-2-one ("A351")

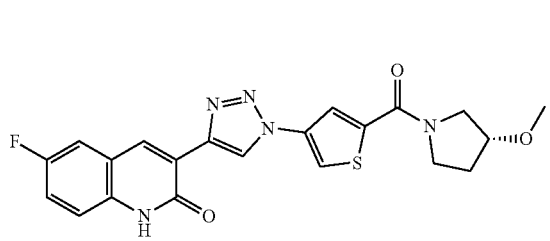 [SMILES: CO[C@@H]1CCN(C(=O)c2cc(-n3cc(-c4cc5cc(F)ccc5[nH]c4=O)nn3)cs2)C1]

UPLC/MS 0.71 min, [M+H]⁺ 440;
¹H NMR (500 MHz, DMSO-d₆) 1:1 mixture of rotamers δ 12.30 (s, 1H), 9.35 (s, 0.5H), 9.34 (s, 0.5H), 8.85 (s, 1H), 8.42 (d, J=1.4 Hz, 1H), 8.22 (d, J=1.5 Hz, 0.5H), 8.19 (d, J=1.5 Hz, 0.5H), 7.82 (dd, J=9.3, 2.8 Hz, 1H), 7.46 (td, J=8.8, 2.8 Hz, 1H), 7.42 (dd, J=9.1, 4.9 Hz, 1H), 4.20-3.87 (m, 3H), 3.75-3.47 (m, 2H), 3.29 (s, 1.5H), 3.27 (s, 1.5H), 2.25-1.90 (m, 2H).

The following examples relate to medicaments:

Example A: Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula I are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I are introduced into hard gelatine capsules in a conventional manner in such a way that each capsule contains 20 mg of the active ingredient.

Example H: Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. Medicaments comprising at least one compound of the formula I

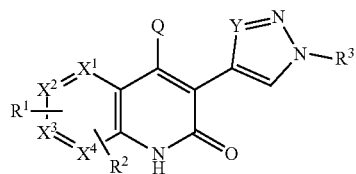

I in which
$X^1$, $X^2$, $X^3$, $X^4$ each, independently of one another, denote CH or N,
Y denotes N or CH,
Q denotes H or $CH_3$,
$R^1$ denotes H, F, Cl, Br, CN, $CH_3$, $CF_3$ or $OCH_3$,
$R^2$ denotes H, F or Cl,
$R^3$ denotes phenyl, pyridyl, pyrimidinyl, indolyl, indazolyl, thiophenyl, dihydroisoindolyl or benzimidazolyl, each of which is unsubstituted or mono-, di- or trisubstituted by Hal, CN, $NO_2$, A, $(CR^4)_nOR^4$, $(CR^4)_nN(R^4)_2$, $(CR^4)_nS(O)_mR^4$, $(CR^4)_nCON(R^4)_2$, $(CR^4)_nCOHet$, $(CR^4)_nSO_2N(R^4)_2$, $(CR^4)_nSO_2Het$, $(CR^4)_nN(R^4)_2$, $(CR^4)_nHet$, $O(CR^4)_nCOHet$, $(CR^4)_nO(CR^4)_nHet$, $(CR^4)_nN(R^4)(CR^4)_nHet$, $(CR^4)_nCON(R^4)(CR^4)_nHet$, $(CR^4)_nCON(R^4)(CR^4)_nN(R^4)_2$, $(CR^4)_nN(R^4)COA$, $(CR^4)_nN(R^4)COHet'$, $(CR^4)_nOCyc$ and/or $(CR^4)_nCOOR^4$,
$R^4$ denotes H or A',
A denotes unbranched or branched alkyl with 1-10 C-atoms, wherein two adjacent carbon atoms may form a double bond and/or one or two non-adjacent CH- and/or $CH_2$-groups may be replaced by N-, O- and/or S-atoms and wherein 1-7 H-atoms may be replaced by $R^5$, or cyclic alkyl having 3-7 C atoms,
A' denotes unbranched or branched alkyl with 1-6 C-atoms, wherein one or two non-adjacent CH- and/or $CH_2$-groups may be replaced by O-atoms,
Cyc denotes cyclobutyl, cyclopentyl or cyclohexyl, each of which is unsubstituted or mono- or disubstituted by A, Hal, $OR^4$, $N(R^4)_2$, Het', $(CR^4)_nO(CR^4)_nHet'$, $CON(R^4)_2$ and/or =O,
$R^5$ denotes F, Cl or OH,
Het denotes pyrrolidinyl, morpholinyl, piperidinyl, piperazinyl, [1,4]-diazepanyl, oxazolidinyl, hexahydropyrrolo[3,4-c]pyrrolyl, 2-oxa-6-aza-spiro[3.4]octanyl, 2-oxa-6-aza-spiro[3.5]nonanyl, 2-oxa-7-aza-spiro[3.5]nonanyl, 2,5-dioxa-8-aza-spiro[3.5]nonanyl, oxetanyl, 2-oxa-5-aza-spiro[3.4]octanyl, 2-oxa-6-aza-spiro[3.3]heptanyl, 3-aza-bicyclo[3.1.0]hexanyl, 2-oxa-7-aza-spiro[3.5]nonanyl, isoxazolidinyl, azetidinyl, 2,6-di-aza-spiro[3.4]octanyl, hexahydro-pyrrolo[3,4-b]pyrrolyl, tetrahydrofuranyl or isothiazolidinyl, each of which is unsubstituted or mono-, di- or trisubstituted by A, Hal, $OR^4$, OCOA, COA, $(CR^4)_nN(R^4)_2$, $(CR^4)_nHet'$, $(CR^4)_nO(CR^4)_nHet'$, $CON(R^4)_2$, $COHet'$, $(CR^4)_nS(O)_mR^4$, and/or =O,
Het' denotes pyrrolidinyl, morpholinyl, piperidinyl, oxetanyl, tetrahydrofuranyl, tetrahydropyranyl, pyridyl, pyrazolyl or piperazinyl, each of which is unsubstituted or mono- or disubstituted by A, Hal, $OR^4$, $N(R^4)_2$ and/or =O,
Hal denotes F, Cl, Br or I,
n denotes 0, 1, 2 or 3,
m denotes 0, 1 or 2,
with the proviso that no more than two of $X^1$, $X^2$, $X^3$, $X^4$ denote N,
and/or pharmaceutically acceptable salts, tautomers and stereoisomers thereof, including mixtures thereof in all ratios, and optionally a pharmaceutically acceptable carrier, excipient or vehicle.

2. The medicaments of claim 1 further comprising at least one further medicament active ingredient.

3. The medicaments of claim 1, where
$R^1$ denotes H, F, Cl, Br, CN, $CH_3$, $CF_3$ or $OCH_3$,
$R^2$ denotes H or F,
and pharmaceutically acceptable salts, tautomers and stereoisomers thereof, including mixtures thereof in all ratios.

4. The medicaments of claim 1, wherein
$R^3$ denotes phenyl, pyridyl, pyrimidinyl, indolyl, indazolyl, thiophenyl, dihydroisoindolyl or benzimidazolyl, each of which is unsubstituted or mono-, di- or trisubstituted by Hal, A, $(CR^4)_nOR^4$, $(CR^4)_nN(R^4)_2$, $(CR^4)_nS(O)_mR^4$, $(CR^4)_nCON(R^4)_2$, $(CR^4)_nCOHet$, (CR⁴)ₙSO₂Het, (CR⁴)ₙHet, O(CR⁴)ₙCOHet, (CR⁴)ₙO(CR⁴)ₙHet, (CR⁴)ₙN(R⁴)(CR⁴)ₙHet, (CR⁴)ₙCON(R⁴)(CR⁴)ₙHet, (CR⁴)ₙCON(R⁴)(CR⁴)ₙN(R⁴)₂, (CR⁴)ₙN(R⁴)COA, (CR⁴)ₙN(R⁴)COHet', (CR⁴)ₙOCyc and/or (CR⁴)ₙCOOR⁴, and pharmaceutically acceptable salts, tautomers and stereoisomers thereof, including mixtures thereof in all ratios.

5. The medicaments of claim 1, wherein
A denotes unbranched or branched alkyl with 1-10 C-atoms, wherein two adjacent carbon atoms may form a double bond and/or one or two non-adjacent CH- and/or CH₂-groups may be replaced by N- and/or O-atoms and wherein 1-7 H-atoms may be replaced by R⁵,
and pharmaceutically acceptable salts, tautomers and stereoisomers thereof, including mixtures thereof in all ratios.

6. The medicaments of claim 1, wherein
Het' denotes pyrrolidinyl,
and pharmaceutically acceptable salts, tautomers and stereoisomers thereof, including mixtures thereof in all ratios.

7. The medicaments of claim 1, wherein
X, X², X³, X⁴ each, independently of one another, denote CH or N,
Y denotes N or CH,
Q denotes H or CH₃,
R¹ denotes H, F, Cl, Br, CN, CH₃, CF₃ or OCH₃,
R² denotes H or F,
R³ denotes phenyl, pyridyl, pyrimidinyl, indolyl, indazolyl, thiophenyl, dihydroisoindolyl or benzimidazolyl, each of which is unsubstituted or mono-, di- or trisubstituted by Hal, A, (CR⁴)ₙOR⁴, (CR⁴)ₙN(R⁴)₂, (CR⁴)ₙS(O)ₘR⁴, (CR⁴)ₙCON(R⁴)₂, (CR⁴)ₙCOHet, (CR⁴)ₙSO₂Het, (CR⁴)ₙHet, O(CR⁴)ₙCOHet, (CR⁴)ₙO(CR⁴)ₙHet, (CR⁴)ₙN(R⁴)(CR⁴)ₙHet, (CR⁴)ₙCON(R⁴)(CR⁴)ₙHet, (CR⁴)ₙCON(R⁴)(CR⁴)ₙN(R⁴)₂, (CR⁴)ₙN(R⁴)COA, (CR⁴)ₙN(R⁴)COHet', (CR⁴)ₙOCyc and/or (CR⁴)ₙCOOR⁴,
R⁴ denotes H or A',
A denotes unbranched or branched alkyl with 1-10 C-atoms, wherein two adjacent carbon atoms may form a double bond and/or one or two non-adjacent CH- and/or CH₂-groups may be replaced by N- and/or O-atoms and wherein 1-7 H-atoms may be replaced by R⁵,
Cyc denotes cyclobutyl, cyclopentyl or cyclohexyl, each of which is unsubstituted or mono- or disubstituted by A, Hal, OR⁴, N(R⁴)₂, Het', (CR⁴)ₙO(CR⁴)ₙHet', CON(R⁴)₂ and/or =O,
A' denotes unbranched or branched alkyl with 1-6 C-atoms, wherein one or two non-adjacent CH- and/or CH₂-groups may be replaced by O-atoms,
R⁵ denotes F, Cl or OH,
Het denotes pyrrolidinyl, morpholinyl, piperidinyl, piperazinyl, [1,4]-diazepanyl, oxazolidinyl, hexahydro-pyrrolo[3,4-c]pyrrolyl, 2-oxa-6-aza-spiro[3.4]octanyl, 2-oxa-6-aza-spiro[3.5]nonanyl, 2-oxa-7-aza-spiro[3.5]nonanyl, 2,5-dioxa-8-aza-spiro[3.5]nonanyl, oxetanyl, 2-oxa-5-aza-spiro[3.4]octanyl, 2-oxa-6-aza-spiro[3.3]heptanyl, 3-aza-bicyclo[3.1.0]hexanyl, 2-oxa-7-aza-spiro[3.5]nonanyl, isoxazolidinyl, azetidinyl, 2,6-di-aza-spiro[3.4]octanyl, hexahydro-pyrrolo[3,4-b]pyrrolyl, tetrahydrofuranyl or isothiazolidinyl, each of which is unsubstituted or mono-, di- or trisubstituted by A, Hal, OR⁴, OCOA, COA, (CR⁴)ₙN(R⁴)₂, (CR⁴)ₙHet', (CR⁴)ₙO(CR⁴)ₙHet', CON(R⁴)₂, COHet', (CR⁴)ₙS(O)ₘR⁴, and/or =O,
Het' denotes pyrrolidinyl, oxetanyl, tetrahydrofuranyl, tetrahydropyranyl, pyridyl or pyrazolyl,
Hal denotes F, Cl, Br or I,
N denotes 0, 1, 2 or 3,
m denotes 0, 1 or 2,
and pharmaceutically acceptable salts, tautomers and stereoisomers thereof, including mixtures thereof in all ratios.

8. The medicaments of claim 1, selected from the group consisting of
6-fluoro-3-{1-[4-(morpholine-4-carbonyl)-phenyl]-1H-[1,2,3]triazol-4-yl}-1H-quinolin-2-one,
3-{1-[4-(morpholine-4-carbonyl)-phenyl]-1H-[1,2,3]triazol-4-yl}-1H-quinolin-2-one,
N,N-dimethyl-4-[4-(2-oxo-1,2-dihydro-[1,8]naphthyridin-3-yl)-[1,2,3]triazol-1-yl]-benzamide,
N,N-dimethyl-4-[4-(2-oxo-1,2-dihydro-quinolin-3-yl)-[1,2,3]triazol-1-yl]-benzamide,
3-[1-(4-dimethylaminomethyl-phenyl)-1H-[1,2,3]triazol-4-yl]-1H-[1,8]naphthyridin-2-one,
3-(1-phenyl-1H-[1,2,3]triazol-4-yl)-1H-[1,8]naphthyridin-2-one,
3-[1-(4-hydroxymethyl-phenyl)-1H-[1,2,3]triazol-4-yl]-1H-[1,8]naphthyridin-2-one,
N-(2-hydroxy-ethyl)-4-[4-(2-oxo-1,2-dihydro-[1,8]naphthyridin-3-yl)-[1,2,3]triazol-1-yl]-benzamide,
N-(2-methoxy-ethyl)-4-[4-(2-oxo-1,2-dihydro-[1,8]naphthyridin-3-yl)-[1,2,3]triazol-1-yl]-benzamide,
3-[1-(4-methoxy-phenyl)-1H-[1,2,3]triazol-4-yl]-1H-quinolin-2-one,
4-[4-(6-chloro-2-oxo-1,2-dihydro-[1,8]naphthyridin-3-yl)-[1,2,3]triazol-1-yl]-N,N-dimethyl-benzamide,
3-[1-(4-fluoro-phenyl)-1H-[1,2,3]triazol-4-yl]-1H-quinolin-2-one,
3-[1-(2-fluoro-phenyl)-1H-[1,2,3]triazol-4-yl]-1H-quinolin-2-one,
3-{1-[4-(2-pyrrolidin-1-yl-ethoxy)-phenyl]-1H-[1,2,3]triazol-4-yl}-1H-quinolin-2-one,
N-(1-methyl-piperidin-4-ylmethyl)-4-[4-(2-oxo-1,2-dihydro-quinolin-3-yl)-[1,2,3]triazol-1-yl]-benzamide,
4-[4-(6-methoxy-2-oxo-1,2-dihydro-[1,8]naphthyridin-3-yl)-[1,2,3]triazol-1-yl]-N,N-dimethyl-benzamide,
4-[4-(2-oxo-1,2-dihydro-quinolin-3-yl)-[1,2,3]triazol-1-yl]-pyridine-2-carboxylic acid methyl ester,
4-[4-(6-fluoro-2-oxo-1,2-dihydro-quinolin-3-yl)-[1,2,3]triazol-1-yl]-N,N-dimethyl-benzamide,
N-(2-hydroxy-ethyl)-4-[4-(2-oxo-1,2-dihydro-quinolin-3-yl)-[1,2,3]triazol-1-yl]-benzamide,
3-[1-(1H-indol-5-yl)-1H-[1,2,3]triazol-4-yl]-1H-quinolin-2-one,
N-(2-morpholin-4-yl-ethyl)-4-[4-(2-oxo-1,2-dihydro-quinolin-3-yl)-[1,2,3]triazol-1-yl]-benzamide,
4-[4-(6-fluoro-2-oxo-1,2-dihydro-quinolin-3-yl)-[1,2,3]triazol-1-yl]-N-(1-methyl-piperidin-4-ylmethyl)-benzamide,
3-[4-(2-oxo-1,2-dihydro-quinolin-3-yl)-[1,2,3]triazol-1-yl]-benzoic acid methyl ester,
3-[1-(3-methoxy-phenyl)-1H-[1,2,3]triazol-4-yl]-1H-quinolin-2-one,
3-{1-[4-(3-oxo-morpholin-4-yl)-phenyl]-1H-[1,2,3]triazol-4-yl}-1H-quinolin-2-one,
3-{1-[4-(2-morpholin-4-yl-ethoxy)-phenyl]-1H-[1,2,3]triazol-4-yl}-1H-quinolin-2-one,
3-(1-phenyl-1H-[1,2,3]triazol-4-yl)-1H-quinolin-2-one, 3-[1-(3H-benzimidazol-5-yl)-1H-[1,2,3]triazol-4-yl]-1H-quinolin-2-one,
3-{1-[4-(morpholine-4-carbonyl)-phenyl]-1H-[1,2,3]triazol-4-yl}-1H-[1,7]naphthyridin-2-one,
7-methyl-3-{1-[4-(morpholine-4-carbonyl)-phenyl]-1H-[1,2,3]triazol-4-yl}-1H-[1,8]naphthyridin-2-one,
6-fluoro-3-{1-[4-(morpholine-4-carbonyl)-phenyl]-1H-[1,2,3]triazol-4-yl}-1H-[1,8]naphthyridin-2-one,
3-{1-[3-fluoro-4-(3-oxo-morpholin-4-yl)-phenyl]-1H-[1,2,3]triazol-4-yl}-1H-quinolin-2-one,
6-fluoro-3-{1-[3-fluoro-4-(3-oxo-morpholin-4-yl)-phenyl]-1H-[1,2,3]triazol-4-yl}-1H-quinolin-2-one,
3-{1-[6-(3-oxo-morpholin-4-yl)-pyridin-3-yl]-1H-[1,2,3]triazol-4-yl}-1H-quinolin-2-one,
3-{1-[2-methyl-4-(morpholine-4-carbonyl)-phenyl]-1H-[1,2,3]triazol-4-yl}-1H-quinolin-2-one,
3-{1-[4-(1-hydroxy-1-methyl-ethyl)-phenyl]-1H-[1,2,3]triazol-4-yl}-1H-quinolin-2-one,
3-{1-[3-fluoro-4-(morpholine-4-carbonyl)-phenyl]-1H-[1,2,3]triazol-4-yl}-1H-quinolin-2-one,
3-[1-(3,4,5-trimethoxy-phenyl)-1H-[1,2,3]triazol-4-yl]-1H-quinolin-2-one,
2-fluoro-N-methyl-4-[4-(2-oxo-1,2-dihydro-quinolin-3-yl)-[1,2,3]triazol-1-yl]-benzamide,
3-{1-[3-methyl-4-(morpholine-4-carbonyl)-phenyl]-1H-[1,2,3]triazol-4-yl}-1H-quinolin-2-one,
3-{1-[4-(morpholine-4-carbonyl)-phenyl]-1H-[1,2,3]triazol-4-yl}-1H-[1,6]naphthyridin-2-one,
N,N-dimethyl-4-[4-(2-oxo-1,2-dihydro-[1,7]naphthyridin-3-yl)-[1,2,3]triazol-1-yl]-benzamide,
3-(1-phenyl-1H-pyrazol-4-yl)-1H-[1,8]naphthyridin-2-one,
3-(1-phenyl-1H-pyrazol-4-yl)-1H-[1,7]naphthyridin-2-one,
3-[1-(4-fluoro-phenyl)-1H-[1,2,3]triazol-4-yl]-1H-[1,6]naphthyridin-2-one,
3-(1-phenyl-1H-pyrazol-4-yl)-1H-[1,6]naphthyridin-2-one,
3-{1-[4-(morpholine-4-carbonyl)-phenyl]-1H-[1,2,3]triazol-4-yl}-1H-[1,8]naphthyridin-2-one,
5-fluoro-3-{1-[4-(morpholine-4-carbonyl)-phenyl]-1H-[1,2,3]triazol-4-yl}-1H-quinolin-2-one,
3-{1-[4-(3-oxo-morpholin-4-yl)-phenyl]-1H-[1,2,3]triazol-4-yl}-1H-[1,7]naphthyridin-2-one,
3-{1-[4-(piperazine-1-carbonyl)-phenyl]-1H-[1,2,3]triazol-4-yl}-1H-quinolin-2-one,
4-[4-(2-oxo-1,2-dihydro-[1,8]naphthyridin-3-yl)-[1,2,3]triazol-1-yl]-N-piperidin-4-yl-benzamide,
3-[1-(4-piperazin-1-yl-phenyl)-1H-[1,2,3]triazol-4-yl]-1H-quinolin-2-one,
6-fluoro-3-{1-[4-(piperazine-1-carbonyl)-phenyl]-1H-[1,2,3]triazol-4-yl}-1H-quinolin-2-one,
3-[1-(2-piperazin-1-yl-pyrimidin-5-yl)-1H-[1,2,3]triazol-4-yl]-1H-quinolin-2-one,
3-[1-(4-[1,4]diazepan-1-yl-phenyl)-1H-[1,2,3]triazol-4-yl]-1H-quinolin-2-one,
6-fluoro-3-{1-[4-(4-methyl-piperazine-1-carbonyl)-phenyl]-1H-[1,2,3]triazol-4-yl}-1H-quinolin-2-one,
3-{1-[4-(4-methyl-piperazine-1-carbonyl)-phenyl]-1H-[1,2,3]triazol-4-yl}-1H-quinolin-2-one,
N-(1-Methyl-piperidin-4-yl)-4-[4-(2-oxo-1,2-dihydro-quinolin-3-yl)-[1,2,3]triazol-1-yl]-benzamide,
N-methyl-N-(1-methyl-piperidin-4-yl)-4-[4-(2-oxo-1,2-dihydro-quinolin-3-yl)-[1,2,3]triazol-1-yl]-benzamide,
3-{1-[4-(1-methyl-piperidin-4-ylmethoxy)-phenyl]-1H-[1,2,3]triazol-4-yl}-1H-quinolin-2-one,
3-{1-[4-(4-dimethylamino-piperidine-1-carbonyl)-phenyl]-1H-[1,2,3]triazol-4-yl}-1H-quinolin-2-one,
3-{1-[4-(4-methyl-piperazine-1-carbonyl)-phenyl]-1H-[1,2,3]triazol-4-yl}-1H-[1,6]naphthyridin-2-one,
3-{1-[4-(4-methyl-piperazine-1-carbonyl)-phenyl]-1H-[1,2,3]triazol-4-yl}-1H-[1,7]naphthyridin-2-one,
3-{1-[4-(4-methyl-piperazine-1-carbonyl)-phenyl]-1H-[1,2,3]triazol-4-yl}-1H-[1,8]naphthyridin-2-one,
7-methyl-3-{1-[4-(4-methyl-piperazine-1-carbonyl)-phenyl]-1H-[1,2,3]triazol-4-yl}-1H-[1,8]naphthyridin-2-one,
3-{1-[2-(4-methyl-piperazin-1-yl)-pyrimidin-5-yl]-1H-[1,2,3]triazol-4-yl}-1H-quinolin-2-one,
6-fluoro-3-{1-[4-(4-methyl-piperazine-1-carbonyl)-phenyl]-1H-[1,2,3]triazol-4-yl}-1H-[1,8]naphthyridin-2-one,
3-{1-[4-(4-methyl-2-oxo-piperazin-1-yl)-phenyl]-1H-[1,2,3]triazol-4-yl}-1H-quinolin-2-one,
3-{1-[4-(4-methyl-[1,4]diazepan-1-yl)-phenyl]-1H-[1,2,3]triazol-4-yl}-1H-quinolin-2-one,
6-fluoro-3-{1-[4-(4-methyl-piperazin-1-yl)-phenyl]-1H-[1,2,3]triazol-4-yl}-1H-quinolin-2-one,
6-fluoro-3-{1-[4-(4-methyl-2-oxo-piperazin-1-yl)-phenyl]-1H-[1,2,3]triazol-4-yl}-1H-quinolin-2-one,
3-(1-{4-[2-(4-methyl-piperazin-1-yl)-ethoxy]-phenyl}-1H-[1,2,3]triazol-4-yl)-1H-quinolin-2-one,
3-{1-[4-(piperazine-1-carbonyl)-phenyl]-1H-pyrazol-4-yl}-1H-quinolin-2-one,
3-{1-[4-(4-methyl-piperazine-1-carbonyl)-phenyl]-1H-pyrazol-4-yl}-1H-quinolin-2-one,
3-(1-phenyl-1H-pyrazol-4-yl)-1H-quinolin-2-one,
3-{1-[3-(morpholine-4-carbonyl)-phenyl]-1H-[1,2,3]triazol-4-yl}-1H-quinolin-2-one,
4-[4-(2-Oxo-1,2-dihydro-[1,8]naphthyridin-3-yl)-[1,2,3]triazol-1-yl]-benzoic acid,
3-{1-[3-(piperazine-1-carbonyl)-phenyl]-1H-[1,2,3]triazol-4-yl}-1H-quinolin-2-one,
3-{1-[3-(4-methyl-piperazine-1-carbonyl)-phenyl]-1H-[1,2,3]triazol-4-yl}-1H-quinolin-2-one,
3-[1-(4-isopropenyl-phenyl)-1H-[1,2,3]triazol-4-yl]-1H-quinolin-2-one,
3-{1-[4-(1-methanesulfonyl-methyl-ethyl)-phenyl]-1H-[1,2,3]triazol-4-yl}-1H-quinolin-2-one,
7-chloro-3-{1-[4-(morpholine-4-carbonyl)-phenyl]-1H-[1,2,3]triazol-4-yl}-1H-quinolin-2-one,
7-fluoro-3-{1-[4-(morpholine-4-carbonyl)-phenyl]-1H-[1,2,3]triazol-4-yl}-1H-quinolin-2-one,
7-methyl-3-{1-[4-(morpholine-4-carbonyl)-phenyl]-1H-[1,2,3]triazol-4-yl}-1H-quinolin-2-one,
3-{1-[4-(morpholine-4-carbonyl)-phenyl]-1H-[1,2,3]triazol-4-yl}-1H-[1,5]naphthyridin-2-one,
6-fluoro-3-(1-{4-[4-(3-methoxy-propyl)-piperazine-1-carbonyl]-phenyl}-1H-[1,2,3]triazol-4-yl)-1H-quinolin-2-one,
5-fluoro-3-(1-{4-[4-(3-methoxy-propyl)-piperazine-1-carbonyl]-phenyl}-1H-[1,2,3]triazol-4-yl)-1H-quinolin-2-one,
6-fluoro-3-(1-{4-[4-(3-methoxy-propyl)-piperazine-1-carbonyl]-phenyl}-1H-[1,2,3]triazol-4-yl)-1H-[1,8]naphthyridin-2-one,
3-(1-{4-[4-(3-methoxy-propyl)-piperazine-1-carbonyl]-phenyl}-1H-[1,2,3]triazol-4-yl)-1H-[1,8]naphthyridin-2-one,
5,7-difluoro-3-{1-[4-(morpholine-4-carbonyl)-phenyl]-1H-[1,2,3]triazol-4-yl}-1H-quinolin-2-one,
7-bromo-3-{1-[4-(morpholine-4-carbonyl)-phenyl]-1H-[1,2,3]triazol-4-yl}-1H-quinolin-2-one, 6-fluoro-3-{1-[4-(4-methyl-3-oxo-piperazine-1-carbonyl)-phenyl]-1H-[1,2,3]triazol-4-yl}-1H-quinolin-2-one,
7-methoxy-3-{1-[4-(morpholine-4-carbonyl)-phenyl]-1H-[1,2,3]triazol-4-yl}-1H-quinolin-2-one,
6-{1-[4-(Morpholine-4-carbonyl)-phenyl]-1H-[1,2,3]triazol-4-yl}-8H-pyrido[2,3-d]pyrimidin-7-one,
6-fluoro-3-{1-[3-(2-morpholin-4-yl-ethoxy)-phenyl]-1H-[1,2,3]triazol-4-yl}-1H-quinolin-2-one,
5,7-difluoro-3-{1-[4-(4-methyl-3-oxo-piperazine-1-carbonyl)-phenyl]-1H-[1,2,3]triazol-4-yl}-1H-quinolin-2-one,
6-chloro-3-{1-[4-(4-methyl-3-oxo-piperazine-1-carbonyl)-phenyl]-1H-[1,2,3]triazol-4-yl}-1H-quinolin-2-one,
7-chloro-3-{1-[4-(4-methyl-3-oxo-piperazine-1-carbonyl)-phenyl]-1H-[1,2,3]triazol-4-yl}-1H-quinolin-2-one,
6-fluoro-3-{1-[4-(2-oxo-oxazolidin-3-yl)-phenyl]-1H-[1,2,3]triazol-4-yl}-1H-quinolin-2-one,
3-{1-[4-(1,1-dioxo-1l6-isothiazolidin-2-yl)-phenyl]-1H-[1,2,3]triazol-4-yl}-6-fluoro-1H-quinolin-2-one,
3-{1-[4-([1,3']bipyrrolidinyl-1'-carbonyl)-phenyl]-1H-[1,2,3]triazol-4-yl}-6-fluoro-1H-quinolin-2-one,
3-(1-{4-[2-(4-acetyl-piperazin-1-yl)-ethoxy]-phenyl}-1H-[1,2,3]triazol-4-yl)-6-fluoro-1H-quinolin-2-one,
3-(1-{4-[2-(4-acetyl-piperazin-1-yl)-ethoxy]-phenyl}-1H-[1,2,3]triazol-4-yl)-6,7-difluoro-1H-quinolin-2-one,
acetic acid 1-{4-[4-(6-fluoro-2-oxo-1,2-dihydro-quinolin-3-yl)-[1,2,3]triazol-1-yl]-benzoyl}-piperidin-4-yl ester,
acetic acid 1-{4-[4-(6-fluoro-2-oxo-1,2-dihydro-quinolin-3-yl)-[1,2,3]triazol-1-yl]-benzoyl}-piperidin-3-yl ester,
3-{1-[4-([1,3']bipyrrolidinyl-1'-carbonyl)-phenyl]-1H-[1,2,3]triazol-4-yl}-6,7-difluoro-1H-quinolin-2-one,
3-{1-[4-([1,3']bipyrrolidinyl-1'-carbonyl)-phenyl]-1H-[1,2,3]triazol-4-yl}-5,7-difluoro-1H-quinolin-2-one,
6-fluoro-3-{1-[4-(3-methoxymethyl-pyrrolidine-1-carbonyl)-phenyl]-1H-[1,2,3]triazol-4-yl}-1H-quinolin-2-one,
3-{1-[3-([1,3']bipyrrolidinyl-1'-carbonyl)-phenyl]-1H-[1,2,3]triazol-4-yl}-6-fluoro-1H-quinolin-2-one,
3-{1-[3-([1,3']bipyrrolidinyl-1'-carbonyl)-phenyl]-1H-[1,2,3]triazol-4-yl}-6,7-difluoro-1H-quinolin-2-one,
6,7-difluoro-3-{1-[4-(3-methoxymethyl-pyrrolidine-1-carbonyl)-phenyl]-1H-[1,2,3]triazol-4-yl}-1H-quinolin-2-one,
6-fluoro-3-{1-[4-(4-methyl-5-oxo-[1,4]diazepane-1-carbonyl)-phenyl]-1H-[1,2,3]triazol-4-yl}-1H-quinolin-2-one,
6-fluoro-3-{1-[4-((R)-3-methoxy-pyrrolidine-1-carbonyl)-phenyl]-1H-[1,2,3]triazol-4-yl}-1H-quinolin-2-one,
6-fluoro-3-{1-[4-((S)-3-methoxy-pyrrolidine-1-carbonyl)-phenyl]-1H-[1,2,3]triazol-4-yl}-1H-quinolin-2-one,
6,7-difluoro-3-{1-[4-((R)-3-methoxy-pyrrolidine-1-carbonyl)-phenyl]-1H-[1,2,3]triazol-4-yl}-1H-quinolin-2-one,
6,7-difluoro-3-{1-[4-((S)-3-methoxy-pyrrolidine-1-carbonyl)-phenyl]-1H-[1,2,3]triazol-4-yl}-1H-quinolin-2-one,
3-{1-[4-(2-dimethylamino-ethyl)-phenyl]-1H-[1,2,3]triazol-4-yl}-6,7-difluoro-1H-quinolin-2-one,
3-{1-[4-(2-diethylamino-ethoxy)-phenyl]-1H-[1,2,3]triazol-4-yl}-6,7-difluoro-1H-quinolin-2-one,
7-fluoro-3-{1-[4-(piperazine-1-carbonyl)-phenyl]-1H-[1,2,3]triazol-4-yl}-1H-quinolin-2-one,
7-fluoro-3-{1-[4-(4-methyl-piperazine-1-carbonyl)-phenyl]-1H-[1,2,3]triazol-4-yl}-1H-quinolin-2-one,
5-fluoro-3-{1-[4-(piperazine-1-carbonyl)-phenyl]-1H-[1,2,3]triazol-4-yl}-1H-quinolin-2-one,
8-fluoro-3-{1-[4-(piperazine-1-carbonyl)-phenyl]-1H-[1,2,3]triazol-4-yl}-1H-quinolin-2-one,
3-{1-[4-(piperazine-1-carbonyl)-phenyl]-1H-[1,2,3]triazol-4-yl}-1H-[1,8]naphthyridin-2-one,
6-fluoro-3-{1-[4-(piperazine-1-carbonyl)-phenyl]-1H-[1,2,3]triazol-4-yl}-1H-[1,8]naphthyridin-2-one,
6-chloro-3-{1-[4-(piperazine-1-carbonyl)-phenyl]-1H-[1,2,3]triazol-4-yl}-1H-quinolin-2-one,
3-[1-(4-[1,4]diazepan-1-yl-phenyl)-1H-[1,2,3]triazol-4-yl]-6-fluoro-1H-[1,8]naphthyridin-2-one,
6-fluoro-3-{1-[3-(piperazine-1-carbonyl)-phenyl]-1H-[1,2,3]triazol-4-yl}-1H-quinolin-2-one,
7-chloro-3-{1-[4-(piperazine-1-carbonyl)-phenyl]-1H-[1,2,3]triazol-4-yl}-1H-quinolin-2-one,
5,6-difluoro-3-{1-[4-(piperazine-1-carbonyl)-phenyl]-1H-[1,2,3]triazol-4-yl}-1H-quinolin-2-one,
6,7-difluoro-3-{1-[4-(piperazine-1-carbonyl)-phenyl]-1H-[1,2,3]triazol-4-yl}-1H-quinolin-2-one,
6-fluoro-3-{1-[4-(piperazine-1-sulfonyl)-phenyl]-1H-[1,2,3]triazol-4-yl}-1H-quinolin-2-one,
6,7-difluoro-3-{1-[4-(2-piperazin-1-yl-ethoxy)-phenyl]-1H-[1,2,3]triazol-4-yl}-1H-quinolin-2-one,
6-fluoro-3-{1-[4-(3-piperazin-1-yl-propoxy)-phenyl]-1H-[1,2,3]triazol-4-yl}-1H-quinolin-2-one,
6-fluoro-3-{1-[4-(piperidine-4-carbonyl)-phenyl]-1H-[1,2,3]triazol-4-yl}-1H-quinolin-2-one,
6-fluoro-3-{1-[4-(2-piperidin-4-yl-ethoxy)-phenyl]-1H-[1,2,3]triazol-4-yl}-1H-quinolin-2-one,
6,7-difluoro-3-{1-[4-(2-piperidin-4-yl-ethoxy)-phenyl]-1H-[1,2,3]triazol-4-yl}-1H-quinolin-2-one,
6,7-difluoro-3-{1-[4-(3-piperazin-1-yl-propoxy)-phenyl]-1H-[1,2,3]triazol-4-yl}-1H-quinolin-2-one,
6,7-difluoro-3-{1-[4-(piperidine-4-carbonyl)-phenyl]-1H-[1,2,3]triazol-4-yl}-1H-quinolin-2-one,
6-methyl-3-{1-[4-(piperazine-1-carbonyl)-phenyl]-1H-[1,2,3]triazol-4-yl}-1H-quinolin-2-one,
5,7-difluoro-3-{1-[1-(2-oxo-2-piperazin-1-yl-ethyl)-1H-indol-5-yl]-1H-[1,2,3]triazol-4-yl}-1H-quinolin-2-one,
6,7-difluoro-3-{1-[1-(2-oxo-2-piperazin-1-yl-ethyl)-1H-indol-5-yl]-1H-[1,2,3]triazol-4-yl}-1H-quinolin-2-one,
6,7-difluoro-3-{1-[4-(2-oxo-2-piperazin-1-yl-ethoxy)-phenyl]-1H-[1,2,3]triazol-4-yl}-1H-quinolin-2-one,
6-fluoro-3-{1-[4-(2-oxo-2-piperazin-1-yl-ethoxy)-phenyl]-1H-[1,2,3]triazol-4-yl}-1H-quinolin-2-one,
3-{1-[4-(piperazine-1-carbonyl)-phenyl]-1H-[1,2,3]triazol-4-yl}-7-trifluoromethyl-1H-quinolin-2-one,
3-{1-[4-(4-amino-piperidine-1-carbonyl)-phenyl]-1H-[1,2,3]triazol-4-yl}-6,7-difluoro-1H-quinolin-2-one,
3-{1-[4-(4-amino-piperidine-1-carbonyl)-phenyl]-1H-[1,2,3]triazol-4-yl}-6-fluoro-1H-quinolin-2-one,
6,7-difluoro-3-{1-[4-(2-oxo-piperazin-1-yl)-phenyl]-1H-[1,2,3]triazol-4-yl}-1H-quinolin-2-one,
6,7-difluoro-3-{1-[1-(2-oxo-2-piperazin-1-yl-ethyl)-1H-indazol-5-yl]-1H-[1,2,3]triazol-4-yl}-1H-quinolin-2-one,
6-fluoro-7-methoxy-3-{1-[4-(piperazine-1-carbonyl)-phenyl]-1H-[1,2,3]triazol-4-yl}-1H-quinolin-2-one,
6-chloro-7-fluoro-3-{1-[4-(piperazine-1-carbonyl)-phenyl]-1H-[1,2,3]triazol-4-yl}-1H-quinolin-2-one, 5-fluoro-3-{1-[4-(4-methyl-piperazine-1-carbonyl)-phenyl]-1H-[1,2,3]triazol-4-yl}-1H-quinolin-2-one,
8-fluoro-3-{1-[4-(4-methyl-piperazine-1-carbonyl)-phenyl]-1H-[1,2,3]triazol-4-yl}-1H-quinolin-2-one,
6-chloro-3-{1-[4-(4-methyl-piperazine-1-carbonyl)-phenyl]-1H-[1,2,3]triazol-4-yl}-1H-quinolin-2-one,
5,7-difluoro-3-{1-[4-(4-methyl-piperazine-1-carbonyl)-phenyl]-1H-[1,2,3]triazol-4-yl}-1H-quinolin-2-one,
6-Fluoro-3-{1-[3-(4-methyl-piperazine-1-carbonyl)-phenyl]-1H-[1,2,3]triazol-4-yl}-1H-quinolin-2-one,
7-chloro-3-{1-[4-(4-methyl-piperazine-1-carbonyl)-phenyl]-1H-[1,2,3]triazol-4-yl}-1H-quinolin-2-one,
6-fluoro-3-{1-[4-(4-methyl-[1,4]diazepan-1-yl)-phenyl]-1H-[1,2,3]triazol-4-yl}-1H-[1,8]naphthyridin-2-one,
5,6-difluoro-3-{1-[4-(4-methyl-piperazine-1-carbonyl)-phenyl]-1H-[1,2,3]triazol-4-yl}-1H-quinolin-2-one,
6,7-difluoro-3-{1-[4-(4-methyl-piperazine-1-carbonyl)-phenyl]-1H-[1,2,3]triazol-4-yl}-1H-quinolin-2-one,
6-fluoro-3-{1-[4-(4-methyl-piperazine-1-sulfonyl)-phenyl]-1H-[1,2,3]triazol-4-yl}-1H-quinolin-2-one,
6,7-difluoro-3-(1-{4-[2-(4-methyl-piperazin-1-yl)-ethoxy]-phenyl}-1H-[1,2,3]triazol-4-yl)-1H-quinolin-2-one,
6-fluoro-3-(1-{4-[3-(4-methyl-piperazin-1-yl)-propoxy]-phenyl}-1H-[1,2,3]triazol-4-yl)-1H-quinolin-2-one,
6-fluoro-3-{1-[4-(1-methyl-piperidine-4-carbonyl)-phenyl]-1H-[1,2,3]triazol-4-yl}-1H-quinolin-2-one,
6,7-difluoro-3-(1-{4-[3-(4-methyl-piperazin-1-yl)-propoxy]-phenyl}-1H-[1,2,3]triazol-4-yl)-1H-quinolin-2-one,
6-fluoro-3-(1-{4-[2-(1-methyl-piperidin-4-yl)-ethoxy]-phenyl}-1H-[1,2,3]triazol-4-yl)-1H-quinolin-2-one,
6,7-difluoro-3-{1-[4-(1-methyl-piperidine-4-carbonyl)-phenyl]-1H-[1,2,3]triazol-4-yl}-1H-quinolin-2-one,
6-fluoro-3-(1-{4-[2-(4-methyl-piperazin-1-yl)-2-oxo-ethoxy]-phenyl}-1H-[1,2,3]triazol-4-yl)-1H-quinolin-2-one,
6,7-difluoro-3-(1-{4-[2-(1-methyl-piperidin-4-yl)-ethoxy]-phenyl}-1H-[1,2,3]triazol-4-yl)-1H-quinolin-2-one,
6,7-difluoro-3-(1-{4-[2-(4-methyl-piperazin-1-yl)-2-oxo-ethoxy]-phenyl}-1H-[1,2,3]triazol-4-yl)-1H-quinolin-2-one,
6-methyl-3-{1-[4-(4-methyl-piperazine-1-carbonyl)-phenyl]-1H-[1,2,3]triazol-4-yl}-1H-quinolin-2-one,
6,7-difluoro-3-(1-{4-[2-(4-methyl-piperazin-1-yl)-2-oxo-ethyl]-phenyl}-1H-[1,2,3]triazol-4-yl)-1H-quinolin-2-one,
3-{1-[4-(4-methyl-piperazine-1-carbonyl)-phenyl]-1H-[1,2,3]triazol-4-yl}-7-trifluoromethyl-1H-quinolin-2-one,
3-{1-[4-(4-dimethylamino-piperidine-1-carbonyl)-phenyl]-1H-[1,2,3]triazol-4-yl}-6,7-difluoro-1H-quinolin-2-one,
3-{1-[4-(4-dimethylamino-piperidine-1-carbonyl)-phenyl]-1H-[1,2,3]triazol-4-yl}-6-fluoro-1H-quinolin-2-one,
6,7-difluoro-3-(1-{1-[2-(4-methyl-piperazin-1-yl)-2-oxo-ethyl]-1H-indazol-5-yl}-1H-[1,2,3]triazol-4-yl)-1H-quinolin-2-one,
6,7-difluoro-3-{1-[4-(4-methyl-2-oxo-piperazin-1-yl)-phenyl]-1H-[1,2,3]triazol-4-yl}-1H-quinolin-2-one,
6-Fluoro-3-(1-{4-[4-(2-methoxy-ethyl)-piperazine-1-carbonyl]-phenyl}-1H-[1,2,3]triazol-4-yl)-1H-[1,8]naphthyridin-2-one,
6-fluoro-3-(1-{4-[2-(4-methyl-piperazin-1-yl)-ethoxy]-phenyl}-1H-[1,2,3]triazol-4-yl)-1H-quinolin-2-one,
3-{1-[4-(morpholine-4-carbonyl)-phenyl]-1H-[1,2,3]triazol-4-yl}-2-oxo-1,2-dihydro-quinoline-7-carbonitrile,
6-fluoro-3-(1-{1-[2-(4-methyl-piperazin-1-yl)-2-oxo-ethyl]-1H-indol-5-yl}-1H-[1,2,3]triazol-4-yl)-1H-quinolin-2-one,
acetic acid (R)-1-{4-[4-(6-fluoro-2-oxo-1,2-dihydro-quinolin-3-yl)-[1,2,3]triazol-1-yl]-benzoyl}-pyrrolidin-3-yl ester,
acetic acid (S)-1-{4-[4-(6-fluoro-2-oxo-1,2-dihydro-quinolin-3-yl)-[1,2,3]triazol-1-yl]-benzoyl}-pyrrolidin-3-yl ester,
6-fluoro-3-{1-[4-((R)-3-hydroxy-pyrrolidine-1-carbonyl)-phenyl]-1H-[1,2,3]triazol-4-yl}-1H-quinolin-2-one,
6-fluoro-3-{1-[4-((S)-3-hydroxy-pyrrolidine-1-carbonyl)-phenyl]-1H-[1,2,3]triazol-4-yl}-1H-quinolin-2-one,
6-fluoro-3-{1-[4-(4-hydroxy-piperidine-1-carbonyl)-phenyl]-1H-[1,2,3]triazol-4-yl}-1H-quinolin-2-one,
6-fluoro-3-{1-[4-(3-hydroxy-piperidine-1-carbonyl)-phenyl]-1H-[1,2,3]triazol-4-yl}-1H-quinolin-2-one,
4-methyl-3-{1-[4-(morpholine-4-carbonyl)-phenyl]-1H-[1,2,3]triazol-4-yl}-1H-quinolin-2-one,
6,7-Difluoro-3-{1-[4-(2-pyrrolidin-1-yl-ethoxy)-phenyl]-1H-[1,2,3]triazol-4-yl}-1H-quinolin-2-one,
N-(2-diethylamino-ethyl)-4-[4-(6,7-difluoro-2-oxo-1,2-dihydro-quinolin-3-yl)-[1,2,3]triazol-1-yl]-benzamide,
4-[4-(7-chloro-6-fluoro-2-oxo-1,2-dihydro-quinolin-3-yl)-[1,2,3]triazol-1-yl]-N-(2-diethylamino-ethyl)-benzamide,
3-(1-{4-[4-(2-diethylamino-ethyl)-piperazine-1-carbonyl]-phenyl}-1H-[1,2,3]triazol-4-yl)-6,7-difluoro-1H-quinolin-2-one,
6-fluoro-3-{1-[4-(4-methoxy-piperidine-1-carbonyl)-phenyl]-1H-[1,2,3]triazol-4-yl}-1H-quinolin-2-one,
6,7-difluoro-3-{1-[4-(4-methoxy-piperidine-1-carbonyl)-phenyl]-1H-[1,2,3]triazol-4-yl}-1H-quinolin-2-one,
6,7-difluoro-3-{1-[4-((R)-3-methoxy-piperidine-1-carbonyl)-phenyl]-1H-[1,2,3]triazol-4-yl}-1H-quinolin-2-one,
6,7-difluoro-3-{1-[4-((S)-3-methoxy-piperidine-1-carbonyl)-phenyl]-1H-[1,2,3]triazol-4-yl}-1H-quinolin-2-one,
6-fluoro-3-{1-[4-((R)-3-methoxy-piperidine-1-carbonyl)-phenyl]-1H-[1,2,3]triazol-4-yl}-1H-quinolin-2-one,
6-fluoro-3-{1-[4-((S)-3-methoxy-piperidine-1-carbonyl)-phenyl]-1H-[1,2,3]triazol-4-yl}-1H-quinolin-2-one,
N-(2-diethylamino-ethyl)-4-[4-(6-fluoro-2-oxo-1,2-dihydro-quinolin-3-yl)-[1,2,3]triazol-1-yl]-benzamide,
6-fluoro-3-{1-[4-((S)-2-hydroxymethyl-pyrrolidine-1-carbonyl)-phenyl]-1H-[1,2,3]triazol-4-yl}-1H-quinolin-2-one,
6-fluoro-3-{1-[4-((R)-2-methoxymethyl-pyrrolidine-1-carbonyl)-phenyl]-1H-[1,2,3]triazol-4-yl}-1H-quinolin-2-one,
6-fluoro-3-{1-[4-((R)-3-methoxymethyl-pyrrolidine-1-carbonyl)-phenyl]-1H-[1,2,3]triazol-4-yl}-1H-quinolin-2-one,
6,7-difluoro-3-{1-[4-((R)-3-methoxymethyl-pyrrolidine-1-carbonyl)-phenyl]-1H-[1,2,3]triazol-4-yl}-1H-quinolin-2-one,
6,7-difluoro-3-{1-[4-((S)-3-methoxymethyl-pyrrolidine-1-carbonyl)-phenyl]-1H-[1,2,3]triazol-4-yl}-1H-quinolin-2-one,
6-fluoro-3-{1-[4-((S)-3-methoxymethyl-pyrrolidine-1-carbonyl)-phenyl]-1H-[1,2,3]triazol-4-yl}-1H-quinolin-2-one,

- 3-(1-{4-[3-(2-diethylamino-ethoxy)-pyrrolidine-1-carbonyl]-phenyl}-1H-[1,2,3]triazol-4-yl)-6-fluoro-1H-quinolin-2-one,
- 6-fluoro-3-{1-[4-(2-oxa-7-aza-spiro[4.4]nonane-7-carbonyl)-phenyl]-1H-[1,2,3]triazol-4-yl}-1H-quinolin-2-one,
- 6-fluoro-3-{1-[4-(2-oxa-6-aza-spiro[3.4]octane-6-carbonyl)-phenyl]-1H-[1,2,3]triazol-4-yl}-1H-quinolin-2-one,
- 6-fluoro-3-{1-[4-(3-hydroxymethyl-pyrrolidine-1-carbonyl)-phenyl]-1H-[1,2,3]triazol-4-yl}-1H-quinolin-2-one,
- 3-{1-[4-(3-dimethylamino-pyrrolidine-1-carbonyl)-phenyl]-1H-[1,2,3]triazol-4-yl}-6-fluoro-1H-quinolin-2-one,
- 6-fluoro-3-(1-{4-[3-(4-hydroxy-piperidin-1-yl)-pyrrolidine-1-carbonyl]-phenyl}-1H-[1,2,3]triazol-4-yl)-1H-quinolin-2-one,
- 6-fluoro-3-(1-{4-[3-(2-morpholin-4-yl-ethoxy)-pyrrolidine-1-carbonyl]-phenyl}-1H-[1,2,3]triazol-4-yl)-1H-quinolin-2-one,
- 6-fluoro-3-(1-{4-[(R)-3-(2-methoxy-ethoxymethyl)-pyrrolidine-1-carbonyl]-phenyl}-1H-[1,2,3]triazol-4-yl)-1H-quinolin-2-one,
- 4-[4-(6-fluoro-2-oxo-1,2-dihydro-quinolin-3-yl)-[1,2,3]triazol-1-yl]-N-(2-methoxy-ethyl)-N-methyl-benzamide,
- 4-[4-(6,7-difluoro-2-oxo-1,2-dihydro-quinolin-3-yl)-[1,2,3]triazol-1-yl]-N-(2-methoxy-ethyl)-N-methyl-benzamide,
- 6-fluoro-3-{1-[4-((R)-3-hydroxymethyl-morpholine-4-carbonyl)-phenyl]-1H-[1,2,3]triazol-4-yl}-1H-quinolin-2-one,
- 6-fluoro-3-{1-[4-(2-hydroxymethyl-piperidine-1-carbonyl)-phenyl]-1H-[1,2,3]triazol-4-yl}-1H-quinolin-2-one,
- 6-fluoro-3-{1-[4-((S)-2-methoxymethyl-pyrrolidine-1-carbonyl)-phenyl]-1H-[1,2,3]triazol-4-yl}-1H-quinolin-2-one,
- 6-fluoro-3-{1-[4-((S)-3-hydroxymethyl-morpholine-4-carbonyl)-phenyl]-1H-[1,2,3]triazol-4-yl}-1H-quinolin-2-one,
- 3-{1-[4-((2S,5S)-2,5-bis-methoxymethyl-pyrrolidine-1-carbonyl)-phenyl]-1H-[1,2,3]triazol-4-yl}-6-fluoro-1H-quinolin-2-one,
- 3-{1-[4-((2R,5R)-2,5-bis-methoxymethyl-pyrrolidine-1-carbonyl)-phenyl]-1H-[1,2,3]triazol-4-yl}-6-fluoro-1H-quinolin-2-one,
- 3-{1-[4-((2S,5S)-2,5-bis-methoxymethyl-pyrrolidine-1-carbonyl)-phenyl]-1H-[1,2,3]triazol-4-yl}-6,7-difluoro-1H-quinolin-2-one,
- 3-{1-[4-((2R,5R)-2,5-bis-methoxymethyl-pyrrolidine-1-carbonyl)-phenyl]-1H-[1,2,3]triazol-4-yl}-6,7-difluoro-1H-quinolin-2-one,
- 6,7-difluoro-3-(1-{4-[3-(2-morpholin-4-yl-ethoxy)-pyrrolidine-1-carbonyl]-phenyl}-1H-[1,2,3]triazol-4-yl)-1H-quinolin-2-one,
- 6-fluoro-7-methyl-3-{1-[4-(4-methyl-piperazine-1-carbonyl)-phenyl]-1H-[1,2,3]triazol-4-yl}-1H-quinolin-2-one,
- 6,7-difluoro-3-(1-{4-[(R)-3-(2-methoxy-ethoxymethyl)-pyrrolidine-1-carbonyl]-phenyl}-1H-[1,2,3]triazol-4-yl)-1H-quinolin-2-one,
- 6-fluoro-3-(1-{4-[3-(2-pyrrolidin-1-yl-ethoxy)-pyrrolidine-1-carbonyl]-phenyl}-1H-[1,2,3]triazol-4-yl)-1H-quinolin-2-one,
- 6,7-difluoro-3-(1-{4-[3-(2-pyrrolidin-1-yl-ethoxy)-pyrrolidine-1-carbonyl]-phenyl}-1H-[1,2,3]triazol-4-yl)-1H-quinolin-2-one,
- (R)-1-{4-[4-(6-fluoro-2-oxo-1,2-dihydro-quinolin-3-yl)-[1,2,3]triazol-1-yl]-benzoyl}-pyrrolidine-3-carboxylic acid amide,
- 6-fluoro-3-{1-[4-((2S,4R)-4-hydroxy-2-hydroxymethyl-pyrrolidine-1-carbonyl)-phenyl]-1H-[1,2,3]triazol-4-yl}-1H-quinolin-2-one,
- 6-fluoro-3-{1-[4-(2-oxa-6-aza-spiro[3.5]nonane-6-carbonyl)-phenyl]-1H-[1,2,3]triazol-4-yl}-1H-quinolin-2-one,
- 6-fluoro-3-{1-[4-(2-oxa-7-aza-spiro[3.5]nonane-7-carbonyl)-phenyl]-1H-[1,2,3]triazol-4-yl}-1H-quinolin-2-one,
- 6-fluoro-3-{1-[4-(4-oxetan-3-yl-piperazine-1-carbonyl)-phenyl]-1H-[1,2,3]triazol-4-yl}-1H-quinolin-2-one,
- 3-{1-[4-(2,5-dioxa-8-aza-spiro[3.5]nonane-8-carbonyl)-phenyl]-1H-[1,2,3]triazol-4-yl}-6-fluoro-1H-quinolin-2-one,
- 4-[4-(6-fluoro-2-oxo-1,2-dihydro-quinolin-3-yl)-[1,2,3]triazol-1-yl]-N-oxetan-3-yl-benzamide,
- 6,7-difluoro-3-(1-{4-[(S)-3-(2-methoxy-ethoxymethyl)-pyrrolidine-1-carbonyl]-phenyl}-1H-[1,2,3]triazol-4-yl)-1H-quinolin-2-one,
- 6-fluoro-3-{1-[4-(2-oxa-5-aza-spiro[3.4]octane-5-carbonyl)-phenyl]-1H-[1,2,3]triazol-4-yl}-1H-quinolin-2-one,
- 6-fluoro-3-{1-[4-(2-oxa-6-aza-spiro[3.3]heptane-6-carbonyl)-phenyl]-1H-[1,2,3]triazol-4-yl}-1H-quinolin-2-one,
- 6-fluoro-3-(1-{4-[(S)-3-(2-methoxy-ethoxymethyl)-pyrrolidine-1-carbonyl]-phenyl}-1H-[1,2,3]triazol-4-yl)-1H-quinolin-2-one,
- 3-{1-[4-((3R,4S)-3,4-dimethoxy-pyrrolidine-1-carbonyl)-phenyl]-1H-[1,2,3]triazol-4-yl}-6-fluoro-1H-quinolin-2-one,
- 4-[4-(6-fluoro-2-oxo-1,2-dihydro-quinolin-3-yl)-[1,2,3]triazol-1-yl]-N,N-bis-(2-methoxy-ethyl)-benzamide,
- 3-{1-[4-(3-diethylaminomethyl-pyrrolidine-1-carbonyl)-phenyl]-1H-[1,2,3]triazol-4-yl}-6,7-difluoro-1H-quinolin-2-one,
- N-(3-acetyl-3-aza-bicyclo[3.1.0]hex-6-yl)-4-[4-(6-fluoro-2-oxo-1,2-dihydro-quinolin-3-yl)-[1,2,3]triazol-1-yl]-benzamide,
- 6-fluoro-3-{1-[4-((2S,4R)-2-hydroxymethyl-4-methoxy-pyrrolidine-1-carbonyl)-phenyl]-1H-[1,2,3]triazol-4-yl}-1H-quinolin-2-one,
- (S)-1-{4-[4-(6-fluoro-2-oxo-1,2-dihydro-quinolin-3-yl)-[1,2,3]triazol-1-yl]-benzoyl}-pyrrolidine-2-carboxylic acid amide,
- (S)-1-{4-[4-(6-fluoro-2-oxo-1,2-dihydro-quinolin-3-yl)-[1,2,3]triazol-1-yl]-benzoyl}-pyrrolidine-3-carboxylic acid amide,
- 6-fluoro-3-{1-[4-((2R,4R)-2-hydroxymethyl-4-methoxy-pyrrolidine-1-carbonyl)-phenyl]-1H-[1,2,3]triazol-4-yl}-1H-quinolin-2-one,
- 6-fluoro-3-{1-[4-(2-oxa-5-aza-spiro[3.5]nonane-5-carbonyl)-phenyl]-1H-[1,2,3]triazol-4-yl}-1H-quinolin-2-one,
- 6-chloro-3-{1-[4-((S)-2-hydroxymethyl-pyrrolidine-1-carbonyl)-phenyl]-1H-[1,2,3]triazol-4-yl}-1H-quinolin-2-one,
- 6-chloro-3-{1-[4-((2R,4R)-2-hydroxymethyl-4-methoxy-pyrrolidine-1-carbonyl)-phenyl]-1H-[1,2,3]triazol-4-yl}-1H-quinolin-2-one, 6-chloro-3-{1-[4-((2S,4R)-2-hydroxymethyl-4-methoxy-pyrrolidine-1-carbonyl)-phenyl]-1H-[1,2,3]triazol-4-yl}-1H-quinolin-2-one,
6-chloro-3-(1-{4-[3-(4-hydroxy-piperidin-1-yl)-pyrrolidine-1-carbonyl]-phenyl}-1H-[1,2,3]triazol-4-yl)-1H-quinolin-2-one,
6-chloro-3-{1-[4-(4-oxetan-3-yl-piperazine-1-carbonyl)-phenyl]-1H-[1,2,3]triazol-4-yl}-1H-quinolin-2-one,
6-fluoro-3-(1-{4-[(S)-3-(2-methoxy-ethoxy)-pyrrolidine-1-carbonyl]-phenyl}-1H-[1,2,3]triazol-4-yl)-1H-quinolin-2-one,
6-fluoro-3-(1-{4-[(R)-3-(2-methoxy-ethoxy)-pyrrolidine-1-carbonyl]-phenyl}-1H-[1,2,3]triazol-4-yl)-1H-quinolin-2-one,
6-chloro-3-{1-[4-((S)-2-methoxymethyl-pyrrolidine-1-carbonyl)-phenyl]-1H-[1,2,3]triazol-4-yl}-1H-quinolin-2-one,
6-chloro-3-{1-[4-(3-dimethylamino-pyrrolidine-1-carbonyl)-phenyl]-1H-[1,2,3]triazol-4-yl}-1H-quinolin-2-one,
6-chloro-3-{1-[4-(2-hydroxymethyl-piperidine-1-carbonyl)-phenyl]-1H-[1,2,3]triazol-4-yl}-1H-quinolin-2-one,
6-chloro-3-{1-[4-(2-oxa-7-aza-spiro[3.5]nonane-7-carbonyl)-phenyl]-1H-[1,2,3]triazol-4-yl}-1H-quinolin-2-one,
6-chloro-3-{1-[4-(2-oxa-6-aza-spiro[3.4]octane-6-carbonyl)-phenyl]-1H-[1,2,3]triazol-4-yl}-1H-quinolin-2-one,
6-chloro-3-{1-[4-(2-oxa-6-aza-spiro[3.3]heptane-6-carbonyl)-phenyl]-1H-[1,2,3]triazol-4-yl}-1H-quinolin-2-one,
6-chloro-3-(1-{4-[(S)-3-(2-methoxy-ethoxy)-pyrrolidine-1-carbonyl]-phenyl}-1H-[1,2,3]triazol-4-yl)-1H-quinolin-2-one,
6-chloro-3-(1-{4-[(R)-3-(2-methoxy-ethoxy)-pyrrolidine-1-carbonyl]-phenyl}-1H-[1,2,3]triazol-4-yl)-1H-quinolin-2-one,
6-fluoro-3-(1-{4-[(R)-3-(2-methoxy-ethoxy)-pyrrolidine-1-carbonyl]-phenyl}-1H-pyrazol-4-yl)-1H-quinolin-2-one,
(R)-1-{4-[4-(6-fluoro-2-oxo-1,2-dihydro-quinolin-3-yl)-[1,2,3]triazol-1-yl]-benzoyl}-pyrrolidine-2-carboxylic acid amide,
3-{1-[4-((3R,4R)-3,4-dimethoxy-pyrrolidine-1-carbonyl)-phenyl]-1H-[1,2,3]triazol-4-yl}-6-fluoro-1H-quinolin-2-one,
3-{1-[4-((3S,4S)-3,4-dimethoxy-pyrrolidine-1-carbonyl)-phenyl]-1H-[1,2,3]triazol-4-yl}-6-fluoro-1H-quinolin-2-one,
6-fluoro-3-{1-[4-((S)-3-fluoro-pyrrolidine-1-carbonyl)-phenyl]-1H-[1,2,3]triazol-4-yl}-1H-quinolin-2-one,
6-chloro-3-{1-[4-((S)-3-fluoro-pyrrolidine-1-carbonyl)-phenyl]-1H-[1,2,3]triazol-4-yl}-1H-quinolin-2-one,
3-{1-[4-(3,3-difluoro-pyrrolidine-1-carbonyl)-phenyl]-1H-[1,2,3]triazol-4-yl}-6-fluoro-1H-quinolin-2-one,
6-chloro-3-{1-[4-(3,3-difluoro-pyrrolidine-1-carbonyl)-phenyl]-1H-[1,2,3]triazol-4-yl}-1H-quinolin-2-one,
6-fluoro-3-{1-[4-((R)-3-fluoro-pyrrolidine-1-carbonyl)-phenyl]-1H-[1,2,3]triazol-4-yl}-1H-quinolin-2-one,
6-chloro-3-{1-[4-((R)-3-fluoro-pyrrolidine-1-carbonyl)-phenyl]-1H-[1,2,3]triazol-4-yl}-1H-quinolin-2-one,
6-chloro-3-{1-[4-((3R,4R)-3,4-dimethoxy-pyrrolidine-1-carbonyl)-phenyl]-1H-[1,2,3]triazol-4-yl}-1H-quinolin-2-one,
6-chloro-3-{1-[4-((3S,4S)-3,4-dimethoxy-pyrrolidine-1-carbonyl)-phenyl]-1H-[1,2,3]triazol-4-yl}-1H-quinolin-2-one,
6-fluoro-3-{1-[4-(pyrrolidine-1-carbonyl)-phenyl]-1H-[1,2,3]triazol-4-yl}-1H-quinolin-2-one,
6-fluoro-3-{1-[4-((R)-4-hydroxy-isoxazolidine-2-carbonyl)-phenyl]-1H-[1,2,3]triazol-4-yl}-1H-quinolin-2-one,
6-chloro-3-{1-[4-((R)-4-hydroxy-isoxazolidine-2-carbonyl)-phenyl]-1H-[1,2,3]triazol-4-yl}-1H-quinolin-2-one,
6-fluoro-3-{1-[4-((S)-4-hydroxy-isoxazolidine-2-carbonyl)-phenyl]-1H-[1,2,3]triazol-4-yl}-1H-quinolin-2-one,
6-chloro-3-{1-[4-((S)-4-hydroxy-isoxazolidine-2-carbonyl)-phenyl]-1H-[1,2,3]triazol-4-yl}-1H-quinolin-2-one,
6-fluoro-3-{1-[4-((R)-2-pyrrolidin-1-ylmethyl-pyrrolidine-1-carbonyl)-phenyl]-1H-[1,2,3]triazol-4-yl}-1H-quinolin-2-one,
6-fluoro-3-{1-[4-((S)-2-pyrrolidin-1-ylmethyl-pyrrolidine-1-carbonyl)-phenyl]-1H-[1,2,3]triazol-4-yl}-1H-quinolin-2-one,
3-{1-[4-(azetidine-1-carbonyl)-phenyl]-1H-[1,2,3]triazol-4-yl}-6-fluoro-1H-quinolin-2-one,
6-fluoro-3-(1-{4-[2-(4-methyl-piperazine-1-carbonyl)-pyrrolidine-1-carbonyl]-phenyl}-1H-[1,2,3]triazol-4-yl)-1H-quinolin-2-one,
6-fluoro-3-{1-[4-((R)-3-methanesulfonyl-pyrrolidine-1-carbonyl)-phenyl]-1H-[1,2,3]triazol-4-yl}-1H-quinolin-2-one,
6-fluoro-3-{1-[4-((S)-3-methanesulfonyl-pyrrolidine-1-carbonyl)-phenyl]-1H-[1,2,3]triazol-4-yl}-1H-quinolin-2-one,
6-fluoro-3-{1-[4-(3-methanesulfonylmethyl-pyrrolidine-1-carbonyl)-phenyl]-1H-[1,2,3]triazol-4-yl}-1H-quinolin-2-one,
6-fluoro-3-(1-{4-[2-(1-methyl-1H-pyrazol-4-yl)-pyrrolidine-1-carbonyl]-phenyl}-1H-[1,2,3]triazol-4-yl)-1H-quinolin-2-one,
6-fluoro-3-{1-[4-(2-pyridin-3-yl-pyrrolidine-1-carbonyl)-phenyl]-1H-[1,2,3]triazol-4-yl}-1H-quinolin-2-one,
6-fluoro-3-(1-{4-[2-(4-methyl-piperazin-1-ylmethyl)-pyrrolidine-1-carbonyl]-phenyl}-1H-[1,2,3]triazol-4-yl)-1H-quinolin-2-one,
6-fluoro-3-{1-[4-(2-methyl-pyrrolidine-1-carbonyl)-phenyl]-1H-[1,2,3]triazol-4-yl}-1H-quinolin-2-one,
6-fluoro-3-{1-[4-(2-methyl-2,6-diaza-spiro[3.4]octane-6-carbonyl)-phenyl]-1H-[1,2,3]triazol-4-yl}-1H-quinolin-2-one,
6-chloro-3-{1-[4-(2-methyl-2,6-diaza-spiro[3.4]octane-6-carbonyl)-phenyl]-1H-[1,2,3]triazol-4-yl}-1H-quinolin-2-one,
6-fluoro-3-{1-[4-((3aR,6aR)-5-methyl-hexahydro-pyrrolo[3,4-b]pyrrole-1-carbonyl)-phenyl]-1H-[1,2,3]triazol-4-yl}-1H-quinolin-2-one,
6-chloro-3-{1-[4-((R)-2-methyl-pyrrolidine-1-carbonyl)-phenyl]-1H-[1,2,3]triazol-4-yl}-1H-quinolin-2-one,
3-{1-[4-(2,2-dimethyl-pyrrolidine-1-carbonyl)-phenyl]-1H-[1,2,3]triazol-4-yl}-6-fluoro-1H-quinolin-2-one,
6-fluoro-3-(1-{4-[3-(4-methyl-piperazine-1-carbonyl)-pyrrolidine-1-carbonyl]-phenyl}-1H-[1,2,3]triazol-4-yl)-1H-quinolin-2-one,
6-fluoro-3-{1-[4-((R)-2-methyl-pyrrolidine-1-carbonyl)-phenyl]-1H-pyrazol-4-yl}-1H-quinolin-2-one, 6-fluoro-3-{1-[4-(4-methyl-piperazine-1-carbonyl)-phenyl]-1H-pyrazol-4-yl}-1H-quinolin-2-one,
6-fluoro-3-{1-[4-((S)-3-methoxy-pyrrolidine-1-carbonyl)-phenyl]-1H-pyrazol-4-yl}-1H-quinolin-2-one,
6-fluoro-3-{1-[4-((R)-3-methoxy-pyrrolidine-1-carbonyl)-phenyl]-1H-pyrazol-4-yl}-1H-quinolin-2-one,
6-fluoro-3-(1-{4-[(S)-3-(2-methoxy-ethoxy)-pyrrolidine-1-carbonyl]-phenyl}-1H-pyrazol-4-yl)-1H-quinolin-2-one,
3-{1-[4-((3R,4R)-3,4-dimethoxy-pyrrolidine-1-carbonyl)-phenyl]-1H-pyrazol-4-yl}-6-fluoro-1H-quinolin-2-one,
6-fluoro-3-{1-[4-((2S,4R)-2-hydroxymethyl-4-methoxy-pyrrolidine-1-carbonyl)-phenyl]-1H-pyrazol-4-yl}-1H-quinolin-2-one,
6-fluoro-3-{1-[4-((2R,4R)-2-hydroxymethyl-4-methoxy-pyrrolidine-1-carbonyl)-phenyl]-1H-pyrazol-4-yl}-1H-quinolin-2-one,
3-{1-[4-((3S,4S)-3,4-dimethoxy-pyrrolidine-1-carbonyl)-phenyl]-1H-pyrazol-4-yl}-6-fluoro-1H-quinolin-2-one,
6,7-difluoro-3-{1-[4-(4-methyl-piperazine-1-carbonyl)-phenyl]-1H-pyrazol-4-yl}-1H-quinolin-2-one,
6-chloro-3-{1-[4-(4-methyl-piperazine-1-carbonyl)-phenyl]-1H-pyrazol-4-yl}-1H-quinolin-2-one,
3-{1-[4-((S)-3-amino-pyrrolidine-1-carbonyl)-phenyl]-1H-[1,2,3]triazol-4-yl}-6-fluoro-1H-quinolin-2-one,
6,7-difluoro-3-{1-[4-((cis)-hexahydro-pyrrolo[3,4-c]pyrrole-2-carbonyl)-phenyl]-1H-[1,2,3]triazol-4-yl}-1H-quinolin-2-one,
6-fluoro-3-{1-[4-((cis)-hexahydro-pyrrolo[3,4-c]pyrrole-2-carbonyl)-phenyl]-1H-[1,2,3]triazol-4-yl}-1H-quinolin-2-one,
3-{1-[4-((R)-3-amino-piperidine-1-carbonyl)-phenyl]-1H-[1,2,3]triazol-4-yl}-6,7-difluoro-1H-quinolin-2-one,
3-{1-[4-((S)-3-amino-piperidine-1-carbonyl)-phenyl]-1H-[1,2,3]triazol-4-yl}-6,7-difluoro-1H-quinolin-2-one,
6-Fluoro-3-{1-[4-((R)-3-methylamino-pyrrolidine-1-carbonyl)-phenyl]-1H-[1,2,3]triazol-4-yl}-1H-quinolin-2-one,
6-fluoro-3-{1-[4-((S)-3-methylamino-pyrrolidine-1-carbonyl)-phenyl]-1H-[1,2,3]triazol-4-yl}-1H-quinolin-2-one,
3-{1-[4-((R)-3-amino-pyrrolidine-1-carbonyl)-phenyl]-1H-[1,2,3]triazol-4-yl}-6-fluoro-1H-quinolin-2-one,
6-fluoro-3-{1-[4-((R)-3-hydroxymethyl-piperazine-1-carbonyl)-phenyl]-1H-[1,2,3]triazol-4-yl}-1H-quinolin-2-one,
6-fluoro-3-{1-[4-((S)-2-hydroxymethyl-piperazine-1-carbonyl)-phenyl]-1H-[1,2,3]triazol-4-yl}-1H-quinolin-2-one,
6-fluoro-3-{1-[4-((R)-2-hydroxymethyl-piperazine-1-carbonyl)-phenyl]-1H-[1,2,3]triazol-4-yl}-1H-quinolin-2-one,
3-{1-[4-(6-amino-3-aza-bicyclo[3.1.0]hexane-3-carbonyl)-phenyl]-1H-[1,2,3]triazol-4-yl}-6-fluoro-1H-quinolin-2-one,
6-chloro-3-{1-[4-((S)-2-dimethylaminomethyl-pyrrolidine-1-carbonyl)-phenyl]-1H-[1,2,3]triazol-4-yl}-1H-quinolin-2-one,
3-{1-[4-((S)-2-dimethylaminomethyl-pyrrolidine-1-carbonyl)-phenyl]-1H-[1,2,3]triazol-4-yl}-6-fluoro-1H-quinolin-2-one,
3-{1-[4-((R)-2-dimethylaminomethyl-pyrrolidine-1-carbonyl)-phenyl]-1H-[1,2,3]triazol-4-yl}-6,7-difluoro-1H-quinolin-2-one,
3-{1-[4-((R)-2-dimethylaminomethyl-pyrrolidine-1-carbonyl)-phenyl]-1H-[1,2,3]triazol-4-yl}-6-fluoro-1H-quinolin-2-one,
6-chloro-3-{1-[4-((R)-2-dimethylaminomethyl-pyrrolidine-1-carbonyl)-phenyl]-1H-[1,2,3]triazol-4-yl}-1H-quinolin-2-one,
3-{1-[4-((S)-2-dimethylaminomethyl-pyrrolidine-1-carbonyl)-phenyl]-1H-[1,2,3]triazol-4-yl}-6,7-difluoro-1H-quinolin-2-one,
3-{1-[4-((S)-2-dimethylaminomethyl-pyrrolidine-1-carbonyl)-phenyl]-1H-pyrazol-4-yl}-6-fluoro-1H-quinolin-2-one,
3-{1-[4-((R)-2-dimethylaminomethyl-pyrrolidine-1-carbonyl)-phenyl]-1H-pyrazol-4-yl}-6-fluoro-1H-quinolin-2-one,
3-{1-[4-((S)-3-dimethylaminomethyl-pyrrolidine-1-carbonyl)-phenyl]-1H-[1,2,3]triazol-4-yl}-6-fluoro-1H-quinolin-2-one,
6-fluoro-3-{1-[4-((cis)-5-methyl-hexahydro-pyrrolo[3,4-c]pyrrole-2-carbonyl)-phenyl]-1H-[1,2,3]triazol-4-yl}-1H-quinolin-2-one,
3-{1-[4-((R)-3-dimethylamino-piperidine-1-carbonyl)-phenyl]-1H-[1,2,3]triazol-4-yl}-6,7-difluoro-1H-quinolin-2-one,
3-{1-[4-((S)-3-dimethylamino-piperidine-1-carbonyl)-phenyl]-1H-[1,2,3]triazol-4-yl}-6,7-difluoro-1H-quinolin-2-one,
3-{1-[4-(6-dimethylamino-3-aza-bicyclo[3.1.0]hexane-3-carbonyl)-phenyl]-1H-[1,2,3]triazol-4-yl}-6-fluoro-1H-quinolin-2-one,
3-{1-[4-((R)-3-dimethylamino-piperidine-1-carbonyl)-phenyl]-1H-[1,2,3]triazol-4-yl}-6-fluoro-1H-quinolin-2-one,
3-{1-[4-((S)-3-dimethylamino-piperidine-1-carbonyl)-phenyl]-1H-[1,2,3]triazol-4-yl}-6-fluoro-1H-quinolin-2-one,
3-{1-[4-((R)-3-dimethylamino-piperidine-1-carbonyl)-phenyl]-1H-[1,2,3]triazol-4-yl}-7-fluoro-1H-quinolin-2-one,
3-{1-[4-((R)-3-dimethylaminomethyl-pyrrolidine-1-carbonyl)-phenyl]-1H-[1,2,3]triazol-4-yl}-6-fluoro-1H-quinolin-2-one,
3-{1-[4-((R)-3-dimethylaminomethyl-pyrrolidine-1-carbonyl)-phenyl]-1H-[1,2,3]triazol-4-yl}-6,7-difluoro-1H-quinolin-2-one,
3-{1-[4-((S)-3-dimethylamino-piperidine-1-carbonyl)-phenyl]-1H-[1,2,3]triazol-4-yl}-7-fluoro-1H-quinolin-2-one,
3-{1-[4-((S)-3-diethylamino-piperidine-1-carbonyl)-phenyl]-1H-[1,2,3]triazol-4-yl}-6-fluoro-1H-quinolin-2-one,
3-{1-[4-((R)-3-diethylamino-piperidine-1-carbonyl)-phenyl]-1H-[1,2,3]triazol-4-yl}-6-fluoro-1H-quinolin-2-one,
3-{1-[4-(4-dimethylamino-3,3-difluoro-pyrrolidine-1-carbonyl)-phenyl]-1H-[1,2,3]triazol-4-yl}-6-fluoro-1H-quinolin-2-one,
3-{1-[4-((S)-3-dimethylaminomethyl-pyrrolidine-1-carbonyl)-phenyl]-1H-pyrazol-4-yl}-6-fluoro-1H-quinolin-2-one,
3-{1-[4-((trans)-3-dimethylamino-4-fluoro-pyrrolidine-1-carbonyl)-phenyl]-1H-[1,2,3]triazol-4-yl}-6-fluoro-1H-quinolin-2-one,
6-fluoro-3-[1-(4-methylamino-phenyl)-1H-[1,2,3]triazol-4-yl]-1H-quinolin-2-one, (R)-tetrahydro-furan-2-carboxylic acid {4-[4-(6-fluoro-2-oxo-1,2-dihydro-quinolin-3-yl)-[1,2,3]triazol-1-yl]-phenyl}-methyl-amide, (S)-tetrahydro-furan-2-carboxylic acid {4-[4-(6-fluoro-2-oxo-1,2-dihydro-quinolin-3-yl)-[1,2,3]triazol-1-yl]-phenyl}-methyl-amide, tetrahydro-pyran-4-carboxylic acid {4-[4-(6-fluoro-2-oxo-1,2-dihydro-quinolin-3-yl)-[1,2,3]triazol-1-yl]-phenyl}-methyl-amide, (R)—N-{4-[4-(6-fluoro-2-oxo-1,2-dihydro-quinolin-3-yl)-[1,2,3]triazol-1-yl]-phenyl}-2-methoxy-N-methyl-propionamide, (2S,4S)-4-methoxy-pyrrolidine-2-carboxylic acid {4-[4-(6-fluoro-2-oxo-1,2-dihydro-quinolin-3-yl)-[1,2,3]triazol-1-yl]-phenyl}-methyl-amide, (S)—N-{4-[4-(6-fluoro-2-oxo-1,2-dihydro-quinolin-3-yl)-[1,2,3]triazol-1-yl]-phenyl}-2-methoxy-N-methyl-propionamide, 1-methyl-piperidine-4-carboxylic acid {4-[4-(6-fluoro-2-oxo-1,2-dihydro-quinolin-3-yl)-[1,2,3]triazol-1-yl]-phenyl}-methyl-amide, 6-fluoro-3-{1-[5-((S)-3-methoxy-pyrrolidine-1-carbonyl)-thiophen-3-yl]-1H-[1,2,3]triazol-4-yl}-1H-quinolin-2-one, 6-fluoro-3-{1-[5-((R)-3-methoxy-pyrrolidine-1-carbonyl)-thiophen-3-yl]-1H-[1,2,3]triazol-4-yl}-1H-quinolin-2-one, N-{4-[4-(6,7-difluoro-2-oxo-1,2-dihydro-quinolin-3-yl)-[1,2,3]triazol-1-yl]-phenyl}-N-methyl-acetamide, N-{4-[4-(6-fluoro-2-oxo-1,2-dihydro-quinolin-3-yl)-[1,2,3]triazol-1-yl]-phenyl}-N-methyl-acetamide, 6-fluoro-3-[1-(2-methyl-1-oxo-2,3-dihydro-1H-isoindol-5-yl)-1H-[1,2,3]triazol-4-yl]-1H-quinolin-2-one, 6-Fluoro-3-{1-[4-((trans)-3-methoxy-cyclopentyloxy)-phenyl]-1H-[1,2,3]triazol-4-yl}-1H-quinolin-2-one, 6-chloro-3-{1-[4-((1S,3R)-3-methoxy-cyclopentyloxy)-phenyl]-1H-[1,2,3]triazol-4-yl}-1H-quinolin-2-one, 6-fluoro-3-[1-(4-methoxy-phenyl)-1H-[1,2,3]triazol-4-yl]-1H-quinolin-2-one, 6-fluoro-3-{1-[4-((R)-3-methoxy-pyrrolidine-1-sulfonyl)-phenyl]-1H-[1,2,3]triazol-4-yl}-1H-quinolin-2-one, 6-chloro-3-{1-[4-((R)-3-methoxy-pyrrolidine-1-sulfonyl)-phenyl]-1H-[1,2,3]triazol-4-yl}-1H-quinolin-2-one, 6-fluoro-3-{1-[4-((S)-3-methoxy-pyrrolidine-1-sulfonyl)-phenyl]-1H-[1,2,3]triazol-4-yl}-1H-quinolin-2-one, 6-chloro-3-{1-[4-((S)-3-methoxy-pyrrolidine-1-sulfonyl)-phenyl]-1H-[1,2,3]triazol-4-yl}-1H-quinolin-2-one, 6-fluoro-3-{1-[4-((1S,2S)-2-methoxy-cyclopentyloxy)-phenyl]-1H-[1,2,3]triazol-4-yl}-1H-quinolin-2-one, 6-chloro-3-[1-(4-cyclopentyloxy-phenyl)-1H-[1,2,3]triazol-4-yl]-1H-quinolin-2-one, 3-[1-(4-cyclopentyloxy-phenyl)-1H-[1,2,3]triazol-4-yl]-6-fluoro-1H-quinolin-2-one, 6-fluoro-3-{1-[4-(tetrahydro-furan-3-yloxy)-phenyl]-1H-[1,2,3]triazol-4-yl}-1H-quinolin-2-one, 6-chloro-3-{1-[4-(tetrahydro-furan-3-yloxy)-phenyl]-1H-[1,2,3]triazol-4-yl}-1H-quinolin-2-one, 6-fluoro-3-{1-[4-((R)-1-methyl-pyrrolidin-3-yloxy)-phenyl]-1H-[1,2,3]triazol-4-yl}-1H-quinolin-2-one, 6-chloro-3-{1-[4-((S)-1-methyl-pyrrolidin-3-yloxy)-phenyl]-1H-[1,2,3]triazol-4-yl}-1H-quinolin-2-one, 6-chloro-3-{1-[4-((R)-1-methyl-pyrrolidin-3-yloxy)-phenyl]-1H-[1,2,3]triazol-4-yl}-1H-quinolin-2-one, 6-fluoro-3-{1-[4-((S)-1-methyl-pyrrolidin-3-yloxy)-phenyl]-1H-[1,2,3]triazol-4-yl}-1H-quinolin-2-one, 6-fluoro-3-{1-[4-(1-methyl-piperidin-4-ylmethyl)-phenyl]-1H-[1,2,3]triazol-4-yl}-1H-quinolin-2-one, 6,7-difluoro-3-{1-[4-((S)-1-methyl-pyrrolidin-3-yloxy)-phenyl]-1H-[1,2,3]triazol-4-yl}-1H-quinolin-2-one, 6,7-difluoro-3-{1-[4-((R)-1-methyl-pyrrolidin-3-yloxy)-phenyl]-1H-[1,2,3]triazol-4-yl}-1H-quinolin-2-one, 6-chloro-3-{1-[4-(1-methyl-piperidin-4-ylmethyl)-phenyl]-1H-[1,2,3]triazol-4-yl}-1H-quinolin-2-one, 6-fluoro-3-{1-[4-(1-methyl-piperidin-4-yloxy)-phenyl]-1H-[1,2,3]triazol-4-yl}-1H-quinolin-2-one, 6-chloro-3-{1-[4-(1-methyl-piperidin-4-yloxy)-phenyl]-1H-[1,2,3]triazol-4-yl}-1H-quinolin-2-one, and pharmaceutically acceptable salts, tautomers and stereoisomers thereof, including mixtures thereof in all ratios.

* * * * *